US012665077B2

(12) United States Patent
Durlach et al.

(10) Patent No.: US 12,665,077 B2
(45) Date of Patent: ***Jun. 23, 2026

(54) CAREGIVER ASSISTANCE SYSTEM

(71) Applicant: Stryker Corporation, Kalamazoo, MI (US)

(72) Inventors: Thomas Joseph Durlach, Portage, MI (US); Ross Michael Nave, Kalamazoo, MI (US)

(73) Assignee: Stryker Corporation, Portage, MI (US)

(*) Notice: Subject to any disclaimer, the term of this patent is extended or adjusted under 35 U.S.C. 154(b) by 28 days.

This patent is subject to a terminal disclaimer.

(21) Appl. No.: 18/780,073

(22) Filed: Jul. 22, 2024

(65) Prior Publication Data

US 2024/0379218 A1     Nov. 14, 2024

Related U.S. Application Data

(63) Continuation of application No. 17/622,593, filed as application No. PCT/US2020/039587 on Jun. 25, 2020, now Pat. No. 12,046,359.

(Continued)

(51) Int. Cl.
    *A61G 7/015*         (2006.01)
    *A61B 5/00*          (2006.01)
    (Continued)

(52) U.S. Cl.
    CPC ............. *G16H 40/20* (2018.01); *A61B 5/002* (2013.01); *A61B 5/1117* (2013.01);
    (Continued)

(58) Field of Classification Search
    CPC ..... G16H 40/20; A61B 5/1117; A61B 5/0077; A61B 2562/0219
    See application file for complete search history.

(56) References Cited

U.S. PATENT DOCUMENTS

2020/0203007 A1* 6/2020 Durlach ................. A61G 7/002
2020/0203010 A1* 6/2020 Durlach ................... A61G 7/00
2022/0122724 A1* 4/2022 Durlach ............... A61B 5/1117

FOREIGN PATENT DOCUMENTS

EP          3348192 A1      7/2018
JP          2014-219957     11/2014
                (Continued)

OTHER PUBLICATIONS

Office Action in co-pending Japanese Patent Application JP 2021-578247, mailed May 7, 2024.

*Primary Examiner* — Reginald R Reyes
(74) *Attorney, Agent, or Firm* — Gardner, Linn, Burkhart & Ondersma LLP

(57)          ABSTRACT

A caregiver assistance system helps caregivers manage the care of patients and the beds that support the patients. The system monitors tasks associated with the patients, such as caregiver rounding tasks, bed sore assessments, and/or fall risk assessments, and forwards completed tasks to an EMR server. The system also monitors the state of the beds and determines compliance with one or more healthcare facility protocols. Over time, the system gathers data from multiple beds regarding how often the beds are in compliance with the healthcare facility protocols and produces reports of the compliance levels to assist administrators in managing their healthcare facilities. The system may further monitor how quickly caregivers responds to one or more alert conditions relating to the beds and/or patients, and generate reports for the administrators regarding such response times.

20 Claims, 64 Drawing Sheets

Related U.S. Application Data

(60) Provisional application No. 62/868,947, filed on Jun. 30, 2019, provisional application No. 62/868,387, filed on Jun. 28, 2019, provisional application No. 62/868,360, filed on Jun. 28, 2019.

(51) Int. Cl.

| | |
|---|---|
| *A61B 5/11* | (2006.01) |
| *G16H 40/20* | (2018.01) |
| *G16H 40/67* | (2018.01) |

(52) U.S. Cl.
CPC .......... *A61B 5/6892* (2013.01); *A61B 5/6898* (2013.01); *A61B 5/7275* (2013.01); *A61B 5/746* (2013.01); *G16H 40/67* (2018.01); *A61B 5/1128* (2013.01); *A61B 5/7435* (2013.01); *A61B 5/7475* (2013.01)

(56) References Cited

FOREIGN PATENT DOCUMENTS

| | | |
|---|---|---|
| JP | 2017-033056 | 2/2017 |
| JP | 2018-163644 | 10/2018 |
| WO | 2019032991 A1 | 2/2019 |

* cited by examiner

226

CAREGIVER ASSISTANCE SYSTEM

CROSS-REFERENCE TO RELATED APPLICATIONS

This application claims priority to U.S. patent application Ser. No. 17/622,593 (corresponding to PCT patent application PCT/US2020/039587) filed Dec. 23, 2021, by inventors Thomas Durlach et al. and entitled CAREGIVER ASSISTANCE SYSTEM, which in turn claims priority to the following U.S. provisional patent applications: Ser. No. 62/868,947 filed Jun. 30, 2019, by inventors Thomas Durlach et al. and entitled CAREGIVER ASSISTANCE SYSTEM, Ser. No. 62/868,387 filed Jun. 28, 2019, by inventors Thomas Durlach et al. and entitled CAREGIVER ASSISTANCE SYSTEM, and Ser. No. 62/868,360 filed Jun. 28, 2019, by inventors Thomas Durlach et al. and entitled CAREGIVER ASSISTANCE SYSTEM, the complete disclosures of all of which are incorporated herein by reference.

This application is related to, and incorporates by reference, the following applications in their entirety: U.S. patent application Ser. No. 62/781,831 filed Dec. 19, 2018, and entitled SYSTEM FOR MANAGING PATIENT SUPPORT APPARATUSES AND CLINICAL ROUNDS; U.S. patent application Ser. No. 62/868,387 filed Jun. 28, 2019, and entitled CAREGIVER ASSISTANCE SYSTEM; U.S. patent application Ser. No. 62/826,187 filed Mar. 29, 2019, and entitled SYSTEM FOR MANAGING PATIENT SUPPORT APPARATUSES AND PATIENT FALL RISKS; U.S. patent application Ser. No. 62/868,360 filed Jun. 28, 2019, and entitled CAREGIVER ASSISTANCE SYSTEM; U.S. patent application Ser. No. 62/781,879 filed Dec. 19, 2018, and entitled SYSTEM FOR MANAGING PATIENT SUPPORT APPARATUSES AND CLINICAL ROUNDS; and U.S. patent application Ser. No. 62/826,195 filed Mar. 29, 2019, and entitled SYSTEM FOR MANAGING PATIENT SUPPORT APPARATUSES AND BED SORE RISKS.

BACKGROUND

The present disclosure relates to patient support apparatuses, such as beds, cots, stretchers, operating tables, recliners, or the like. More specifically, the present disclosure relates to a system for assisting caregivers with both the management of such patient support apparatuses and the performance of other tasks, such as, but not limited to, their rounding tasks.

Hospitals typically expect nurses and/or other caregivers to perform a variety of different duties when caring for patients. These duties include administering medications and/or therapies, taking vital sign readings, installing and removing IV drips, taking blood samples, ensuring patient compliance with prescribed activities and/or medications, assisting the patient into and out of bed, regularly visiting the patient, configuring the patient's bed to be in a desired state, documenting one or more of these activities, and generally being responsive to the patient's needs. One of these duties including performing what are customarily known as patient rounds. Such rounding duties involve the caregiver personally checking on the wellbeing of the patient at certain specified intervals. Hospital administrators typically specify a minimum frequency at which the caregivers are to perform these rounding duties, such as, for example, at least once every two hours. In some situations, the rounding frequencies may vary based on the medical condition of the patient, the wing or section of the hospital, and/or other factors.

Hospitals also typically expect nurses and/or other caregivers to help reduce the risk of patients falling. In many hospitals, patients are to be assigned a fall risk and, if the fall risk exceeds a certain threshold, certain steps are to be taken by the caregiver in order to reduce the likelihood of the patient falling while in the hospital. Such fall risk reduction steps often involve placing one or more components of the hospital bed into one or more desired states, such as, for example, arming an exit detection system, activating a brake, etc. Still further, hospitals also typically expect nurses and/or other caregivers to ensure that patients do not develop bed sores while they are in the healthcare facility, and/or to ensure that any existing bed sores do not get worse.

In addition to the foregoing tasks, hospitals also typically expect the nurses to ensure that the patient's bed is configured properly. The proper configuration may involve any one or more of the following: ensuring the bed is plugged into an electrical outlet; ensuring the bed is properly connected to a nurse call system; ensuring an exit detection system is armed; ensuring a monitoring system on the bed is armed; and/or other ensuring one or more other aspects of the bed are in a desired state.

The tasks and responsibilities of nurses and other caregivers are therefore manifold and substantial, and technology that assists these caregivers in meeting their responsibilities and providing quality healthcare to their patients is desirable.

SUMMARY

According to various embodiments, a tool for assisting caregivers in carrying out multiple ones of their patient care responsibilities is provided herein. According to some embodiments, a tool is specifically provided for facilitating one of more of the following: carrying out bed sore risk reduction duties, carrying out fall risk reduction duties, carrying out bed configuration duties, carrying out rounding duties, and carrying out other periodic duties for which a reminder may be set. The tool may assist with the caregiver's duties by displaying screens that show various status data regarding the bed, as well as notifications and reminders associated with one or more duties of the caregiver. The status data regarding the bed may indicate whether the bed is operating in accordance with one or more healthcare facility protocols, such as a protocol to reduce fall risks, a protocol to reduce bed sore risks, a protocol to reduce ventilator associated pneumonia (VAP), and/or other protocols. The status data may also include data indicating whether the bed is operating on battery power or power from an electrical outlet, a state of a battery on the bed, whether the bed is properly coupled to a nurse call system, whether the bed is able to wirelessly communicate with a hospital network, whether the bed needs servicing, whether an exit detection system of the bed is armed and, if so, what sensitivity level it is armed at; and/or other aspects of the bed.

Still further, the tool provides alerts to the caregiver of a variety of different unperformed tasks. Such tasks may involve setting various states of the bed to desired states, evaluating one or more aspects of the patient's health (e.g. whether the patient is at risk for falling, and/or other undesirable conditions); documenting one or more aspects of the patient's care, and/or other tasks. By combining reminders and notifications for these disparate tasks into a single tool, the tool eliminates the need for caregivers to access and/or utilize separate tools for performing such disparate patient care tasks. In some embodiments, the tool comprises a server-based caregiver assistance application that communicates with the patients' beds and mobile electronic devices carried by the caregivers, as well as stationary electronic devices that display information for beds that are located in predesignated areas of the hospital.

The tool may also or alternatively inform healthcare facility administrators of response times of caregivers to alert conditions and how well caregivers are administrating various healthcare facility protocols. Such information may be gathered for multiple beds over the course of different time periods, averaged, graphed, and/or separated according to various parameters, such as, but not limited to caregivers, wards, floors, etc. The tool may also allow caregivers to easily view instructions for carrying out any one or more of these protocols, and/or instructions for operating any one or more features of the beds.

A caregiver assistance system according to an embodiment of the present disclosure includes a plurality of beds and a server-based caregiver assistance application. The beds each include a litter frame; a support deck supported on the litter frame and configured to support a patient thereon; a memory containing an identifier uniquely identifying the bed; a nurse call cable port adapted to couple to a first end of a nurse call cable having a second end adapted to couple to a nurse call outlet to thereby enable the bed to communicate with a nurse call system; a sensor adapted to detect a state of the respective bed; a network transceiver; and a controller in communication with the memory, the network transceiver, and the sensor. The controller is adapted to activate an alert if the sensor detects that the bed is in an undesired state and to deactivate the alert when a caregiver responds to the alert. The controller is further adapted to forward the identifier, a first alert message, and a second alert message to the caregiver assistance application via the network transceiver. The first alert message is sent in response to the alert being activated and the second alert message is sent in response to the alert being deactivated. The caregiver assistance application is adapted to receive the identifier, the first alert message, and the second alert message from the bed, and to perform the following: (i) record a time interval for each bed from which the caregiver assistance application receives the first alert message and the second alert message wherein the time interval corresponds to an amount of time between receipt of the first alert message and receipt of the second alert message; (ii) forward the time interval to an electronic device; and (iii) display the time interval on a display of the electronic device.

According to another aspect of the present disclosure, the caregiver assistance application is further adapted to average multiple time intervals together and display the average of the multiple time intervals on the display of the electronic device.

In some embodiments, the caregiver assistance application is further adapted to perform the following: (i) determine a first average for a first set of multiple time intervals gathered over a first time period; (ii) determine a second average for a second set of multiple time intervals gathered over a second time period; and (iii) simultaneously display both the first average and the second average on the electronic device.

The first and/or second time periods may be configurable by an administrator and may include, but are not limited to, a day, a week, a month, a year, etc.

In some embodiments, the sensor is an exit detection system and the undesired state is a state in which the respective patient has exited from the respective bed. In some other embodiments, the sensor may also, or alternatively be, a member of a set of sensors monitored by a bed monitoring system. In these latter embodiments, the undesired state may include any one or more of the following: a brake on the respective bed is not activated; a set of siderails on the respective bed is not raised; a height of the litter frame of the respective bed is not at a minimum height, or an exit detection system of the respective bed is not activated.

In some embodiments, each of the plurality of beds includes a timer and the controller is adapted to utilize the timer to determine the time interval and to send the time interval to the caregiver assistance application. In other embodiments, the caregiver assistance application includes a timer and is adapted to utilize the timer to determine the time interval.

In some embodiments, the caregiver assistance application is adapted to record multiple time intervals and to categorize each of the multiple time intervals according to at least one of the following: a caregiver, a location, a time of day, and a type of patient.

The caregiver assistance application, in some embodiments, is further adapted to perform any one or more of the following: (a) receive bed sore risk data from the caregiver regarding each patient's risk of developing bed sores and determine a bed sore risk assessment score from the bed sore risk data; (b) receive fall risk data from the caregiver regarding each patient's risk of falling and determine a fall risk assessment score from the fall risk data; (c) receive completion data from the caregiver indicating when the caregiver has completed a rounding task for each patient; (d) display a bed sore risk assessment indicator on the display of the electronic device, the bed sore risk assessment indicator indicating each patient's risk of developing bed sores; (e) display a fall risk assessment indicator on the display of the electronic device, the fall risk assessment indicator indicating each patient's risk of falling; (f) display a time until a next rounding task is to be completed for each patient; (g) display a reminder to perform a rounding task with each patient; (h) display a reminder to perform a bed sore risk assessment for each patient; (i) display a reminder to perform a fall risk assessment for each patient; ( ) activate an exit detection system onboard each bed using the electronic device; and (k) receive an exit alert when each patient exits from his or her respective bed.

In some embodiments, one or more of the beds further comprise a battery and a battery sensor adapted to detect a status of the battery. In such embodiments, the controller is adapted to send the status of the respective battery to the caregiver assistance application and the caregiver assistance application is further adapted to display on the display of the electronic device a battery status indicator. The battery status indicator indicates the status of the respective battery.

In some embodiments, the bed further comprises a short range transceiver adapted to communicate with a headwall-mounted short range transmitter of a location beacon. The short range transmitter is adapted to forward location data and beacon battery status data to an adjacent one of the plurality of beds. The location data is indicative of a location of the adjacent bed and the beacon battery status data is indicative of a status of a battery of the location beacon. The adjacent bed is adapted to forward the beacon battery status data to the caregiver assistance application, which is further adapted to display a beacon status indicator on the display of the electronic device. The beacon status indicator indicates a current status of the battery of the location beacon.

In some embodiments, each controller is further adapted to forward signal strength data to the caregiver assistance application. The signal strength data is indicative of a strength of a signal between the respective transceiver and a wireless access point of a healthcare facility. The caregiver assistance application is further adapted to display a signal strength indicator on the display of the electronic device, and the signal strength indicator indicates the strength of the signal between the respective transceiver and the wireless access point of the healthcare facility.

In some embodiments, the alert indicates that the nurse call cable port is not communicatively coupled to the nurse call system.

In some embodiments, the sensor is adapted to determine whether the respective bed is currently operating on power from a battery or power from an electrical wall outlet, and the alert indicates that the respective bed is currently operating on battery power.

In some embodiments, each controller is further adapted to determine if the respective bed should be serviced and to forward servicing data to the caregiver assistance application when the respective bed should be serviced. The caregiver assistance application is further adapted to display a bed service indicator on the display of the electronic device.

The caregiver assistance application, in some embodiments, is further adapted to display instructions for using a feature of at least one of the beds on the electronic device.

According to another embodiment of the present disclosure, a caregiver assistance system is disclosed that includes a plurality of beds and a server-hosted caregiver assistance application. Each of the plurality of beds includes a litter frame; a support deck supported on the litter frame and configured to support a respective patient thereon; a memory containing an identifier uniquely identifying the respective bed; a nurse call cable port adapted to couple to a first end of a nurse call cable having a second end adapted to couple to a nurse call outlet to thereby enable the respective bed to communicate with a nurse call system; an occupancy detector adapted to detect when the respective patient is occupying the respective bed and not occupying the respective bed; a sensing system adapted to sense an alert condition of the respective bed when the sensing system is activated and to not sense the alert condition when the sensing system is deactivated; a network transceiver; and a controller in communication with the memory, the network transceiver, and the sensing system. The controller is adapted to forward occupancy data and activation data off the respective bed via the network transceiver. The occupancy data indicates when the respective patient is occupying the respective bed and not occupying the respective bed, and the activation data indicates when the respective sensing system is activated and deactivated. The caregiver assistance application is adapted to receive the identifier, the activation data, and the occupancy data, and to perform the following: (i) determine whether each bed is currently in compliance with a healthcare facility protocol based upon the activation data and the occupancy data; (ii) record a compliance value indicative of how many beds are currently in compliance with the healthcare facility protocol and how many beds are currently out of compliance with the healthcare facility protocol; and (iii) display the compliance value on a display of an electronic device in communication with the caregiver assistance application.

According to other aspects of the present disclosure, the caregiver assistance application may further be configured to generate a report showing the compliance value as measured over a time period.

In some embodiments, the sensing system of each bed is an exit detection system adapted to detect when the respective patient exits from the respective bed. In other embodiments, the sensing system of each bed is a bed monitoring system adapted to monitor a plurality of conditions of the respective bed. In still other embodiments, the sensing system of each bed is lockout control adapted to prevent a pivotable head section of the support deck from pivoting below a threshold angle when activated. In such embodiments, the healthcare facility protocol is a Ventilator Associated Pneumonia (VAP) prevention protocol.

In still other embodiments, multiple sensing systems may be included. For example, in some embodiments, each bed further comprises a second sensing system adapted to sense a second alert condition of the respective bed when the second sensing system is activated and to not sense the second alert condition when the second sensing system is deactivated. In such embodiments, the controller is further adapted to send second activation data to the caregiver assistance application that indicates when the second sensing system is activated and deactivated. The caregiver assistance application is further adapted to perform the following: (i) determine whether each bed is currently in compliance with the healthcare facility protocol based upon the second activation data and the occupancy data; (ii) record a second compliance value indicative of how many beds are currently in compliance with the healthcare facility protocol based upon the second activation data and the occupancy data, and how many beds are currently out of compliance with the healthcare facility protocol based upon the second activation data and the occupancy data; and (iii) display the second compliance value on a display of an electronic device in communication with the caregiver assistance application.

In some embodiments, each bed is further configured to communicate an alert to both the caregiver assistance application via the network transceiver and to the nurse call system via the nurse call cable port when the sensing system senses the alert condition.

In those embodiments with a bed monitoring system, the bed monitoring system may be adapted to monitor at least the following: a state of a brake on the respective bed; states of a set of siderails on the respective bed; a height of the litter frame of the respective bed; and an activation/deactivation state of an exit detection system on the respective bed.

In some embodiments, the caregiver assistance application is further adapted to generate a report of the compliance value for beds associated with a specific caregiver.

The healthcare facility protocol, in some embodiments, defines when the sensing system of the respective bed is to be activated based upon whether a particular patient assigned to the respective bed has a fall risk assessment score above a threshold. Alternatively, or additionally, the healthcare facility protocol may define when the sensing system of the respective bed is to be activated based upon whether a particular patient assigned to the respective bed has a bed sore risk assessment score above a threshold.

The caregiver assistance application may further be configured to receive fall risk assessment data from a mobile electronic device associated with a particular caregiver and to generate the fall risk assessment score from the fall risk assessment data. Similarly, the caregiver assistance application may further be configured to receive bed sore risk assessment data from a mobile electronic device associated with a particular caregiver and to generate the bed sore risk assessment score from the bed sore risk assessment data.

In some embodiments, the caregiver assistance application is further adapted to communicate with a mobile electronic device associated with a particular caregiver and to display at least the following data for a particular bed associated with the particular caregiver: (a) a state of a battery onboard the particular bed; (b) a signal strength indicator indicating a strength of a wireless signal between the network transceiver of the particular bed and a wireless access point of a healthcare facility local area network; (c) an indicator indicating if the nurse call cable port of the particular bed is not communicatively coupled to the nurse call system; and (d) an indicator indicating if the particular bed is currently operating on power from a battery or power from an electrical wall outlet.

In some embodiments, the caregiver assistance application is further adapted to send a notification to a mobile electronic device associated with a particular caregiver if a particular bed associated with the particular caregiver is not in compliance the healthcare facility protocol.

The caregiver assistance application may further be adapted to display instructions for using a feature of at least one of the beds on the electronic device.

According to another embodiment of the present disclosure, a caregiver assistance system is provided that includes a bed and a server-hosted caregiver assistance application. The bed includes a litter frame; a support deck supported on the litter frame and configured to support a patient thereon; a memory containing an identifier uniquely identifying the bed; a nurse call cable port adapted to couple to a first end of a nurse call cable having a second end adapted to couple to a nurse call outlet to thereby enable the bed to communicate with a nurse call system; a sensor adapted to detect a state of the bed; a network transceiver; and a controller in communication with the memory and the network transceiver. The controller is adapted to transmit the identifier and data from the sensor off the bed via the network transceiver. The caregiver assistance application is adapted to receive the identifier and the sensor data and to perform the following: (i) display the sensor data on a mobile electronic device associated with a caregiver assigned to the patient; and (ii) display instructions for using a feature of the bed on the mobile electronic device.

According to other aspects of the present disclosure, the instructions may include a video stored in a memory location accessible to the caregiver assistance application. In such embodiments, the caregiver assistance application is configured to deliver the video to the mobile electronic device.

In some embodiments, the bed further comprises a sensing system adapted to sense an alert condition of the bed when the sensing system is activated and to not sense the alert condition when the sensing system is deactivated; and an occupancy detector adapted to detect when the patient is occupying the bed and not occupying the bed. In such embodiments, the controller may further be adapted to forward occupancy data and activation data off the bed to the caregiver assistance application via the network transceiver. The occupancy data indicates when the patient is occupying the bed and not occupying the bed, and the activation data indicates when the respective sensing system is activated and deactivated. The caregiver assistance application is further adapted to: determine whether the bed is currently in compliance with a healthcare facility protocol based upon the activation data and the occupancy data; and, if the bed is currently out of compliance with the healthcare facility protocol, display data indicating non-compliance on the mobile electronic device.

In some embodiments, the controller is further adapted to activate an alert if the sensor detects the bed is in an undesired state and to deactivate the alert when a caregiver responds to the alert, as well as to forward a first alert message and a second alert message to the caregiver assistance application via the network transceiver. The caregiver assistance application is further adapted to record a time interval corresponding to an amount of time between receipt of the first alert message and receipt of the second alert message; forward the time interval to a second mobile electronic device associated with a supervisor of a healthcare facility; and display the time interval on a display of the second mobile electronic device. The sensor may be an exit detection system, a bed monitoring system, a component of either of these systems, or still another type of sensor.

In any of the embodiments disclosed herein, the mobile electronic devices may be a smart phone, a tablet computer, a laptop computer, or another type of mobile electronic device.

Additionally, in any of the embodiments disclosed herein, the mobile electronic device may include a browser app that the mobile electronic device uses to communicate with the caregiver assistance application by accessing at least one Uniform Resource Locator (URL) associated with the server. The caregiver assistance application may be adapted to send an alert to the mobile electronic device that is processed by an app other than the browser app, such as, but not limited to, a phone app, an email app, or a messaging app.

A caregiver assistance system according to an embodiment of the present disclosure includes a first bed, a second bed, and a server-based caregiver assistance application. Each of the first and second beds includes a litter frame, a support deck supported on the litter frame and configured to support a patient thereon, a memory containing an identifier uniquely identifying the respective bed, a sensor adapted to detect a state of a component of the respective bed, a transceiver, and a controller. The controller is adapted to transmit the identifier and data from the sensor off the respective bed to the server on which the caregiver assistance application is hosted. The caregiver assistance application is adapted to receive first sensor data from the first bed and second sensor data from the second bed and to perform the following: forward the first sensor data to a first mobile electronic device associated with a first caregiver assigned to a first patient on the first bed; forward the second sensor data to a second mobile electronic device associated with a second caregiver assigned to a second patient on the second bed; receive a share request; forward the first sensor data to the second mobile electronic device if the caregiver assistance application receives acceptance of the share request; and not forward the first sensor data to the second mobile electronic device if the caregiver assistance application does not receive the acceptance of the share request.

According to other aspects of the present disclosure, the caregiver assistance application may be adapted to receive the share request from the first mobile electronic device and to receive the acceptance from the second mobile electronic device.

In some embodiments, the caregiver assistance application is adapted to receive the share request and the acceptance from the second mobile electronic device.

The caregiver assistance application, in some embodiments, is further adapted to designate the second caregiver as a primary caregiver for the first patient after receiving the acceptance. The caregiver assistance application thereafter forwards alerts from the first bed to the second mobile electronic device while the second caregiver is designated as the primary caregiver for the first patient. The caregiver assistance application also does not forward the alerts from the first bed to the first mobile electronic device while the second caregiver is designated as the primary caregiver for the first patient.

The caregiver assistance application is further adapted, in some embodiments, to receive an unshare request, and in response to the unshare request, to stop forwarding the first sensor data to the second mobile electronic device if the caregiver assistance application receives acceptance of the unshare request.

In some embodiments, the caregiver assistance application is further adapted to forward additional data regarding the first patient to the second mobile electronic device if the caregiver assistance application receives acceptance of the share request, and to not forward the additional data to the second mobile electronic device if the caregiver assistance application does not receive the acceptance of the share request. The additional data may include a reminder to perform at least one of the following tasks: to make a rounding visit to the first patient, to assess a bed sore risk of the first patient, to assess a fall risk of the first patient, to start a therapy on the first patient, and to change a setting on the first bed.

The caregiver assistance application is further adapted in some embodiments to receive patient data from the second mobile electronic device after receiving acceptance of the share request. The patient data from the second mobile electronic device relates to a condition of the first patient and the caregiver assistance application is further adapted to forward the patient data to an electronic medical records server for entry in a patient record corresponding to the first patient.

The caregiver assistance application is configured in some embodiments to obtain a location of the first mobile electronic device from a real time location server. In such embodiments, the caregiver assistance application is adapted to display a first screen on the first mobile electronic device if the first mobile electronic device is in a first location and to display a second screen on the first mobile electronic device if the first mobile electronic device is in a second location. The caregiver assistance application may further be configured to obtain a location of the second mobile electronic device from the real time location server and to display a third screen on the second mobile electronic device if the second mobile electronic device is in the first location and to display a fourth screen on the second mobile electronic device if the second mobile electronic device is in the second location.

According to another aspect of the present disclosure, a caregiver assistance system for helping a caregiver to perform patient care tasks is provided. The caregiver assistance system includes a plurality of beds and each bed includes a litter frame, a support deck supported on the litter frame and configured to support a patient thereon, a memory containing an identifier uniquely identifying the respective bed, a sensor adapted to detect a state of a component of the respective bed, a transceiver, and a controller. The controller is adapted to transmit the identifier and sensor data from the respective bed to a server on which the caregiver assistance application is hosted. The caregiver assistance application is configured to receive the sensor data and the identifier and to perform the following: communicate with a mobile electronic device carried by a caregiver; determine a set of patients assigned to the caregiver; obtain a location of the caregiver; determine if the location corresponds to any room in which a patient from the set of patients is staying; display a first screen on the mobile electronic device if the caregiver is in any room to which a patient from the set of patients is staying; and display a second screen on the mobile electronic device if the caregiver is not located in any room in which a patient from the set of patients is staying.

According to other aspects of the present disclosure, the caregiver assistance application may be configured such that the first screen displays the sensor data from a particular one of the plurality of beds wherein the particular one of the plurality of beds is located in the same room as the caregiver.

In some embodiments, the second screen displays a listing of rooms that identifies all of the rooms in which the caregiver's set of patients are located.

In some embodiments, the second screen displays a state of multiple beds that are located in the rooms in which the caregiver's set of patients are located.

The sensor data displayed on the first screen may include data indicating whether a bed exit system onboard the particular one of the plurality of beds is armed or not armed. Alternatively or additionally, the sensor data displayed on the first screen includes data indicating whether a bed monitoring system onboard the particular one of the plurality of beds is armed or not armed. Still further, the sensor data displayed on the first screen may include any one or more of the following: (a) data indicating if a brake onboard the particular one of the plurality of beds is activated; (b) data indicating a low height status of the litter frame of the particular one of the plurality of beds; (c) data indicating if a power cable onboard the particular one of the plurality of beds is plugged into an electrical outlet; and/or (d) data indicating if a nurse call cable onboard the particular one of the plurality of beds is plugged into a nurse call outlet.

A caregiver assistance application according to another embodiment of the present disclosure includes a plurality of beds and a server-based caregiver assistance application. Each of the beds includes a litter frame, a support deck supported on the litter frame and configured to support a patient thereon, a memory containing an identifier uniquely identifying the respective bed, a plurality of sensors adapted to detect states of a plurality of components of the respective bed, a transceiver, and a controller. The controller transmits the identifier and sensor data from the plurality of sensors off of the respective bed to the server of the caregiver assistance application. The caregiver assistance application is adapted to receive the sensor data and the identifier and to perform the following: communicate with a mobile electronic device carried by a caregiver; determine a set of patients assigned to the caregiver; determine room numbers for the set of patients; identify a set of beds from the plurality of beds wherein each bed in the set of beds is associated with a corresponding patient from the set of patients; and display a first screen on the mobile electronic device. The first screen includes a listing of the room numbers of the set of patients and a status indicator for at least one bed from the set of beds, wherein the status indicator is derived from the sensor data received from the at least one bed.

According to other aspects of the present disclosure, the caregiver assistance application determines a set of patients assigned to the caregiver by communicating with both an Admission, Discharge, and Tracking (ADT) server and a nurse call system server.

In some embodiments, the status indicator indicates whether the at least one bed is in compliance with a set of criteria. The set of criteria may be defined by a fall risk reduction protocol, a bed sore risk reduction protocol, and/or any one of more of the following: an activated brake onboard the at least one bed, an activated exit detection system onboard the at least one bed, a plurality of raised siderails onboard the at least one bed, and a low height of the litter frame onboard the at least one bed.

In some embodiments, the caregiver assistance application is further adapted to display on the first screen a fall risk indicator if any patients from the set of patients have an elevated risk of falling and/or a bed sore risk indicator if any patients from the set of patients have an elevated risk of developing a bed sore.

A caregiver assistance system according to another embodiment of the present disclosure includes a bed and a server-based caregiver assistance application. The bed includes a litter frame, a support deck supported on the litter frame and configured to support a patient thereon, an inflatable mattress positioned on the support deck and adapted to turn the patient while the patient is supported thereon, a sensor adapted to detect a state of a component of the bed, a memory containing an identifier uniquely identifying the bed, a transceiver, and a controller. The controller transmits the identifier and sensor data from the sensor off the bed to the server hosting the caregiver assistance application. The caregiver assistance application receives the identifier and the sensor data and is adapted to perform the following: receive login credentials from a user's mobile electronic device, determine if the login credentials are valid, determine if the login credentials correspond to a caregiver or a technician, and if the login credentials correspond to a caregiver, display data on a display of the user's mobile electronic device that includes the sensor data and that includes patient information relating to a patient assigned to the bed; or if the login credentials correspond to a technician, display data on the display of the user's mobile electronic device that includes the sensor data and none of the patient information.

According to other aspects of the present disclosure, if the login credentials correspond to the technician, the caregiver assistance application is further configured to perform the following: communicate with a geographically remote equipment management system; send a request for a service history of the bed to the geographically remote equipment management system using the identifier; receive the service history of the bed from the geographically remote equipment management system; and display the service history of the bed on the display of the user's mobile electronic device.

In some embodiments, if the login credentials correspond to the caregiver, the caregiver assistance application is configured to not display any service history of the bed on the user's mobile electronic device.

In some embodiments, if the login credentials correspond to the technician, the caregiver assistance application is configured to receive maintenance information regarding the bed from the user's mobile electronic device and to forward the maintenance information to the geographically remote equipment management system.

In some embodiments, if the login credentials correspond to the technician, the caregiver assistance application is configured to receive both maintenance information regarding the bed and confirmation data from the user's mobile electronic device, to analyze the confirmation data to confirm the technician's presence at the bed, and to send the confirmation data and the maintenance information to the geographically remote equipment management system.

In some embodiments, the caregiver assistance application is further adapted to receive a bed code from the user's mobile electronic device. The bed code is captured by the user's mobile electronic device and uniquely identifies the bed. The bed may be adapted to display the bed code on a display of the bed such that the user's mobile electronic device is able to capture an image of the bed code. Alternatively or additionally, the bed may be adapted to wirelessly transmit the bed code via a short range transmitter to a short range transmitter onboard the user's mobile electronic device.

In some embodiments, if the login credential correspond to the caregiver, the caregiver assistance application is configured to use the bed code to automatically select what type of screen to display on the display of the user's mobile electronic device. The type of screen may be selected from the following: a first screen showing sensor data from the bed, and a second screen showing sensor data from a plurality of beds.

In some embodiments, the caregiver assistance application is further configured to determine if the login credentials correspond to an administrator, and if the login credential do correspond to an administrator, to display all of the following: the sensor data from the bed, the patient information relating to the patient assigned to the bed, and a service history of the bed.

In some embodiments, if the login credentials correspond to the caregiver, the caregiver assistance application is further configured to receive a share request from the caregiver, to forward the share request to another mobile electronic device associated with a second caregiver, and if the second caregiver accepts the share request, to forward the sensor data from the bed and the patient information to the another mobile electronic device.

A caregiver assistance system according to another embodiment of the present disclosure includes a bed and a server-based caregiver assistance application. The bed includes a litter frame; a support deck supported on the litter frame and configured to support a patient thereon; a memory containing an identifier uniquely identifying the bed; a nurse call cable port adapted to couple to a first end of a nurse call cable having a second end adapted to couple to a nurse call outlet to thereby enable the bed to communicate with a nurse call system; a sensor adapted to detect if the nurse call cable port is electrically coupled to the nurse call system via the nurse call cable; a transceiver; and a controller in communication with the memory, the transceiver, and the sensor. The controller is adapted to transmit the identifier and data from the sensor off the bed to the server on which the caregiver assistance application is hosted. The caregiver assistance application is adapted to receive the identifier and the sensor data from the bed and to perform the following: forward the sensor data to a mobile electronic device associated with the caregiver assigned to the patient, and display a connection indicator on a display of the mobile electronic device. The connection indicator indicates whether or not the nurse call cable port is communicatively connected to the nurse call system.

According to other aspects of the present disclosure, the caregiver assistance application is further adapted to display a time on the mobile electronic device indicating when the caregiver should perform a rounding task for the patient. The caregiver assistance application may further be adapted to receive completion data from the caregiver indicating when the caregiver has completed the rounding task. Additionally, the caregiver assistance application may be adapted to forward the completion data to an electronic medical record server for entry in a patient record corresponding to the patient. Still further, the mobile electronic device may be configured to obtain confirmation data confirming a presence of the caregiver adjacent the bed when the caregiver completes the rounding task. The mobile electronic device forwards the confirmation data to the caregiver assistance application.

In some embodiments, the caregiver assistance application is adapted to also forward the sensor data to a stationary electronic device and to display on a display of the stationary electronic device the connection indicator.

The bed, in some embodiments, further comprises a short range transceiver adapted to communicate with a headwall-mounted short range transmitter of a location beacon. The short range transmitter forwards location data and beacon battery status data to the bed. The location data is indicative of a location of the bed and the beacon battery status data is indicative of a status of a battery of the location beacon. In such embodiments, the bed is adapted to forward the beacon battery status data to the caregiver assistance application and the caregiver assistance application is further adapted to display a beacon status indicator on the display of the mobile electronic device. The beacon status indicator indicates a current status of the battery of the location beacon. The current status of the battery of the location beacon may refer to a current charge amount of the beacon battery, an indication of whether or not the location beacon battery should be replaced, and/or another indication regarding the charge and/or health of the location beacon battery.

In some embodiments, the controller is further adapted to determine if the bed should be serviced and to forward servicing data to the caregiver assistance application when the bed should be serviced. The caregiver assistance application is further adapted to display a bed service indicator on the display of the mobile electronic device if the bed should be serviced.

The controller of the bed, in some embodiments, is further adapted to forward signal strength data to the caregiver assistance application. The signal strength data is indicative of a strength of a signal between the transceiver and a wireless access point of a healthcare facility. In such embodiments, the caregiver assistance application is further adapted to display a signal strength indicator on the display of the mobile electronic device. The signal strength indicator indicates the strength of the signal between the transceiver and the wireless access point of the healthcare facility. The signal strength data is forwarded to the caregiver assistance application using the transceiver, in at least some embodiments.

In some embodiments, the caregiver assistance application is further adapted to display a wireless connection indicator on the display of the mobile electronic device. The wireless connection indicator comprises a first form indicating the bed is unable to wirelessly communicate with the caregiver assistance application, and a second form indicating the bed is able to wirelessly communicate with the caregiver assistance application.

In some embodiments, the caregiver assistance application is further adapted to query an Admission, Discharge, and Tracking server for patient-room assignment information and to use the patient-room assignment information to determine if the bed is unable to communicate wirelessly with the caregiver assistance application.

A caregiver assistance system according to another embodiment of the present disclosure includes a bed and a server-hosted caregiver assistance application. The bed includes a litter frame; a support deck supported on the litter frame and configured to support a patient thereon; a memory containing an identifier uniquely identifying the bed; a short range transceiver adapted to communicate with a short range transmitter of a location beacon mounted to headwall of a healthcare facility room; a network transceiver; and a controller. The short range transceiver is adapted to receive location data and beacon battery status data from the location beacon. The location data is indicative of a location of the bed and the beacon battery status data is indicative of a current status of a battery of the location beacon. The controller communicates with the memory, the network transceiver, and the short range transceiver, and is adapted to transmit the identifier, the location data, and the beacon battery status data off the bed to the server on which the caregiver assistance application is hosted. The caregiver assistance application is adapted to perform the following: (i) determine a location of the bed using the location data; (ii) forward the beacon battery status data to a mobile electronic device associated with the caregiver assigned to the patient; and (iii) display a beacon battery status indicator on a display of the mobile electronic device, the beacon battery status indicator indicating the current status of the battery of the location beacon.

A caregiver assistance application according to still another embodiment of the present disclosure includes a bed and a server-hosted caregiver assistance application. The bed includes a litter frame; a support deck supported on the litter frame and configured to support a patient thereon; a memory containing an identifier uniquely identifying the bed; a short range transceiver adapted to receive location data from a short range transmitter of a location beacon mounted to headwall of a healthcare facility room; a network transceiver adapted to wirelessly communicate with a wireless access point of a healthcare facility network; and a controller in communication with the memory, the short range transceiver, and the network transceiver. The controller is adapted to transmit the identifier and location data off the bed via the network transceiver to the caregiver assistance application. The caregiver assistance application is adapted to perform the following: (i) determine a location of the bed using the location data; (ii) forward the location to a mobile electronic device associated with the caregiver assigned to the patient; (iii) display the location on display of the mobile electronic device; and (iv) display a wireless connection indicator on the display of the mobile electronic device. The wireless connection indicator comprises a first form indicating the bed is unable to wirelessly communicate with the caregiver assistance application using the network transceiver, and a second form indicating the bed is able to wirelessly communicate with the caregiver assistance application using the network transceiver.

A caregiver assistance application according to still another embodiment of the present disclosure includes a bed and a server-hosted caregiver assistance application. The bed includes a litter frame; a support deck supported on the litter frame and configured to support a patient thereon; a memory containing an identifier uniquely identifying the bed; a battery; a power cable adapted to couple to an electrical outlet; a sensor adapted to determine if the bed is operating on power from the battery or power from the power cable; a transceiver; and a controller in communication with the memory, the transceiver, and the sensor. The controller is adapted to transmit the identifier and data from the sensor off the bed to the server hosting the caregiver assistance application. The caregiver assistance application is adapted to receive the identifier and the sensor data from the bed and to perform the following: (i) forward the sensor data to a mobile electronic device associated with the caregiver assigned to the patient; and (ii) display a power status indicator on a display of the mobile electronic device.

The power status indicator indicates whether the bed is currently operating on power from the battery or power from the power cable.

In some embodiments, the bed further comprises a nurse call cable port adapted to couple to a first end of a nurse call cable having a second end adapted to couple to a nurse call outlet to thereby enable the bed to communicate with a nurse call system, and a sensor adapted to detect if the nurse call cable port is electrically coupled to the nurse call system via the nurse call cable. In such embodiments, the controller may be further adapted to transmit data from the sensor to the caregiver assistance application and the caregiver assistance application may be further adapted to display a connection indicator on the display of the mobile electronic device. The connection indicator indicates whether or not the nurse call cable port is communicatively connected to the nurse call system.

In some embodiments, the bed further comprises a battery and a battery sensor adapted to detect a status of the battery. In such embodiments, the controller is adapted to send the status of the battery to the caregiver assistance application, and the caregiver assistance application is further adapted to display on the display of the mobile electronic device a battery status indicator. The battery status indicator indicates the status of the battery, and may indicate a current amount of charge of the battery, whether the battery should be replaced or not, and/or other data regarding the charge and/or health of the location beacon battery.

In some embodiments, the caregiver assistance application is further adapted to display a wireless connection indicator on the display of the mobile electronic device. The wireless connection indicator comprises a first form indicating the bed is unable to wirelessly communicate with the caregiver assistance application, and a second form indicating the bed is able to wirelessly communicate with the caregiver assistance application. In some embodiments, the caregiver assistance application is further adapted to query an Admission, Discharge, and Tracking server for patient-room assignment information and to use the patient-room assignment information to determine if the bed is unable to communicate wirelessly with the caregiver assistance application.

The caregiver assistance application, in some embodiments, is further adapted to perform the following: (a) display a time on the display of the mobile electronic device indicating when the caregiver should perform a rounding task for the patient; (b) receive completion data from the caregiver indicating when the caregiver has completed the rounding task; and (c) forward the completion data to an electronic medical record server for entry in a patient record corresponding to the patient. In some of these embodiments, the mobile electronic device may be further adapted to obtain confirmation data confirming a presence of the caregiver adjacent the bed when the caregiver completes the rounding task, and to forward the confirmation data to the caregiver assistance application.

A caregiver assistance system according to another embodiment of the present disclosure includes a bed and a server-based caregiver assistance application. The bed includes a litter frame; a support deck supported on the litter frame and configured to support a patient thereon; a memory containing an identifier uniquely identifying the bed; a sensor adapted to detect a state of a component of the bed; a short range transceiver adapted to receive location data from a short range transmitter of a location beacon mounted to headwall of a healthcare facility room; a network transceiver; and a controller in communication with the memory, the short range transceiver, and the network transceiver. The controller is adapted to transmit the identifier, location data, and sensor data off the bed. The caregiver assistance application is adapted to receive the location data, the sensor data and the identifier, and to perform the following: (i) communicate with a mobile electronic device associated with the caregiver; (ii) communicate with a stationary electronic device; (iii) determine a room in which the bed is located using the location data; (iv) determine a set of patients assigned to the caregiver; (v) display the sensor data on the display of the mobile electronic device if the patient assigned to the bed is a patient from the set of patients assigned to the caregiver; (vi) not display the sensor data on the display of the mobile electronic device if the patient assigned to the bed is not from the set of patients assigned to the caregiver; (vii) determine a set of room locations associated with the stationary electronic device; (viii) display the sensor data on the display of the stationary electronic device if the room in which the bed is located is from the set of room locations; and (ix) not display the sensor data on the display of the stationary electronic device if the room in which the bed is located is not from the set of room locations.

In some embodiments, the short range transceiver is further adapted to receive beacon battery status data from the location beacon. The beacon battery status data indicates of a status of a battery of the location beacon. In such embodiments, the bed is adapted to forward the beacon battery status data to the caregiver assistance application and the caregiver assistance application is further adapted to perform the following: (i) display a beacon status indicator on the display of the mobile electronic device if the patient assigned to the bed is a patient from the set of patients assigned to the caregiver; (ii) not display the beacon status indicator on the display of the mobile electronic device if the patient assigned to the bed is not a patient from the set of patients assigned to the caregiver; (iii) display the beacon status indicator on the display of the stationary electronic device if the room in which the bed is located is from the set of room locations; and (iv) not display the beacon status indicator on the display of the stationary electronic device if the room in which the bed is located is not from the set of room locations.

In any of the embodiments of the caregiver assistance system disclosed herein, the steps undertaken by the caregiver assistance application, mobile electronic device, and/ or bed may be embodied in one or more methods for assisting the caregiver.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
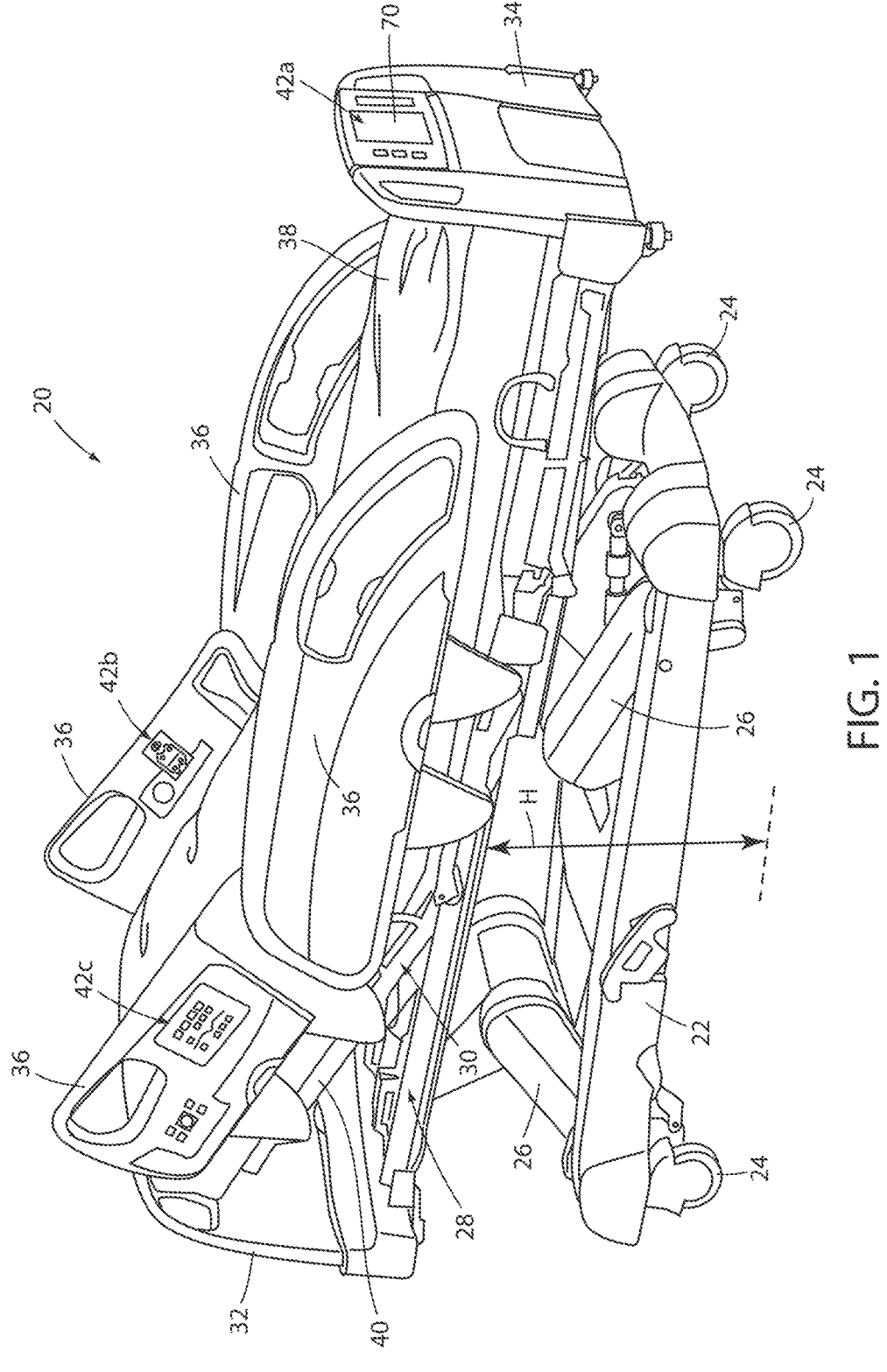
FIG. 1 is a perspective view of a patient support apparatus usable in a caregiver assistance system according to one embodiment of the disclosure.

An illustrative patient support apparatus 20 usable in a caregiver assistance system according to the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient while the patient is in a healthcare facility, such as, but not limited to, a hospital. For purposes of the following written description, patient support apparatus 20 will be primarily described as a bed with the understanding that the following written description applies to these other types of patient support apparatuses.

In general, patient support apparatus 20 includes a base 22 having a plurality of wheels 24, a lift subsystem comprising a pair of lifts 26 supported on the base, a litter frame 28 supported on the lifts 26, and a support deck 30 supported on the litter frame 28. Patient support apparatus 20 further includes a headboard 32, a footboard 34, and a plurality of siderails 36. Siderails 36 are all shown in a raised position in FIG. 1 but are each individually movable to a lower position in which ingress into, and egress out of, patient support apparatus 20 is not obstructed by the lowered siderails 36. In some embodiments, siderails 36 may be moved to one or more intermediate positions as well.

Lifts 26 are configured to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end and a foot end, each of whose height can be independently adjusted by the nearest lift 26. Patient support apparatus 20 is designed so that when an occupant lies thereon, his or her head will be positioned adjacent the head end and his or her feet will be positioned adjacent the foot end.

Litter frame 28 provides a structure for supporting support deck 30, the headboard 32, footboard 34, and siderails 36. Support deck 30 provides a support surface for a mattress 38, or other soft cushion, so that a person may lie and/or sit thereon. Support deck 30 is made of a plurality of sections, some of which are pivotable about generally horizontal pivot axes. In the embodiment shown in FIG. 1, support deck 30 includes a head section 40, which is also sometimes referred to as a Fowler section or a backrest section. Head section 40 is pivotable about a generally horizontal pivot axis between a generally horizontal orientation (not shown in FIG. 1) and a plurality of raised positions (one of which is shown in FIG. 1). Support deck 30 may include additional sections that are pivotable about one or more horizontal pivot axes, such as an upper leg or thigh section and/or a lower leg or foot section (not labeled).

Patient support apparatus 20 further includes a plurality of control panels 42 that enable a user of patient support apparatus 20, such as a patient and/or an associated caregiver, to control one or more aspects of patient support apparatus 20. In the embodiment shown in FIG. 1, patient support apparatus 20 includes a footboard control panel 42a, a pair of inner siderail control panels 42b (only one of which is visible), and a pair of outer siderail control panels 42c (only one of which is visible). Footboard control panel 42a and outer siderail control panels 42c are intended to be used by caregivers, or other authorized personnel, while inner siderail control panels 42b are intended to be used by the patient associated with patient support apparatus 20. Not all of the control panels 42 include the same controls and/or functionality. In the illustrated embodiment, footboard control panel 42a includes a substantially complete set of controls for controlling patient support apparatus 20 while control panels 42b and 42c include a selected subset of those controls. One or more of any of control panels 42a, b, and/or c may include a height adjustment control that, when activated, changes a height of litter frame 28 relative to base 22.

Control panels 42a and/or 42c may include controls for allowing a user to do one or more of the following: activate and deactivate a brake for wheels 24, arm an exit detection system 46, take a weight reading of the patient, activate and deactivate a propulsion system, and communicate with a healthcare facility computer network installed in the healthcare facility in which patient support apparatus 20 is positioned. Inner siderail control panels 42b may also include a nurse call control that enables a patient to call a nurse. A speaker and microphone are included on, or adjacent to, inner siderail control panel 42b in order to allow the patient to aurally communicate with the remotely positioned nurse.

Footboard control panel 42a is implemented in the embodiment shown in FIG. 1 as a touchscreen display 70 having a plurality of controls 72 positioned alongside the touchscreen display 70. Controls 72 may be implemented as buttons, dials, switches, or other devices. Either or both of control panels 42*b* or 42*c* may also include a display for displaying information regarding patient support apparatus 20, and such a display may be a touchscreen in some embodiments. Alternatively, any one or more of control panels 42*a-c* may omit a touchscreen display and instead include only dedicated controls 72, or some other form of non-display controls.

The mechanical construction of those aspects of patient support apparatus 20 not explicitly described herein may be the same as, or nearly the same as, the mechanical construction of the Model FL27 InTouch Critical Care bed manufactured and sold by Stryker Corporation of Kalamazoo, Michigan. This mechanical construction is described in greater detail in the Stryker Maintenance Manual for the Model FL27 InTouch Critical Care Bed (Version 2.4; 2131-409-002 REV B), published by Stryker Corporation of Kalamazoo, Michigan, the complete disclosure of which is incorporated herein by reference. It will be understood by those skilled in the art that those aspects of patient support apparatus 20 not explicitly described herein can alternatively be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of those aspects of patient support apparatus 20 not explicitly described herein may also take on forms different from what is disclosed in the aforementioned references.

Figure 2:
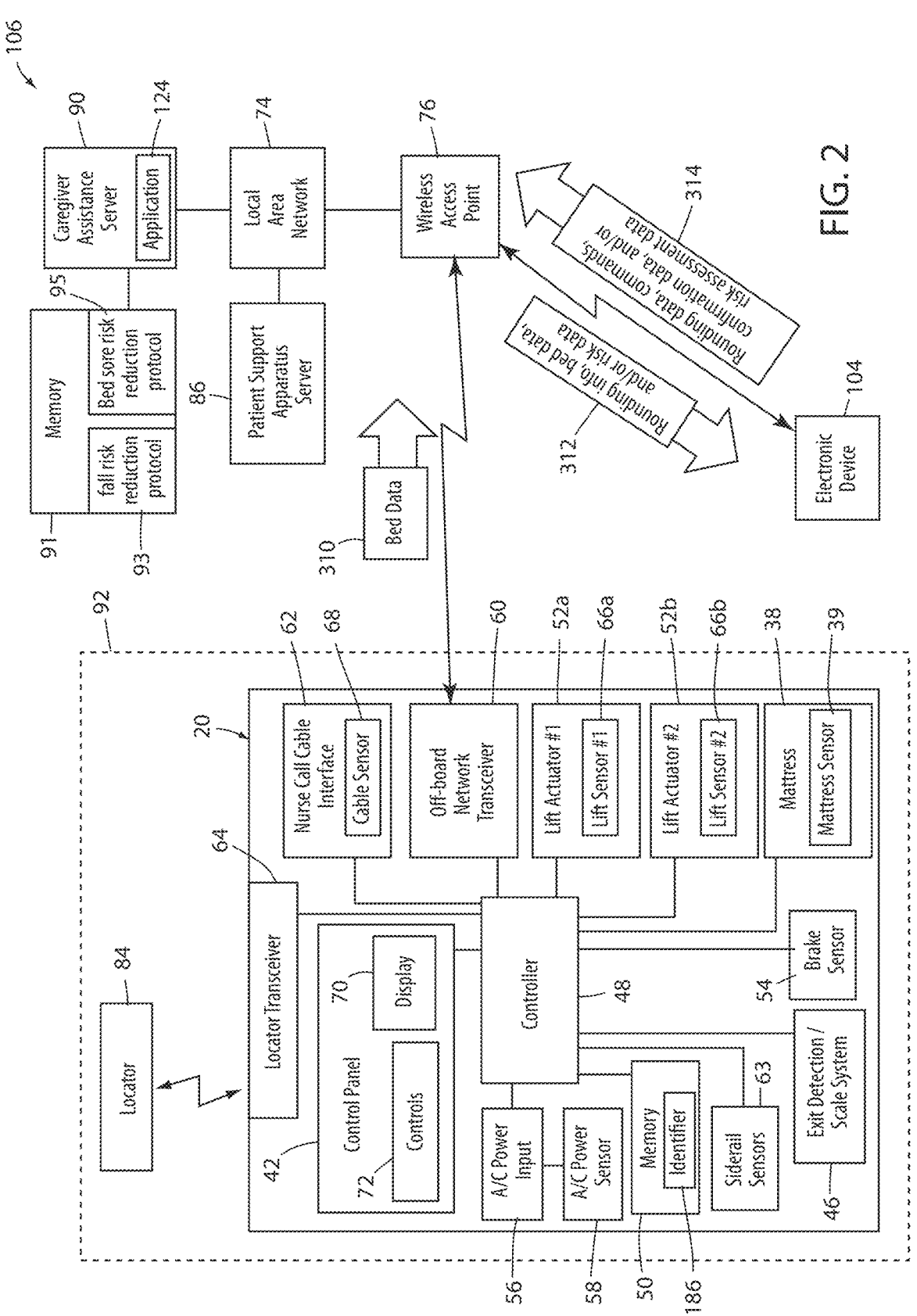
FIG. 2 is a block diagram of a first embodiment of the caregiver assistance system of the present disclosure showing a detailed set of components of the patient support apparatus of FIG. 1, a server-based caregiver assistance application, and a portion of a local area network in which the patient support apparatus is in communication.

FIG. 2 illustrates a first embodiment of a caregiver assistance system 106 according to the present disclosure. Caregiver assistance system 106 includes patient support apparatus 20 in communication with a caregiver assistance server 90, and one or more electronic devices 104 that are adapted to communicate with caregiver assistance server 90. Caregiver assistance system 106 may also include a conventional patient support apparatus server 86 that is separate from caregiver assistance server 90, or the functionality of caregiver assistance server 90 may be modified to include the functionality of patient support apparatus server 86, thereby allowing patient support apparatus server 86 to be omitted. As will be discussed in greater detail below with respect to FIG. 4, caregiver assistance system 106 communicates with a plurality of conventional servers on a local area network 74 of the healthcare facility and uses those communications to obtain some of the information it needs to perform its caregiver assistance functions.

FIG. 2 illustrates in greater detail some of the internal components of patient support apparatus 20. As shown therein, patient support apparatus 20 includes a controller 48, a memory 50, a first lift actuator 52*a*, a second lift actuator 52*b*, a brake sensor 54, an scale/exit detection system 46, an Alternating Current (A/C) power input 56, an A/C power sensor 58, one or more control panels 42, an off-board network transceiver 60 having a signal strength detector 75, a nurse call cable interface 62, a plurality of siderail sensors 63, a location transceiver 64, a head of bed (HOB) angle sensor 69, a battery 71, and a battery monitor 73. Additionally, patient support apparatus 20 includes a first lift sensor 66*a*, a second lift sensor 66*b*, a cable sensor 68, display 70, and one or more controls 72 incorporated into one or more of the control panels 42. Still further, patient support apparatus 20 includes a mattress 38 having at least one mattress sensor 39 positioned therein. It will be understood by those skilled in the art that patient support apparatus 20 may be modified to include additional components not shown in FIG. 2, as well modified to include fewer components from what is shown in FIG. 2.

Controller 48 (FIG. 2) is constructed of any electrical component, or group of electrical components, that are capable of carrying out the functions described herein. In many embodiments, controller 48 is a conventional microcontroller, or group of conventional microcontrollers, although not all such embodiments need include a microcontroller. In general, controller 48 includes any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units as part of an embedded network. When implemented to include an embedded network, the embedded network may include multiple nodes that communicate using one or more of the following: a Controller Area Network (CAN); a Local Interconnect Network (LIN); an I-squared-C serial communications bus; a serial peripheral interface (SPI) communications bus; any of RS-232, RS-422, and/or RS-485 communication interfaces; a LonWorks network, and/or an Ethernet. The instructions followed by controller 48 in carrying out the functions described herein, as well as the data necessary for carrying out these functions, are stored in memory 50, and/or in one or more other memories accessible to the one or more microprocessors, microcontrollers, or other programmable components of controller 48. Memory 50 also includes a unique identifier 186 that uniquely identifies the particular patient support apparatus into which it is incorporated, such as, but not limited to, a serial number.

When controller 48 is implemented to communicate using an on-board Ethernet, the on-board Ethernet may be designed in accordance with any of the Ethernet-carrying patient support apparatuses disclosed in commonly assigned U.S. patent application Ser. No. 14/622,221 filed Feb. 13, 2015, by inventors Krishna Bhimavarapu et al. and entitled COMMUNICATION METHODS FOR PATIENT HANDLING DEVICES, the complete disclosure of which is incorporated herein by reference. In some embodiments, controller 48 may be implemented to include multiple nodes that communicate with each other utilizing different communication protocols. In such embodiments, controller 48 may be implemented in accordance with any of the embodiments disclosed in commonly assigned U.S. patent application Ser. No. 15/903,477 filed Feb. 23, 2018, by inventors Krishna Bhimavarapu et al. and entitled PATIENT CARE DEVICES WITH ON-BOARD NETWORK COMMUNICATION, the complete disclosure of which is incorporated herein by reference.

Controller 48 is shown in FIG. 2 as including a usage monitor 77. Usage monitor 77 monitors the usage of the various components of patient support apparatus 20 and determines if servicing of any of these components should be performed. In some embodiments, usage monitor 77 is carried out purely within controller 48 based upon inputs from the various components of the patient support apparatus 20. In other embodiments, usage monitor 77 may include one or more electrical circuits and/or devices separate from controller 48 that operate in conjunction with controller 48 to monitor the usage, and servicing of, the various components of patient support apparatus 20.

In at least one embodiment, usage monitor 77 includes a data logger that keeps track of the number of times each of the serviceable components (e.g. any component that moves, such as siderails 36, actuators 52, etc.) are moved, activated, or otherwise used. Once the number reaches a threshold-without having been serviced-controller 48 issues a notification and/or alert. As will be discussed in greater detail below with respect to FIG. 80, the notification/alert may be sent to an electronic device 104 so that caregivers are apprised of the need for servicing one or more components of the patient support apparatus 20. As is also discussed below with respect to FIGS. 71-73, such servicing may be documented using a caregiver assistance application 124 (discussed below), either alone or in conjunction with a standalone equipment management system 918. The documenting of the servicing is forwarded to controller 48, which then resets the appropriate counter(s) and/or other usage parameters.

In some embodiments, usage monitor 77 is implemented to perform the functions of the data logger disclosed in commonly assigned U.S. Pat. No. 7,690,059 issued Apr. 6, 2017, to Lemire et al. and entitled HOSPITAL BED, the complete disclosure of which is incorporated herein by reference. In some embodiments, usage monitor 77 may alternatively, or additionally, perform any of the functions of the diagnostic and control system disclosed in the aforementioned '059 patent. In some embodiments, usage monitor 77 may perform, either alone or in addition to other structures, any of the servicing, monitoring, and/or event detection functions of the equipment management system disclosed in commonly assigned PCT patent publication WO 2018/013666 filed Jul. 12, 2017, by inventors David Becker et al. and entitled EQUIPMENT MANAGEMENT SYSTEM, the complete disclosure of which is incorporated herein by reference. Usage monitor 77 may alternatively or additionally perform still other usage and/or diagnostic monitoring.

First and second lift actuators 52*a* and 52*b* (FIG. 2) are components of lifts 26 and are configured to raise and lower litter frame 28 with respect to base 22. A first one of lift actuators 52*a* powers a first one of the lifts 26 positioned adjacent a head end of patient support apparatus 20 and a second one of lift actuators 52*b* powers a second one of the lifts 26 positioned adjacent a foot end of patient support apparatus 20. Lift actuators 52*a* and 52*b* may be conventional linear actuators having electric motors therein that, when driven, expand or contract the length of the linear actuator, thereby moving the litter frame upward or downward and changing its height H (FIG. 1) relative to the floor.

Each lift actuator 52*a* and 52*b* includes a corresponding lift sensor 66*a* and 66*b*, respectively. Each of the sensors 66*a*, 66*b* detects a position and/or angle of its associated actuator 52*a*, 52*b* and feeds the sensed position/angle to controller 48. Controller 48 uses the outputs from sensors 66 as inputs into a closed-loop feedback system for controlling the motion of the actuators 52*a*, 52*b* and the litter deck. Controller 48 also uses the outputs from sensors 66*a*, 66*b* to determine the height H of litter frame 28 above the floor. In some embodiments, actuators 52 are constructed in any of the same manners as the actuators 34 disclosed in commonly assigned U.S. patent application Ser. No. 15/449,277 filed Mar. 3, 2017, by inventors Anish Paul et al. and entitled PATIENT SUPPORT APPARATUS WITH ACTUATOR FEEDBACK, the complete disclosure of which is incorporated herein by reference. In such embodiments, sensors 66*a* and 66*b* may be constructed to include any of the encoders and/or switch sensors disclosed in the aforementioned '277 application.

Scale/exit detection system 46 is configured to determine a weight of a patient positioned on support deck 30 and/or when the patient is moving and is likely to exit patient support apparatus 20. The particular structural details of the exit detection system can vary widely. In some embodiments, scale/exit detection system 46 includes a plurality of load cells arranged to detect the weight exerted on litter frame 28. By summing the outputs from each of the load cells, the total weight of the patient is determined (after subtracting the tare weight). Further, by using the known position of each of the load cells, controller 48 determines a center of gravity of the patient and monitors the center of gravity for movement beyond one or more thresholds. One method of computing the patient's center of gravity from the output of such load cells is described in more detail in commonly assigned U.S. Pat. No. 5,276,432 issued to Travis and entitled PATIENT EXIT DETECTION MECHANISM FOR HOSPITAL BED, the complete disclosure of which is incorporated herein by reference. Other methods for determining a patient's weight and/or the weight of non-patient objects supported on litter frame 28 are disclosed in commonly assigned U.S. patent application Ser. No. 14/776,842, filed Sep. 15, 2015, by inventors Michael Hayes et al. and entitled PATIENT SUPPORT APPARATUS WITH PATIENT INFORMATION SENSORS, and commonly assigned U.S. patent application Ser. No. 14/873,734 filed Oct. 2, 2015, by inventors Marko Kostic et al. and entitled PATIENT SUPPORT APPARATUSES WITH MOTION MONITORING, the complete disclosures of both of which are incorporated herein by reference. Other systems for determining a patient's weight and/or detecting a patient's exit from patient support apparatus 20 may alternatively be used.

Mattress 38 is an inflatable mattress in many embodiments. In some embodiments, mattress 38 includes its own internal controller (not shown) that controls the inflation and deflation of various bladders contained within mattress under the instructions of controller 48. It will therefore be understood that the control of mattress 38 carried out by controller 48 may include both the direct control over the blower(s), pump(s), valve(s), and other components of mattress 38, or an indirect control over on onboard mattress controller that itself carries out the direct controls of the blower(s), pump(s), valve(s), and other components of mattress 38. In either situation, controller 48 may communicate with mattress 38 using a serial cable, or other cable, that extends between patient support apparatus 20 and mattress 38. In at least one alternative embodiment, the communication between patient support apparatus 20 and mattress 38 may be carried out wirelessly, such as in any of the manners disclosed in commonly assigned U.S. Pat. No. 9,289,336 issued to Lambarth et al. and entitled PATIENT SUPPORT WITH ENERGY TRANSFER, the complete disclosure of which is incorporated herein by reference. Other manners for wireless communication may, of course, be used.

In some embodiments, mattress 38 is constructed in accordance with any of the mattresses disclosed in commonly assigned U.S. Pat. No. 9,468,307 issued to Lafleche et al. and entitled INFLATABLE MATTRESS AND CONTROL METHODS, the complete disclosure of which is incorporated herein by reference. In other embodiments, mattress 38 is constructed in accordance with any of the mattresses disclosed in commonly assigned U.S. Pat. No. 8,413,271 issued to Blanchard and entitled PATIENT SUPPORT APPARATUS, the complete disclosure of which is also incorporated herein by reference. Other mattresses may also be used. Regardless of the specific construction of mattress 38, mattress 38 may be configured to carry out one or more different therapy procedures for the patient supported thereon. Such therapy procedures may include, but are not limited to, any of the following: rotation, percussion, vibration, maximum inflation, and turn assistance. Mattress 38 may also be able to be inflated to different states, thereby changing the distribution of pressure on the patient's skin while supported thereon. These various therapies and/or states are often used in order to reduce the likelihood of a patient developing a bed sore, or exacerbating an already existing bed sore. Caregiver assistance system 106 is adapted to suggest, encourage, and/or enforce the utilization of one or more of these therapies and/or states if a patient's skin assessment score is higher than a threshold, as will be discussed in greater detail below with respect to bed sore risk reduction algorithm 141 (see FIG. 28).

Controller 48 communicates with network transceiver 60 (FIG. 2) which, in at least one embodiment, is a Wi-Fi radio communication module configured to wirelessly communicate with wireless access points 76 of local area network 74. In such embodiments, network transceiver 60 may operate in accordance with any of the various IEEE 802.11 standards (e.g. 802.11b, 802.11n, 802.11g, 802.11ac, 802.11ah, etc.). In other embodiments, network transceiver 60 may include, either additionally or in lieu of the Wi-Fi radio and communication module, a wired port for connecting a network wire to patient support apparatus 20. In some such embodiments, the wired port accepts a category 5e cable (Cat-5e), a category 6 or 6a (Cat-6 or Cat-6a), a category 7 (Cat-7) cable, or some similar network cable, and transceiver 60 is an Ethernet transceiver. In still other embodiments, network transceiver 60 may be constructed to include the functionality of the communication modules 56 disclosed in commonly assigned U.S. patent application Ser. No. 15/831,466 filed Dec. 5, 2017, by inventor Michael Hayes et al. and entitled NETWORK COMMUNICATION FOR PATIENT SUPPORT APPARATUSES, the complete disclosure of which is incorporated herein by reference.

Regardless of the specific structure included with network transceiver 60, controller 48 is able to communicate with the local area network 74 (FIG. 2) of a healthcare facility in which the patient support apparatus is positioned. When network transceiver 60 is a wireless transceiver, it communicates with local area network 74 via one or more wireless access points 76. When network transceiver 60 is a wired transceiver, it communicates directly via a cable coupled between patient support apparatus 20 and a network outlet positioned within the room of the healthcare facility in which patient support apparatus 20 is positioned. As will be discussed in greater detail below with respect to FIG. 4, local area network 74 includes a plurality of servers that are utilized in different manners by the caregiver assistance system disclosed herein, and patient support apparatus 20 communicates with one or more of those servers via transceiver 60 as part of the caregiver assistance system.

When network transceiver 60 is implemented as a wireless transceiver, it may include a signal strength detector 75 that detects the signal strength of the wireless signals it is receiving from the wireless access point 76 with which it is in communication. In some embodiments, such as ones in which network transceiver 60 is a WiFi transceiver, the signal strength detector 75 may be part of the conventional WiFi circuitry that determines the Received Signal Strength Indicator (RSSI), in which case the signal strength may be measured as an RSSI value. In other embodiments, the signal strength may be measured as an actual value in milliwatts (or other units), and signal strength detector 75 may be comprised of any conventional circuitry configured to measure the signal strength in this manner. In still other embodiments, signal strength detector 75 and/or patient support apparatus 20 may have any of the spectrum analysis functionality built into either or both of them that is disclosed in commonly assigned U.S. patent application Ser. No. 15/236,452 filed Sep. 29, 2016, by inventors Krishna Bhimavarapu et al. and entitled PERSON SUPPORT APPARATUSES WITH COMMUNICATION CHANNEL MONITORING, the complete disclosure of which is incorporated herein by reference.

Regardless of whether signal strength detector 75 measures signals using a relative RSSI value or an actual milliwatt value (e.g. -dBm), signal strength detector 75 is configured to forward its results to controller 48 which then displays the value on display 70 and also forwards the value to caregiver assistance application 124 via network transceiver 60. As will be discussed in greater detail below, particularly with respect to FIG. 80, caregiver assistance application 124 may forward this signal strength value to one or more electronic devices 104 for display thereon.

Figure 4:
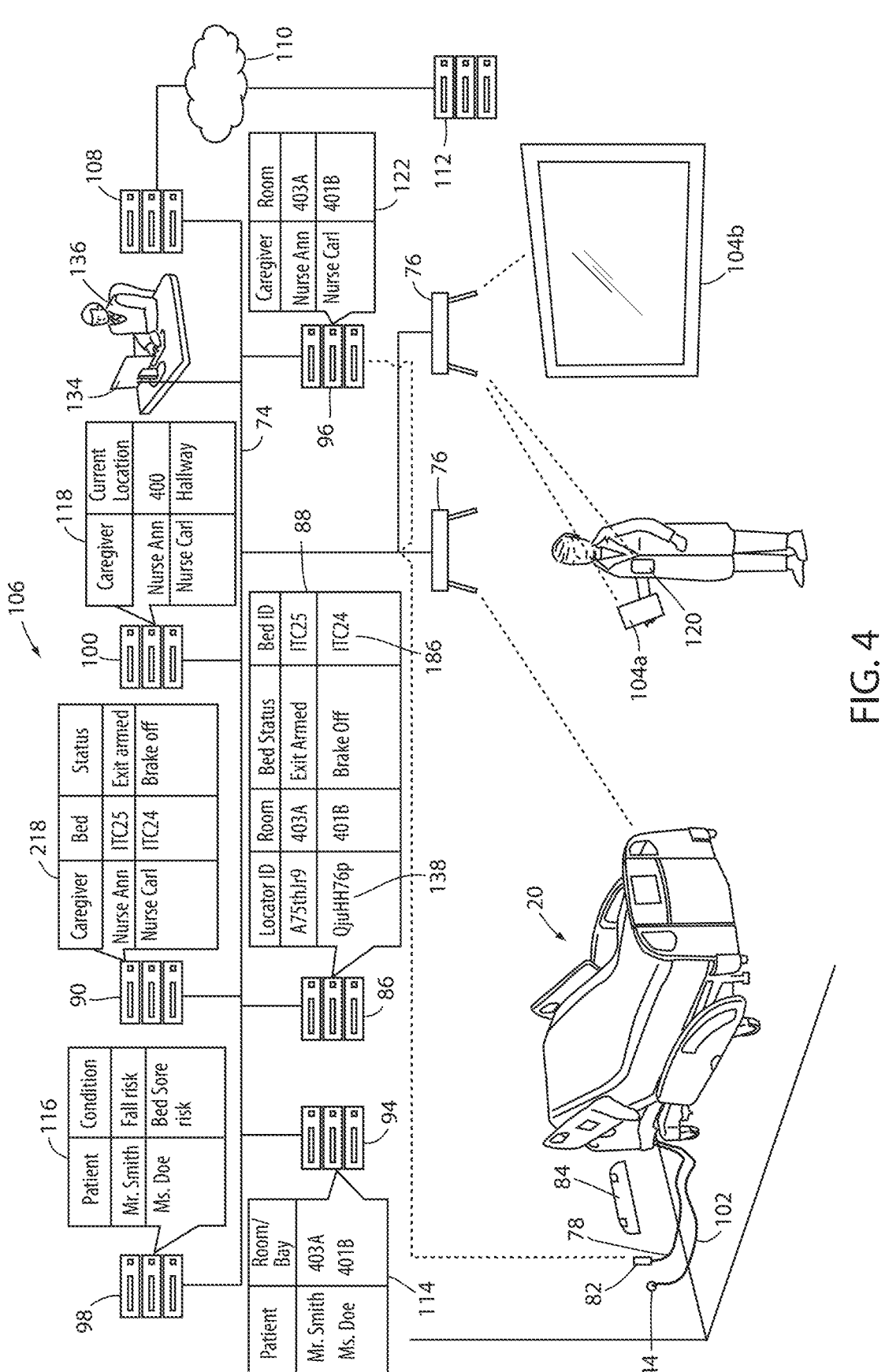
FIG. 4 is a block diagram of the caregiver assistance system shown integrated into a local area network of a healthcare facility.

Nurse call cable interface 62 is an interface adapted to couple to one end of a nurse call cable 78 (FIG. 4). The other end of the nurse call cable 78 couples to a nurse call outlet 82 (FIG. 4) that is typically built into each headwall of each of the patient rooms within a healthcare facility. In many embodiments, nurse call outlet 82 is a 37 pin outlet that cable 78 couples to, thereby enabling patient support apparatus 20 to communicate directly with a conventional nurse call system 80. In some embodiments, nurse call cable interface 62 is constructed in accordance with any of the cable interfaces 92 disclosed in commonly assigned U.S. patent application Ser. No. 15/945,437 filed Apr. 4, 2018, by inventors Krishna Bhimavarapu et al. and entitled PATIENT SUPPORT APPARATUSES WITH RECONFIGURABLE COMMUNICATION, the complete disclosure of which is incorporated herein by reference.

In other embodiments, nurse call cable interface 62 may be replaced with a wireless nurse call communication system that wirelessly communicates with nurse call outlet 82. For example, in some embodiments, nurse call cable interface 62 is replaced with a radio module, such as the radio module 60 disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference. In such wireless headwall embodiments, a headwall module, such as headwall module 38 disclosed in the aforementioned '844 application, is included and coupled to nurse call outlet 82. Such a headwall module may replace and/or supplement the functions of location beacon 84, described below. Still other types of wireless communication between the patient support apparatus and nurse call outlet 82 may be implemented.

Regardless of whether nurse call interface 62 uses a wired cable connection to a nurse call outlet on the headwall of the hospital room or it uses a wireless connection, nurse call interface 62 may also, or alternatively, perform any of the functions of the nurse call interfaces disclosed in commonly assigned U.S. patent application Ser. No. 62/833,943 filed Apr. 15, 2019, by inventors Alexander Bodurka et al. and entitled PATIENT SUPPORT APPARATUSES WITH NURSE CALL AUDIO MANAGEMENT, the complete disclosure of which is also incorporated herein by reference.

Siderail sensors 63, which may be conventional siderail sensors, are configured to detect when the siderails 36 are in a raised or lowered position. In most embodiments, a single siderail sensor 63 is included for each of the siderails 36. Therefore, in the embodiment of FIG. 1, patient support apparatus 20 includes four siderail sensors 63, one for detecting the position of each of the four siderails 36. In alternative embodiments, more than one siderail sensor 63 may be included for each siderail 36, such as a first siderail sensor 63 that detects when the siderail is raised and/or locked in its raised position, and a second siderail sensor 63 that detects when the siderail 36 is in its lower position, and/or locked in its lowered position. In general, any switch or other type of sensor that is able to detect when the respective siderail 36 is in its raised and/or locked orientation can be used with patient support apparatus 20. The outputs of siderail sensors 63 are fed to controller 48 and are periodically sent to caregiver assistance server 90 as part of the patient support apparatus status updates that are discussed in greater detail below. Further, as will also be discussed in greater detail below, the position of one or more siderails 36 is monitored for compliance with a desired state, such as, but not limited to, a desired state defined by a fall risk reduction protocol 93 discussed in more detail below.

Location transceiver 64 (FIG. 2) is adapted to detect a wireless signal emitted from a nearby location beacon 84 (FIG. 4) that is positioned at a fixed and known location within the healthcare facility. Although FIG. 4 only illustrates a single one of these location beacons 84, it will be understood that a particular healthcare facility includes many of these location beacons 84 mounted throughout the healthcare facility. Each location beacon 84 includes a wireless short range transmitter (not shown) that broadcasts a wireless, short range signal containing a unique identifier. The short range signal, in some embodiments, is broadcast via an infrared transmitter and is only detectable by receivers (e.g. location transceivers 64) that are positioned within several feet of the location beacon 84. Consequently, location transceivers 64, which are adapted to detect the signals transmitted from location beacons 84, are only able to detect these signals when patient support apparatuses 20 are positioned adjacent (e.g. within several feet) of one of these location beacons 84. If/when location transceiver 64 is able to detect the unique signal from a particular location beacon 84, the corresponding patient support apparatus 20 can therefore be concluded to be currently positioned adjacent that particular location beacon 84. This allows the current location of the patient support apparatus 20 to be identified. In some healthcare facilities, one or more of the patient rooms may not be completely private rooms, but instead may be shared with one or more other patients. In such situations, it is typical to mount two or more location beacons 84 within such a room-one on the headwall at the bay where the first patient support apparatus 20 normally resides and the other on the headwall at the bay where the second patient support apparatus 20 normally resides (and still more if the room is shared by more than two patients).

When location transceiver 64 receives a signal from an adjacent location beacon 84, controller 48 forwards the received signal, including the unique ID of the beacon 84, to a patient support apparatus server 86 (FIG. 2) which is sometimes alternately referred to herein as a bed server 86. Patient support apparatus server 86 includes a location table 88 (FIG. 4), or has access to such a table 88, that correlates beacon IDs to locations within the healthcare facility. Patient support apparatus server 86 is thereby able to determine the location of each patient support apparatus 20 within the healthcare facility (at least all of those that are positioned adjacent a location beacon 84).

In some embodiments, location beacons 84 (FIG. 2) function both as locators and as wireless links to the nurse call outlet 82 integrated into the adjacent headwall. When equipped with this dual function, patient support apparatuses 20 may omit the nurse call cable interface 62, yet still be able to communicate with the nurse call system server 62b. In the illustrated embodiment of FIG. 4, however, patient support apparatus 20 includes a nurse call cable 78 that communicatively couples the patient support apparatus 20 to nurse call outlet 82, thereby enabling the patient support apparatus 20 to communicate directly with the nurse call system 80. Further details about the function of location beacons 84, whether operating solely as locators or both as locators and wireless portals to the nurse call system outlets 82, may be found in any of the following commonly assigned U.S. patent references: U.S. Pat. No. 8,102,254 issued Jan. 24, 2012 to Becker et al. and entitled LOCATION DETECTION SYSTEM FOR A PATIENT HANDLING DEVICE; patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION; patent application Ser. No. 62/600,000 filed Dec. 18, 2017, by inventor Alex Bodurka, and entitled SMART HOSPITAL HEADWALL SYSTEM; and patent application Ser. No. 62/598,787 filed Dec. 14, 2017, by inventors Alex Bodurka et al. and entitled HOSPITAL HEADWALL COMMUNICATION SYSTEM, the complete disclosures of all of which are incorporated herein by reference.

Location beacon 84 also includes, in at least some embodiments, a beacon battery 79 and a beacon battery monitor 81. Beacon battery 79 provide electrical power to location beacon 84, either exclusively or, in at least some embodiments, when location beacon 84 is unplugged, or electrical power is otherwise unavailable from an electrical outlet. Beacon battery monitor 81 monitors the charge state of beacon battery 79 and reports measurements of this charge to patient support apparatus 20. That is, the measurements taken by beacon battery monitor 81 are forwarded wirelessly by locator beacon 84 to patient support apparatus 20 via the built-in transmitter of location beacon 84. These measurements are received by location transceiver 64 onboard patient support apparatus 20 and forwarded to controller 48. Controller 48 then displays these measurements on display 70 and/or forwards them to caregiver assistance application 124 via network transceiver 60. As will be discussed in more detail below (particularly with respect to FIG. 80), caregiver assistance application 124 may forward these battery charge measurements to one or more electronic devices 104.

In some embodiments, beacon battery monitor 81 may monitor one or more additional factors regarding beacon battery 79, such as, but not limited to, the overall health of beacon battery 79. Such overall health may be measured in terms of the charge capacity of the battery, the number of times the battery has been recharged, the rate at which the battery discharges, the rate at which the battery re-charges, and/or in other manners. In some embodiments, beacon battery monitor 81 may be implemented in the same manner as, and/or configured to monitor and measure any one or more of the same battery parameters as, the battery monitors disclosed in commonly assigned U.S. patent publication 2016/0331614 published Nov. 17, 2016, and filed by inventors Aaron Furman et al. and entitled BATTERY MANAGEMENT FOR PATIENT SUPPORT APPARATUSES, the complete disclosure of which is incorporated herein by reference.

In some embodiments, locator beacon 84 may be incorporated into a wireless headwall module that communicates with patient support apparatus 20 over multiple communication channels. In such embodiments, the first communication channel between location beacon 84 and patient support apparatus 20 may be a short range channel (e.g. infrared) and the second one may be a longer range channel (e.g. Bluetooth). In such embodiments, the transmission of the data from beacon battery monitor 81 to patient support apparatus 20, as well as the transmission of the location identifier of locator beacon 84 to patient support apparatus 20, may occur over either or both of the two communication channels.

Controller 48 of patient support apparatus 20 (FIG. 2) communicates with A/C power sensor 58, which informs controller 48 whether or not an A/C power cable 102 (FIG. 4) is coupled between patient support apparatus 20 and a conventional A/C power outlet 44. In other words, A/C power sensor 58 lets controller 48 know whether patient support apparatus 20 is receiving electrical power from an off-board power supply (e.g. power outlet 44). In some cases, patient support apparatus 20 includes one or more batteries that are able to power patient support apparatus 20, including controller 48, when patient support apparatus 20 is not coupled to a source of electrical power. As will be discussed more below, the status of the A/C power cord 102 (e.g. whether patient support apparatus 20 is operating on battery power or on power from an A/C outlet) is communicated from A/C power sensor 58 to controller 48, which then forwards that status via network transceiver 60 to patient support apparatus server 86 and/or to caregiver assistance server 90.

Controller 48 also communicates with brake sensor 54 (FIG. 2). Brake sensor 54 informs controller 48 whether or not a brake has been applied on patient support apparatus 20. When the brake is applied, one or more of wheels 24 are braked to resist rotation. When the brake is not applied, wheels 24 are free to rotate. As with the data from the A/C power cord sensor 58, the data from the brake sensor 54 is forwarded by controller 48 to patient support apparatus server 86 and/or to caregiver assistance server 90, via network transceiver 60. Caregiver assistance server 90 shares this information with caregivers via one or more electronic devices that are in communication with server 90, as will be discussed in greater detail below.

Controller 48 also communicates with head of bed angle sensor 69. Head of bed angle sensor 69 measure the angular orientation of head section 40 of patient support apparatus 20, either with respect to horizontal or with respect to the general plane of litter frame 28. In some embodiments, head of bed angle sensor 69 is implemented as one or more accelerometers that are mounted to head section 40. In other embodiments, head of bed angle sensor 69 may be implemented as an encoder counter, or other type of counter, that monitors the extension and retraction of the actuator that pivots head section 40. Still other types of sensors may be used to measure the angle of head section 40.

Regardless of the specific type of sensor used for HOB sensor 69, HOB sensor 69 reports its readings to controller 48, which in turn displays them on display 70 and/or forwards them to caregiver assistance application 124 via network transceiver 60. As will be discussed in more detail below (particularly with respect to FIGS. 74-77), caregiver assistance application 124 may forward the HOB angle reading to one or more electronic devices 104 for display thereon, thereby enabling caregivers to remotely view the current angle of head section 40 of patient support apparatus 20.

In some embodiments, patient support apparatus 20 may include one or more batteries 71 that are used to provide power to patient support apparatus 20, or certain components thereof, when patient support apparatus 20 is not electrically coupled to a conventional electrical power outlet. For example, in some embodiments, patient support apparatus 20 may include a first battery (or first set of batteries) that are used for all functions on the bed except for powering an onboard propulsion system, and a second battery (or second set of batteries) that are used for powering the onboard propulsion system. One example of such a patient support apparatus 20 is disclosed in commonly assigned U.S. patent application Ser. No. 62/823,324 filed Mar. 25, 2019, by inventors Zane Shami et al. and entitled PATIENT CARE SYSTEM WITH POWER MANAGEMENT, the complete disclosure of which is incorporated herein by reference. In other embodiments, patient support apparatus 20 includes only a single battery 71 (or a single set of batteries 71) that are used for powering all of the electrical functions of patient support apparatus 20. In many instances, whether one or more batteries 71 are included, such batteries 71 are typically rechargeable batteries 71.

In the embodiment shown in FIG. 2, patient support apparatus 20 further includes a battery monitor 73 that is adapted to monitor the charge state (and/or other parameters) of battery 71, or each of the batteries 71 (if there are more than one) of patient support apparatus 20. Battery monitor 73, in addition to monitoring the charge state of one or more batteries 71, may also monitor any of the same parameters of batteries 71 that beacon battery monitor 81 may monitor with respect to beacon battery 79, as discussed above. To that end, battery monitor 73 may be implemented in any of the same manners as, and/or perform any of the same functions as, the battery monitors disclosed in commonly assigned U.S. patent publication 2016/0331614 published Nov. 17, 2016, and filed by inventors Aaron Furman et al. and entitled BATTERY MANAGEMENT FOR PATIENT SUPPORT APPARATUSES, the complete disclosure of which has been incorporated herein by reference.

Regardless of which specific criteria battery monitor 73 monitors for one or more of the batteries 71 of patient support apparatus 20, battery monitor 73 reports the results to controller 48. Controller 48, in turn, displays one or more of the results on display 70 and/or forwards one or more of the results to caregiver assistance application 124. Caregiver assistance application 124 then forwards these results to one or more mobile electronic devices 104a, as discussed in more detail below. The electronic devices 104 include a display and are adapted to display information about the monitored state(s) of battery(ies) 71. If patient support apparatus 20 contains more than one battery, controller 48 forwards the monitored data for each battery (or set of batteries) to caregiver assistance application 124, which in turn forwards this data to one or more electronic devices 104. The recipient electronic device 104 displays the received data separately for each set of batteries. In this manner, caregivers who are remote from patient support apparatus 20 are able to review the status of each of the batteries onboard patient support apparatus 20.

Each of the control panels 42 includes one or more controls 72 that are used to control various functions of the patient support apparatus 20 (FIG. 2). For example, one or more of the control panels 42 includes a motion control 72 for controlling movement of the lift actuators 52*a* and 52*b*. Additional controls 72 may be provided for activating and deactivating the brake for wheels 24, arming and disarming exit detection function of scale/exit detection system 46, taking a weight reading of the patient using the scale function of scale/exit detection system 46, activating and deactivating a propulsion system (if included), and communicating with one or more servers on local area network 74. It will be understood that in some embodiments, one or more of controls 72 may be integrated into a touchscreen display, such as display 70. In such embodiments, one or more of the controls may only appear when the user navigates to specific screens displayed on the touchscreen.

Patient support apparatus 20 communicates with the caregiver assistance server 90 of local area network 74 (FIG. 2). Caregiver assistance server 90 is adapted to assist the caregivers in performing a plurality of tasks. In general, caregiver assistance server 90 includes software—a caregiver assistance application 124—that, when executed, assists the caregivers in ensuring that the patient support apparatuses 20 are maintained in a desirable state, assists the caregiver in performing their rounding tasks, assists the caregivers in performing fall and/or skin assessments, assists the caregivers with setting reminders and receiving notifications of the reminders, as well as assists the caregivers with receiving alerts and/or status information about the patients under their care while the caregivers go about their duties.

Caregiver assistance server 90 includes a memory 91 storing various data used by the caregiver assistance application 124 (as well as, in some cases, storing the executable instructions of caregiver assistance application 124). Memory 91 stores such items as, but not limited to, a fall risk reduction protocol 93 and a bed sore risk reduction protocol 95. Memory 91 may be physically included within server 90 and/or it may be distributed across one or more other physical locations that are accessible to server 90.

Caregiver assistance application 124 uses the fall risk reduction protocol 93 when application 124 executes the patient fall risk reduction algorithm 143, as will be discussed in greater detail below. In general, patient fall risk reduction algorithm 143 enables a caregiver to utilize one or more of the electronic devices 104 to assess the fall risk of a patient and to subsequently ensure that the patient support apparatus 20 is in a state specified by the healthcare facility for that patient's particular fall risk. Fall risk reduction protocol 93 specifies the desired state of patient support apparatus 20 for one or more fall risk levels. Fall risk reduction algorithm 143 is discussed in more detail below with respect to FIGS. 18-27.

Caregiver assistance application 124 uses the bed sore risk reduction protocol 95 when application 124 executes the patient bed sore risk reduction algorithm 141. In general, patient bed sore risk reduction algorithm 141 enables a caregiver to utilize the same electronic devices used with the fall risk reduction algorithm 143 (and other algorithms discussed herein) to assess the bed sore risk of a patient and to carry out monitoring, compliance, and implementation of appropriate bed sore risk reductions steps. The particular bed sore risk reduction steps for a particular patient are, in some cases, automatically suggested by caregiver assistance application 124 based upon a bed sore risk score determined for that particular patient. Bed sore risk reduction algorithm 141 is discussed in more detail below with respect to FIGS. 28-58.

Figure 3:
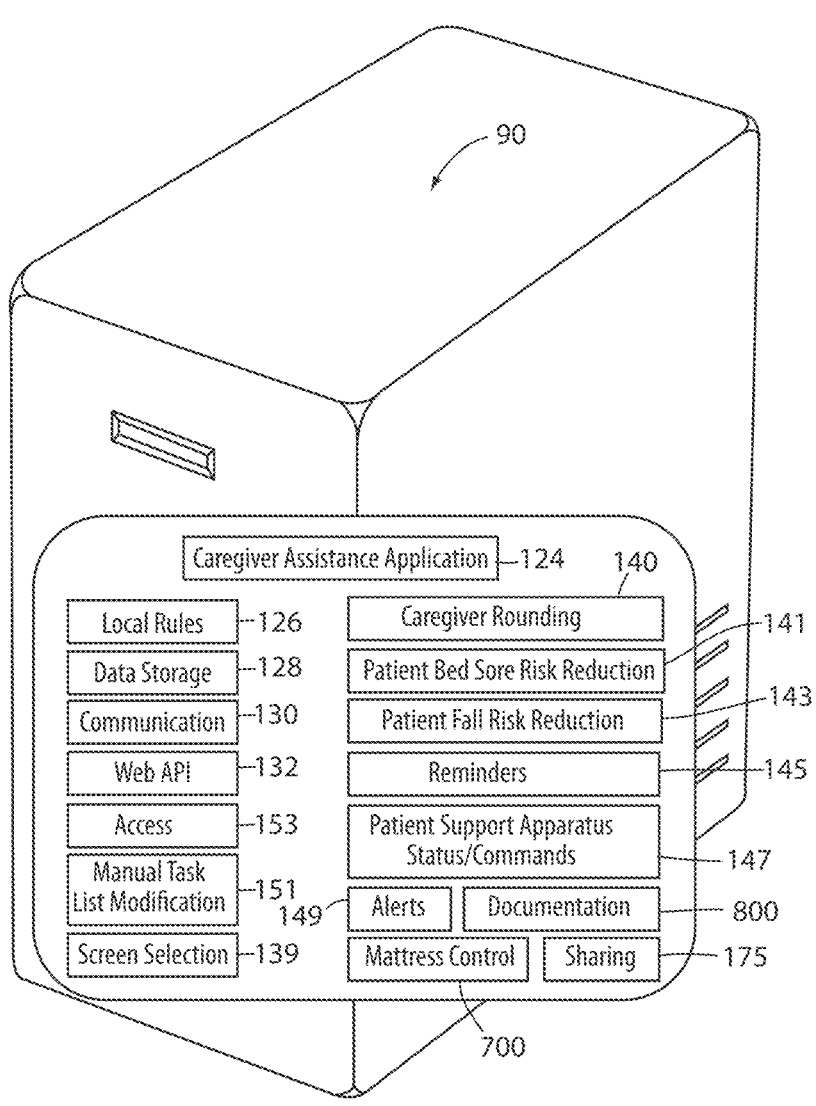
FIG. 3 is a block diagram of a set of components of the server-based caregiver assistance application.

FIG. 3 illustrates in greater detail some of the specific functionality and components of caregiver assistance server 90. Caregiver assistance server 90 is adapted to host and execute a caregiver assistance application 124 that performs a plurality of algorithms and that utilizes a plurality of components. The algorithms includes a screen selection algorithm 139, a caregiver rounding algorithm 140, the bed sore risk reduction algorithm 141, the patient fall risk reduction algorithm 143, a reminder algorithm 145, a status/command algorithm 147, an alerting algorithm 149, a manual task list modification algorithm 151, an access algorithm 153, a sharing algorithm 175, a mattress control algorithm 700, a documentation algorithm 800, and a wireless disconnection detection algorithm 990. Caregiver assistance application 124 may be modified to execute only a subset of these algorithms and/or it may be modified to execute still other algorithms. Further, the content and function of each of these algorithms may be modified from the specific content and functions that are described in more detail below.

Screen selection algorithm 139 automatically selects a type of screen to display on one or more of the mobile electronic devices 104*a* based upon the location of the caregiver and his/her associated mobile electronic device. Further details regarding algorithm 139 are described below with respect to FIG. 63.

Caregiver rounding algorithm 140 assists a caregiver in performing his or her rounding duties, as well as assisting the caregiver to ensure that patient support apparatuses 20 are properly configured in accordance with the policies of the particular healthcare facility that employs the caregivers and operates the patient support apparatuses 20. In general, caregiver rounding algorithm 140 allows a caregiver to document his or her individual rounding actions while simultaneously reminding the caregiver of any actions that need to be taken to configure the patient support apparatus 20 properly. Such patient support apparatus configurations include, but are not limited to, setting a brake, moving the litter frame to its lowest height (or within a specified range of its lowest height), positioning the siderails in a correct position, arming the exit detection system, plugging in the nurse call cable, plugging in the A/C power cable, and/or arming a patient support apparatus monitoring system.

Bed sore risk reduction algorithm 141 assists the caregiver in assessing a particular patient's risk of developing bed sores and/or in managing the care of a patient's existing bed sores. Fall risk reduction algorithm 143 assists the caregiver in assessing the fall risk of a particular patient and/or in ensuring that patient support apparatus 20 is placed in a desired state for reducing the risk of a patient falling. Reminder algorithm 145 assists the caregiver by keeping track of any or all tasks that the caregiver is to complete that have time deadlines, including issuing reminders to the caregiver of when those tasks are due and/or are approaching their deadlines. Status/command algorithm 147 functions to provide the caregivers with up-to-date information of the status of each of the patient support apparatuses 20 having a patient to which that caregiver is assigned, as well as to allow the caregiver to remotely control one or more aspects of those patient support apparatuses 20. Alerting algorithm 149 provides alerts to caregivers when a status of a patient support apparatus 20 is changed to an out-of-compliance state, when a reminder deadline approaches or is reached, and/or whenever any information from any of the other algorithms 140, 141, 143, 145, and/or 147 yields information to which the caregivers should be alerted.

Manual task list modification algorithm 151 allows a caregiver to manually add tasks to, and/or remove tasks from, a task list maintained by caregiver assistance application 124, as well as to change the reminders (timing, frequency, recipients, etc.) that are associated with any of those tasks. Many of the tasks on the task list are automatically populated by one or more of the other algorithms executed by caregiver assistance algorithm 124 (e.g. bed sore risk reduction algorithm 141, fall risk reduction algorithm 143, etc.), but algorithm 151 allows the caregiver to manually modify the list, including tasks on the list that have been automatically populated by caregiver assistance application 124. Further details of one embodiment of a manual task list modification algorithm 151 are discussed below with respect to FIG. 57.

Access algorithm 153 controls which individuals are allowed to use caregiver assistance system 106, as well as what information is viewable to the authorized users of caregiver assistance system 106. Further details of one embodiment of access algorithm 153 that may be executed by caregiver assistance system 106 are provided below with respect to the discussion of FIG. 62.

Sharing algorithm 175 allows caregivers to share and unshare their responsibilities with each other so that, for example, while a first caregiver is temporarily unavailable, a second caregiver will receive alerts, updates, and other information on his or her mobile electronic device 104a regarding the patient(s) whose first caregiver is temporarily unavailable. Further description of sharing algorithm 175 is provided below with respect to FIGS. 64-67.

Mattress control algorithm 700 allows a caregiver to remotely control one or more aspects of the mattress 38, including, but not limited to, sending mattress parameters to the mattress 38 that are thereafter stored and utilized by the mattress 38 during a mattress therapy session, or utilized at other times. In some embodiments, mattress control algorithm 700 is also configured to ensure that the mattress settings and/or therapies utilized by a caregiver conform to the healthcare facility's bed sore reduction protocol. Mattress control algorithm 700 is discussed in greater detail below with respect to FIGS. 42-49.

Documentation algorithm 800 allows a caregiver to utilize caregiver assistance application 124 to document various tasks and/or patient data to the patient's corresponding electronic medical record. Such tasks and data include, but are not limited to, tasks and data that relate to the patient's bed sore risks, existing bed sores, and/or other information related to condition and/or treatment of the patient's skin. Documentation algorithm 800 is discussed in greater detail below with respect to FIGS. 50-56.

Figure 82:
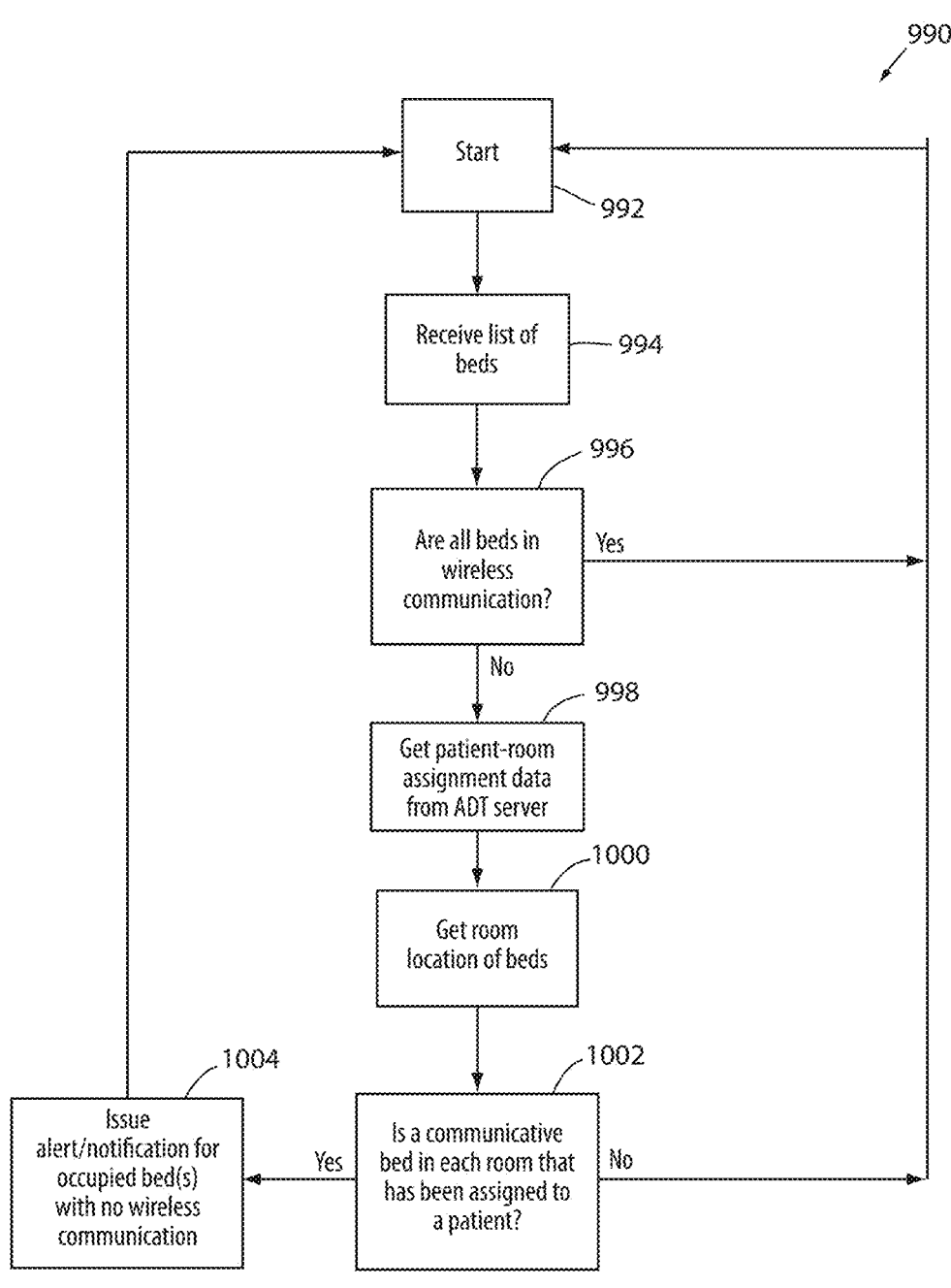
FIG. 82 is a flow diagram of a detection algorithm for detecting an absent communication connection between a patient support apparatus and the caregiver assistance application.

Wireless disconnection detection algorithm 990 is adapted to detect when one or more of the patient support apparatuses 20 lose their communication connection to local area network 74 and/or caregiver assistance application 124. In some embodiments, as will be discussed more below with respect to FIG. 82, wireless disconnection detection algorithm 990 is adapted to determine not only which patient support apparatuses 20 are not in communication with caregiver assistance application 124, but which ones of those uncommunicative patient support apparatuses 20, if any, are assigned to patients and which ones, if any, are not assigned to patients. By determining this information, wireless disconnection detection algorithm 990 can avoid sending an alert or notification regarding disconnected patient support apparatuses 20 that may be in storage, may be unused, or that otherwise do not have patients assigned to them. This helps reduce alert fatigue for the caregivers by avoiding alerts and/or notifications that do not relate to relevant safety conditions.

The non-algorithm components of caregiver assistance application 124 include a set of local rules 126, a data repository 128, a communication interface 130, and a web Application Programming Interface 132 (FIG. 3). The set of local rules 126 is initially defined prior to the installation of caregiver assistance application 124 within a particular healthcare facility, in at least some embodiments. In other embodiments, the set of local rules 126 is defined during or after installation of caregiver assistance application 124. In all embodiments discussed herein, however, local rules 126 are modifiable by authorized personnel from the healthcare facility. Such modifications are made by way of one or more computers 134 that are in communication with local area network 74 (FIG. 4). An authorized individual 136 (FIG. 4) utilizes computer 134 to communicate with caregiver assistance application 124 and add, delete, or modify one or more of the local rules 126.

Local rules 126 (FIG. 3) include, but are not limited to, the following: rules indicating how frequently caregivers are to perform their rounding duties (e.g. once every two hours, once every three hours, etc.); rules indicating what state patient support apparatuses 20 are to be placed in (e.g. one or more fall risk reduction protocols 93, bed sore risk reduction protocols 95, VAP protocols, etc.); rules specifying who is to be notified, and when, if a rounding duty is not performed within the desired time period; rules specifying who is to be notified, and when, if a patient support apparatuses is not placed in the desired state and/or is moved out of the desired state; rules specifying how such notifications are to be communicated (e.g. email, phone call, texts, etc.); rules specifying what personnel within the healthcare facility are authorized to view what data using caregiver assistance application 124; and rules specifying if and/or how rounding duties are to be verified and/or documented in the EMR server 98. Both the rules for caregiver assistance frequency and the desired states of the patient support apparatuses 20 may be configured by authorized individuals 136 to vary based upon one or more factors. For example, both the caregiver assistance frequency and desired states of patient support apparatuses may vary for different wings of the healthcare facility, different units of the healthcare facility, different times of day and/or different shifts, different models of patient support apparatuses, different patient health conditions, different patient treatments, different data stored in the EMR server 98, etc.

Local rules 126 (FIG. 3) also include additional administrative data that is stored on caregiver assistance server 90, or stored in a memory otherwise accessible to caregiver assistance application 124. Such administrative data includes, but is not limited to, the IP address, or other network address, of each of the servers with which caregiver assistance application 124 is to communicate (e.g. EMR server 98, ADT server 94, patient support apparatus server 86, RTLS server 100, and nurse call server 96), and/or the IP addresses or other configuration data necessary for caregiver assistance application 124 to communicate with one or more middleware software applications that act as gateways to one or more of these servers. The administrative data also may also include the email addresses, passwords, phone numbers, user names, access levels, and other information about those hospital personnel who have been authorized to use caregiver assistance application 124. The email address and/or phone numbers are used in some embodiments of the alerting algorithm 149 in order for caregiver assistance application 124 to make contact with mobile electronic devices 104a (FIG. 4) carried by the caregivers when there is an alert, or other information to which the caregiver's attention is desirably directed.

Data repository 128 (FIG. 3) stores data that is received by caregiver assistance application 124 during the course of its operation. This data includes patient support apparatus status data sent from patient support apparatuses 20 (via patient support apparatus server 86 in some embodiments, and directly in other embodiments), alert data (e.g. when alerts occurred, causes, remedies, notifications, etc.), rounding completion/incompletion data, verification data verifying caregiver assistance (discussed more below), patient data from bed sore risk reduction and fall risk reduction algorithms 141 and 143, and other data. Data repository 128 may be physically located on server 90 (or another server), or it may be cloud-based, or it may be a combination of both cloud-based storage and local storage maintained at the healthcare facility.

Communication interface 130 (FIG. 3) controls the communications between caregiver assistance application 124 and the electronic devices 104 with which it is in communication. Communication interface 130 also controls the communications between caregiver assistance application 124 and the servers with which it is in communication. All of these communications, in at least one embodiment, are carried out using conventional Internet packet routing. That is, patient support apparatuses 20 send data in packets that have an IP address corresponding to patient support apparatus server 86 and/or caregiver assistance server 90, and servers 86 and/or 90 send message packets back to patient support apparatuses 20 that include an IP address corresponding to the particular patient support apparatus(es) 20 to which the messages are intended. In some embodiments, each patient support apparatus 20 includes a static IP address that is stored on the patient support apparatus 20, while in other embodiments, the patient support apparatuses 20 consult a local Dynamic Host Configuration Protocol (DHCP) server (not shown) on local area network 74 and the DHCP server assigns a network address to the patient support apparatus.

When communicating with other servers within the healthcare facility, communication interface 130 may utilize different communication protocols, such as, but not limited to, Link Layer Protocol (LLP), Hyper-Text Transfer Protocol Secure (HTTPS), and/or Simple Mail Transfer Protocol (SMTP), etc. In order to facilitate the communication between caregiver assistance server 90 and the other servers of local area network 74, communication interface 130 may utilize a conventional interface engine, such as, but not limited to, the Redox cloud platform that is commercially available from Redox, Inc. of Madison, Wisconsin. Alternatively, or additionally, communication interface 130 may utilize a conventional iGUANA interface engine (HL-7 or otherwise) available from iNTERFACEWARE, Inc. of Toronto, Ontario. Such interfaces allow caregiver assistance application 124 to communicate with different types and/or brands of Electronic Health Record (EHR) systems, such as, but not limited to, those marketed by Cerner corporation, Epic Corporation, Allscripts, etc.

Web API 132 (FIG. 3) provides a portal for authorized devices, software applications and/or servers to access the data of caregiver assistance application 124. In some embodiments, electronic devices 104 communicate with caregiver assistance application 124 via the web API 132 by using a web browser built into the device 104 that accesses one or more Uniform Resource Locators (URLs) that direct the web browser to caregiver assistance application 124. Web API 132, in some embodiments, uses JavaScript Object Notation (JSON) to communicate with the web browsers of the electronic devices 104. In other embodiments, web API 132 use Extensible Markup Language (XML) to communicate with the web browsers of the electronic devices 104. Still other types of communication may be used.

Web API 132 may be configured to communicate with the electronic devices 104 using the conventional GET, POST, DELETE, and UPDATE verbs of the Hyper-Text Transfer Protocol (HTTP). These are used for providing RESTful service (i.e. Representational State Transfers) between web API and the electronic devices 104. For those aspects of caregiver assistance application 124 that utilize two way interactive communication, conventional web socket protocols (e.g. IETF RFC 6455, or the WebSocket API in Web IDL (Interface Description Language) that is standardized by the World Wide Web Consortium (W3C)) may be used for communication between web API 132 and the electronic devices 104. Alternatively, or additionally, conventional pull and push requests may be used for this communication, as well as, but not limited to, server-sent events and/or long polling. Still other communication techniques may be used. In some embodiments, such communications are encrypted such that at least those messages containing patient data are secured against interception. Such encryption takes place, in at least one embodiment, as part of a RESTulf Web service (RWS).

Web API 132 may also be utilized for carrying out additional communications with any of the servers on network 74 and/or for communicating with other software applications that are cloud-based (e.g. equipment management system 918, discussed below) and/or unrelated to caregiver assistance application 124.

In general, caregiver rounding algorithm 140, status/command algorithm 147, and alerting algorithm 149 of caregiver assistance application 124 performs the following functions: gather data from patient support apparatuses 20 about their current states; communicate the patient support apparatus data to electronic devices 104 that are remote from caregiver assistance server 90; cause the electronic devices 104 to display the patient support apparatus status data thereon; cause the electronic devices 104 to display reminders and/or other information on their displays to assist caregivers in performing their rounding tasks, fall prevention tasks, skin care tasks, and other tasks; receive patient data (rounding, skin, fall, etc.) that is input into electronic devices 104 by caregivers during or after the performance of their various tasks; communicate alerts to the caregivers if the patient support apparatus status data indicates the patient support apparatus 20 is not in a desired state or if a timer associated with the patient or the patient support apparatus 20 has expired; forward patient support apparatus commands received from caregivers (via electronic devices 104) to patient support apparatuses 20; receive verification data from electronic devices 104 and/or patient support apparatuses 20 verifying the caregivers' presence adjacent the patient support apparatus 20 when performing the rounding tasks; document to an Electronic Medical Record server 98 (FIG. 4) the successful completion of the caregiver's tasks, as well as the current state of the patient support apparatus status data at the time of completion of the tasks; confirm that the caregiver is following one or more of the healthcare facility's protocols; automatically display a screen on the electronic device that is selected based on the location of the caregiver; temporarily share bed data, alerts, and reminders with other caregivers; and communicate with, and utilize the functionality of, a remote equipment maintenance system that monitors the usage and service history of the beds, as well as other information. Still other functions and features are provided by caregiver assistance application 124. However, it will be understood that, in some embodiments, caregiver assistance application 124 may be modified such that one or more of these functions and/or algorithms are modified, supplemented, and/or omitted. That is, in one embodiment, caregiver assistance application 124 includes only a single one of the algorithms and/or features disclosed herein, in another embodiment it includes all of the algorithms and/or features disclosed herein, and in still other embodiments it includes any combinations of two or more of these algorithms/features but less than all of the algorithms/ features.

Patient support apparatus 20 is shown in FIG. 2 positioned in a room 92 of a representative example of a healthcare facility. FIG. 2 also depicts patient support apparatus 20 in communication with local area network 74 of the healthcare facility. It will be understood that the precise structure and contents of the local area network 74 will vary from healthcare facility to healthcare facility. FIG. 4 illustrates in greater detail the contents of a common hospital's local area network 74, along with caregiver assistance server 90 and other components of caregiver assistance system 106.

As shown in FIG. 4, local area network 74 includes a plurality of servers, including a conventional Admission, Discharge, and Tracking (ADT) server 94, a conventional nurse call system server 96, a conventional Electronic Medical Records server 98, a conventional real time location system (RTLS) server 100, and a plurality of conventional wireless access points 76. Local area network 74 also includes caregiver assistance server 90 that, together with one or more patient support apparatuses 20 and one or more electronic devices (e.g. mobile electronic devices 104*a* or stationary electronic devices 104*b*) implement one embodiment of the caregiver assistance system 106 according to the present disclosure. Still further, network 74 includes a conventional Internet gateway 108 that couples local area network 74 to the Internet 110, thereby enabling the servers and/or patient support apparatuses 20 to communicate with computers outside of the healthcare facility, such as, but not limited to, a geographically remote server 112. In some embodiments, all or some of the functions of caregiver assistance server 90 are carried out by geographically remote server 112, while in other embodiments caregiver assistance server 90 is configured to implement all of its functions without accessing geographically remote server 112.

ADT server 94 stores patient information, including the identity of patients and the corresponding rooms 92 and/or bays within rooms to which the patients are assigned. That is, ADT server 94 includes a patient-room assignment table 114, or functional equivalent to such a table. The patient-room assignment table correlates rooms, as well as bays within multi-patient rooms, to the names of individual patients within the healthcare facility. The patient's names are entered into the ADT server 94 by one or more healthcare facility staff whenever a patient checks into the healthcare facility and the patient is assigned to a particular room within the healthcare facility. If and/or when a patient is transferred to a different room and/or discharged from the healthcare facility, the staff of the healthcare facility update ADT server 94. ADT server 94 therefore maintains an up-to-date table 114 that correlates patient names with their assigned rooms. ADT server 94 may be a conventional server marketed by Cerner Corporation of North Kansas City, Missouri; EPIC Systems of Madison, Wisconsin; Allscripts Healthcare Solutions, Inc. of Chicago, Illinois; and/or by other companies. Still other types of ADT servers 94 may, of course, be used.

EMR server 98 (FIG. 4) stores individual patient records. Such patient records identify a patient by name and the medical information associated with that patient. Such medical information may include all of the medical information generated from the patient's current stay in the healthcare facility as well as medical information from previous visits. EMR table 116 shows an abbreviated example of two types of medical information entries that are commonly found within a patient's medical records: a fall risk entry indicating whether the patient is a fall risk, and a bed sore risk entry indicating whether the patient is at risk for developing bed sores. Although FIG. 4 shows the data for these entries to be expressed as text, it will be understood that this data may be stored within a medical record in numeric format. For example, the fall risk data may be stored as a numeric value generated from a conventional fall risk assessment tool, such as, but not limited to, the Morse fall risk scale or the Hester-Davis fall risk scale. Similarly, the bed sore data may be stored as a numeric value generated from a conventional bed sore risk assessment tool, such as, but not limited to, the Braden scale. As noted, EMR server 98 includes far more additional information in the medical records of each patient than what is shown in table 116 of FIG. 4, and some of that additional data, such as rounding data, is discussed in more detail below. It will be understood that the term "EMR server," as used herein, also includes Electronic Health Records servers, or EHR servers for short, and that the present disclosure does not distinguish between electronic medical records and electronic health records. EMR server 98 may be a conventional server marketed by Cerner Corporation of North Kansas City, Missouri; EPIC Systems of Madison, Wisconsin; Allscripts Healthcare Solutions, Inc. of Chicago, Illinois; and/or by other companies. Still other types of EMR servers 98 may, of course, be used.

RTLS server 100 (FIG. 4) is a conventional server that may be present within a given healthcare facility. When present, RTLS server 100 keeps track of the current location of people and equipment within the healthcare facility. In many instances, the RTLS server keeps track of the current location of one or more tags 120 (FIG. 4) that are worn by personnel and/or that are attached to equipment. Such tags 120 may be RF ID tags, or other types of tags. RTLS table 118 provides an example of the type of location data that RTLS server 100 may contain with respect to caregivers. As shown therein, table 118 shows the current location of two caregivers, one by room number (e.g. room 400) and another by general location (e.g. "hallway"). Other types of location data may be included. Further, as noted, some healthcare facilities may not include such an RTLS server 100 and caregiver assistance system 106 is able to fully function without such a server. RTLS server 100 may be a conventional Centrak server marketed by Halma plc of Amersham, United Kingdom, or it may be a conventional RTLS server marketed by Stanley Healthcare of Waltham, Massachusetts. Still other types of RTLS servers 100 may, of course, be used.

Nurse call server 96 is shown in FIG. 4 to include a caregiver assignment table 122 that matches caregivers to specific rooms and/or bays within the healthcare facility. Although table 122 only shows caregivers assigned to a single room, it will be understood that each caregiver is typically assigned to multiple rooms. In some nurse call systems 80, caregivers are assigned to specific patients, rather than to specific rooms. Caregiver assistance system 106 is configured to work with both types of nurse call systems 80. Caregiver assistance system 106 is also adapted to work with healthcare facilities that utilize a separate caregiver assignment server (not shown), rather than nurse call server 96, to assign caregivers to rooms and/or patients. Nurse call server 96 may be a conventional server marketed by Rauland (now owned by Ametek, Inc. of Berwyn, Pennsylvania); by West-Com Nurse Call System, Inc. of Fairfield, California; and/or by other companies.

Regardless of whether caregiver assignment table 122 is stored within nurse call server 96 or some other server on network 74, nurse call system server 96 is configured to communicate with caregivers and patients. That is, whenever a patient on a patient support apparatus 20 presses, or otherwise activates, a nurse call, the nurse call signals pass through nurse call cable 78 to nurse call outlet 82. Nurse call outlet 82 is coupled via wire to nurse call server 96 and/or to another structure of nurse call system 80 that then routes the call to the appropriate nurse. The nurse is thereby able to communicate with the patient from a remote location. In some nurse call systems 80, nurse call server 96 is also able to forward alerts and/or other communications to portable wireless devices carried by caregivers and/or to audio stations positioned within patient rooms 92. Such portable wireless devices are the same as mobile electronic devices 104a discussed herein, in at least one embodiment.

Local area network 74 may include additional structures not shown in FIG. 4, such as, but not limited to, one or more conventional work flow servers and/or charting servers that monitor and/or schedule patient-related tasks for particular caregivers, and/or one or more conventional communication servers that forward communications to particular individuals within the healthcare facility, such as via one or more portable devices (smart phones, pagers, beepers, laptops, etc.). The forwarded communications may include data and/or alerts that originate from patient support apparatuses 20 as well as data and/or alerts that originate from caregiver assistance server 90.

Wireless access points 76 are configured, in at least some embodiments, to operate in accordance with any one or more of the IEEE 802.11 standards (e.g. 802.11g, 802.11n, 802.11ah, etc.). As such, patient support apparatuses 20 and electronic devices 104a, 104b that are equipped with Wi-Fi capabilities, and that have the proper authorization credentials (e.g. password, SSID, etc.), can access local area network 74 and the servers hosted thereon. This allows patient support apparatus 20 to send messages to, and receive messages from, patient support apparatus server 86 and/or caregiver assistance server 90. This also allows electronic devices 104 to send messages to, and receive messages from, patient support apparatus server 86 and/or caregiver assistance server 90. As noted previously, alternatively, or additionally, patient support apparatuses 20 may include a wired port for coupling a wired cable (e.g. a Category 5, Category 5e, etc.) between the patient support apparatus 20 and one or more routers/gateways/switches, etc. of network 74, thereby allowing patient support apparatuses 20 to communicate via wired communications with servers 86 and/or 90.

In still other embodiments, one or more of the patient support apparatuses 20 are equipped with alternative wireless transceivers enabling them to communicate directly with patient support apparatus server 86 and/or caregiver assistance server 90 via an antenna and transceiver that is directly coupled to servers 86 and/or 90 and that is separate from LAN 74, thereby allowing patient support apparatuses 20 to bypass LAN 74 in their communications with servers 86 and/or 90. One example of patient support apparatuses equipped to communicate directly with a server on a healthcare facility's local area network without utilizing the LAN is disclosed in commonly assigned U.S. patent application Ser. No. 15/831,466 filed Dec. 5, 2017, by inventors Michael Hayes and entitled NETWORK COMMUNICATION FOR PATIENT SUPPORT APPARATUSES, the complete disclosure of which is incorporated herein by reference. In some embodiments, patient support apparatuses 20 include communication modules, such as the communication modules 66 disclosed in the aforementioned '466 application, and servers 86 and/or 90 are coupled directly to a receiver, such as the enterprise receiver 90 disclosed in the aforementioned '466 application. In such embodiments, patient support apparatuses 20 are able to both send and receive messages directly to and from servers 86 and/or 90 without utilizing access points 76 or any of the hardware of network 74 (other than servers 86 and/or 90).

Caregiver assistance server 90 constructs a table 218 (FIG. 4) that correlates specific caregivers with the patient support apparatuses 20 assigned to them. As shown in FIG. 4, table 218 correlates individual patient support apparatuses 20 and their current statuses to the specific caregivers who are assigned to those patient support apparatuses 20. Although not shown in FIG. 4, table 218 also may correlate caregivers and their patient support apparatuses 20 to specific rooms within the healthcare facility. In order to construct table 218, caregiver assistance application 124 receives the unique patient support apparatus identifiers 186, along with the current status of the patient support apparatuses 20 from patient support apparatus server 86. Caregiver assistance application 124 determines which caregivers are associated with each of these patient support apparatuses 20 based on the caregiver-to-room assignment data it receives from nurse call server 96 (i.e. the data of table 122) and the room-to-patient support apparatus data it receives from patient support apparatus server 86 (i.e. the data from table 88). Caregiver assistance server 90 is therefore supplied with sufficient data to know the current status of each patient support apparatus 20, the room in which each patient support apparatus 20 is assigned, the caregiver assigned to that room and/or patient support apparatus 20, the patient assigned to each patient support apparatus 20, and the fall risk and/or bed sore risk (if known) of each patient. Still further, in those embodiments where an RTLS server 100 is included, caregiver assistance server 90 is also supplied with sufficient data to know the current location of each caregiver.

In some embodiments, caregiver assistance application 124 is configured to determine patient-to-room, patient-to-bed, patient-to-bed-bay, patient-to-caregiver, caregiver-to-room, caregiver-to-patient-support-apparatus, and/or caregiver-to-bed-bay correlations in any of the manners disclosed in commonly assigned U.S. patent application Ser. No. 62/826,097, filed Mar. 29, 2019 by inventors Thomas Durlach et al. and entitled PATIENT CARE SYSTEM, the complete disclosure of which is incorporated herein by reference. In some embodiments, caregiver assistance application 124 may further be modified to carry out any of the staffing errors, and other error-notification functions, disclosed in the aforementioned '097 application.

Figure 5:
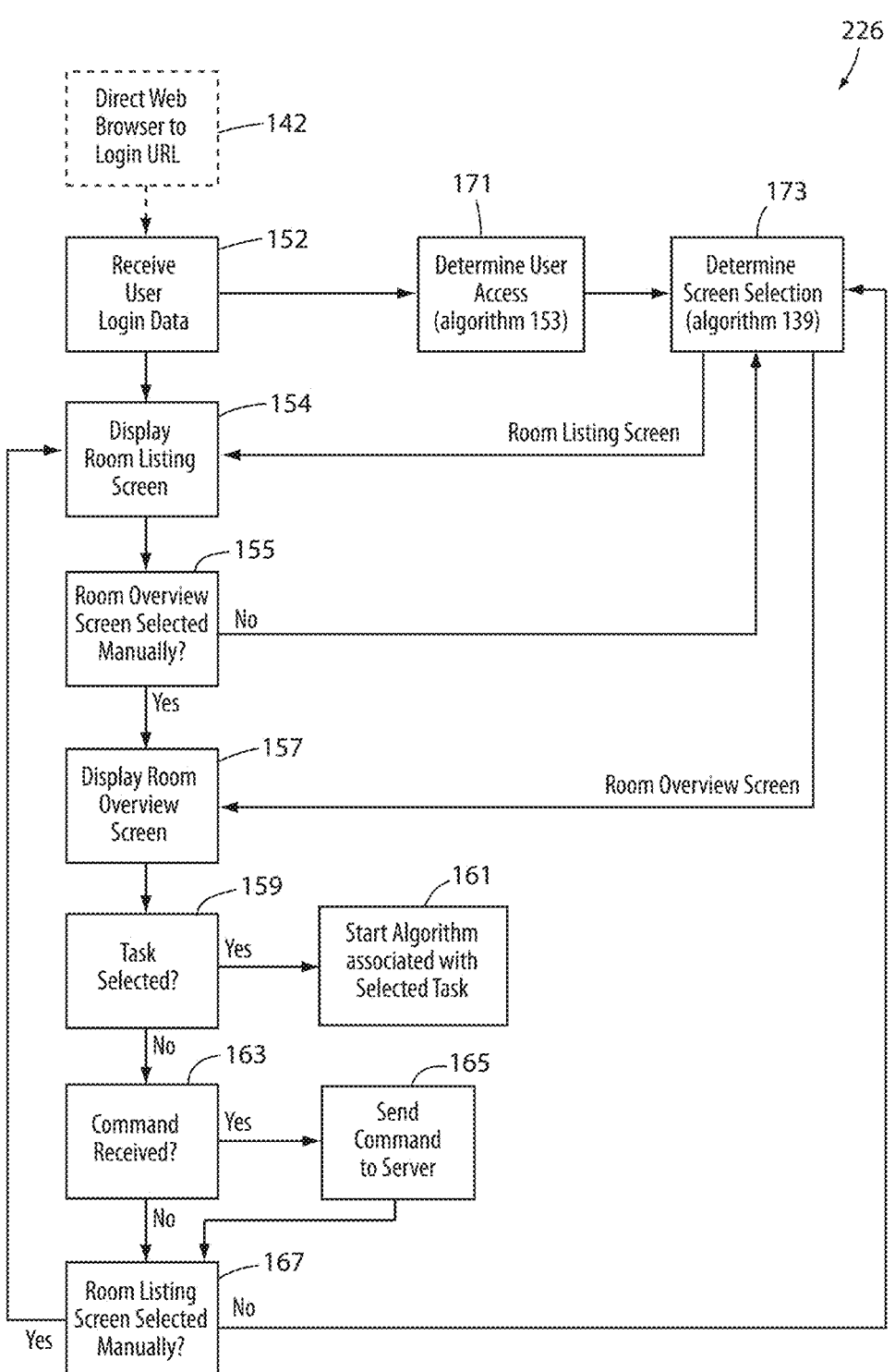
FIG. 5 is a flow diagram of a general algorithm that may be executed by the caregiver assistance application.

FIG. 5 illustrates a main algorithm 226 executed by caregiver assistance application 124 in at least one embodiment of the present disclosure. Main algorithm 226 is carried out by the one or more processors of caregiver assistance server 90 when caregiver assistance server 90 is executing caregiver assistance application 124. Main algorithm 226 begins at an initial access step 142 where a user accesses caregiver assistance application 124. Initial step 142 is illustrated in FIG. 5 as a window having dashed lines. The dashed lines are presented in order to indicate that step 142 is performed by a user, rather than caregiver assistance application 124 itself. The remaining steps of algorithm 226 are carried out by caregiver assistance application 124.

Initial step 142 is carried out by a user by manipulating one of the electronic devices 104 that are used in conjunction with caregiver assistance application 124. Caregiver assistance system 106 includes one or more electronic devices 104 that communicate with caregiver assistance server 90 and its caregiver assistance application 124. These electronic devices 104 utilize caregiver assistance application 124 to receive status data from patient support apparatuses 20 and to send and receive caregiver assistance data. In other words, caregiver assistance application 124 functions as an intermediary between the electronic devices 104 and the patient support apparatuses 20, as well as an intermediary between the electronic devices 104 and other servers, such as EMR server 98 and/or the nurse call server 96. Caregiver assistance application 124 also performs other functions, as described below.

Electronic devices 104 come in a variety of different forms. As shown in FIG. 4, some electronic devices 104a are mobile electronic devices intended to be carried by a user (e.g. caregiver) while other electronic devices 104b are stationary electronic devices that generally remain in one location. Mobile electronic devices 104a may take on different forms, such as, but not limited to, smart phones, tables, laptop computers, Computers on Wheels (COWs), and others. Stationary electronic devices 104b may also take on different forms, such as, but not limited to, televisions, displays, Personal Computers (PCs), and others. For purposes of the following written description, caregiver assistance system 106 will be described with reference to electronic devices 104 that access caregiver assistance system 106 via a conventional web browser. It will be understood, however, that in other embodiments, electronic devices 104 may be modified to execute a specialized software application that is downloaded to the electronic device 104 and that is tailored to be executed by the particular operating system of the electronic device (e.g. Android, iOS, Windows, etc.). The specialized software application is executed by the microcontroller(s) of the electronic device 104 and carries out the functions of caregiver assistance system 106.

In order for a caregiver associated with an electronic device 104 to access caregiver assistance system 106, the caregiver utilizes the web-browsing application contained within the electronic device 104 to go to a particular web page, or other URL, associated with caregiver assistance application 124. Any conventional web-browsing software may be used for this purpose, including, but not limited to, Microsoft's Bing or Internet Explorer web browsers, Google's Chrome web browser, Apple's Safari web browser, Mozilla's Firefox web browser, etc. The particular URL accessed with the web browser may vary for different healthcare facilities and can be customized by authorized IT personnel at the healthcare facility. In some embodiments, a domain name may be associated with caregiver assistance application 124 that is resolved by a local DNS server to the IP address of caregiver assistance server 90 (e.g. www.caregiver-assistance-app.com). In other embodiments, access to caregiver assistance system 106 may be achieved in other manners.

Figure 7:
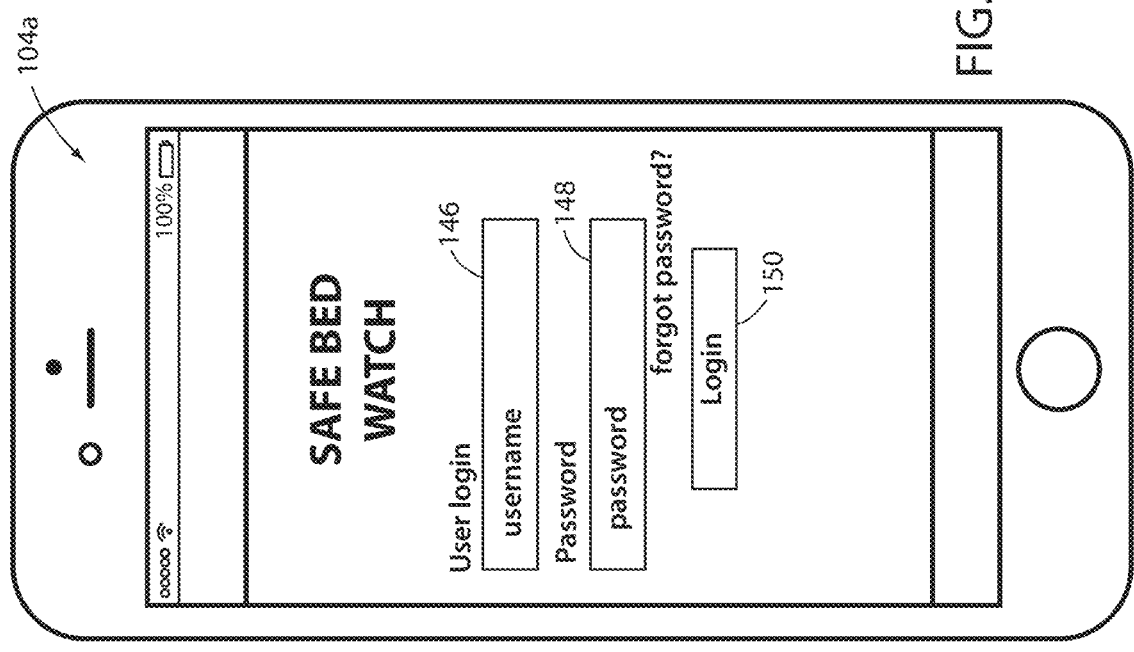
FIG. 7 is a plan view of a portable electronic device usable with the caregiver assistance system wherein the portable electronic device is shown displaying a login screen for the caregiver assistance application.

Once at the initial web page corresponding to caregiver assistance application 124, caregiver assistance application 124 instructs the web browser of the electronic device 104 to display a login screen on the display of the electronic device 104. FIG. 7 illustrates an example of such a login screen 144. Login screen 144 is shown in FIG. 7 as being displayed on a mobile electronic device (smart phone) 104a. This is done merely for purposes of illustrating one specific type of electronic device 104 with which caregiver assistance system 106 may be utilized. Other types of devices 104 may be used and the various drawings depict illustrative screens of caregiver assistance system 106 that do not show the specific type of electronic device 104 on which they are displayed (other than FIGS. 7 and 65-67), which is intended to re-emphasize the device agnostic nature of caregiver assistance system 106.

Login screen 144 includes a username field 146 in which a user is asked to input his or her username, as well as a password field 148 in which the user is asked to input his or her password. In order for the user to input this information, he or she utilizes the conventional input features of the electronic device 104. Thus, for example, when the electronic device 104 includes a touch screen display and the user touches or otherwise selects either of the fields 146, 148, the electronic device 104 shows on its display, in some embodiments, an image of an alphanumeric keyboard that can be used by the user to input his or her username and password. After this information is typed into fields 146, 148, the user either presses the "enter" or "return" button, or touches the login icon 150 shown on login screen 144. If electronic device 104 does not include a touch screen display, the user may enter the username and login information using a conventional keyboard, a mouse or other pointer, or other methods.

Figure 62:
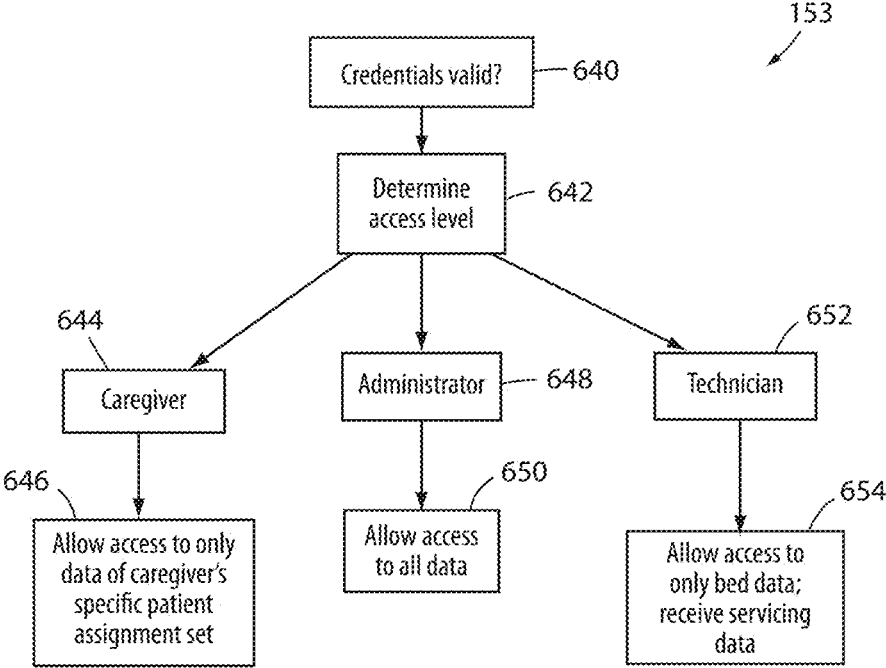
FIG. 62 is a flow diagram of an access algorithm that may be executed by the caregiver assistance application.

Caregiver assistance application 124 receives the user's username and password at step 152 of main algorithm 226 (FIG. 5). That is, the entry of the user's username and password into electronic device 104 is communicated by the electronic device 104 to caregiver assistance server 90. As was noted, this may be done in a conventional manner utilizing the WiFi, or other network communication, abilities of the electronic device 104. Once caregiver assistance application 124 receives the username and password, it proceeds to step 171 where it determines the level of access, if any, that is to be granted the user. In many embodiments, this determination is carried out in accordance with the steps set forth in access algorithm 153, which is illustrated in FIG. 62. As discussed in the description of access algorithm 153, caregiver assistance application 124 may utilize rules repository 126 to see if the username and password match an approved user. Local rules repository 126 contains information input into application 124 by an authorized representative of the healthcare facility in which caregiver assistance application 124 is installed. This information includes a list of those individuals who are authorized to use caregiver assistance application 124, including their usernames and passwords (and other data, such as their authorization level, email address, phone number, etc.), as well as what level of access to grant each such individual.

If the user's username and password match an authorized entry within local rules repository 126, caregiver assistance application 124 determines at step 171 (via algorithm 153) what level of access to grant the user. For purposes of the following description of main algorithm 226, it will be assumed that the user is a caregiver, although as set forth in the discussion of FIG. 62, the user might alternatively be an administrator or a technician (and still other categories are possible). After determining that the user is an authorized caregiver, algorithm 226 proceeds to step 173 where it determines what screen to display on the user's electronic device 104. The selection of a screen to display at step 173 is carried out, in some embodiments, in accordance with screen selection algorithm 139 which, as noted, is described further below with respect to FIG. 63. In the example shown in FIG. 5, algorithm 226 is configured to select between two basic screen types: a room listing screen and a room overview screen. FIGS. 8, 59, 84, and 91 show four examples of room listing screens 156, 156a, 156b, and 156c, while numerous drawings show examples of room overview screens (e.g. room overview screen 162 of FIG. 9, room overview screen 162a of FIG. 58, etc.). If caregiver assistance application 124 determines at step 173 to display a room listing screen, it proceeds to step 154. If caregiver assistance application 124 determines at step 173 to display a room overview screen, it proceeds to step 157.

Figure 8:
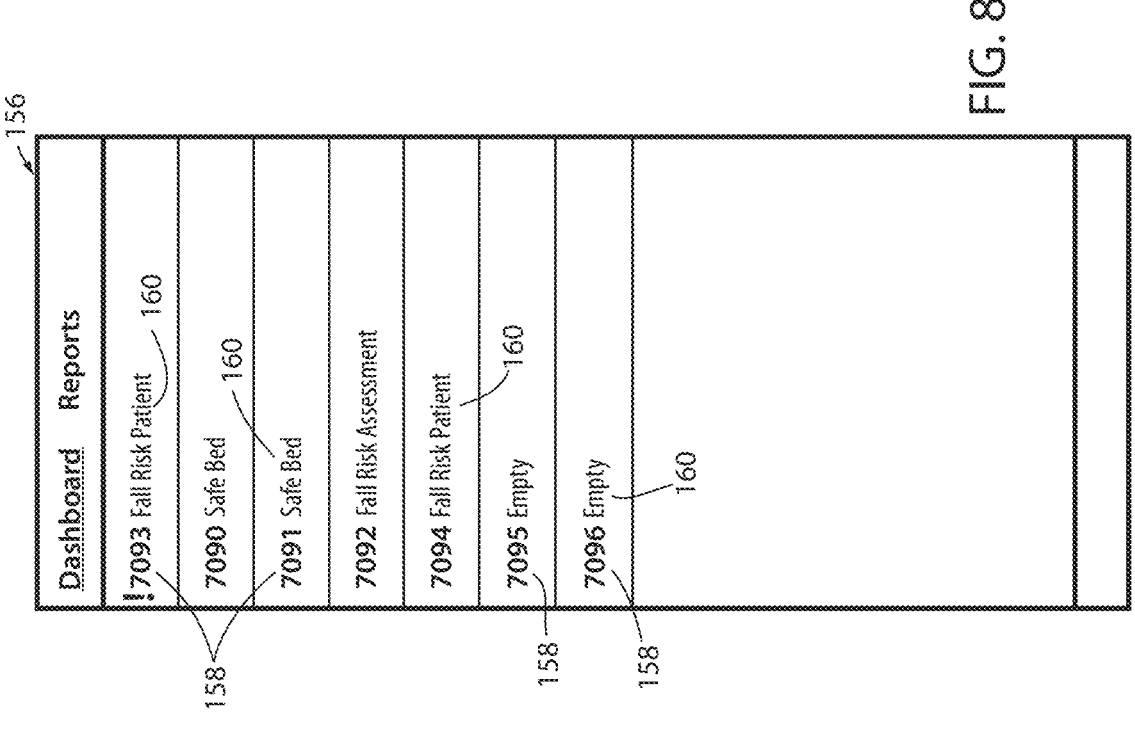
FIG. 8 is an illustrative room listing screen that is displayable on an electronic device of the caregiver assistance system.

As can be seen from FIG. 8, room listing screen 156 displays a plurality of rows and each row includes a room identifier 158 that identifies a particular room 92 within the healthcare facility in which caregiver assistance system 106 is installed. The particular selection of which rooms to list in room listing screen 156 corresponds, in the illustrated embodiment, to the particular person who has just logged into caregiver assistance application 124. That is, each caregiver is assigned a level of administrative access to the data contained within caregiver assistance application 124 (see algorithm 153; FIG. 62). This assignment is carried out by one or more of the authorized individuals 136 who initially set up caregiver assistance application 124. In at least one embodiment, caregivers are assigned an access level that only permits them to view rooms that they themselves have been assigned. Caregiver managers may be granted a higher access level that permits them to view all of the rooms of all of the caregivers which they oversee. Administrators may be granted an even higher access that allows them to see all of the rooms in the entire healthcare facility. Still other types of access levels may be used and/or created, and the rules defining the access level architecture are stored within local rules repository 126.

Caregiver assistance application 124 automatically determines which rooms a particular caregiver has been assigned by communicating with a server on local area network 74 that maintains room assignments for caregivers. In the example illustrated in FIG. 4, nurse call server 96 is shown to include a caregiver-room assignment table 122 that stores the room assignments for the caregivers within the healthcare facility. As noted previously, caregiver-room assignment table 122 may be stored on a different server. During installation of caregiver assistance application 124, an authorized administrator inputs the IP address of the server containing caregiver room assignment table 122 (and/or other data necessary to gain access to caregiver-room assignment table 122). Similar data is also input for all of the other servers and tables discussed herein. After a user successfully logins at step 152 of algorithm 140, caregiver assistance application 124 sends a message to the server having caregiver room assignment table 122. The message requests an up-to-date listing of the rooms that are assigned to the caregiver who has just logged in. After receiving this information, caregiver assistance application 124 displays those rooms on the display of the electronic device 104 (or, more precisely, causes the web browser to display those rooms on the display of the electronic device 104). Thus, in the example of FIG. 8, caregiver assistance application 124 displays rooms 7090 through 7096, which correspond to the rooms assigned to the particular caregiver who is using caregiver assistance application 124.

In some healthcare facilities, caregivers may be assigned to specific patients instead of specific rooms. In such instances, caregiver assistance application 124 may be configured in at least two alternative manners. In a first manner, caregiver assistance application 124 continues to display a room listing, such as the room listing screen 156 of FIG. 8. In a second manner, caregiver assistance application 124 displays a patient listing screen that, instead of rows of the rooms the caregiver has been assigned, displays rows of each of the patients the caregiver has been assigned to. When configured in either manner, caregiver assistance application 124 determines the data to display by sending a request to the particular server(s) within the healthcare facility that maintain data sufficient to correlate specific caregivers to specific patients. In the particular embodiment illustrated in FIG. 4, there is no server that correlates patients to caregivers. However, by utilizing patient-room assignment table 114 in conjunction with another server that stores caregiver to room assignments (e.g. table 122), caregiver assistance application 124 is able to determine which particular patients are assigned to a particular caregivers, and which rooms 92 those particular patients are located in within the healthcare facility.

For example, if caregiver assistance application 124 is configured to display room listing screen 156 (FIG. 8) in a healthcare facility that assigns caregivers to specific patients, rather than to specific rooms, caregiver assistance application 124 sends a first request message and a second request message. The first request message is sent to whatever server maintains a table correlating caregivers and the particular patient they have been assigned to care for. The second request is sent to ADT server 94 and requests a listing of the specific rooms in which the caregiver's assigned patients are located. By using the data retrieved from these two requests, caregiver assistance application 124 is able to determine which particular patients the caregivers has been assigned, along with the rooms those patients have been assigned. Caregiver assistance application 124 is thereby able to display room listing screen 156 in a manner that is tailored to the particular caregiver who is using caregiver assistance application 124.

In those embodiments where caregiver assistance application 124 is configured to display rows of the patients assigned to a particular caregiver, rather than the patient room listing screen 156, caregiver assistance application 124 need not send the first request message mentioned above. Instead, it can send a single request message to the particular server that stores the table (or other data structure) that correlates caregivers to particular patients. Caregiver assistance application 124 then displays on the display screen of the electronic device used by that particular caregiver the listing of those patients who are assigned to that particular caregiver.

Still further, in some embodiments, a particular healthcare facility may assign rooms to particular caregivers but may desire to have room listing screen 156 replaced by a patient listing screen that identifies the particular patients assigned to a particular caregiver. Caregiver assistance application 124 may be configured to accommodate this desire. In order to do so, caregiver assistance application 124 sends a message to nurse call server 96 requesting the room assignments for a particular caregiver and also sends a message to ADT server 94 requesting the patient assignments to particular rooms. By using the data from both of these requests, caregiver assistance application 124 is able to determine which patients have been assigned to which caregivers, and is therefore able to display a patient listing screen instead of, or in addition to, room listing screen 156. This is configurable by an authorized individual 136 and is stored in rule repository 126.

It should be noted that, although most electronic devices 104 are associated with a particular caregiver, this is not always the case, particularly for stationary electronic devices 104*b*. Stationary electronic devices 104*b*, which may include large screen smart televisions, may be associated with a particular unit of a healthcare facility, a particular nurse's station, wing, floor, and/or other section of the healthcare facility. For these devices, the login credentials may be tailored to the particular location and/or intended function of that particular electronic device 104*b*. For example, a stationary electronic device 104*b* may be associated with an oncology unit, an east wing, nurse's station XYZ, the second floor, or rooms A through G, or something else. In such instances, caregiver assistance application 124 may be configured to assign a username and password to each such electronic device 104 that is custom tailored to that specific device. Thus, for example, if a particular electronic device 104 is positioned at a nurse's station within a pediatric oncology unit, the device 104 may be assigned a username of "pediatric oncology display" and have its own specific password. Once an authorized user has logged into caregiver assistance application 124 via that device, caregiver assistance application displays the rooms and/or patient data corresponding to the pediatric oncology unit on that particular device. The room and/or patient data may include rooms and/or patients that are assigned to multiple caregivers, thereby allowing the electronic device 104 to display information beyond that associated with a single caregiver.

Regardless of whether caregiver assistance application 124 displays room listing screen 156 at step 154 or a patient listing screen at step 154 (FIG. 5), caregiver assistance application 124 is also configured to display a status indicator 160 (FIG. 8) on the screen selected at step 154. Status summaries 160 provide additional information about the status of the patient in the room and/or the patient support apparatus 20 assigned to that room. Thus, for example, the status indicator 160 may indicate that a patient is a fall risk or a bed sore risk, that the patient support apparatus 20 is currently empty, that the patient support apparatus 20 is in a compliant or non-compliant state, and/or that one or more tasks (e.g. a fall risk assessment, a skin care assessment, rounding, etc.) are waiting to be performed for that particular patient and/or room.

Caregiver assistance application 124 receives the data necessary for displaying status summaries 160 by communicating with one or more of the servers on local area network 74. In some embodiments, caregiver assistance application 124 receives all of the patient support apparatus data from patient support apparatus server 86, which may be a commercially available bed status server, such as, but not limited to, the iBed server available from Stryker Corporation of Kalamazoo, Michigan. Further details of the iBed server are found in the Stryker Installation/Configuration Manual for the iBed Server 2.0 (document 5212-209-001 REV A), published in May of 2016 by Stryker Corporation of Kalamazoo, Michigan, the complete disclosure of which is incorporated herein by reference. In other embodiments, caregiver assistance application 124 is configured to receive the patient support apparatus status data directly from the patient support apparatuses 20 themselves, rather than through an intermediary server, such as the above-noted iBed server.

Caregiver assistance application 124 receives the patient data and protocol data from EMR server 98 and/or ADT server 94. ADT server 94 may contain, in addition to patient room assignments, requirements data identifying one or more protocols that the healthcare facility requires its caregivers to follow when caring for one or more patients. Such requirements data, for example, may specify what assessments are to be performed on a patient, such as an assessment of the patient's fall risk and/or bed sore risk. Alternatively, such requirements data may be stored elsewhere, such as, but not limited to, local rules repository 126. In some embodiments, the requirements data that specifies which assessments (fall, skin, etc.) are to be performed for a given patient may depend upon the location of the patient within the healthcare facility. For example, some healthcare facilities may configure local rules repository 126 such that all patients within a particular wing, floor, or other section, receive both a fall risk assessment and a skin assessment, while patients within a different location are to receive only one or none of these assessments. Caregiver assistance application 124 automatically checks these local rules when a new patient is admitted to the healthcare facility (as determined from communication with ADT server 94) and, if no assessment is recorded in EMR server 98 (which may be sent there either by caregiver assistance application 124 itself or another device), it displays a reminder on various screens associated with that patient that such an assessment needs to be performed.

Thus, when a new patient enters the healthcare facility, caregiver assistance application 124 automatically determines from server 94 and/or rules repository 126 (or another location) if a particular patient is supposed to have a fall assessment, bed sore assessment, or other assessment performed. If so, caregiver assistance application 124 further sends an inquiry to EMR server 98 to determine if such an assessment has been completed for that particular patient. If it has not, caregiver assistance application 124 displays this lack of completion in the status indicator 160 (FIG. 8). In the example shown in FIG. 8, the patient in room 7092 has not yet had a fall risk assessment performed, and this information is shown in the status indicator 160 corresponding to room 7092.

Turning more particularly to the examples shown in FIG. 8, caregiver assistance application 124 receives the data necessary to indicate that the patient in room 7093 is a fall risk either from EMR server 98 or from data repository 128. Caregiver assistance application 124 requests and receives the data indicating "safe bed" for rooms 7090 and 7091 from patient support apparatus server 86. The term "safe bed" displayed in the status indicator 160 for rooms 7090 and 7091 of FIG. 8 means that the patient support apparatuses 20 in those rooms are currently configured in their desired state. The "desired state" may be a pre-programmed part of caregiver assistance system 106, it may be defined by a fall risk reduction protocol 93, a bed sore risk reduction protocol 95, or another healthcare facility protocol, and/or it may be modified and/or customized by an authorized individual 136. In any of these situations, the definition of the desired state, or "safe bed," is stored in local rules repository 126. In some embodiments, a particular patient support apparatus 20 is considered to be in the "safe bed" state if all of the following are true: the exit detection system 46 is armed, the brake is activated, the litter frame 28 is at its lowest height (or within a specified range of its lowest height), and at least three of the siderails 36 are in their raised position. As noted, this "safe bed" state may be modified to include, among other things, one or more of the following: a requirement that the A/C cable 102 is plugged into an A/C power outlet; a requirement that the nurse call cable 78 is plugged into the nurse call outlet 82; a requirement that a monitoring function for the patient support apparatus 20 is armed; and/or other requirements. Still further, the "safe bed" state may be modified to remove one or more of the aforementioned criteria.

As was noted previously, caregiver assistance application 124 determines if a patient in a particular room needs to have an assessment performed by checking EMR server 98, data repository 128, and/or one or more other servers on the local area network that define what assessments are to be performed, when they are to be performed, and if they are to be re-performed (and, if so, when). In some embodiments, caregiver assistance application 124 records the completion of one or more of these assessments in data repository 128 in addition to, or in lieu of, sending this data to EMR server 98. As will be discussed in more detail below, one or more of these assessments may be completed, in at least some embodiments, using electronic devices 104 and/or patient support apparatuses 20, and sent to EMR server 98 from either or both of these devices. Alternatively, such assessments may be performed by other devices who forward their results to EMR server 98. In the particular example shown in FIG. 8, caregiver assistance application 124 has determined that the patient in room 7092 has not yet had a fall risk assessment performed, and therefore displays "fall risk assessment" in the status indicator 160 associated with room 7092.

Similarly, caregiver assistance application 124 is configured to display in the status indicator 160 the results of any patient assessments that a caregiver should be aware of. Thus, in the example of FIG. 8, caregiver assistance application 124 displays "fall risk patient" for the status indicator 160 associated with room 7094. This indicates that a fall risk assessment has been performed for the patient in room 7094 and that assessment has indicated that that particular patient is at a higher risk for falling. The results of this fall risk assessment are typically stored in EMR server 98 and/or data repository 128, and caregiver assistance application 124 is configured to request these results from either or both locations and display them in status indicator 160, if a fall risk (or bed sore risk, or other risk) has been detected.

Caregiver assistance application 124 is also configured to display in the status indicator 160 whether or not a patient support apparatus 20 is currently occupied by a patient or not. This information is obtained from the weight sensors, such as load cells, that are included within the scale/exit detection system 46 of each patient support apparatus 20. Each patient support apparatus 20 periodically transmits its weight readings to patient support apparatus server 86. Those weight readings are forwarded to caregiver assistance server 90. If the weight readings are less than a threshold (e.g. 50 pounds), caregiver assistance application 124 concludes that the patient support apparatus 20 is unoccupied and may display this information in status indicator 160 (or it may display other information that is configured to have a higher priority, such as, but not limited to, any assessments that need to be performed for that particular patient). Such information may be displayed in status indicator 160 with the words "weight not detected," or "patient out of bed," or some other text that indicates that the patient support apparatus 20 is not detecting the patient.

In the example shown in FIG. 8, caregiver assistance application 124 is displaying the word "empty" for rooms 7095 and 7096. This indicates that those rooms currently do not have any patients assigned to them. Caregiver assistance application 124 determines this information by sending a request to ADT server 94 server asking it for patient information for those rooms 92 that are assigned to the particular caregivers who are using caregiver assistance system 106. In this example, ADT server 94 instructed caregiver assistance application 124 that rooms 7095 and 7096 were not assigned to any patients. Accordingly, caregiver assistance application 124 displays "empty" in the status indicator 160 for these rooms.

It will be understood that the examples of information displayed in the status indicators 160 shown in FIG. 8 are merely several examples of the types of information that may be displayed on room listing screen 156. Caregiver assistance application 124 may be modified to show less, more, and/or different information in status summaries 160 and/or to eliminate them entirely. Still further, caregiver assistance application 124 may be configured to display the status summaries 160 in different colors, depending upon the informational content of the status indicator 160. Thus, for example, tasks that need to be completed may be highlighted in a different color (e.g. orange); information indicating a task has not been complete within a designated time period and/or a patient support apparatus 20 that is out of compliance with a desired state may be highlighted in yet another color (e.g. red); and information indicating that no tasks or no out-of-compliance states exist may be indicated in yet another color (e.g. green). Indications of alerts may be displayed in status summary through flashing text, or still other manners.

Returning to main algorithm 226 of caregiver assistance system 106 (FIG. 5), main algorithm 226 proceeds from step 154 to step 155. At step 155 of main algorithm 226, caregiver assistance application 124 determines whether or not a caregiver has manually selected a particular room from amongst the rooms listed in room listing screen 156. If the caregiver has not manually selected a particular room, algorithm 226 returns to step 173 and re-executes algorithm 139 to determine whether or not to change the screen currently being displayed. The result of the re-execution of algorithm 139 is that caregiver assistance application 124 will either continue to display the room listing screen 156 (by returning to step 154 after re-executing algorithm 139 at step 173), or it will automatically start displaying the room overview screen at step 157. The triggers for this automatic display of the room overview screen are discussed further below with respect to algorithm 139.

Figure 9:
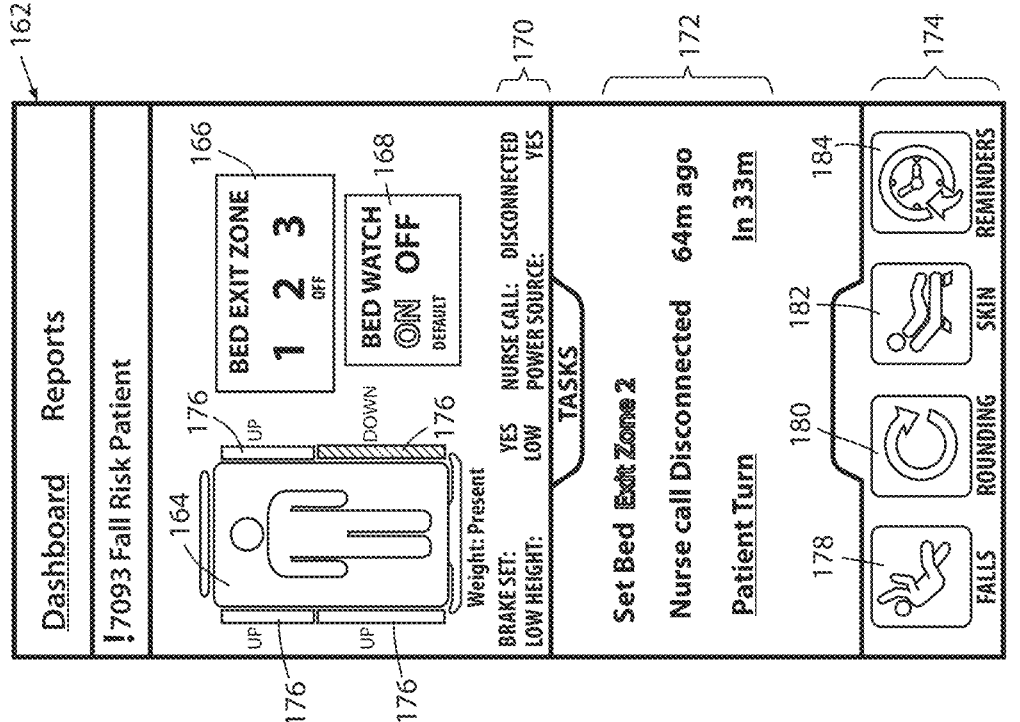
FIG. 9 is an illustrative room overview screen that is displayable on an electronic device of the caregiver assistance system.
Figures 58, 59:
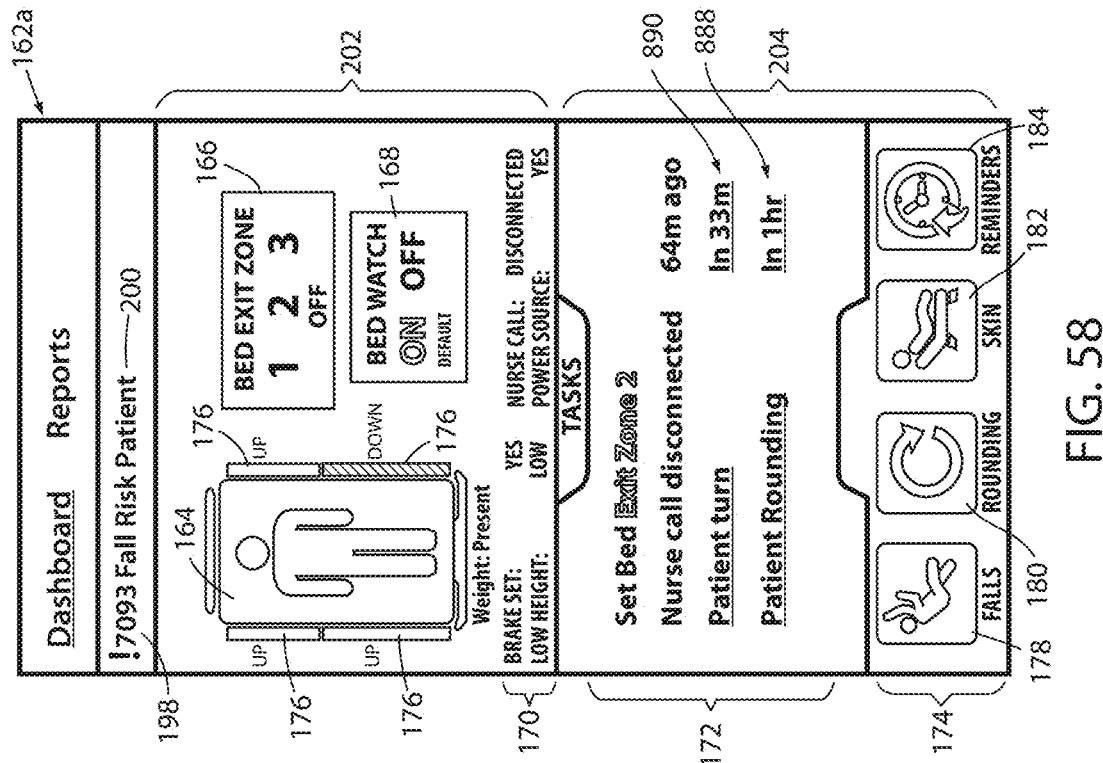
FIG. 58 is an illustrative alternative room overview screen that is displayable on an electronic device of the caregiver assistance system.
FIG. 59 is an illustrative alternative room listing screen that is displayable on an electronic device of the caregiver assistance system.

Regardless of whether caregiver assistance application 124 arrives at step 157 from step 155 or step 173, caregiver assistance application 124 displays on the screen of electronic device 104 a room overview screen 162, such as the room overview screen 162 of FIG. 9 (or the room overview screen 162a of FIG. 58). Thus, if a user manually navigates to (or is automatically brought to) the room listing screen 156 at any point while using caregiver assistance application 124, he or she can press on (or otherwise select) a particular room listed on room listing screen 156. Caregiver assistance application 124 responds to this selection by displaying a room overview screen 162 that corresponds to the particular room 92 selected by the user. The particular room overview screen 162 shown in FIG. 9 is therefore displayed by caregiver assistance application 124 when a user specifically selects room 7093 from room listing screen 156. Caregiver assistance application 124 may also include other tools for allowing a user to navigate to room overview screen 162, such as, but not limited to, a search function in which room numbers may be entered/searched.

Room overview screen 162 (FIG. 9) displays information about a particular room 92 within the healthcare facility and the patient associated with that room 92. It will be understood that room overview screen 162 may be changed to a bay overview screen, or other type of overview screen, if the particular room that the caregiver has selected is a semi-private room containing more than one patient support apparatus 20 or patient. In such embodiments, caregiver assistance application 124 displays a bay overview screen (not shown) similar to room overview screen 162 that is specific to the particular bay that the caregiver has selected the within semi-private room (or it displays an overview screen listing a combination of both rooms and bays).

Room overview screen 162 (or a similar bay overview screen) includes a bed icon 164, an exit detection system status indicator 166, a bed watch status indicator 168, a bed status bar 170, a summary area 172, and a task menu 174 (FIG. 9). Bed icon 164 includes a plurality of siderail icons 176 positioned along the sides of bed icon 164. Within each siderail icon 176 is an indicator (not labeled) that includes the word "up" or "down." Caregiver assistance application 124 selectively displays the "up" or "down" down indication within the siderail icons 176 based upon the current status of the siderails 36 of the patient support apparatus 20 within room 7093. Caregiver assistance application 124 receives the up/down status of each siderail 36 from patient support apparatus server 86 and displays "up" or "down" to match the current siderail status of patient support apparatus 20. Caregiver assistance application 124 is also configured, in at least some embodiments, to display the siderail icons 176 in a different color if they are in the down state, such as, but not limited to, amber. This distinguishes the siderail icons 176 from those corresponding to siderails 36 that are in an up position, which may be displayed in a green color, or some other color.

Exit detection system status indicator 166 (FIG. 9) indicates the current status of the scale/exit detection system 46 of the corresponding patient support apparatus 20 (e.g. the patient support apparatus 20 positioned in room 7093). That is, status indicator 166 indicates if the exit detection system 46 is currently armed or not. It also indicates what zone of the exit detection system the user has selected, if the exit detection system is armed and includes multiple zones. Many exit detection systems are configured to allow a user to select different zones of permitted movement. The different zones allow a patient to move different amounts before the exit detection system issues an alert. In the example of FIG. 9, the patient support apparatus 20 includes an exit detection system 46 having three zones, the second of which is highlighted. The exit detection system 46 is indicated in FIG. 9 as being disarmed (off). Caregiver assistance application 124 displays an "armed" or "on" indicator when the exit detection system 46 is armed, and also highlights the selected zone (1, 2, or 3). Further information about the zones and/or operation of an exit detection system that may be incorporated into patient support apparatus 20 and utilized in caregiver assistance system 106 are found in commonly assigned U.S. patent application Ser. No. 14/918,003 filed Oct. 20, 2015, by inventors Marko Kostic et al. and entitled EXIT DETECTION SYSTEM WITH COMPENSATION, the complete disclosure of which is incorporated herein by reference.

Bed watch status indicator 168 (FIG. 9) indicates whether the bed watch system of the patient support apparatus 20 is turned on or off. The bed watch system is a monitoring feature that is included in some embodiments of patient support apparatuses 20, but may be omitted in other embodiments. In general, the bed watch system, when activated, causes controller 48 to monitor the status of a plurality of components of the patient support apparatus 20 to issue an alert when any of those components are changed from a desired state to an undesired state. In several embodiments, the particular features that are monitored by the bed watch system are defined by the patient fall risk reduction protocol 93 (FIG. 2). The patient fall risk reduction protocol 93 also defines what the desired states are for each of the particular components that are being monitored by the bed watch system.

For example, if the bed watch system is activated and includes the monitoring of the siderails 36 of the patient support apparatus 20, controller 48 of patient support apparatus 20 will issue an alert if one or more of the siderails are lowered, or otherwise moved to an undesired state. Generally speaking, when the bed watch system is incorporated into a particular patient support apparatus 20, the bed watch system will monitor and issue an alert—when armed—if any of the following changes on the patient support apparatus 20 are detected: the exit detection system 46 is disarmed, a siderail 36 is lowered, the patient exits the patient support apparatus 20, the brake is deactivated, the height of the bed is raised beyond a specified level, the A/C power cord 102 is unplugged, and/or the nurse call cable 78 is unplugged. The particular components of the patient support apparatus 20 that are monitored by the bed watch system and that, when changed, trigger an alert can be selected by an authorized user, such as authorized individual 136. This selection may take place via one of the control panels 42 of the patient support apparatus 20, one of electronic devices 104, and/or via a computer in communication with caregiver assistance server 90. The alert issued by patient support apparatus 20 in response to the bed watch system detecting an undesired state may be a local alert (at patient support apparatus 20), a remote alert (e.g. sent to patient support apparatus server 86 and/or to caregiver assistance application 124), or a combination of both a local and a remote alert. The user may select from these different types of alerts via patient support apparatus 20, electronic devices 104, and/or a computer in communication with server 90.

Bed status bar 170 provides additional information about the current status of patient support apparatus 20 (FIG. 9). This includes an indication of whether or not the brake on the patient support apparatus 20 is activated or not; information indicating whether litter frame 28 is at its lowest height or not; information indicating whether the nurse call cable 78 is plugged into nurse call outlet 82 or not; and information indicating whether the A/C power cable 102 is plugged into an A/C outlet or not. All of the information shown in status bar 170 (as well as all of the patient support apparatus 20 data displayed by caregiver assistance application 124) is sent by the patient support apparatuses 20 (via transceiver 60) to patient support apparatus server 86, which then forwards it to caregiver assistance server 90 and caregiver assistance application 124. Although, in some modified embodiments, caregiver assistance application 124 and caregiver assistance server 90 are configured to receive this information directly from patient support apparatuses 20, thereby avoiding the need for a separate patient support apparatus server 86.

The data displayed in bed status bar 170 (FIG. 9) is updated in real time, or near real time. In most embodiments of patient support apparatuses 20, the patient support apparatuses 20 are configured to automatically (and nearly imme-diately) communicate their status to patient support appa-ratus server 86 whenever a change occurs in their status. Thus, for example, if the nurse call cable 78 gets unplugged from the nurse call outlet 82, the patient support apparatus 20 sends a message automatically and almost immediately thereafter to patient support apparatus server 86. The patient support apparatus server 86 automatically, and immediately or nearly immediately, forwards this status update to care-giver assistance application 124. Caregiver assistance appli-cation 124, in turn, updates the information displayed in bed status bar 170 to indicate that the nurse call cable has been unplugged. A caregiver, who may be remote from a particu-lar room 92 and/or a particular patient support apparatus 20, thereby gets a real time, or near real time, update of the status of patient support apparatus 20 when utilizing care-giver assistance application 124.

Summary area 172 of room overview screen 162 (FIG. 9) lists one or more items of information about the patient, the patient's patient support apparatus 20, the room assigned to that particular patient, and/or any data generated from the reminder algorithm 145. In the example shown in FIG. 9, the summary area 172 includes a reminder to set, or arm, exit detection system 46, and more specifically to select zone 2 when arming it. This data comes from a task list 886 (FIG. 57) discussed below that is populated by any one or more of the algorithms 140, 141, and 143 and/or by a manual task list modification algorithm 151. The manual task list modifica-tion algorithm 151 allows a caregiver to select one or more tasks associated with a patient and/or patient support appa-ratus 20, schedule those tasks, have reminders issued via caregiver assistance application 124, and display data about those reminders in summary area 172.

Summary area 172 also includes an entry re-iterating the fact that the nurse call cable 78 has been disconnected. Still further, summary area 172 includes an entry reminding the caregiver of any upcoming tasks that are scheduled for this particular patient, room, and/or patient support apparatus 20. In the specific example of FIG. 7, the summary area 172 of room overview screen 162 includes a reminder to turn the patient in room 7093 in thirty-three minutes. This task data is input into caregiver assistance application 124 by a caregiver and/or authorized individual 136 using the manual task list modification algorithm 151 and/or automatically by one or more of the various algorithm 140, 141, and/or 143. The automatically populated reminders include, but are not limited to, reminders to perform a fall risk assessment, to perform a bed sore risk assessment, to perform a rounding duty, to carry out one or more therapies, to configure patient support apparatus 20 and/or various of its components in desired states, etc. The reminders themselves include, in some embodiments, an indication of the amount of time until the task is supposed to be completed (e.g. a time until the next patient turn or next rounding task) and/or an amount of time that has elapsed since the time the task was last completed (e.g. the amount of time since the patient was last turned or the amount of time since the rounding duties were last performed).

Task menu 174 of room overview screen 162 (FIG. 9) identifies a plurality of different tasks that may be under-taken by a caregiver utilizing caregiver assistance applica-tion 124. In the example shown in FIG. 9 and elsewhere (e.g. FIGS. 10-17), task menu 174 includes four separate task icons: a fall task icon 178, a rounding task icon 180, a skin task icon 182, and a reminders task icon 184. If a caregiver selects one of these task icons 174-182 at step 159, caregiver assistance application 124 begins execution of a corresponding algorithm 140, 141, 143, and 151 at step 161 (FIG. 5). More specifically, if a caregiver selects fall task icon 178 at step 159, caregiver assistance application 124 begins execu-tion of fall risk reduction algorithm 143 at step 161. If a caregiver selects rounding task icon 180 at step 159, care-giver assistance application 124 begins execution of round-ing algorithm 140 (FIG. 6) at step 161. If a caregiver selects skin task icon 182 at step 159, caregiver assistance appli-cation 124 begins execution of skin care algorithm 141 (also referred to herein as a bed sore risk reduction algorithm) at step 161. Finally, if a caregiver selects reminder task icon 184 at step 157, caregiver assistance application 124 begins executing manual task list modification algorithm 151 at step 161.

The selection of these various icons and their associated algorithms cause caregiver assistance application 124 to bring up different screens corresponding to the selected task. The different screens enable a user to perform one or more tasks with respect to that particular patient. If the user selects the fall task icon 178, caregiver assistance application 124 begins execution of fall risk reduction algorithm 143 and causes the display of electronic device 104 to display one or more screens allowing a caregiver to perform one or more fall risk reduction steps associated with reducing the likeli-hood of a patient falling, such as, but not limited to, the screens shown in FIGS. 19-27. These steps include, but are not limited to, performing a fall risk assessment and con-figuring the patient support apparatus 20 according to a fall risk reduction protocol (e.g. in a manner that helps to reduce or minimize a patient's fall risk). The particular screen that is displayed by caregiver assistance application 124 in response to a user selecting the fall task icon 178 (or any of the other task icons of task menu 174) may be an initial screen that is part of a larger set of screens that are displayable by caregiver assistance application 124 in order to assist the caregiver with the selected task. In some embodiments, this initial screen is of the type shown in FIG. 19, although other screens may be initially shown.

If a caregiver selects skin task 182 (FIG. 9) at step 159 (FIG. 5), caregiver assistance application 124 proceeds to executes skin care algorithm 141, which causes it to display an initial skin care screen (not shown) that assists the caregiver in performing a bed sore risk assessment, docu-menting one or more existing skin states or conditions, and/or setting one or more reminders or configurations on the patient support apparatus 20 to assist in preventing the development and/or worsening of a patient's bed sores. As with fall task icon 178, the selection of skin task icon 182 causes caregiver assistance application 124 to display an initial screen associated with caring for a patient's skin that is part of a larger set of screens adapted to assist the caregiver in caring for the patient's skin. The additional screens within that larger set are accessible through the initial screen, or through one or more of the other screens that are accessible from the initial screen.

If a caregiver selects reminder task icon 184 step 159 (FIG. 5), caregiver assistance application 124 proceeds to execute task list modification algorithm 151 and display an initial screen showing existing reminders, such as a room overview screen 162 (FIG. 9) or a room listing screen 156 (FIG. 8). Algorithm 151 thereafter allows the caregiver to set, edit, and/or cancel reminders associated with caring for a particular patient or room. Such reminders include, but are not limited to, reminders to turn the patient, reminders to perform one or more therapies on the patient (e.g. a percus-sion therapy or maximum inflation therapy using mattress 38), reminders to perform caregiver rounds, and other reminders. Whatever the specific reminder, caregiver assistance application 124 is configured to display the reminder in summary area 172 of room overview screen 162, in the status indicator 160 of room listing screen 156, and/or on other screens of caregiver assistance application 124. The display may include not only an indication of the reminder, but also a time remaining until the reminder deadline is met (or, if the reminder deadline has passed, an amount of time that has passed since the reminder deadline expired). Still further, in some embodiments of caregiver assistance system 106, caregiver assistance application 124 is configured to send a notification to the caregiver when a reminder deadline is reached (or at one or more configurable times ahead of the reminder deadline and/or at one or more configurable times after the reminder deadline if the task remains uncompleted). The notifications include, in some embodiments, an email, a text, a phone call, or some other type of notification, as will be discussed more below.

During the performance of any of the tasks identified in task menu 174, caregiver assistance application 124 is configured to continue to display task menu 174 on the screens that are specifically associated with those tasks. If the user selects a task icon corresponding to a task different from the one currently being executed, caregiver assistance application 124 switches to performing the algorithm associated with that particular task. In the specific case of the rounding algorithm 140, if the caregiver selects rounding task icon 180 from one of the screens associated with task icons 178, 182, or 184, caregiver assistance application switches to step 192 of rounding algorithm 140 (FIG. 6), as will be discussed in more detail below.

If the caregiver does not select any of the tasks from task menu 174, main algorithm 226 (FIG. 5) of caregiver assistance application 124 proceeds to step 163 where it determines if a caregiver has input a command to control one or more aspects of the patient support apparatus 20. If the caregiver has input such a command, algorithm 226 proceeds to step 165 where it sends the command to the patient support apparatus 20. The routing of this command is through caregiver assistance server 90, in at least one embodiment. That is, the command to control one or more aspects of the patient support apparatus 20 is sent from the electronic device 104 to caregiver assistance application 124 (via one or wireless access points 76). After being received, caregiver assistance application 124 forwards the command either directly to the corresponding patient support apparatus 20 using wireless access points 76, or it forwards the command to patient support apparatus server 86, which then forwards the command to the patient support apparatus 20 using one or more wireless access points 76. When the command is received at the patient support apparatus 20, controller 48 checks to see if the command is an authorized command and, if so, implements the command.

After both steps 163 and 165 of main algorithm 226 (FIG. 5), caregiver assistance application 124 proceeds to step 167 where it checks to see if the caregiver has manually input a command to change the currently displayed room overview screen 162 back to the room listing screen 156 of FIG. 8. If the caregiver has, algorithm 226 returns back to step 154 and proceeds in the manner previously described. If the caregiver has not, algorithm returns back to step 173 where it either continues to display the room listing screen or it automatically changes the screen to the room overview screen.

It should be noted that the display of different screens within caregiver assistance application 124 is not only controlled by the area that a user presses/selects on a particular screen, but also by the caregiver's use of the conventional "back" and "forward" functions of the web browser that the caregiver is using to access caregiver assistance application 124. Thus, for example, if a user is viewing room overview screen 162 of FIG. 9 and wishes to return to viewing room listing screen 156 of FIG. 8, he or she can simply press, or otherwise activate, the "back" function of the web browser the caregiver is using. These and other navigation features (e.g. a "home" icon, a menu icon, etc.) are not shown in FIG. 5 but are included in at least some embodiments of caregiver assistance application 124.

It should also be noted that main algorithm 226 may be modified substantially from what is shown in FIG. 5 and what has been described above. Such modifications include the addition of one or more steps or screens not described with respect to FIG. 5, as well as the removal of one or more steps and/or a changing of sequence of one or more steps. In one specific embodiment, main algorithm 226 omits the automatic screen selection feature of step 173. In another embodiment, main algorithm 226 includes one or more icons on one or more of the displayed screens that allow a user to perform the sharing and unsharing functions described below with respect to FIGS. 64-67. Still other modifications are possible.

Figure 6:
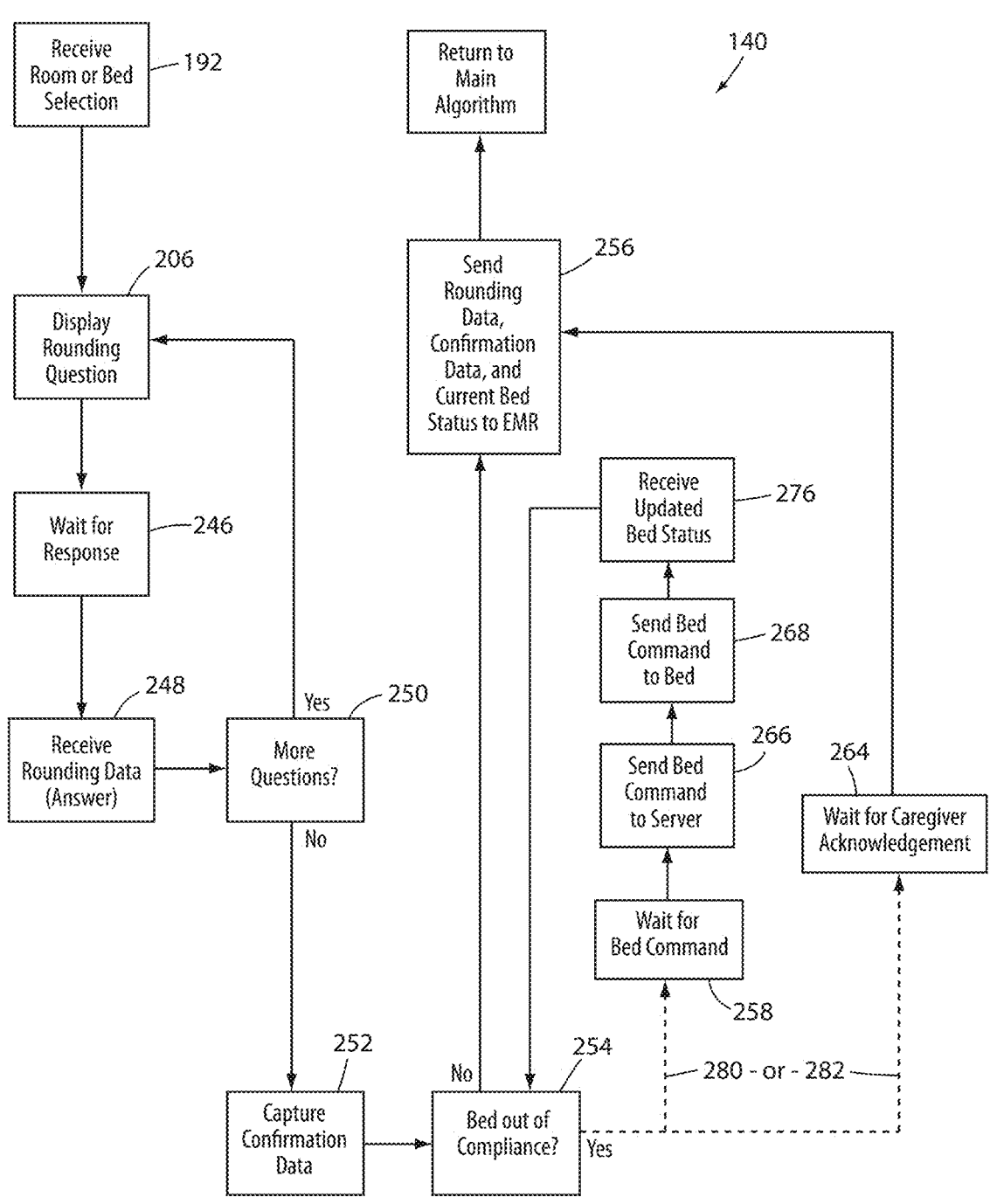
FIG. 6 is a flow diagram of a caregiver assistance algorithm that may be executed by the caregiver assistance application.

If a caregiver selects rounding task icon 180 (FIG. 9) at step 159 of main algorithm 226 (FIG. 5), caregiver assistance application 124 begins executing rounding algorithm 140 of FIG. 6. Rounding algorithm 140 begins at a step 192 where caregiver assistance application 124 receives and/or verifies a room selection or bed selection. In response to such a room selection or bed selection, caregiver assistance application 124 proceeds to displaying a first rounding screen 190, such as the first rounding screen 190 shown in FIG. 10. The caregiver's selection of a specific room or patient support apparatus is used by caregiver assistance application 124 in order for caregiver assistance application 124 to know what patient and/or room rounding information to display on screen 190 (and its subsequent rounding screens). If a caregiver navigates to screen 190 from a screen, such as screen 162 of FIG. 9, caregiver assistance application displays information on screen 190 that corresponds to the same bed and/or room as was selected in screen 162. Thus, because screen 162 was displaying information for room 7093 in FIG. 9, if a user navigates to screen 190 of FIG. 10 by pressing on the rounding task icon 180 of FIG. 9, caregiver assistance application will automatically display the rounding information on screen 190 that also corresponds to room 7093.

However, there may be situations where the first rounding screen 190 is called up by the caregiver without having previously selected a particular room and/or patient, or there may be situations where the caregiver wants to utilize first rounding screen 190 for a different room or patient than what was selected on a previously displayed screen. In those situations, first rounding screen 190 may be modified and/or supplemented by a screen, or input field, in which the caregiver can select a particular room and/or patient for carrying out the rounding tasks associated with first rounding screen 190. In some embodiments, the particular patient support apparatus 20 may be selected at step 192 by having the user manually enter the room number of the patient whose rounding information he or she is intending to collect. In other embodiments, patient support apparatus 20 may have a short range wireless transmitter (e.g. one or more near field transmitters and/or a Bluetooth transmitter) that communicates automatically with the mobile electronic device 104a and tells the device 104a which patient support apparatus 20 it is. In response, caregiver assistance application 124 automatically associates the first rounding screen 190 with the patient support apparatus 20 identified in the wireless communication it received from the patient support apparatus 20. In still other embodiments, caregiver assistance application 124 may be configured to automatically associate first rounding screen 190 with a particular room or patient based on the current location of the mobile electronic device 104a at the time the first rounding screen 190 was first accessed. Such current location information may be received from RTLS server 100.

Figures 10, 11:
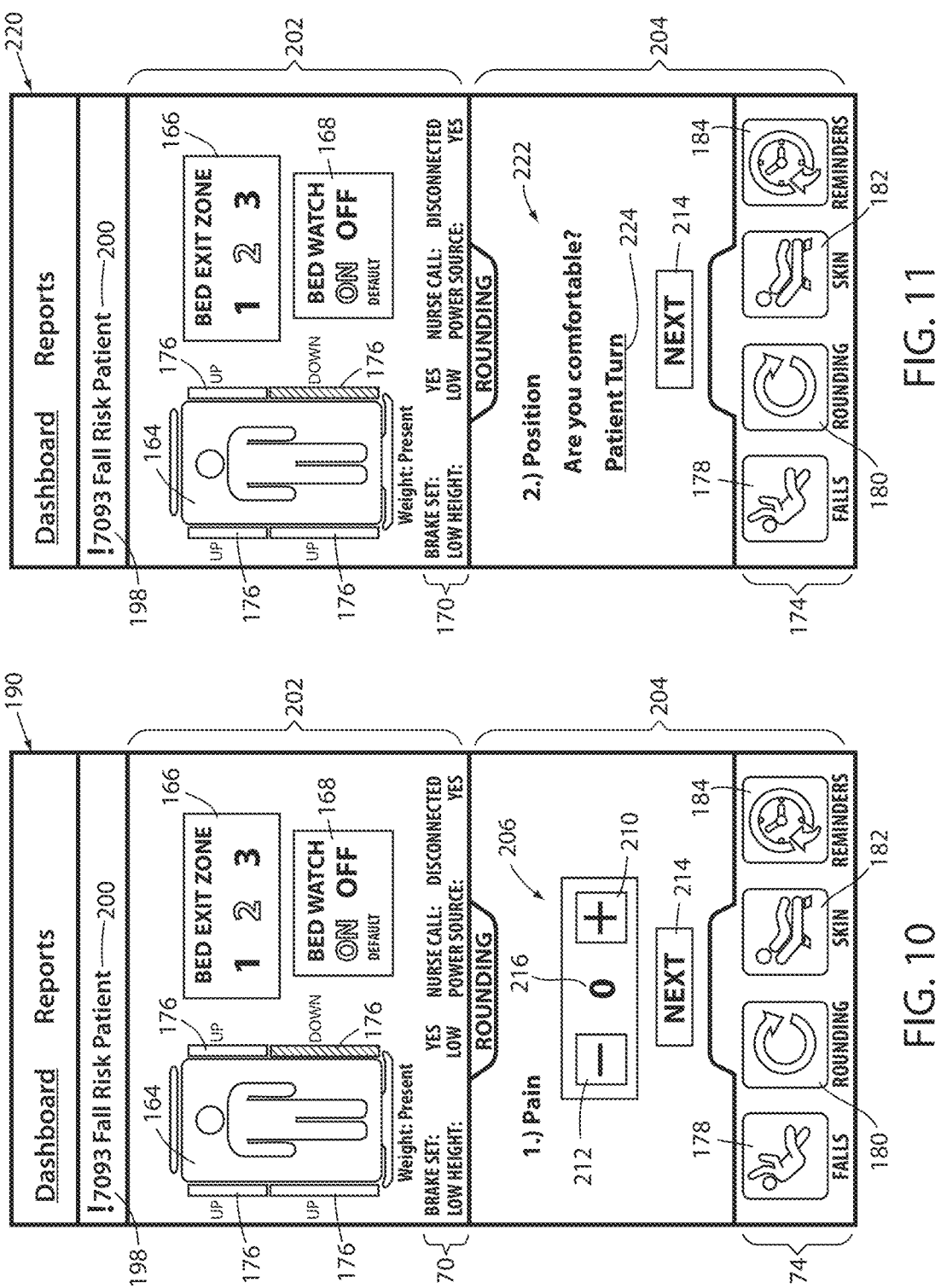
FIG. 10 is an illustrative first rounding question screen that is displayable on an electronic device of the caregiver assistance system.
FIG. 11 is an illustrative second rounding question screen that is displayable on an electronic device of the caregiver assistance system.

Regardless of the specific manner in which the room for first rounding screen 190 is selected, caregiver assistance application 124 displays the selected room in a room identifier location 198 (FIG. 10). Caregiver assistance application 124 may also display the same content of status indicator 160 (of room listing screen 156) in a status location 200 adjacent the room identifier location 198. First rounding screen 190 also includes a top portion 202 and a bottom portion 204. Top portion 202 includes the same information displayed in the top half of room overview screen 162 (FIG. 9). Specifically, it includes the bed icon 164, exit detection system status indicator 166, bed watch status indicator 168, and bed status bar 170. Bottom portion 204, however, does not include summary area 172 of room overview screen 162, but instead includes a first rounding question 206. The first rounding question identifies a question intended to be asked by the caregiver of the patient while the caregiver is performing his or her rounding duties. Caregiver assistance application 124 displays this first question 206 at step 208 of algorithm 140 (FIG. 6).

The specific first rounding question 206 displayed at step 208 of algorithm 140 (illustrated in FIG. 10) is a question regarding the patient's pain level. Specifically, it is a question of the patient's current pain level on a scale of zero through ten with zero being the lowest pain level and ten being the highest. It will be understood that, although first question 206 is described herein as being the "first" question shown after rounding task icon 180 is selected, the particular order of questions displayed by caregiver assistance application 124 may be varied, and the term "first" in the phrase "first rounding question" is merely used to distinguish the question from other rounding question, not to indicate any particular significance to its sequential order.

First rounding question screen 190 (FIG. 10) includes a plus sign icon 210, a minus sign icon 212, a next icon 214, and a current pain level indicator 216. The plus sign icon 210 and minus sign icon 212 are pressed by the caregiver to increase or decrease the patient's pain level, as indicated by the current pain level indicator 216, until the corresponding pain level shown by indicator 216 matches the pain level expressed by the patient. For example, if the user indicates their pain level is a six, the caregiver presses the plus sign icon 212 six times until the current pain level indicator reads a six. The caregiver then presses next icon 214 and caregiver assistance application 124 saves the pain level data and proceeds to display a second rounding question screen, such as second rounding question screen 220 shown in FIG. 11.

In other embodiments, first rounding question screen 190 (FIG. 10) is modified to allow the user to input the patient's current pain level in one or more alternative and/or additional manners. For example, in another embodiment, plus and minus signs 210 and 212 are replaced by a numeric keypad icon and the user simply presses on the numbers of the keypad to directly input the patient's pain level. In yet another embodiment, a slider bar icon is displayed on screen 190 and the user touches the slider bar while moving the sliding portion of the bar to a position corresponding to the number of the patient's pain level. Still other manners of allowing the user to input the patient's pain level are possible.

Second rounding question screen 220 includes all of the same elements of first rounding question screen 190 with the exception of the specific rounding question displayed in bottom portion 204. That is, second rounding question screen 220 displays the room identifier in the room identifier location 298, the status of the room in the room status location 200, and all of the same icons in top portion 202 that are found in the top portion 202 of first rounding screen 190. Bottom portion 204, however, differs from bottom portion 204 of screen 190 in that it is directed to a different rounding question. Specifically, bottom portion 204 of second rounding question screen 220 includes a rounding question 222 inquiring whether the patient is currently in a comfortable position or not. If the patient is not, the caregiver assists the patient to a more comfortable position and documents this movement or turning of the patient by pressing a "patient turn" icon 224 displayed on screen 220. In response to pressing the turn icon 224, caregiver assistance application 124 records the fact that the patient has been turned, along with the identity of the particular caregiver associated with the mobile electronic device 104a from which the turn indication was received. Caregiver assistance application 124 further time stamps this recording and, as will be discussed further below, includes it with other rounding information that is transmitted to the EMR server 98.

Figures 12, 13:
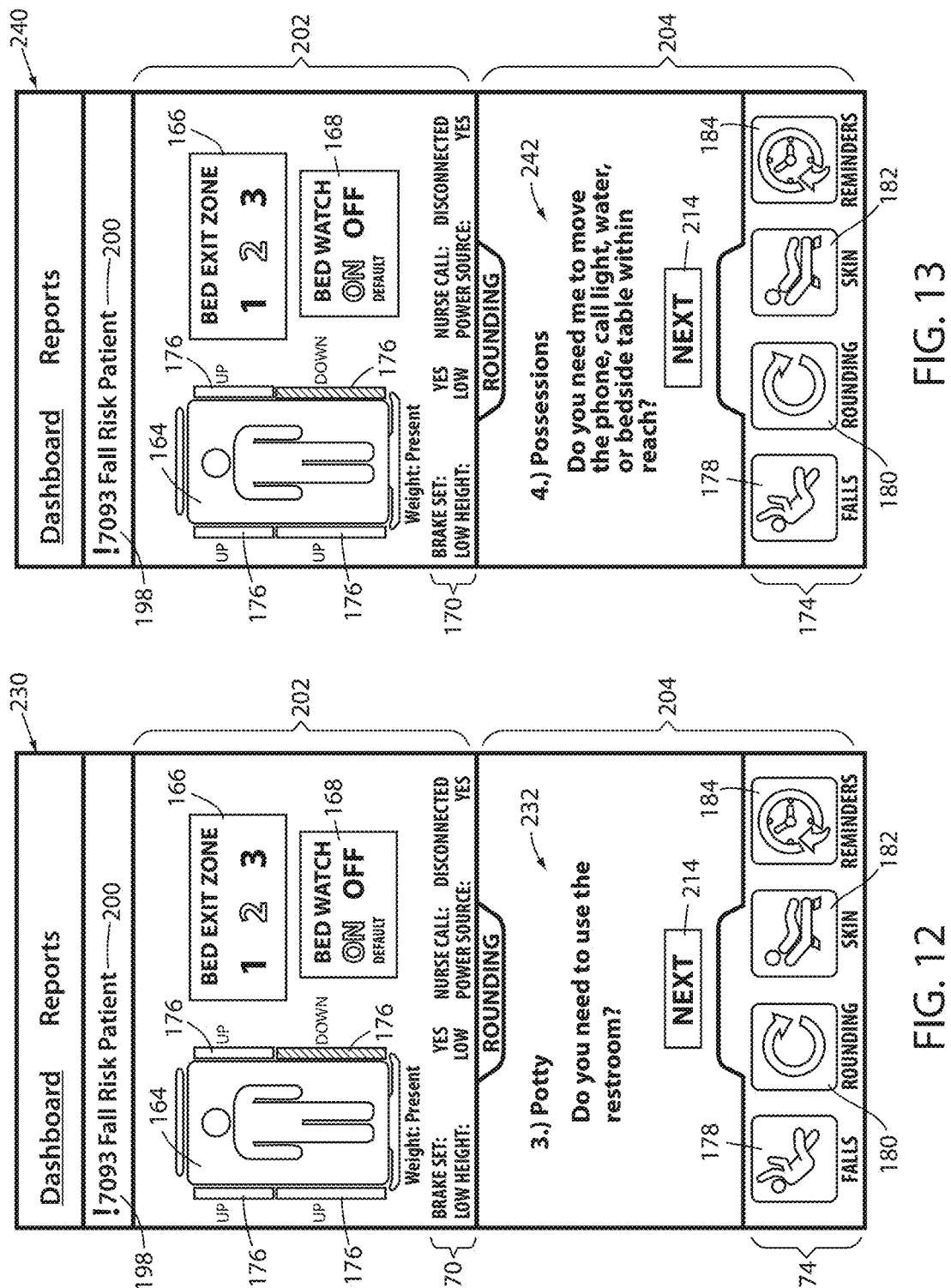
FIG. 12 is an illustrative third rounding question screen that is displayable on an electronic device of the caregiver assistance system.
FIG. 13 is an illustrative fourth rounding question screen that is displayable on an electronic device of the caregiver assistance system.

If the patient does not need to be turned or otherwise repositioned, the caregiver presses the next icon 214 on screen 220 (FIG. 11). The pressing of the next icon 214 on screen 220 causes caregiver assistance application 124 to display a third rounding question screen 230, an example of which is shown in FIG. 12. Third rounding question screen 230 includes a top portion 202 and a bottom portion 204. Top portion 202 include all of the same information as the top portions 202 of first and second rounding question screens 190 and 220. Bottom portion 204 differs from these screens in that it includes a third rounding question 232, which, in this case, is an inquiry into whether the patient needs to use the restroom or not. If the patient needs to use the restroom, the caregiver assists, or otherwise allows, the patient to use the restroom. In some embodiments, third rounding question screen 230 may include an input that, when pressed by the caregiver, sends a message to caregiver assistance application 124 indicating that the patient has used the restroom, and caregiver assistance application 124 saves this information for entry into that particular patient's electronic medical record. If the patient does not need to use the restroom, or has finished using the restroom, the caregiver presses the next icon 214.

In response to pressing the next icon 214 on third rounding question screen 230, caregiver assistance application 124 displays a fourth rounding question screen 240, one example of which is shown in FIG. 13. Fourth rounding question screen 240 includes a top portion 202 and a bottom portion 204. Top portion 202 include all of the same information as the top portions 202 of first, second, and third rounding question screens 190, 220, and 230. Bottom portion 204 differs from these screens in that it includes a fourth rounding question 242, which, in this case, is an inquiry into whether the patient needs any possession or not. If the patient needs a possession, the caregiver retrieves it for the patient, or otherwise moves it into a position within the room 92 that is accessible to the patient without requiring the patient to leave patient support apparatus 20. After ensuring that the patient has access to any of his or her possessions, the caregiver again presses the next icon 214.

It can be seen from FIG. 6 that the input of rounding information utilizing the rounding screens 190, 220, 230, and 240 corresponds to steps 246, 248, and 250 of algorithm 140. That is, at step 208 (FIG. 4), caregiver assistance application 124 displays a first rounding question. This step is accomplished by displaying first rounding question screen 190 and its associated first rounding question 206. After displaying this information, caregiver assistance application 124 waits for a response from the caregiver at step 248. After waiting for the response, algorithm 140 receives data from the caregiver at step 248. This data input corresponds to, for example, the caregiver entering the patient's pain level via screen 190, or repositioning the patient and documenting the repositioning step using patient turn icon 224 of screen 220. For some screens, such as screens 230 and 240, the data entry includes the pressing of the next icon 214, which indicates that the corresponding question was asked by the caregiver.

After receiving the caregiver assistance data at step 248 (FIG. 6), caregiver assistance application 124 moves onto step 250 where it determines whether or not there are more caregiver assistance questions to ask. Thus, after displaying first, second, and third rounding question screens 190, 220, and 230, respectively, caregiver assistance application 124 returns back to step 208 and displays the another rounding question screen. However, after displaying the fourth rounding question screen 240 (FIG. 13), caregiver assistance application 124 moves from step 250 to step 252 where it waits for verification data verifying the completion of the rounding task to be input by the caregiver, as will be discussed in greater detail below.

Before proceeding to describe step 252, it is worth noting that the particular number and content of the caregiver assistance questions displayed by caregiver assistance application 124 on electronic devices 104 may be varied from the four shown in FIGS. 10-13. Caregiver assistance application 124 includes an administrative portal that can be accessed by an authorized individual 136 to change the number of questions asked, the content of the questions, the order of the questions, and the content of the data that is to be input into the application 124 in response to receiving the patient's answers.

Figures 14, 15:
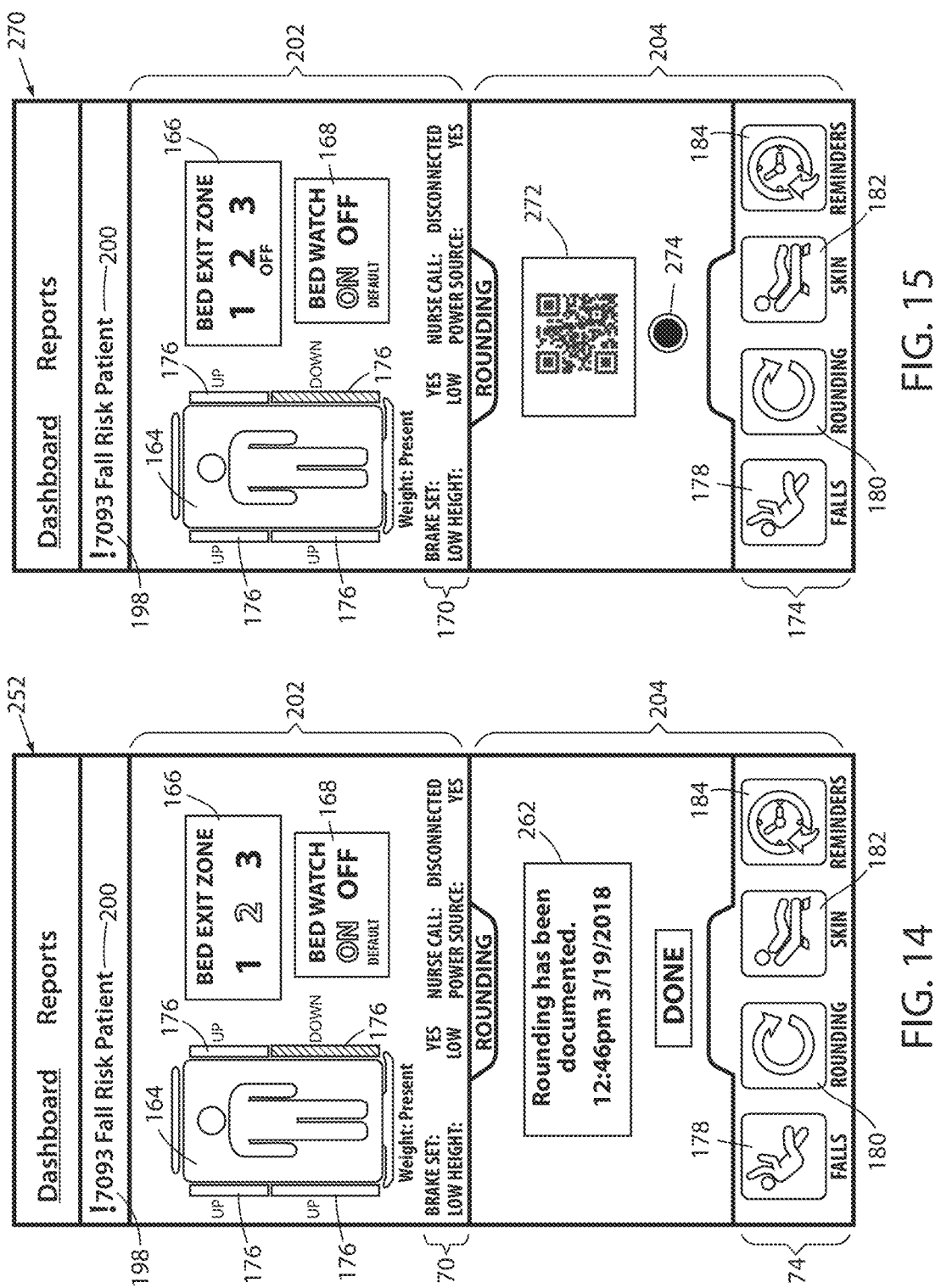
FIG. 14 is an illustrative rounding completion screen that is displayable on an electronic device of the caregiver assistance system.
FIG. 15 is an illustrative first rounding verification screen that is displayable on an electronic device of the caregiver assistance system.

At step 252 (FIG. 6) of rounding algorithm 140, caregiver assistance application 124 displays a rounding completion screen 260 (FIG. 14). The rounding completion screen 260 includes a rounding documentation window 262 that indicates the time (and date) at which the caregiver completed his or her rounding task associated with the particular room shown in room identifier location 198 (or more particularly, the patient in that room), as well as a verification that the information entered by the caregiver (e.g. pain level) has been sent to caregiver assistance server 90 and recorded by caregiver assistance application 124. In some embodiments, as will be discussed more below, caregiver assistance application 124 proceeds to automatically forward this rounding information to EMR server 98 for storage in the patient's electronic medical record. In the embodiments which follow algorithm 140, as shown in FIG. 6, caregiver assistance application 124 does not send this rounding data to EMR server 98 until it receives verification data verifying that the caregiver was actually present at the patient's bedside while he or she accessed and used rounding screens 190, 220, 230, and 240.

Figures 16, 17:
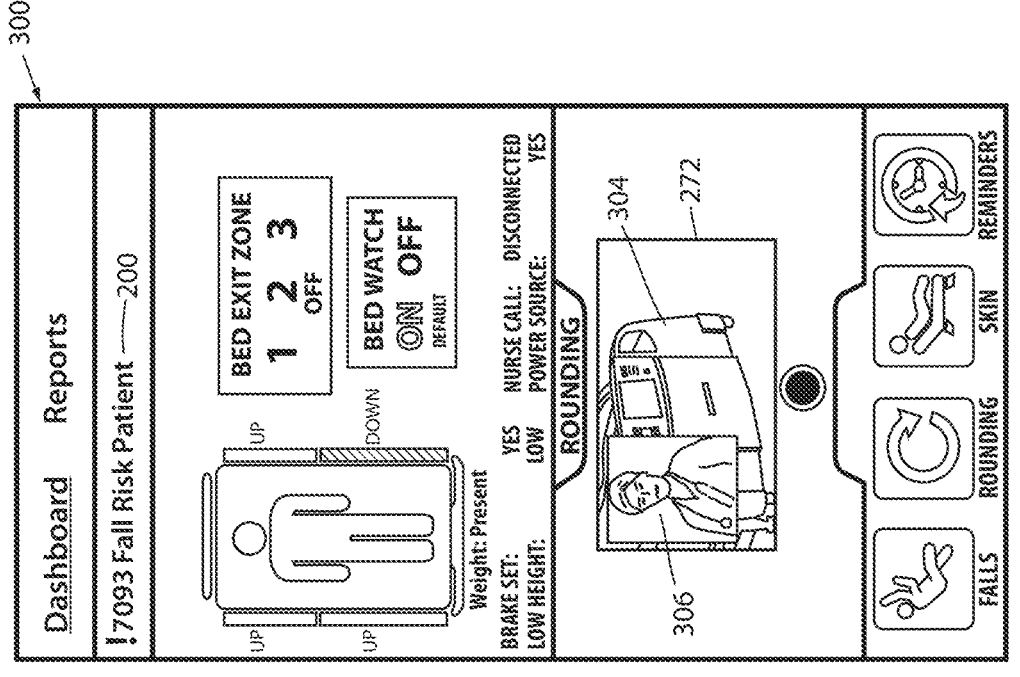
FIG. 16 is an illustrative second rounding verification screen that is displayable on an electronic device of the caregiver assistance system.
FIG. 17 is an illustrative third rounding verification screen that is displayable on an electronic device of the caregiver assistance system.

More specifically, in the embodiment of algorithm 140 shown in FIG. 6, caregiver assistance application 124 proceeds from step 250 (if there are no more rounding questions) to step 252 where it seeks to capture verification data. As noted, the verification data refers to data that is used to verify that the caregiver actually entered the room and performed his or her rounding duties in the patient's room. The particular verification data that is captured at step 252 may vary widely from embodiment to embodiment. FIGS. 15, 16, and 17 illustrate three different verification screens that may be utilized by caregiver assistance application 124 for gathering this verification data. Each of the three screens is intended to gather different verification data. In practice, caregiver assistance application 124 will typically utilize only a single one of the screens shown in FIGS. 15-17. The inclusion of multiple screens in FIGS. 15-17 is intended to show a variety of different types of verification data that may be gathered by caregiver assistance application 124. It will further be understood, of course, that still other types of verification data may be gathered by caregiver assistance application 124 besides the three examples shown in FIGS. 15-17.

Verification screen 270 (FIG. 15) includes a bottom portion 204 having an image window 272 and a capture icon 274. Image window 272 displays an image currently being sensed by the camera built into mobile electronic device 104a. Capture icon 274 is touched by the caregiver when the caregiver is ready to take a picture. The image window 272 in FIG. 15 specifically shows a Quick Response (QR) code because, in the embodiment illustrated therein, each patient support apparatus 20 is configured to display a QR code on its display 70 in response to the caregiver pressing a specific control, or series of controls. Controller 48 of the patient support apparatus 20 generates the QR code in a manner that embeds at least two pieces of information in the QR code: a unique identifier corresponding to that particular patient support apparatus 20 (e.g. identifier 186) and a current time (and day).

Caregiver assistance application 124 is adapted to analyze the QR code to determine the specific patient support apparatus 20 identified in the code and the time at which the photograph was captured by the mobile electronic device 104a. Caregiver assistance application 124 compares the specific patient support apparatus 20 identified in the QR code with the identity of the patient support apparatus 20 positioned in the room identified in the room identifier location 198 to ensure that they match. If they do not match, then the image that the caregiver captured using capture icon 274 is not an image of the patient support apparatus 20 associated with the patient to whom the caregiver just asked the rounding questions. In this case, caregiver assistance application 124 displays an error message and does not proceed to step 254 of algorithm 140 (FIG. 6). If the patient support apparatus 20 identifiers match, then caregiver assistance application 124 proceeds to step 254.

Caregiver assistance application 124 receives patient support apparatus identifiers 186 (FIG. 4) that uniquely identify each patient support apparatus 20 from patient support apparatus server 86. When each patient support apparatus 20 sends these identifiers 186 to patient support apparatus server 86, the patient support apparatus 20 also sends a locator identifier 138 (FIG. 4) that uniquely identifies the location beacon 84 within that room. This information is shared with caregiver assistance application 124. Caregiver assistance application 124 therefore receives not only the unique IDs corresponding to each patient support apparatus 20, but also the location of those patient support apparatuses 20. Alternatively, it receives the unique IDs of the patient support apparatuses 20 and bed location table 88. In either situation, caregiver assistance application 124 receives sufficient information to know the specific patient support apparatus ID of each patient support apparatus 20 and the specific room in which each patient support apparatus is located in. This is the information caregiver assistance application 124 uses to compare against the patient support apparatus identifier contained within the QR code.

For example, if a caregiver takes a picture of a QR code using verification screen 270 and capture icon 274, and the picture is taken in room 7093 (FIG. 15), caregiver assistance application 124 compares the patient support apparatus 20 ID contained within the QR code to the location record it maintains for that particular patient support apparatus 20. If that record also indicates that that particular patient support apparatus 20 is located in room 7093, then caregiver assistance application 124 accepts the QR code as verification that the caregiver was actually present in that room when he or she performed his or her rounding tasks. If the record does not match, caregiver assistance application 124 displays an error message and does not accept the picture of the QR codes as verification of the caregiver's physical presence during the rounding task.

Patient support apparatuses 20 suitable for use with the verification method utilized by verification screen 270 of FIG. 15 include a clock that keeps track of the current time, and a controller 48 configured to embed both the current time and the unique ID of the patient support apparatus 20 into the QR code. Some examples of patient support apparatuses 20 that include internal clocks and that may be utilized with algorithm 140 and the verification process of FIG. 13 are disclosed in commonly assigned U.S. patent application Ser. No. 15/642,621 filed Jul. 6, 2017, by inventors Anuj Sidhu et al. and entitled PATIENT SUPPORT APPARATUSES WITH CLOCKS, the complete disclosure of which is incorporated herein by reference. Other types of patient support apparatuses 20 can, of course, alternatively be used.

The patient support apparatuses 20 utilized with the verification process of FIG. 15 are configured to display the QR code somewhere on their display screen 70. The display of the QR code may be constant with repetitive updates to include the current time (e.g. every minute or so), or the display may be intermittent in response to the caregiver pressing, or otherwise activating, one or more controls on the patient support apparatus 20. With respect to the latter option, one of controls 72 may be specifically dedicated to causing patient support apparatus 20 to display the QR code, or the code may be displayed in response to the caregiver navigating to a specific screen on which the QR code is displayed. Still other manners of getting the patient support apparatus 20 to display the QR code may be utilized.

It will also be noted that there is no requirement that the patient support apparatus 20 specifically utilizes a QR code. That is, other codes may be utilized, such as, but not limited to, a bar code. Still further, in some embodiments, patient support apparatus 20 is configured to not encode the information at all. In such embodiments, patient support apparatus 20 displays, or can be manipulated by the caregiver to display (e.g. using controls 72), a screen on which both the current time and the unique identifier of the patient support apparatus 20 are shown. The caregiver captures an image of that display using the camera function of the mobile electronic device (e.g. smart phone, tablet, etc.) and forwards the image to caregiver assistance application 124. Caregiver assistance application 124 processes the image to extract the ID of the patient support apparatus and the time from the captured image. The extracted patient support apparatus ID is then matched against the record data for that particular room, as discussed above. If the captured patient support apparatus ID data matches the data contained in the records (data repository 128) of caregiver assistance application 124, caregiver assistance application 124 proceeds to step 254, which will now be described.

At step 254 of rounding algorithm 140 (FIG. 6), caregiver assistance application 124 determines whether or not patient support apparatus 20 is in a compliant or non-compliant state. The definition of a compliant state may be determined during the installation of caregiver assistance application 124 (or modified thereafter) in accordance with the particular requirements of the healthcare facility into caregiver assistance application 124 is being installed, or it may be pre-defined by the vendor of caregiver assistance application 124. Alternatively, or additionally, the compliant state may be defined based upon whether or not a fall risk reduction protocol is currently being implemented for the patient assigned to that particular patient support apparatus 20, as will be discussed in greater detail below with respect to FIGS. 18-27. In any of the embodiments, the definition of the compliant state may also or alternatively be modified and/or defined by an authorized individual 136 after installation of system 106. In many embodiments, the compliant state includes the same criteria that are monitored by the bed watch system discussed above. That is, in many instances, healthcare facilities will define a compliant state of a patient support apparatus as one in which all of the following are true: the brake is activated, the litter frame 28 is at its lowest height, the exit detection system 46 is armed, a monitoring feature is armed, at least three of the siderails 36 are up (and/or specific ones of the siderails are up), the A/C power cable 102 is plugged into a wall outlet, and the nurse call cable 78 is plugged into a nurse call outlet 82. Other definitions of a compliant state may, of course, be utilized.

Caregiver assistance application 124 checks to see if the patient support apparatus 20 is in the compliant state or not at step 254. Caregiver assistance application 124 performs this step by asking patient support apparatus server 86 for the current status data of the patient support apparatus 20 when the user reaches step 254. The current status data of each patient support apparatus 20 is maintained by patient support apparatus server 86 in table 88 (FIG. 4). As was noted, patient support apparatuses 20 send their status data to patient support apparatus server 86 whenever they sense a change in their state (or upon a specific request from patient support apparatus server 86). After caregiver assistance application 124 receives the current status data of the patient support apparatus 20 from patient support apparatus server 86, it checks to see if the current status data matches the compliant state criteria discussed above. If caregiver assistance application 124 determines that the patient support apparatus 20 is currently in a compliant state, it moves to step 256 of rounding algorithm 140 (FIG. 6). If caregiver assistance application 124 determines that the patient support apparatus 20 is not currently in a compliant state, it moves to following a first control path 280 (in one embodiment) or to following a second control path 282 (in another embodiment).

At step 256 (FIG. 6), caregiver assistance application 124 sends various data to the EMR server 98 to be documented in the electronic medical record of the patient for whom the caregiver just completed his or her rounding tasks. This transmission occurs without the caregiver having to perform any additional step beyond the ones previously described. The particular data that is sent to EMR server 98 includes the following: (a) the rounding data entered by the caregiver into the mobile electronic device 104*a* during the rounding task (e.g. pain level, whether the patient used the restroom, etc.); (b) the verification data captured during step 252 (or data indicating that the rounding tasks was verified); (c) whether or not the patient support apparatus 20 is in a compliant state or not (or alternatively, the current status of patient support apparatus 20 with respect to its brake, siderails, litter frame height, exit detection system, nurse call cable, and/or power cable); (d) a time and date stamp; and (e) data sufficient to identify the caregiver who is currently logged into the particular mobile electronic device 104*a* from which caregiver assistance application 124 receives the rounding data.

The time and date stamp may include both the time and date at which the data is received by caregiver assistance application 124 from the corresponding mobile electronic device 104*a*, and the time and data that is encoded in the verification data presented on the display 70 of the patient support apparatus 20 and captured by the caregiver in image window 272. Alternatively, or additionally, the time and data stamp may refer to the time at which this data is sent to EMR server 98 by caregiver assistance application 124. EMR server 98, upon receipt of this data, updates the patient's electronic medical record with the new data, and caregiver assistance application 124 returns back to step 154, thereby enabling the caregiver to complete another rounding task and/or another one of the tasks associated with task menu 174.

After completing step 256 (FIG. 6), caregiver assistance application 124 is configured, in at least some embodiments, to update any timer that is associated with the rounding task that was just completed. In other words, caregiver assistance application 124 may be configured to update the task list 886 to reflect that the caregiver just completed one of the rounding tasks on the list. As a result, reminder algorithm 145 resets the reminder timer for that particular rounding task according to the prescribed cadence for re-completing the rounding tasks. Thus, for example, if a caregiver is supposed to perform a rounding task every two hours, and the caregiver has just completed a round for room 1703, caregiver assistance application 124 automatically resets the timer for room 1703 to two hours after step 256 is completed. The corresponding time information displayed on the screens of mobile electronic devices 104*a* is therefore also automatically reset, thereby providing the caregivers with up-to-date indications of how much time is left until the next rounding task is to be performed. Reminder algorithm 145 of caregiver assistance application 124 maintains and updates timers for rounding tasks associated with each room and/or patient as well as timers for other tasks.

Returning to step 254 of algorithm 140 (FIG. 6), if the patient support apparatus 20 is determined by caregiver assistance application 124 to not be compliant at that step, it proceeds to either 1$^{st}$ control path 280 or second control path 282, depending upon the particular embodiment of caregiver assistance application 124. Turning first to the embodiment in which caregiver assistance application 124 proceeds to first control path 280, caregiver assistance application 124 implements the status/command algorithm 147. That is, caregiver assistance application 124 proceeds to step 258 and waits there to receive a command from the caregiver that will remotely change the patient support apparatus 20 to a compliant state. As noted previously, the status/command algorithm 147 allows caregiver assistance application 124 to receive patient support apparatus commands from a caregiver and relay those commands to the corresponding patient support apparatus 20. This enables the caregiver to remotely change the state of the patient support apparatus 20 to be in a compliant state.

For example, if caregiver assistance application 124 determines at step 254 that the patient support apparatus 20 is not in a compliant state because the exit detection system 46 is not currently armed, caregiver assistance application 124 will display an indication informing the caregiver that this is the cause of the non-compliant state. It will also display a control that enables the caregiver to use the mobile electronic device 104*a* to arm the exit detection system. In some embodiments, this control is simply a display of exit detection system status indicator 166 and tapping on this indicator 166 toggles between arming and disarming exit detection system 46. Other types of controls may also or alternatively be displayed. In response to the user tapping on the control to arm the exit detection system 46, the mobile electronic device 104*a* sends a message to caregiver assistance server 90 instructing caregiver assistance application 124 to send a command to the patient support apparatus 20 to arm its exit detection system 46. This message is sent at part of step 266 of algorithm 140.

In response to this message, caregiver assistance application 124 proceeds to step 268 (FIG. 6) where it either sends a command directly to the corresponding patient support apparatus 20 to arm its exit detection system 46, or it sends the command to patient support apparatus server 86, which in turn relays the command to the appropriate patient support apparatus 20. In either scenario, the command is received by the patient support apparatus 20 and controller 48 responds by arming the exit detection system.

The arming of the exit detection system 46 by controller 48 also prompts controller 48 to send a new status message to patient support apparatus server 86 that updates the current status of the patient support apparatus 20. This updated status includes the fact that the exit detection system 46 is now armed. Patient support apparatus server 86 forwards this updated status to caregiver assistance application 124, which receives it at step 276 (FIG. 6). Using this updated status data, caregiver assistance application 124 returns to step 254 where it again checks to see if the patient support apparatus 20 is in a compliant state or not. If it is, it proceeds to step 256 and takes the actions associated with step 256 that were previously described. If the patient support apparatus 20 is still out of compliance, caregiver assistance application 124 returns to first control path 280 and step 258 where it waits to receive another command from the caregiver for changing the state of the patient support apparatus 20.

In some embodiments, caregiver assistance application 124 is configured to only allow the caregiver to remotely change those states of the patient support apparatus 20 that do not involve any motion. That is, the caregiver is only allowed to use his or her mobile electronic device 104*a* at step 266 to send non-movement commands to the patient support apparatus 20. This is done in order to avoid the situation where movement occurs on patient support apparatus 20 when the caregiver may not be present in the room, and such movement may startle the patient and/or be impeded by an obstacle, such as, but not limited to, the patient himself or herself. Such unattended movement may therefore lead to injuries. Therefore, in some embodiments, caregiver assistance application 124 only forwards nonmoving commands, such as, but not limited to, commands to arm/disarm the exit detection system 46, arm/disarm the bed watch system, and turn on/off the brake.

In those embodiments of caregiver assistance application 124 where it follows second control path 282 (FIG. 6), caregiver assistance application proceeds to step 264 after it determines at step 254 that the patient support apparatus 20 in not in a compliant state. At step 264, caregiver assistance application 124 displays a screen (not shown) on the mobile electronic device 104*a* that includes an acknowledgement input. The acknowledgement input is an input that the caregiver must actively touch, or otherwise activate, and includes a message indicating that the patient support apparatus 20 is not in a compliant state. After the caregiver acknowledges that the patient support apparatus 20 is not in a compliant state at step 264, caregiver assistance application 124 proceeds to step 256 and takes the actions associated with step 256 that were previously described. In addition to those actions, caregiver assistance application 124 also sends to EMR server 98 data indicating that the non-compliant state of the patient support apparatus 20 was actively acknowledged (and a time and date of the acknowledgment, in some embodiments). Caregiver assistance application 124 may also send the identity of the caregiver who performed this acknowledgement to EMR server 98.

It can be seen from a comparison of first and second control paths 280 and 282 (FIG. 6) that caregiver assistance application 124 may be configured to either not allow a caregiver to upload rounding data to EMR server 98 if the patient support apparatus 20 is not in a compliant state (first path 280) or to allow the caregiver to upload the rounding data to EMR server 98 for a non-compliant patient support apparatus 20, provided the caregiver actively acknowledges (at step 264) that the patient support apparatus 20 is not in a compliant state (second path 282). Either control path 280 and 282 therefore encourages the caregiver to ensure that the patient support apparatus 20 is in a compliant state, thereby helping the healthcare facility to achieve higher rates of patient support apparatus compliancy.

It will be understood that caregiver assistance application 124 may be modified in still other embodiments to include alternative paths to control paths 280 and 282, and/or to include modifications to these control paths. For example, in at least one embodiment, caregiver assistance application 124 follows a third alternative path (not shown) in which the caregiver has access to an "update status" control on mobile electronic device 104*a*. The "update status" control, when activated by the caregiver, causes the mobile electronic device 104*a* to send a message to caregiver assistance application 124 instructing caregiver assistance application 124 to request an updated status of the patient support apparatus 20 from patient support apparatus server 86. The inclusion of the "update status" control allows a caregiver who is positioned next to the patient support apparatus 20 to directly utilize the controls 72 on patient support apparatus 20 to change the patient support apparatus 20 to a compliant state. Once in the compliant state, pressing the "update status" control causes the now-compliant state of the patient support apparatus 20 to be communicated to caregiver assistance application 124, which then moves to step 256 of rounding algorithm 140, thereby allowing the rounding data to be uploaded to EMR server 98.

One modification to this alternative third control path that may be implemented is to configure caregiver assistance application 124 to repetitively and/or automatically request updated statuses from the patient support apparatuses 20. In this modified embodiment, it is not necessary for a caregiver to press, or otherwise activate, an "update status" control. Instead, caregiver assistance application 124 automatically receives patient support apparatus status updates. Thus, in this embodiment, once the caregiver assistance application 124 receives a status update for the patient support apparatus

20 that indicates that the patient support apparatus 20 is in a compliant state, it automatically moves to step 256 without requiring the caregiver to manually manipulate any controls on the mobile electronic device 104*a*.

In still other embodiments, any of the features of control paths 280, 282, or the third alternative control path described above may be combined together. For example, in some embodiments, caregiver assistance application 124 may be configured to display three options to the caregiver after determining at step 254 that the patient support apparatus 20 is out of compliance: (a) a patient support apparatus command input, (b) an acknowledgement input; and (c) an "update status" input. The caregiver can then decide whether to use the mobile electronic device 104*a* to change the patient support apparatus state (option a); acknowledge the non-compliant state of the patient support apparatus 20 without correcting it (option b); or change the patient support apparatus 20 state using the controls 72 on the patient support apparatus 20 itself and request that the updated status be communicated to caregiver assistance application 124 (option c). Still other variations may be implemented.

Returning now to step 252 of caregiver rounding algorithm 140 (FIG. 6), caregiver assistance system 106 may be modified to capture verification data at step 252 in a variety of manners different from what was previously described above with respect to step 252 and FIG. 15. Two of these different manners are illustrated in FIGS. 16 and 17. After a caregiver has completed the caregiver assistance questions of FIGS. 10-13 and steps 208, 246, 248, and 250, caregiver assistance application may be configured in some embodiments to execute step 252 by having the caregiver take a photograph of the patient support apparatus 20 itself, rather than the QR code, or other code, on the display 70 of the patient support apparatus 20. An example of this type of verification is shown in FIG. 16, which shows a first alternative verification screen 290.

First alternative verification screen 290, like verification screen 270 of FIG. 15, includes a camera image window 272 that shows the image currently being detected by the camera built into mobile electronic device 104*a*. In order for a caregiver to properly verify that he or she has completed a rounding task associated with a particular patient, he or she aims the camera of the mobile electronic device 104*a* such that the camera is pointed at a designated portion of the patient support apparatus 20. In the example shown in FIG. 16, the designated portion includes the foot end of patient support apparatus 20. The designated portion may vary, depending upon the particular patient support apparatus 20, but should include whatever portion of the patient support apparatus 20 includes sufficient information to uniquely identify the patient support apparatus 20 and distinguish it from other patient support apparatuses 20 within the healthcare facility. This identification information may include a sticker with a serial number on it, an engraved serial number, a sticker or other structure coupled to the patient support apparatus 20, and/or any other kind of image information that identifies the particular patient support apparatus 20. Once that portion of the patient support apparatus 20 is within the field of view of the camera of mobile electronic device 104*a*, the caregiver presses the image capture icon 274 and the mobile electronic device 104*a* takes a picture of that portion of the patient support apparatus 20. The mobile electronic device 104*a* also sends the captured image to caregiver assistance application 124 where it is analyzed to verify that the patient support apparatus 20 in the image matches the patient support apparatus assigned to the patient for whom the caregiver just completed his or her rounding tasks, as discussed previously. If there is a match, caregiver assistance application 124 proceeds to step 256 where it uploads the rounding data and other data (including the capture image) to EMR server 98.

In alternative embodiment, caregiver assistance application 124 is configured to have the caregiver capture an image of the patient support apparatus 20 using the camera of mobile electronic device 104a, but the particular portion of patient support apparatus 20 that is captured is immaterial. In this modified embodiment, the caregiver turns on the location feature (GPS, WiFi triangulation, etc.) of the mobile electronic device 104a and has the mobile electronic device automatically append a geographic location to the photograph captured using image window 272. The mobile electronic device 104a forwards the image data (i.e. photograph) to caregiver assistance application 124, along with the location data and, in some cases, the time and date at which the photo was taken. Caregiver assistance application 124 uses knowledge of the geographic location of each room within the healthcare facility (stored in data repository 128, or elsewhere) to determine if the location at which the photograph was taken matches the room in which the corresponding patient is located. If so, it proceeds to step 256 of algorithm 140. If not, it displays an error message.

After a caregiver has completed the caregiver assistance questions of FIGS. 10-13 and steps 208, 246, 248, and 250, caregiver assistance application 124 is configured in some embodiments to display second alternative verification screen 300 of FIG. 17, rather than first alternative verification screen 290 of FIG. 16 (or verification screen 270 of FIG. 15). In such embodiments, the caregiver is instructed to not only capture an image (take a picture) using the camera function of the mobile electronic device 104a, but to also use the selfie feature built into the camera of mobile electronic device 104a that enables the mobile electronic device to simultaneously capture both a forward looking photograph and a rearward looking photograph of the caregiver himself or herself. In other words, caregiver assistance application 124 instructs the caregiver to take a picture using both the forward facing camera of the mobile electronic device 104a and the rearward facing camera of the mobile electronic device 104a. The rearward facing camera is intended to capture an image of the caregiver while the forward facing camera is intended to capture an image of all or a portion of the patient support apparatus 20. An example of this is shown in FIG. 17, which includes a forward-facing image 304 and a rearward facing image 306. The forward facing image 304 captures a portion of the patient support apparatus and the rearward facing image 306 captures an image of the caregiver.

The purpose of the rearward facing camera image of the caregiver is to document the actual presence of the caregiver at the bedside of the patient when he or she has completed the rounding tasks associated with that patient. As with the other verification processes, caregiver assistance application 124 processes the image data from both the forward and rearward facing cameras to identify the patient support apparatus 20 within the forward facing image 304. This image may be of an identifier of the patient support apparatus 20, of a QR or other code, or of any portion of the patient support apparatus 20. Caregiver assistance application 124, in at least one embodiment, also processes the rearward image 306 using conventional facial recognition technology to determine the identity of the caregiver captured therein. In other embodiments, caregiver assistance application 124 does not process the caregiver image data, but instead forwards it to EMR server 98 at step 256 unanalyzed.

In another embodiment, mobile electronic device 104a includes native software onboard that perform facial recognition. In this embodiment, the controller of mobile electronic device 104a is configured to compare an image (taken, for example, by using the digital camera function of the mobile electronic device) of the caregiver with a baseline image taken previously of the caregiver and to determine if there is a match. In other words, in this embodiment, mobile electronic device 104a is programmed to perform facial recognition of the selfie photograph captured by mobile electronic device 104a and, if the selfie is determined to match the authorized caregiver, to forward the captured data to the caregiver assistance application 124. The data forwarded to caregiver assistance application 124 in this embodiment, however, may omit the actual image data of the caregiver, thereby reducing consumed bandwidth, as well as repeated storage of a caregiver's face. Instead of the image data, the mobile electronic device 124 is programmed to send a message confirming that the selfie image captured by the mobile electronic device 104a is of an authorized caregiver (and in some embodiments, the identity of that authorized caregiver). Caregiver assistance application 124 can be configured in this embodiment (as well as other embodiments) to omit any facial recognition software.

It will be appreciated by those skilled in the art that other manners of verifying the caregiver's presence at the patient's bedside during the rounding task may be utilized by caregiver assistance application 124, including verification techniques that do not utilize a camera. For example, in some embodiments, patient support apparatuses 20 include a near field transceiver and/or a short range RF transceiver (e.g. Bluetooth, or infrared) that is detectable by mobile electronic device 104a. By bring the mobile electronic device 104a into sufficiently close proximity to the transceiver, the mobile electronic device 104a is able to wirelessly receive a signal from the patient support apparatus 20 that identifies that particular patient support apparatus 20 and, in some embodiments, also indicates a time. Caregiver assistance application 124 uses the reception of that signal as verification of the caregiver's physical presence at the patient's bedside during the rounding task. The detected signal and/or the fact that the detected signal was received may be forwarded to the EMR server 98 at step 256 (FIG. 6).

It will also be appreciated by those skilled in the art that various other modifications may be made to rounding algorithm 140. These include, but are not limited to, skipping the compliance step 254 completely (along with control paths 280 and/or 282); skipping the capture verification data step 252 and instead proceeding directly from step 250 to step 254; changing the order of one or more steps (e.g. step 192 is moved ahead of step 188 or 154); and/or combinations of one or more of these modifications.

Figure 18:
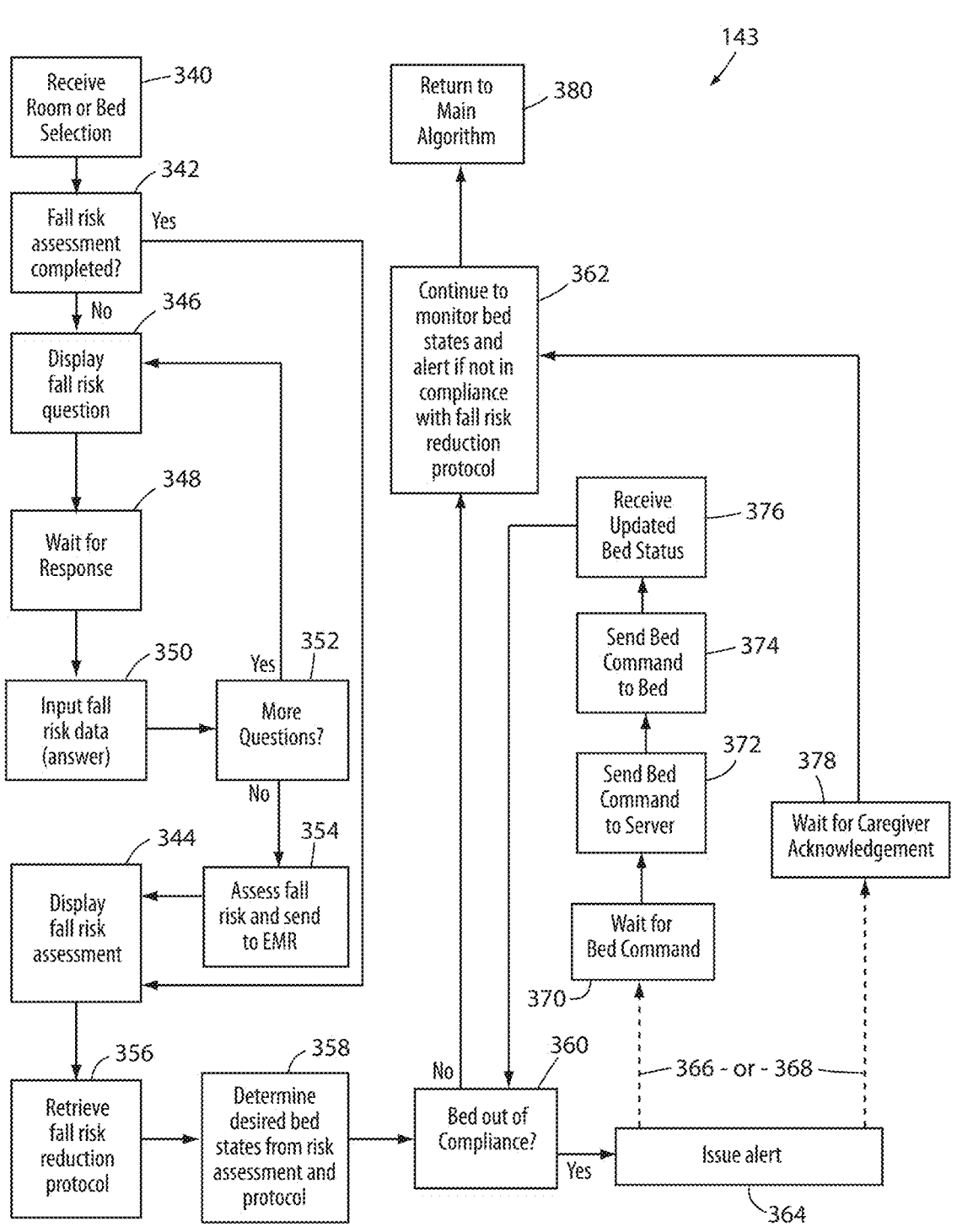
FIG. 18 is a flow diagram of a fall risk reduction algorithm that may be executed by the caregiver assistance application.

Turning now to the patient fall risk reduction algorithm 143 of caregiver assistance system 106, if a caregiver selects fall task icon 178 (FIGS. 9-17) at step 159 of main algorithm 226 (FIG. 5), caregiver assistance application 124 begins executing fall risk reduction algorithm 143. One example of fall risk reduction algorithm 143 is shown in FIG. 18. Fall risk reduction algorithm 143 begins at a step 340 where caregiver assistance application 124 receives or verifies a room selection or a bed selection. In response to such a room selection or a bed selection, caregiver assistance application 124 proceeds to step 342 where it determines if the particular patient assigned to the selected room and/or selected bed has had a fall risk assessment performed or not. Step 342 may be accomplished in several manners. In one particular embodiment, caregiver assistance application sends a request to EMR server 98 requesting the fall risk assessment for the patient assigned to the room or bed identified at step 340. If the EMR server 98 responds that there is no such fall risk assessment currently on file for the patient, fall risk reduction algorithm 143 checks to see if the fall risk assessment is stored elsewhere, such as, but not limited to, data storage 128. If there is no such fall risk assessment stored there, caregiver assistance application 124 may be configured by administrators of the healthcare facility to search in other locations. If no locations contain the fall risk assessment for the particular patient, caregiver assistance application 124 proceeds to step 346. If a fall risk assessment is located for the particular patient, caregiver assistance application 124 proceeds to step 344.

Figure 19:
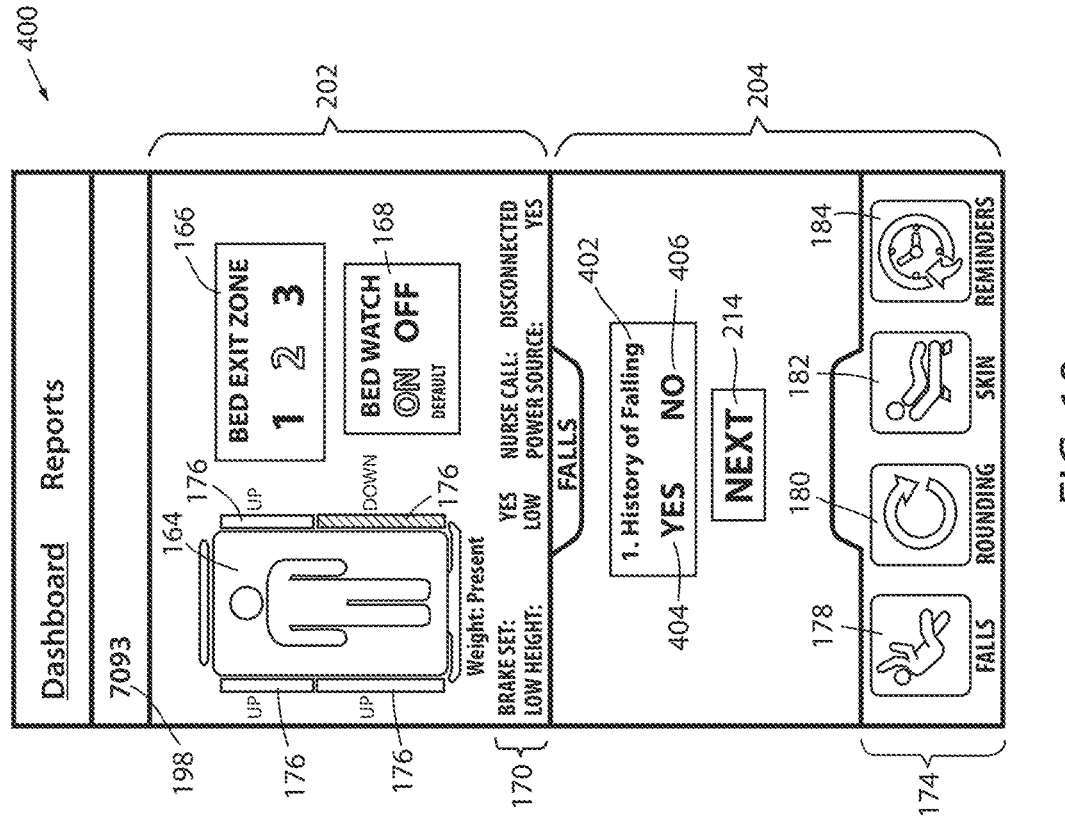
FIG. 19 is an illustrative first fall risk assessment question screen that is displayable on an electronic device of the caregiver assistance system.

When no fall risk assessment has been performed for the patient, caregiver assistance application 124 proceeds from step 342 to step 346. At step 346, caregiver assistance application 124 displays a first fall risk assessment screen 400 that is used to perform a fall risk assessment for the patient assigned to the room or bed identified in step 340. One example of such an initial fall risk assessment screen 400 is shown in FIG. 19. FIG. 19 is the first of six fall risk assessment question screens (FIGS. 19-24) used in one embodiment of caregiver assistance application 124. These six screens are designed to implement the Morse fall risk assessment, which is also sometimes referred to as the Morse fall scale. The Morse fall risk assessment is a numerically scored fall risk assessment that ranks patients into various qualitative categories (e.g. no fall risk, low fall risk, and high fall risk). It will be understood that caregiver assistance application 124 can be configured to implement other fall risk assessments besides the Morse fall risk assessment (e.g. the Hendrich fall risk assessment, the Johns Hopkins fall risk assessment, etc.), and/or it may be supplemented and/or partially modified with other questions. Still other variations may be made to the fall risk assessment by authorized personnel 136 of the healthcare facility, such as by using computer 134 to access and re-configure the settings of caregiver assistance application 124.

Screen 400 includes many of the same elements found in other screens discussed herein, such as, but not limited to, room identifier location 198, top portion 202, bottom portion 204, task menu 174, bed status bar 170, exit detection system status indicator 166, bed watch system status indicator 168, and bed icon 164. Bottom portion 204 differs from the previously described bottom portions in that it includes a first fall risk assessment question 402. The first fall risk question identifies a question intended to be asked by the caregiver of the patient while the caregiver is determining what level of fall risk the patient possesses. Caregiver assistance application 124 displays this first question 402 at step 346 of algorithm 143 (FIG. 18).

The specific first fall risk question 402 displayed at step 346 of algorithm 143 is a question regarding the patient's fall history. Specifically, it is a question of whether or not the patient has ever fallen recently (such as within the last three months, although other time periods can be used). If the patient answers yes, the user touches the "yes" icon 404. If the patient answers no, the user touches the "no" icon. Further, caregiver assistance application 124 assigns a point total to each answer. If the patient answers "yes," application 124 assigns the patient a point value of 25. If the patient answers no, application 124 assigns the patient a point value of zero. Caregiver assistance application 124 sums these point values as the caregiver proceeds through all of the fall risk assessment screens associated with the Morse fall assessment (e.g. FIGS. 19-24). The total score after completing all of the questions is used by caregiver assistance application 124 to determine the patient's qualitative fall risk, as discussed further below.

It will be understood that, although first question 402 is described herein as being the "first" question shown after fall task icon 178 is selected, the particular order of questions displayed by caregiver assistance application 124 may be varied, and the term "first" in the phrase "first fall risk assessment question" is merely used to distinguish the question from other fall risk assessment questions, not to indicate any particular significance to its sequential order.

Returning to fall risk reduction algorithm 143 of FIG. 18, after displaying the first fall risk assessment screen 400 at step 346, caregiver assistance application 124 proceeds to step 348 where it waits for the caregiver to provide an answer to the first fall risk question (e.g. question 402). When the user answers with either a "yes" or a "no" answer, the touching of either the "yes" icon 404 or the "no" icon 406 corresponds to step 350 of algorithm 143. That is, touching either of these icons 404 or 406 inputs the fall risk answer into the electronic device 104, which forwards the data to caregiver assistance application 124. After completing step 350 of algorithm 143, caregiver assistance application 124 proceeds to step 352 where it determines if there are any more fall risk assessment questions that need to be completed as part of the fall risk assessment. Because the example described herein uses the Morse fall risk assessment, which comprises six questions, caregiver assistance application 124 returns at step 352 back to step 346 and displays the next fall risk question (and repeats this another four times).

Figures 20, 21:
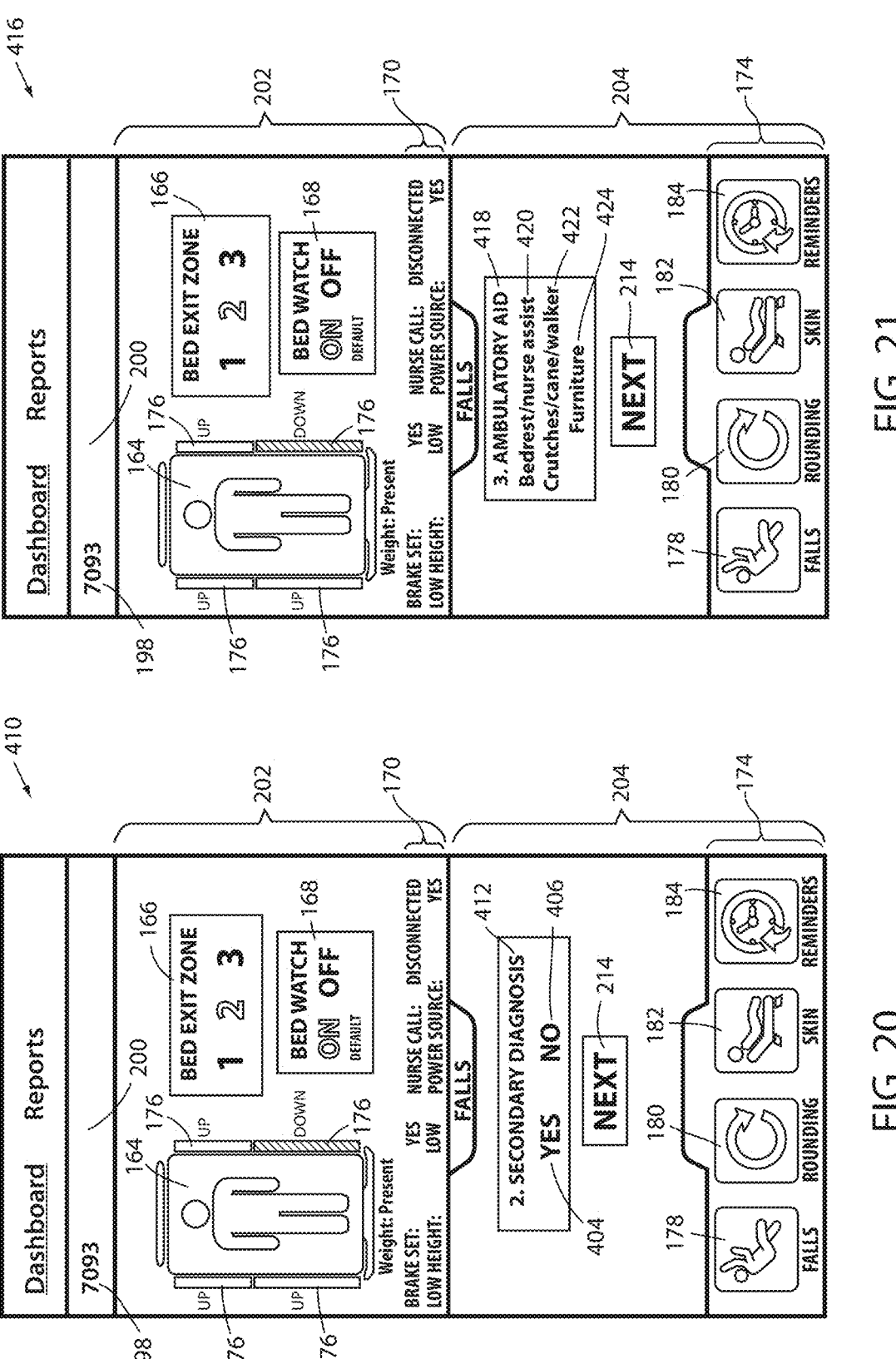
FIG. 20 is an illustrative second fall risk assessment question screen that is displayable on an electronic device of the caregiver assistance system.
FIG. 21 is an illustrative third fall risk assessment question screen that is displayable on an electronic device of the caregiver assistance system.

FIG. 20 illustrates a second fall risk assessment question screen 410. Second fall risk assessment question screen 410 includes a second fall risk assessment question 412 that is answered by the caregiver. Second fall risk assessment question 412 asks if the patient has received more than one medical diagnosis. This may be determined by the caregiver by reviewing the patient's chart or other medical record. If the patient has been assigned two or more medical diagnoses, the caregiver presses the "yes" icon 404. If the patient has only been assigned a single medical diagnosis, the caregiver presses the "no" icon 406. Caregiver assistance application assigns a point value of fifteen to the yes answer and zero to the no answer. After answering the second fall risk assessment question 412, the caregiver presses the "next" icon 214, which brings up third fall risk assessment screen 416 (FIG. 21). The inputting of an answer to second fall risk assessment question 412 corresponds to step 350 of algorithm 143; the pressing of the next icon 214 corresponds to choosing the "yes" option at step 352 of algorithm 143, and the display of third fall risk assessment screen 416 after pressing the next icon 214 corresponds to step 346 of algorithm 143.

Figures 22, 23:
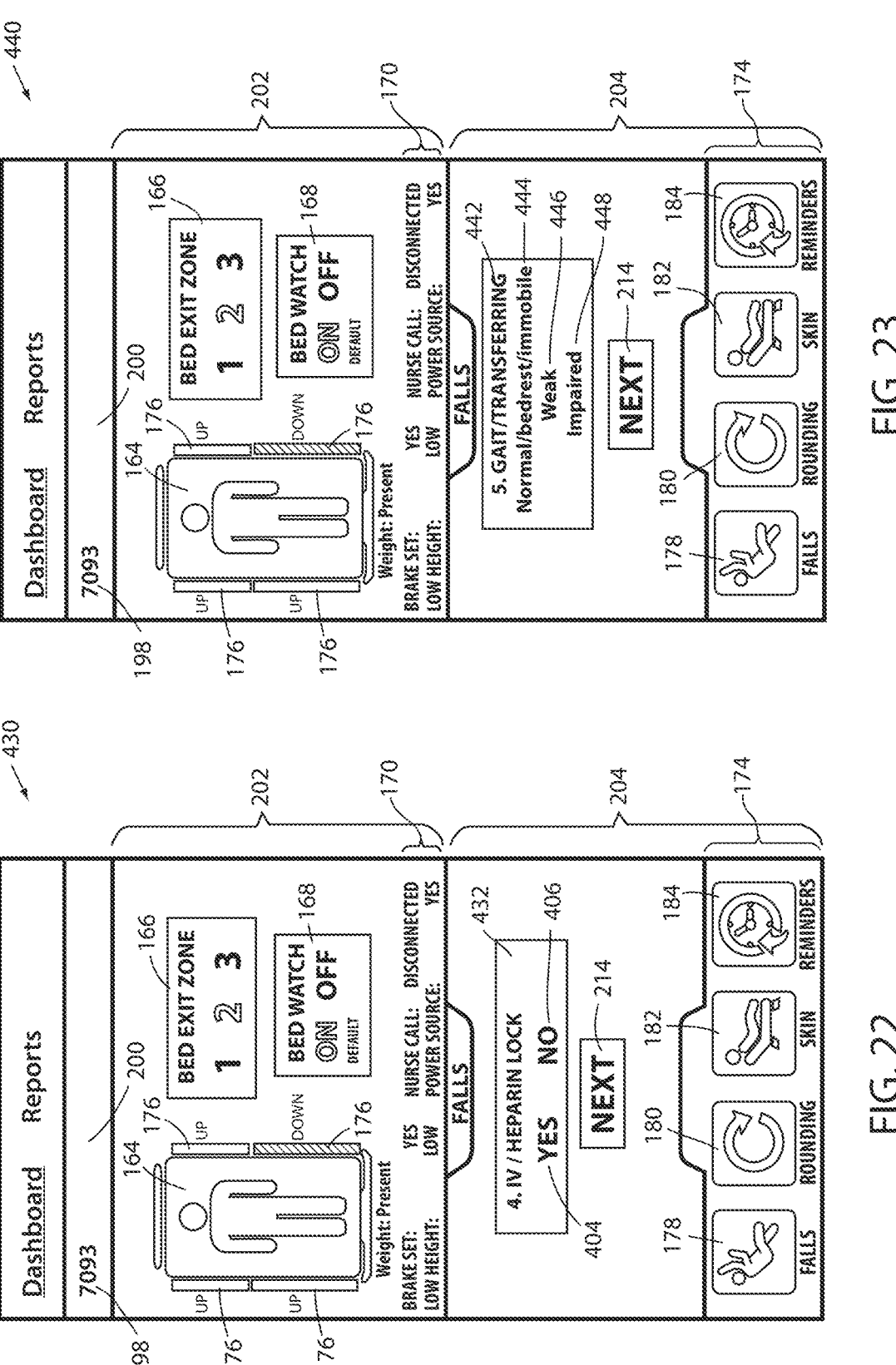
FIG. 22 is an illustrative fourth fall risk assessment question screen that is displayable on an electronic device of the caregiver assistance system.
FIG. 23 is an illustrative fifth fall risk assessment question screen that is displayable on an electronic device of the caregiver assistance system.

Third fall risk assessment question 418 (FIG. 21) comprises three separate sub-questions that are part of the Morse fall risk assessment. In the first sub-question, the caregiver determines if the patient has been assigned to bed rest, or if the patient is able to walk (even with nurse assistance). If either of these conditions is true, the caregiver presses a top icon 420 shown in FIG. 21 that is labeled "bedrest/nurse assist." In response to pressing top icon 420, caregiver assistance application 124 adds a zero value to the patient's fall risk score (which is the sum of the scores previously assigned to the answers to first and second fall risk questions 402 and 412). If neither of these conditions are true, the caregiver determines if the patient needs crutches, a cane, or a walker in order to walk. If the patient needs any of these devices, the caregiver presses a middle icon 422 on screen 416. Middle icon 422 is labeled "crutches/cane/walker" in FIG. 21. In response to pressing middle icon 422, caregiver assistance application 124 add a value of fifteen to the patient's fall risk score. If the patient does not need a crutch, cane, or walker to walk, the caregiver determines if the patient holds onto furniture, or other stable items, when he or she walks. If the patient does this, the caregiver presses a bottom icon 424 on screen 416, which is labeled "furniture" in FIG. 21. In response to pressing bottom icon 424, caregiver assistance application 124 adds a value of thirty to the patient's fall risk score. After choosing one of top, middle, or bottom icons 420, 422, or 424, the caregiver presses the next icon 214, which causes caregiver assistance application 124 to display a fourth fall risk assessment question screen 430, an example of which is shown in FIG. 22.

Fourth fall risk assessment question screen 430 includes a fourth fall risk question 432 displayed in bottom portion 204. Fourth fall risk question 432 asks if the patient has an intravenous (IV) apparatus or heparin lock inserted. If the patient does, the caregiver presses the "yes" icon 404. If the patient does not, the caregiver presses the "no" icon 406. Caregiver assistance application 124 adds a value of twenty to the patient's fall risk score if the caregiver answers "yes" (and adds a value of zero if the caregiver answers no). When the caregiver presses the next icon 214 on screen 430, caregiver assistance application 124 displays a fifth fall risk assessment question screen 440, one example of which is shown in FIG. 23.

Figures 24, 25:
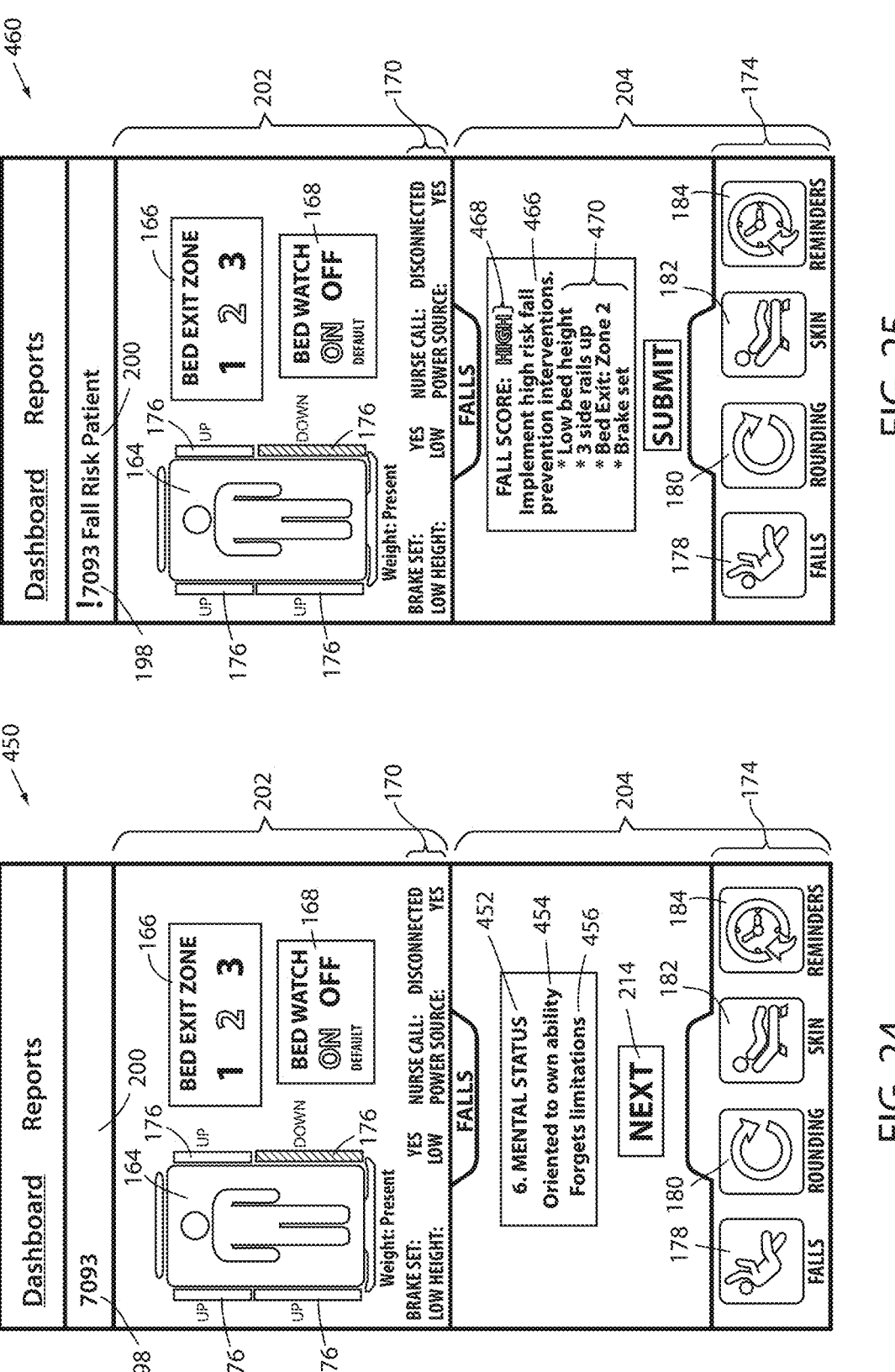
FIG. 24 is an illustrative sixth fall risk assessment question screen that is displayable on an electronic device of the caregiver assistance system.
FIG. 25 is an illustrative fall risk assessment information screen that is displayable on an electronic device of the caregiver assistance system.

Fifth fall risk assessment question screen 440 includes a fifth fall risk question 442 displayed in bottom portion 204. Fifth fall risk question 442 asks the caregiver to assess the patient's gait while he or she walks. More specifically, fifth fall risk question 442 asks the caregiver to qualify the patient's walking gait as one of "normal," "weak", or "impaired." The caregiver characterizes the patient's gait as normal if the patient walks with his or her head erect, his or her arms swinging freely, and takes strides without hesitation. The caregiver characterizes the patient's gait as "weak" if the patient is stooped while walking but is able to lift his or her head while walking without losing his or her balance. The caregiver characterizes the patient's gait as "impaired" if the patient has difficulty rising from a chair, the patient's head is down, and/or he or she watches the ground while walking. An "impaired" assessment may also be assigned if the patient's balance is poor, the patient grasps onto furniture, another person, or some sort of walking aid. Once the caregiver has determined the proper characterization, the caregiver presses the corresponding top icon 444, middle icon 446, or bottom icon 448. Caregiver assistance application 124 adds a value of zero to the patient's fall risk score if the caregiver selects "normal" (top icon 444), adds a value of ten if the caregiver selects "weak" (middle icon 446), and adds a value of twenty if the caregiver selects "impaired" (bottom icon 448). When the caregiver thereafter presses next icon 214, caregiver assistance application displays a sixth fall risk assessment question screen 450, one example of which is shown in FIG. 24.

Sixth fall risk assessment question screen 450 includes a sixth fall risk question 452. Sixth fall risk question 452 asks the patient to assess his or her own abilities at walking (e.g. "do you need assistance walking to the restroom?"). If the patient's answer does not match what the caregiver has observed and determined from the previous questions, the caregiver selects the bottom icon 456 (labeled "forgets limitations" in FIG. 24). If the patient's answer is consistent with what the caregiver has observed and determined from the previous questions, the caregiver selects the top icon 454 (labeled "oriented to own ability"). Caregiver assistance application 124 adds a value of zero to the patient's fall risk score if he or she selects the top icon 454, and adds a value of fifteen if he or she selects bottom icon 456.

After the answer to sixth fall risk assessment question 452 has been provided to caregiver assistance application 124 by the caregiver, caregiver assistance application 124 proceeds to step 354 of algorithm 143 where it analyzes the results of the six questions to determine what level of fall risk the patient possesses. Application 124 does this by summing up all of the values from the six questions of screens 400, 410, 416, 430, 440, and 450, the result of which is the patient's numeric fall risk score. Although different methods of scoring may be used (and/or customized by a particular healthcare facility), in some embodiments caregiver assistance application 124 converts this numeric fall risk score into a qualitative rating, such as zero risk, low risk, moderate risk, and high risk. In one such embodiment, caregiver assistance application assigns a zero risk rating when the numeric fall risk score is zero, assigns a low risk rating if the numeric fall risk score is greater than zero but less than 25; assigns a moderate risk rating if numeric fall risk score is greater than 25 but less than 45; and assigns a high risk rating if the numeric fall risk score is greater than 45. In an alternative embodiment, caregiver assistance application 124 assigns a no risk rating for numeric scores between zero and 25, a low risk rating for numeric scores between 25 and 50, and a high risk for numeric scores greater than 50. Still other qualitative ratings may be used and/or other score ranges may be selected for matching quantitative scores with qualitative scores. Further, the point values assigned to each individual question may also be varied from that described above.

After determining the patient's qualitative fall risk rating, caregiver assistance application sends either or both of the qualitative and quantitative fall risk ratings to the EMR server 98. The fall risk rating is sent by caregiver assistance application 124 along with one or more identifiers that identify which particular patient the just-completed fall risk rating corresponds to. The particular patient to whom the fall risk rating is assigned may be determined in any of the manners previously described, such as by correlating the room number of the patient with the patient's ID, correlating the patient support apparatus's identifier 186 with the room and/or the patient's ID, and/or by performing still other correlations. In this regard, it is to be noted that caregiver assistance application 124 displays the room number (and specific bed bay identifier if the room is a shared room) of the patient to whom the fall risk rating applies during the display of the screens shown in FIGS. 19-24. In the particular example shown, the room number is "7093," and all of the answers to the fall risk questions shown in these screens are assigned to the patient who has been assigned to room 7093. The caregiver therefore is provided with a reminder during the fall risk assessment process of the room number (and thus ultimately the specific patient) to which (or whom) the fall risk assessment is applicable. In some embodiments, caregiver assistance application 124 may be configured to retrieve the actual patient's name from ADT server 98 and display it during the fall risk assessment process so that the caregiver is informed of the specific patient whose fall risk they are assessing. Whether displaying the specific patient name or the specific room number, the caregiver ensures that the fall risk assessment is attributed to the correct individual by assuring that the room number, or patient's name, displayed on the screens 400, 410, 416, 430, 440, and 450 corresponds to the patient (or the patient's room) the caregiver is evaluating for fall risk.

After sending the fall risk assessment and the corresponding patient's name to EMR server 98 at step 354, caregiver assistance application 124 displays the qualitative risk rating at step 344 (FIG. 18). One example of the manner in which the qualitative fall risk rating may be displayed is shown in fall risk screen 460 of FIG. 25. Fall risk screen 460 includes a fall risk warning added to the status location 200. Fall risk screen 460 also includes a summary window 466 displaying multiple pieces of information as a result of the fall risk assessment that was just completed. More specifically, summary window 466 includes both a qualitative fall risk rating identifier 468 and a patient fall risk reduction protocol summary 470. The qualitative fall risk rating identifier 468 corresponds to the qualitative fall risk rating determined after receiving the answers to the six questions shown in FIGS. 19-24. In the particular example shown in FIG. 25, the qualitative fall risk rating identifier 468 is a "high" rating, which indicates that the patient has a high risk of falling.

The fall risk reduction protocol summary 470 summarizes the steps to be taken in order to mitigate the risk of the patient falling. That is, fall risk reduction protocol summary 470 briefly summarizes the fall risk reduction steps contained within fall risk reduction protocol 93 (FIG. 2). In some embodiments, the fall risk reduction protocol 93 is initially set by the manufacturer of caregiver assistance system 106 but is able to be modified by an authorized person 136 of the healthcare facility in order to meet the desires of the healthcare administrators of the particular healthcare facility in which the system 106 installed. In other embodiments, the fall risk reduction protocol 93 may be set by the manufacturer without being customizable, while in still other embodiments, the fall risk reduction protocol 93 may be undefined until the healthcare facility administrators determine its contents.

In general, the fall risk reduction protocol 93 identifies what steps are to be taken by caregivers with respect to the patient support apparatus 20 in order to reduce the risk of the patient falling. Generally speaking, these steps typically include one or more of the following: ensuring the brake on patient support apparatus 20 is activated; placing at least three of the siderails 36 of patient support apparatus 20 in their raised position; arming the exit detection system 46 of the patient support apparatus 20 (including arming a particular zone of the exit detection system 46); lowering the height of litter frame 28 to either its lowest height, or a height that is no taller than a specified threshold; and, in some cases, arming a monitoring system (e.g. the bed watch system identified in the bed watch status indicator 168) that issues an alert if any of the conditions of the fall risk reduction protocol 93 are changed out of their desired states. All of these steps are steps that are taken with respect to fall-risk components of patient support apparatus 20. Fall-risk components are those components of patient support apparatus 20 that have two different states, at least one of which is more likely to reduce the risk of falling. Thus, the fall-risk components include at least the following components of patient support apparatus 20: the siderails 36, the brake, the litter frame 28, exit detection system 46, and the bed watch monitoring system. Fall risk reduction protocol 93 specifies what the desired state is for these fall risk components when the patient has a non-zero fall risk. In most situations, the desired states are those indicated above (e.g. brake on, at least three siderails up, litter frame lowered, exit detection system armed, and bed watch monitoring system (if included) also armed).

In those embodiments where the qualitative fall risk rating has more than two categories (e.g. more than high risk and low risk), fall risk reduction protocol 93 may include different definitions, one for each of the different fall risk rating categories. For example, fall risk reduction protocol 93 may specify that for high fall risk patients, a first set of the fall-risk components must be in their desired states, and that for medium fall risk patients, a second set of the fall-risk components must be in their desired states, wherein the second set is either a subset of the first set, or has some other variation with respect to the first set. In other embodiments, fall risk reduction protocol 93 may be the same for all patients that do not have a zero fall risk rating (e.g. protocol 93 may be the same for high and medium fall risk patients).

Fall risk reduction protocol summary 470 summarizes the desired states for the fall-risk components of the fall risk reduction protocol 93. As shown in FIG. 25, fall risk reduction protocol summary 470 indicates "low bed height," "3 side rails up," "bed exit: zone 2," and "brake set." This means that the particular fall risk reduction protocol 93 shown in this example has identified the litter frame 28, siderails 36, exit detection system 46, and brake as fall-risk components, and that their desired states are a lowered height, or lowest height, for the litter frame 28, a raised position for at least three of the siderails 36, an armed state for exit detection system 46 that is set to zone 2, and an activated brake. Fall risk reduction protocol summary 470 therefore acts as a reminder to the caregiver to ensure that all of these fall-risk components are set to their desired states before the caregiver leaves the room in which patient support apparatus 20 and its associated patient are located.

In order for caregiver assistance application 124 to display the fall risk reduction protocol summary 470 in summary window 466 of FIG. 25, application 124 first retrieves the fall risk reduction protocol 93. This is performed at step 356 of algorithm 143. As indicated in FIG. 2, fall risk reduction protocol 93 may be stored in memory 91. In other embodiments, fall risk reduction protocol 93 may be stored elsewhere. Still further, patient support apparatuses 20 are configured in at least one embodiment to allow a user to make changes to the fall risk reduction protocol 93 using one of the control panels 42. And, as noted, one or more authorized individuals 136 may modify or store fall risk reduction protocol 93 using a computer (e.g. 134) that is in communication with network 74 and caregiver assistance server 90.

Returning to FIG. 18, once caregiver assistance application 124 retrieves the fall risk reduction protocol 93, it determines what the desired states are for each of the fall-risk components. This is accomplished at step 358 of algorithm 143. As noted, the desired states are defined in fall risk reduction protocol 93. After determining these desired states at step 358, caregiver assistance application 124 moves to step 360 where it determines if any of the current states are not in their respective desired states. Caregiver assistance application 124 continuously monitors the states of the fall-risk components of the patient support apparatus 20 within the healthcare facility and uses this repetitively updated state data to determine at step 360 if any of the fall-risk components are not in, or have moved out of, their respective desired states. The updated state data is received from patient support apparatuses 20, which send their state data to caregiver assistance application 124, either directly or, as noted previously, indirectly via patient support apparatus server 86. This state data is alternatively referred to herein as status data, and includes, for example, the current states of the siderails, brake, litter frame, exit detection system, bed watch monitoring system, etc.

If caregiver assistance application 124 determines at step 360 that any of the fall-risk components of the patient support apparatus 20 are not in their desired state according to the patient fall risk reduction protocol 93, it moves to step 364 where it issues an alert, as will be discussed in greater detail below. If it determines at step 360 that none of the fall-risk components of patient support apparatus 20 are out of their desired state, it moves to step 362 where it continues to monitor the fall-risk components and checks to see if they remain in their desired states. From step 362, caregiver assistance application 124 moves to step 380 where it returns to main algorithm 226 (FIG. 5) and allows the caregiver to utilize other functions of caregiver assistance application 124 and/or to display other screens that are not directly related to the patient's fall risk. It is to be noted that the return to main algorithm 226 does not terminate the continuous monitoring of the fall-risk components of the patient support apparatuses, but instead allows this monitoring process to continue in the background. Thus, for example, if the caregiver switches to using the patient rounding function of caregiver assistance application 124 (e.g. by pressing rounding task icon 180) and the patient support apparatus 20 of a patient with a high fall risk has one of its fall-risk components change to an undesired state, caregiver assistance application 124 will still provide the alert of step 364 to the caregiver, even though application 124 may be executing a different algorithm at that particular time.

The alert that is issued at step 364 follows the alerting algorithm 149. Alerting algorithm 149 is described in more detail below with respect to FIG. 61. It generally sends an alert to those electronic device(s) 104 that have been configured to be notified (as defined in local rules 126) for the particular patient support apparatus 20 that has had a fall-risk component moved to an undesired state. The alert is sent to the caregiver's mobile device 104a (and/or to stationary device(s) 104b) regardless of whether or not the caregiver is in the same room, or same ward, as the patient support apparatus 20 that generated the alert. That is, alerting algorithm 149 provides each caregiver with alerts when any of the patient support apparatuses 20 of the patients to whom he or she is assigned have one or more of their fall-risk components change out of their respective desired states. Thus, for example, if a caregiver is currently in, say, room 7030 and that caregiver is assigned to patients in rooms 7031, 7032, and 7033 and those patients are all high fall risks, the caregiver will get an alert on his or her mobile electronic device 104a while they are in room 7030 if any of the patient support apparatuses 20 in rooms 7031, 7032, or 7033 have one or more of their fall-risk components change out of their respective desired states. Further, caregiver assistance application 124 does this for each caregiver who has a mobile electronic device 104a (as well as for all of the stationary electronic devices 104b). As a result, each caregiver is apprised of changes in fall-risk components of the patient support apparatuses 20 used by the particular patients to whom that caregiver is assigned to care for.

Returning to step 364 of algorithm 143, alerting algorithm 149 issues an alert at this step in one or more different manners, depending upon how caregiver assistance application 124 is custom-tailored by an authorized administrator of the healthcare facility, as well as depending upon the particular embodiment of caregiver assistance application 124. In some embodiments of application 124, caregivers access caregiver assistance application 124 on their mobile electronic devices 104a by accessing a particular URL using a conventional web browser. In these embodiments of application 124, alerting algorithm 149 may not be able to always provide an alert to the caregiver via the web browser because the caregiver may have the web browser closed, may be visiting a different web page, and/or may not be currently logged into the application 124 via the web browser. Still further, even if the caregiver is currently logged into the caregiver assistance application 124 via the web browser, it may be difficult to guarantee that the caregiver receives the alert because he or she may have the volume turned down on the mobile electronic device 104a and/or he or she may not be looking at the screen at the time the alert is issued.

In order to account for these and other possibilities, alerting algorithm 149 may be configured to issue an alert in some embodiments by sending a text, email, or phone message to the mobile electronic device 104a of the caregiver to whom the alert is directed. Because the mobile electronic device 104a is typically a smart phone or a tablet computer, the text, email, or phone message is delivered to another application that is being executed by the device 104a (e.g. the text app, the email app, or the phone app). Further, the mobile electronic device 104a can be easily set to issue a specific noise, sound, and/or vibration in response to an incoming text, phone call, and/or email. Still further, this specific noise, sound, and/or vibration happens even in those situations where the web browser on the mobile electronic device 104a is closed, or the caregiver is not logged into application 124, or the volume that sounds from websites are played at by the device 104a (e.g. the media volume on a smart phone) have been turned off or set to low. Therefore, alerting algorithm 149 can utilize a separate mobile app on the device 104 for alerting that is independent of the web browsing app on device 104 in order to ensure that alerts are communicated to the caregivers, even when the web browsing app used to gain access to application 124 is turned off on device 104, or is not logged into application 124.

As was also noted previously, in some alternative embodiments, caregiver assistance application 124 is divided into two specific applications: a server application and a mobile device application. In such embodiments, the caregiver does not access caregiver assistance application 124 via a web browser installed on his or her mobile electronic device 104a, but instead does so by opening the mobile device application of caregiver assistance application 124. The mobile device application is a specialized app that is downloaded to the mobile electronic device 104a and that is specifically designed to work in conjunction with the server application. In this embodiment, the mobile device application is customized to operate with the specific operating system of the mobile electronic device 104a and, as a result, there may be different versions of the mobile device application that are written for the different operating systems (e.g. an Android version, an iOS version, etc.). Such native applications, offer the advantage of being able to operate in the background and cause the mobile electronic device 104a to issue a sound, vibrate, illuminate one or more lights, etc. in response to an incoming alert, even if the user has not manually opened that native application.

Regardless of the specific manner in which caregiver assistance application 124 issues an alert at step 364 (FIG. 18), algorithm 143 branches to different paths after step 365: a first path 366 and a second path 368. First path 366 allows the user to remotely or locally change the state of the fall-risk component on the patient support apparatus 20 that caused the alert to issue. Second path 368 allows the user to acknowledge the alert without changing the state of the fall-risk component. If the caregiver selects second path 368, caregiver assistance application 124 proceeds to step 378 where it waits for the caregiver to acknowledge the alert without making any changes to the fall-risk component(s) that is out of its desired state. Caregiver assistance application 124 may be configured to accept this acknowledgement in several different manners such as, but not limited to, displaying an "acknowledge" or "ignore" icon that must be touched by the caregiver to acknowledge the alert, or otherwise requiring the caregiver to take some positive action with the mobile electronic device 104a that indicates that the caregiver received and is aware of the alert. Once the alert is received by caregiver assistance application 124, algorithm 143 proceeds to step 362 and operates in the manner previously discussed.

If the caregiver wishes to change the state of the fall-risk component that is no longer in its desired state, the caregiver can elect to follow first path 366 (FIG. 18). First path 366 allows the caregiver to change the state of the fall-risk component to its desired state either locally or, in some cases, remotely. To change the state locally, the caregiver must be present in the room in which the alerting patient support apparatus 20 is located. The caregiver makes the local change by utilizing one or more of the control panels 42 of the patient support apparatus 20. To make the change remotely, the caregiver uses mobile electronic device 104a to send a command to the patient support apparatus 20 to change the fall-risk component back to its desired state. In many embodiments, only commands that involve no physical movement on the patient support apparatus 20 are allowed to be carried out remotely, such as arming the exit detection system, arming the bed watch monitoring system, etc.

In order to remotely change the state of the fall-risk component using mobile electronic device 104a (or stationary electronic device 104b), caregiver assistance application 124 waits to receive a command for the patient support apparatus at step 370 (FIG. 18). Once the command is received, the command is sent by the electronic device 104 to the caregiver assistance server 90 at step 372. When it is received by the caregiver assistance application 124 operating on server 90, application 124 forwards the command to the appropriate patient support apparatus 20 at step 374. Thereafter, the patient support apparatus 20 implements the command and sends an updated set of data regarding its fall-risk components, which are received by caregiver assistance application 124 at step 376. Using this updated set of data, caregiver assistance application 124 returns back to step 360 where it checks to see if the patient support apparatus 20 has all of its fall-risk components in their desired states. From step 360, caregiver assistance application 124 proceeds in the manners previously described.

When mobile electronic device 104a is used to send a command to change the state of a fall-risk component of a patient support apparatus 20, it knows which specific patient support apparatus 20 to send the command to based upon the room number (and/or patient name) displayed in status location 200. That is, whatever room number, bed bay identifier, and/or patient identifier is displayed in status location 200 at the time the command is sent identifies where the command will be sent. When caregiver assistance application 124 receives the command at server 90, it knows which patient support apparatus 20 to send it to based on its knowledge of which patient support apparatuses 20 are assigned to which rooms, bed bays, and/or patients.

It will be noted that the monitoring of the states of the fall-risk components of the patient support apparatuses 20 that occurs at steps 360 and 362 of algorithm 143 may involve more monitoring than is performed by the bed watch monitoring system. That is, in at least one embodiment, the patient fall risk reduction protocol 93 may specify that the bed watch monitoring system is turned on for high fall risk patients. In this case, algorithm 143 automatically monitors whether the bed watch monitoring system is turned on or off for those patient support apparatuses 20 to whom high fall risk patients have been assigned, and if it is off, algorithm 143 issues an alert. Thus, the fall risk reduction protocol 93 can provide an additional layer of monitoring beyond what the bed watch monitoring system offers: it can monitor the bed watch monitoring system itself (which does not monitor itself).

It will also be noted that caregiver assistance application 124 also passively monitors all of the states of various components of the patient support apparatuses 20, regardless of whether a patient is a high fall risk or not, and regardless of whether the patient has even been assessed for fall risks or not (and also regardless of whether the bed watch monitoring system is armed or disarmed). The results of this passive monitoring are displayed in top portion 202 of the screen shots shown herein (e.g. FIGS. 19-26). This monitoring provides information to the caregiver of the current state of the patient support apparatus 20 so that the caregiver can remotely know the states of all of the patient support apparatuses 20 which are being used with his or her assigned patients. Further, this passive monitoring may involve the monitoring of a different set of components than the fall-risk components discussed above, such as, but not limited to, whether the patient support apparatus 20 is currently plugged into an electrical outlet, whether the nurse call system cable between the patient support apparatus 20 and the nurse call system is connected or disconnected, etc.

In some embodiments, when caregiver assistance application 124 issues an alert due to a fall-risk component of a patient support apparatus 20 moving out of its desired state, the alert may include a graphical indication of the fall-risk component that has moved out of its desired state. For example, in all of the screens shown in FIGS. 19-27, caregiver assistance application 124 includes a bed icon 164. If any of the siderails are moved out of their desired position, caregiver assistance application 124 may graphically indicate this by changing the color of, or otherwise changing the visual appearance of, the siderail icon 176 corresponding to the siderail 36 that has moved out of its desired state. Additionally, if the height of the litter frame 28 moves above its desired height, caregiver assistance application 124 may change the color or appearance of the top of the litter frame shown in bed icon 164 (e.g. the top portion of the bed icon 164 that surrounds the patient icon). If either the exit detection system 46 or the bed watch monitoring system are changed to an undesired state, caregiver assistance application 124 may graphically indicate this by highlighting, or otherwise changing the appearance of, exit detection system status indicator 166 or bed watch status indicator 168. If the brake moves out of its desired state, the portion of bed status bar 170 indicating the brake status may be highlighted and/or otherwise changed visually. Still other graphical changes may be made for alerts involving a fall-risk component that are moved out of its desired state.

In at least one embodiment, caregiver assistance application 124 allows a user to make changes to the exit detection system aspects of the patient fall risk reduction protocol 93 for a particular patient. More specifically, in at least one embodiment, caregiver assistance application 124 allows a caregiver to override the exit detection system zone that is specified by the fall risk reduction protocol 93. For example, in many embodiments, the fall risk reduction protocol 93 specifies that the exit detection system 46 is armed for a high fall risk patient, and that zone 2 (the middle sensitive zone) is chosen. If the caregiver wishes to arm a different zone, however, caregiver assistance application 124 allows the caregiver to do with without causing an alert when application 124 detects that the incorrect zone is armed at step 360 of algorithm 143.

Figures 26, 27:
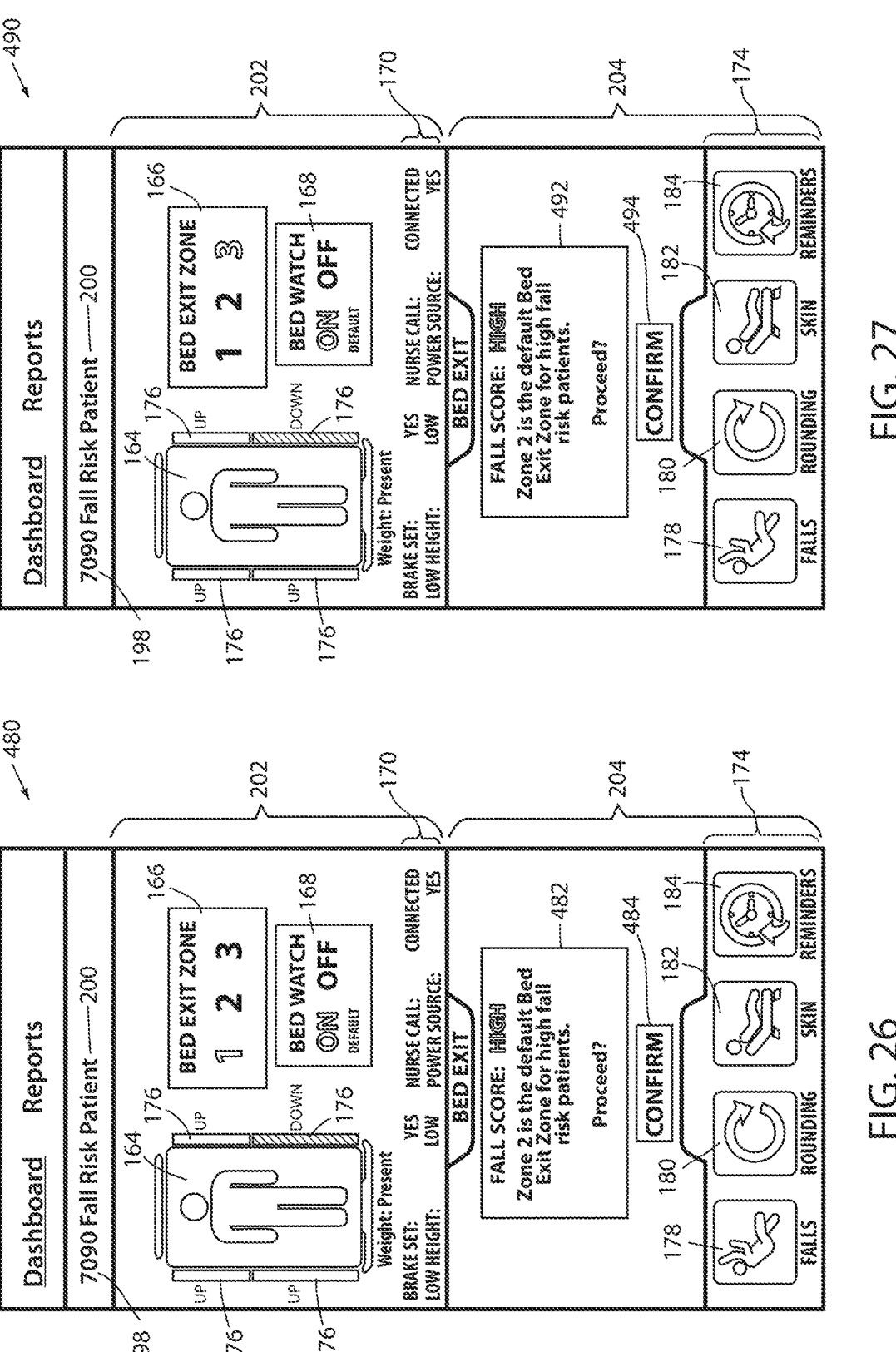
FIG. 26 is an illustrative first bed exit advisory screen that is displayable on an electronic device of the caregiver assistance system.
FIG. 27 is an illustrative second bed exit advisory screen that is displayable on an electronic device of the caregiver assistance system.

Two examples of this customized zone selection are shown in FIGS. 26 and 27. In the screenshot 480 of FIG. 26, the caregiver has selected zone 1 of the exit detection system 46 and caregiver assistance application 124 has displayed a warning window 482 thereon. Warning window 482 notifies the caregiver that zone 2, not zone 1, is the zone specified by patient fall risk reduction protocol 93. If the user wishes to select zone 1 instead of zone 2, however, the user is free to do so by pressing the confirm icon 484. If the user presses the confirm icon 484, caregiver assistance application 124, in at least one embodiment, updates the fall risk reduction protocol 93 for that particular patient only such that no alerts are issued at step 364 because of zone 1 being armed instead of zone 2. In this embodiment, caregiver assistance application 124 automatically changes the fall risk reduction protocol 93 back to zone 2 if a new patient is assigned to that particular patient support apparatus 20, or if the user subsequently switches exit detection system 46 from zone 1 back to zone 2 for that particular patient support apparatus 20.

FIG. 27 illustrates a similar situation where the caregiver wishes to arm zone 3 of exit detection system 46 instead of zone 2. As with the situation shown in FIG. 27, caregiver assistance application 124 displays a warning window 492 on screen 490 that informs the caregiver that zone 2 is the zone specified by fall risk reduction protocol 93. If the user wishes to override this zone choice, however, the user is free to press the confirm icon 494, in which case caregiver assistance application 124 updates the fall risk reduction protocol 93 for that particular patient and no longer issues alerts due to zone 3 being selected instead of zone 2. Caregiver assistance application 124 automatically switches the protocol 93 back to zone 2 for that particular patient support apparatus 20 if a new patient is assigned to it or the caregiver switches exit detection system 46 back to zone 2 from zone 3 on that particular patient support apparatus 20.

In addition to the alerts discussed above with respect to rounding algorithm 140 and fall risk reduction algorithm 143, alerting algorithm 149 is configured to alert caregivers whenever a status of any of the patient support apparatuses 20 assigned to the caregiver changes while the bed watch system is armed. Caregiver assistance application 124 may further be configured to alert the corresponding caregiver whenever any patient support apparatus 20 alert is issued by any of the patient support apparatuses 20 to which the caregiver is assigned (e.g. a patient exit alert, a cord-out alert, etc.). Such alerts may arise when the caregiver is using caregiver assistance application 124 for other purposes, such as one of the other tasks identified in task menu 174, or such alerts may arise while the caregiver is engaged in other tasks that don't involve the use of an electronic device 104. As noted, such alerts are communicated to the caregiver, in at least one embodiment, by sending a text, email, and/or automated phone call to the particular caregiver associated with the patient support apparatus 20 that is issuing the alert. Further, alerting algorithm 149 is configured to allow users to choose how such alerts are issued, in at least some embodiments. Caregivers may therefore receive a text sent to their mobile electronic device 104*a* (or another phone capable of receiving texts), for example, if the exit detection system 46 of a patient support apparatus 20 detects a patient exit, or if the nurse call cable is unplugged, or any other status changes that warrant an alert. The mobile electronic device 104*a* responds to the received text (or email or phone call) with a beep, the illumination of one or more lights, or in any other manner dictated by that particular caregiver's preferences.

It will also be appreciated by those skilled in the art that various other modifications may be made to fall risk reduction algorithm 143. These include, but are not limited to, skipping the fall risk assessment steps 346-354; skipping the sending of bed commands at step 370-376; requiring the caregiver to set the patient support apparatus 20 to a compliant state (and thus omitting acknowledgement step 378); taking additional steps to ensure or encourage compliance with the fall risk reduction protocol 93; changing the order of one or more the steps; and/or combinations of one or more of these modifications.

Figure 28:
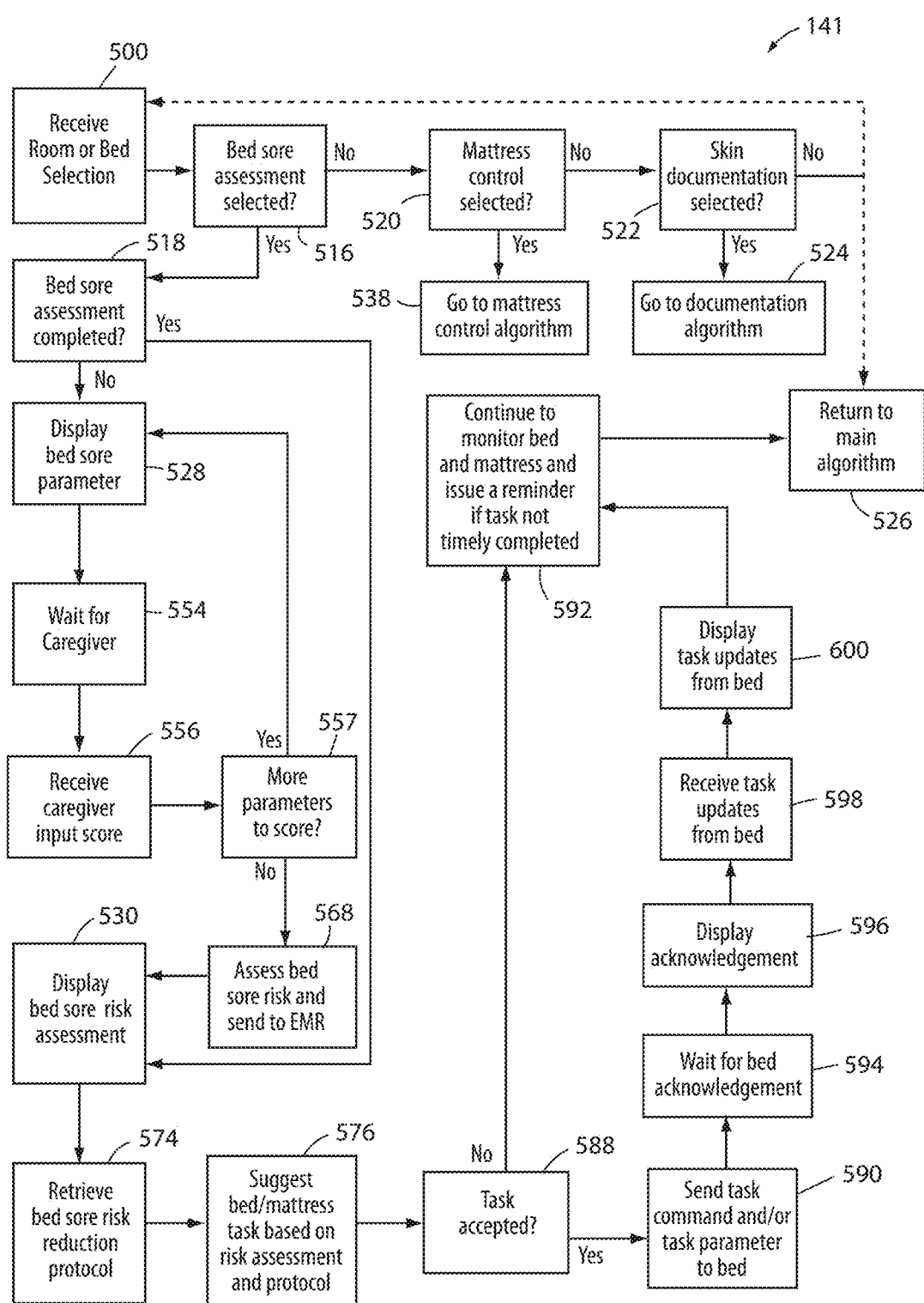
FIG. 28 is a flow diagram of a patient skin care algorithm that may be executed by the caregiver assistance application.

Turning now to the bed sore risk reduction algorithm 141 of caregiver assistance system 106, if a caregiver selects skin task icon 182 (FIG. 9) at step 159 of main algorithm 226 (FIG. 5), caregiver assistance application 124 begins executing skin care algorithm 141. One example of skin care algorithm 141 is shown in FIG. 28. Skin care algorithm 141 begins at a step 500 where caregiver assistance application 124 receives or verifies a room selection or a bed selection. In response to such a room selection or bed selection, caregiver assistance application displays a skin care overview screen, such as skin care overview screen 502 of FIG. 29. Skin care overview screen 502 (as well as most, if not all, of the other skin care screens associated with skin care algorithm 141, e.g. those screens shown in FIGS. 29-41, 43-49, and 51-56, and 58-59) includes many of the same elements of the screens previously discussed herein, such as, but not limited to, room identifier location 198, top portion 202, bottom portion 204, task menu 174, bed status bar 170, exit detection system status indicator 166, bed watch system status indicator 168, and bed icon 164. Bottom portion 204 differs from the previously described bottom portions in that it includes a menu 504 of skin care options.

Menu 504 (FIG. 29) includes a skin assessment icon 506, a patient turn icon 508, a skin documentation icon 510, a maximum inflation icon 512, and a low air loss icon 514. By pressing or touching any of these option, the user is taken to different screens by caregiver assistance application 124 and is able to perform different functions. At step 516 of algorithm 141 (FIG. 28), caregiver assistance application 124 determines if the caregiver has pressed on the skin assessment option 506. If the answer is yes, application 124 proceeds to step 518, as will be discussed more below. If the answer is no, caregiver assistance application 124 proceeds to step 520, where it determines if the user has pressed on any of the mattress control options of menu 504. The mattress control options refer to the patient turn icon 508, the maximum inflation icon 512, and the low air loss icon 514. If caregiver assistance application 124 determines at step 520 that any of these mattress control icons have been selected, caregiver assistance application 124 proceeds to step 538, which takes it to the mattress control algorithm 700 illustrated in FIG. 42 and described in greater detail below.

If caregiver assistance application 124 determines at step 520 (FIG. 28) that none of the mattress control options have been selected, it proceeds to step 522 where it determines if the caregiver has selected the skin documentation icon 510. If the caregiver has selected the skin documentation icon 510, caregiver assistance application 124 proceeds to step 524, which takes it to the skin documentation algorithm 800 shown in FIG. 50 and described in greater detail below. If the caregiver does not select the skin documentation icon 510, caregiver assistance application 124 returns to either main algorithm 226 at step 526 or it continues to display the menu 504 until the caregiver makes a selection (or otherwise navigates away from screen 502). If caregiver assistance application 124 returns to main algorithm 226, application 124 may continue to execute certain monitoring functions of algorithm 141, as discussed in more detail below.

Returning back to step 516, when a caregiver selects skin assessment icon 506 at step 516 (FIG. 28), caregiver assistance application 124 proceeds to step 518 where it determines if the particular patient assigned to the selected room and/or selected bed has had a bed sore risk assessment performed or not. Step 518 may be accomplished in several manners. In one particular embodiment, caregiver assistance application sends a request to EMR server 98 requesting the bed sore risk assessment for the patient assigned to the room or bed identified at step 518. If the EMR server 98 responds that there is no such bed sore risk assessment currently on file for the patient, skin care algorithm 141 checks to see if the bed sore risk assessment is stored elsewhere, such as, but not limited to, data storage 128. If there is no such bed sore risk assessment stored there, caregiver assistance application 124 may be configured by administrators of the healthcare facility to search in other locations. If no locations contain the bed sore risk assessment for the particular patient, caregiver assistance application 124 proceeds to step 528. If a bed sore risk assessment is located for the particular patient, caregiver assistance application 124 proceeds to step 530.

Figures 29, 30:
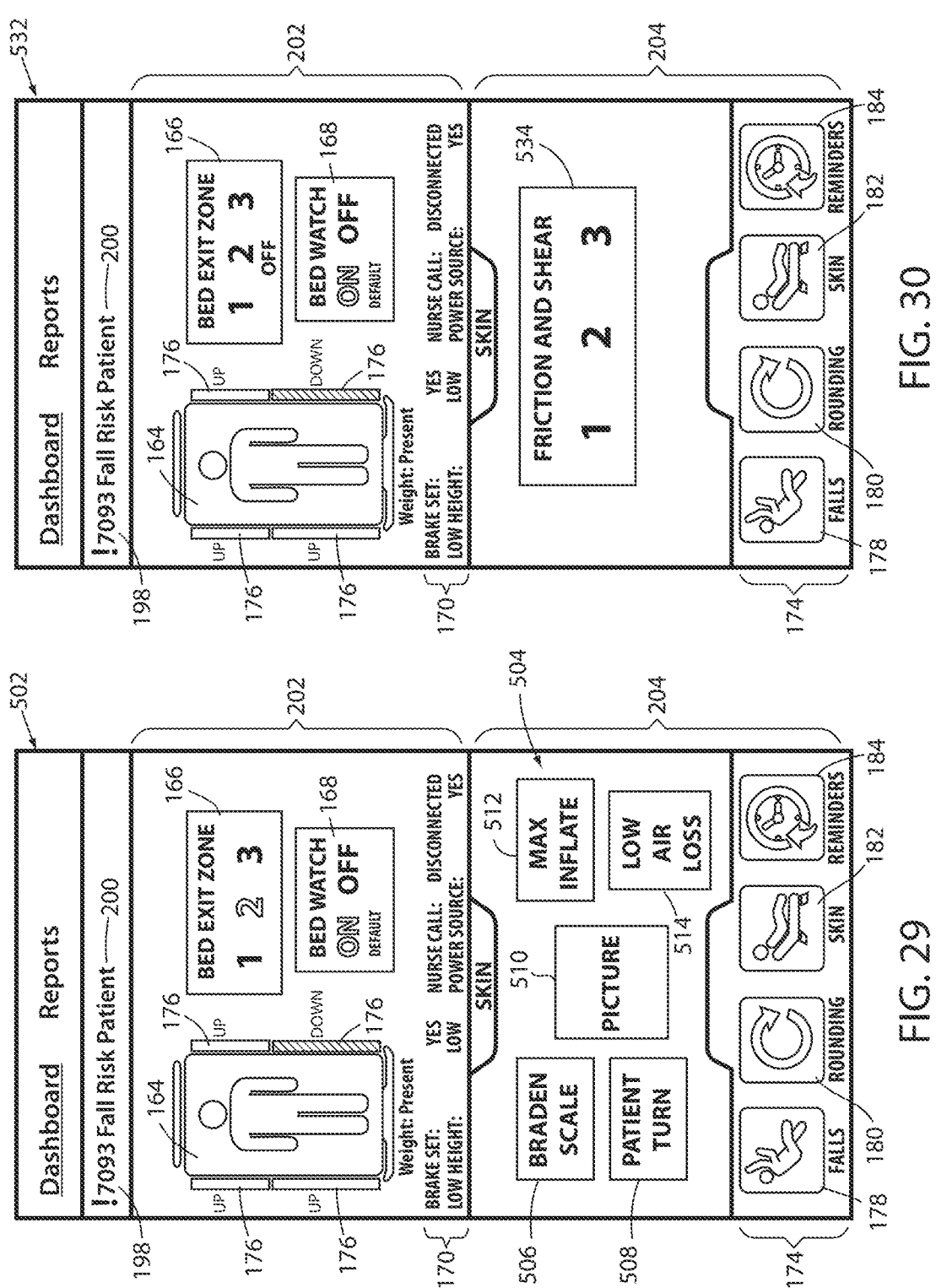
FIG. 29 is an illustrative skin care overview screen that is displayable on an electronic device of the caregiver assistance system.
FIG. 30 is an illustrative first skin assessment question screen that is displayable on an electronic device of the caregiver assistance system.

When no bed sore risk assessment has been performed for the patient, caregiver assistance application 124 proceeds from step 518 to step 528. At step 528, caregiver assistance application 124 displays a first bed sore risk scoring screen 532 that is used to perform a bed sore risk assessment for the patient assigned to the room or bed identified in step 500. One example of such an initial bed sore risk scoring screen 532 is shown in FIG. 30. FIG. 30 is the first of six bed sore risk assessment scoring screens (FIGS. 30-35) used in one embodiment of caregiver assistance application 124. These six screens are designed to implement the Braden bed sore risk assessment, which is also sometimes referred to as the Braden scale. The Braden bed sore risk assessment is a numerically scored bed sore risk assessment that ranks patients into various qualitative categories (e.g. very high risk, high risk, moderate risk, mild risk, no risk, etc.) It will be understood that caregiver assistance application 124 can be configured to implement other bed sore risk assessments besides the Braden bed sore risk assessment (e.g. the Waterlow scale, Norton scale, etc.), and/or it may be supplemented, customized, and/or partially modified with other questions. Still other variations may be made to the bed sore risk assessment by authorized personnel 136 of the healthcare facility, such as by using computer 134 to access and re-configure the settings of caregiver assistance application 124.

The specific first bed sore risk factor displayed at step 528 of algorithm 141 is the amount of friction and/or shear that the patient may experience while in patient support apparatus 20. In general, first risk factor is to be scored based on how much friction and/or shear the patient's body experiences during movement while positioned on the mattress 38 that is positioned on top of support deck 30 of patient support apparatus 20.

Scoring for the friction and shear factor is assigned one of three numeric values: 1, 2, and 3. These score values are shown in a scoring window 534 (FIG. 30). The caregiver selects which value corresponds to the particular patient he or she is analyzing. By selecting the value, caregiver assistance application 124 assigns the selected value to the friction and shear component of the Braden scale assessment and moves onto a second bed sore risk assessment scoring screen, such as the second bed sore risk assessment scoring screen 536 shown in FIG. 31. If the user wishes to know more information about what the different numeric values represent, caregiver assistance application 124 is configured to provide this information to the user. One manner in which this information is provided to the user is in response to the user double tapping, pressing and holding a numeric value, or otherwise choosing a numeric value in some other manner that is different from the manner used to select the value for assigning it to the patient's bed risk score.

Figures 35, 36:
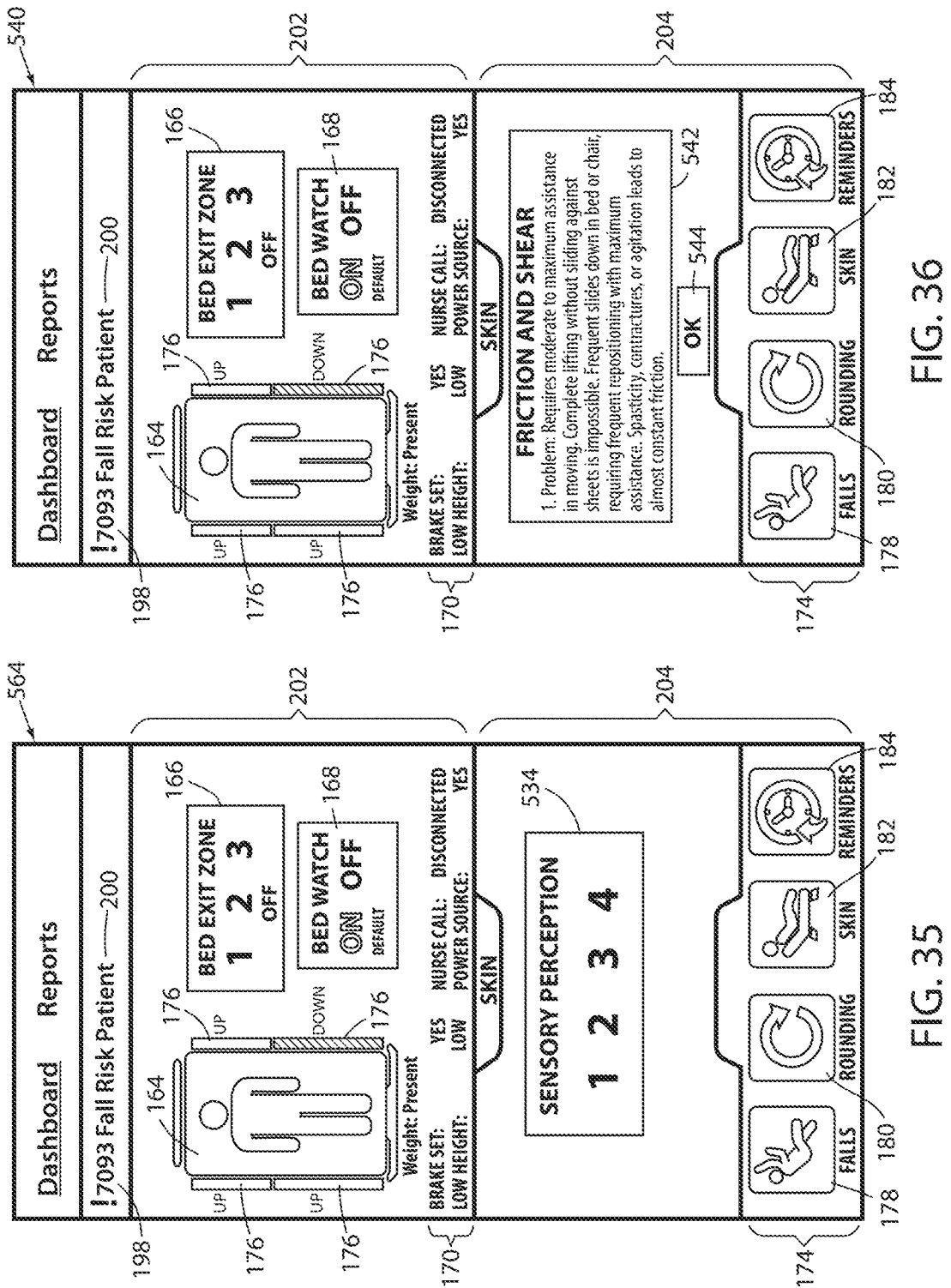
FIG. 35 is an illustrative sixth skin assessment question screen that is displayable on an electronic device of the caregiver assistance system.
FIG. 36 is an illustrative first informational screen that provides additional information regarding a first selection made from the screen of FIG. 30.

In one example, if the user selects and holds value "1" in first bed sore risk scoring screen 532 for a predetermined amount of time, caregiver assistance application 124 is configured to display an explanation of the "1" score. One example of this explanation is shown in first informational screen 540 of FIG. 36. As shown in FIG. 36, caregiver assistance application 124 displays a message window 542 in which the following explanation of the "1" score from screen 532 (FIG. 30) is provided: "Problem: requires moderate to maximum assistance in moving. Complete lifting without sliding against sheets is impossible. Frequently slides down in bed or chair, requiring frequent repositioning with maximum assistance. Spasticity, contractures, or agitation leads to almost constant friction." Other messages, of course, may be displayed in window 542 that provide an explanation of the "1" score for the friction and shear factor of FIG. 30.

Regardless of the specific content of window 542 (FIG. 36), the caregiver uses the information provided therein to determine if the "1" score corresponds to the patient he or she is analyzing. If the information is applicable and the caregiver believes the patient should be assigned a value of "1" for the friction and shear component of the Braden bed sore assessment, he or she may simply press the OK icon 544 shown in FIG. 36. If the caregiver does not wish to assign a "1" score to the patient's friction and shear component of the Braden assessment, he or she may return to first bed sore risk scoring screen 532 by using the mobile electronic device 104's built-in "back" button (not shown), a web-browser's back button (if application 124 is web-based), or caregiver assistance application 124 can be programmed to show a "back" option on screen 540, or some other navigation aid may be used.

Returning to first bed sore risk scoring screen 532, if the user wishes to assign a value of two or three to the friction and shear score components of the patient's overall bed sore risk assessment, the caregiver selects the "2" or "3" value, respectively. If the user presses and holds the "2" value shown in FIG. 30 (or double taps it, etc.), caregiver assistance application 124 displays additional information about the "2" score, such as the second informational screen 546 shown in FIG. 37. Second informational screen 546 includes a message window 548 that contains additional information about the "2" score. In this particular embodiment, second message window 548 explains that a "2" score represents a potential problem, and that the patient "moves feebly or requires minimum assistance. During a move, skin probably slides to some extent against sheets, chair, restraints, or other devices. Maintains relatively good position in chair or bed most of the time but occasionally slides down." Other messages, of course, may be displayed in window 548 that provide an explanation of the "2" score for the friction and shear factor of FIG. 30.

Figures 37, 38:
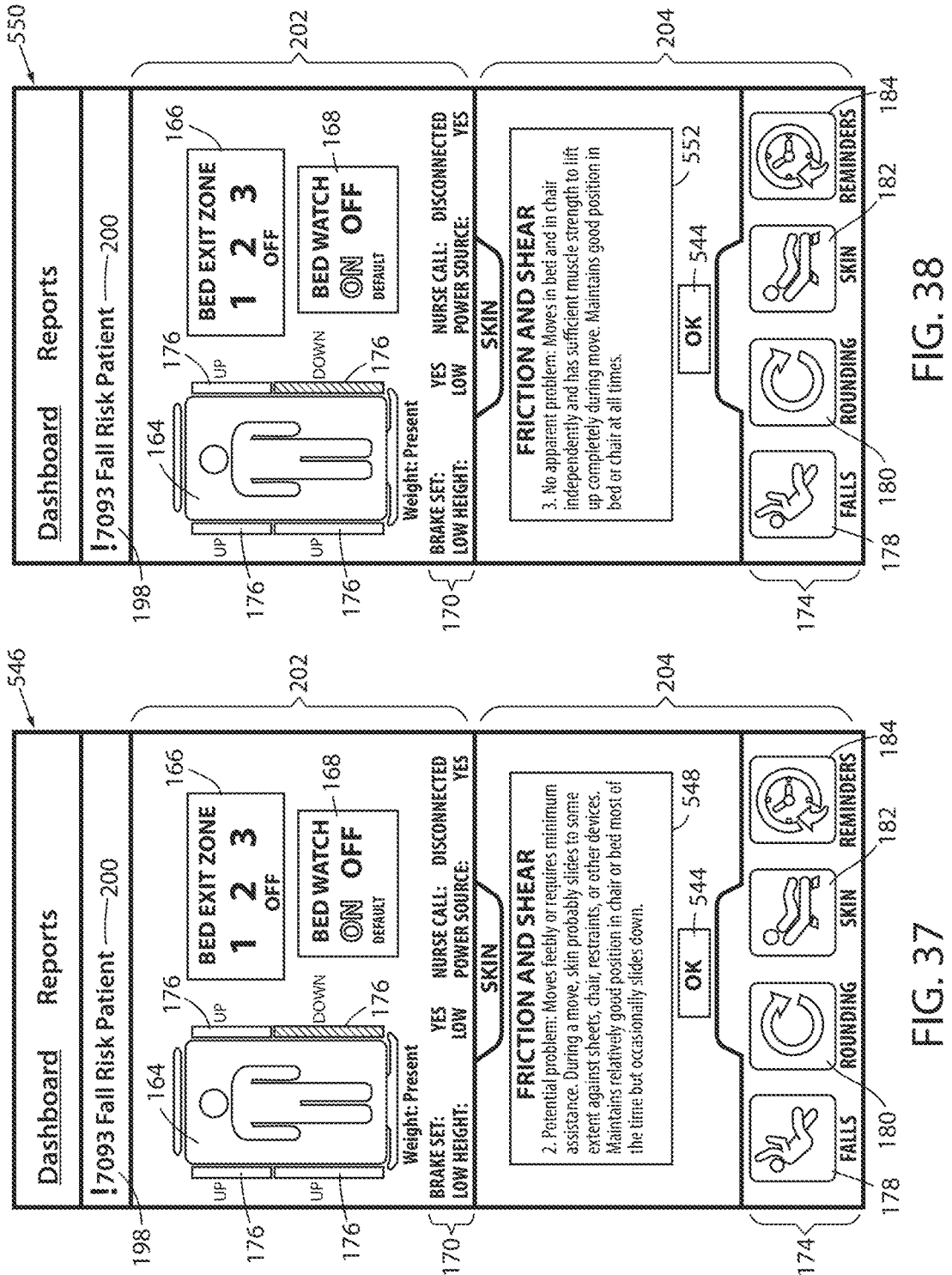
FIG. 37 is an illustrative second informational screen that provides additional information regarding a second selection made from the screen of FIG. 30.
FIG. 38 is an illustrative third informational screen that provides additional information regarding a third selection made from the screen of FIG. 30.
Figures 39, 40:
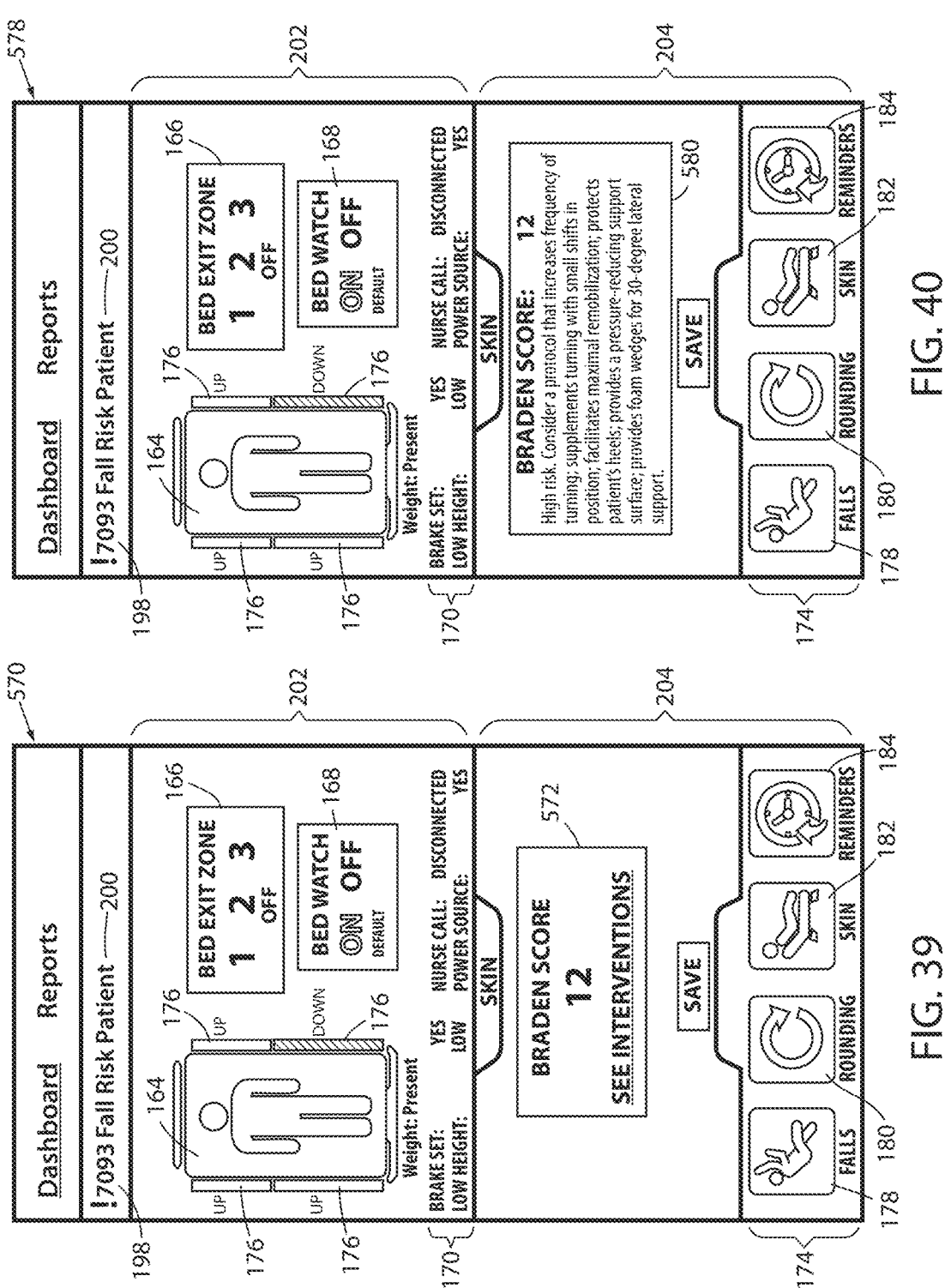
FIG. 39 is an illustrative skin risk assessment score screen that is displayable on an electronic device of the caregiver assistance system.
FIG. 40 is an illustrative general intervention screen that suggests various skin intervention and that is displayable on an electronic device of the caregiver assistance system.

If the user presses and holds the "3" value shown in FIG. 30 (or double taps it, etc.), caregiver assistance application 124 displays additional information about the "3" score, such as the third informational screen 550 shown in FIG. 38. Third informational screen 550 includes a message window 552 that contains additional information about the "3" score. In this particular embodiment, third message window 552 explains that a "3" score represents no apparent problem, and that the patient "moves in bed and in chair independently and has sufficient muscle strength to lift up completely during move. Maintains good position in bed or chair at all times." Other messages, of course, may be displayed in window 552 that provide an explanation of the "3" score for the friction and shear factor of FIG. 30.

Regardless of the specific content of windows 548 and/or 552 (FIGS. 37 & 38), the caregiver uses the information provided therein to determine if the respective score corresponds to the patient he or she is analyzing. If the information is applicable and the caregiver believes the patient should be assigned the corresponding value for the friction and shear component of the Braden bed sore assessment, he or she may simply press the OK icon 544 shown on these screens. If the caregiver does not wish to assign these scores to the patient's friction and shear component of the Braden assessment, he or she may return to first bed sore risk scoring screen 532 by using the mobile electronic device 104's built-in "back" button (not shown), a web-browser's back button (if application 124 is web-based), or caregiver assistance application 124 can be programmed to show a "back" option on screens 546 and 550, or some other navigation aid may be used.

Whichever score the caregiver assigns to the friction and shear component of the Braden bed sore assessment, the assignment of that score corresponds to step 556 of algorithm 141 (FIG. 28). That is, after displaying first bed sore risk scoring screen 532 at step 528, caregiver assistance application 124 moves to step 554 where it waits for the caregiver to assign a "1", "2", or "3" value to the patient's friction and shear factor. Once this value is assigned at step 556, caregiver assistance application 124 moves to step 557, where it determines if there are more factors that are to be scored as part of the bed sore risk assessment. In the particular example shown in the accompanying drawings where the Braden score assessment is being used, there are six factors that are scored by the caregiver. Accordingly, caregiver assistance application 124 returns to step 528 five times after the initial completion of step 528.

The second time caregiver assistance application 124 performs step 528, it displays a second bed sore risk factor to be scored by the caregiver. In the particular example shown in the drawings, the second bed sore risk factor is the patient's nutrition. When caregiver assistance application 124 returns to step 528, it displays the second bed sore risk assessment scoring screen 536 shown in FIG. 31. Screen 536 allows the caregiver to assign four different scoring values to the patient's nutrition, which are shown in the scoring window 534. As with all of the bed assessment screens discussed herein, the user may choose the desired score value by simply touching the numeric value (e.g. "1," "2", "3", or "4), or he or she may access additional information about the each of the particular score values, such as by double tapping on the numeric value, pressing and holding the numeric value for longer than a predetermined time period, or by other means. When the user takes the appropriate action to see this additional information, caregiver assistance application 124 responds by displaying a screen like those shown in FIGS. 36-38, except the message window shown in the screen corresponds to information about the particular value selected by the caregiver. Thus, it will be understood that caregiver assistance application 124 is configured to display additional screens like those shown in FIGS. 36-38 for all of the bed sore risk factors that are to be scored, but for purposes of brevity, such additional drawings have been omitted. The content of these additional screens and their additional message windows is discussed below.

If the caregiver requests additional information about the "1" value of the patient's Braden scale nutritional component, caregiver assistance application 124 displays a message window that contains the following information, or a variant thereof: "Very poor: patient never eats a complete meal. Rarely eats more than ⅓ of any food offered. Eats two servings or less of protein (meat or dairy products) per day. Takes fluids poorly. Does not take a liquid dietary supplement."—OR—"The patient is NP0 (eating nothing by mouth) and/or maintained on clear liquids or an IV for more than five days."

If the caregiver requests additional information about the "2" value of the patient's Braden scale nutritional component, caregiver assistance application 124 displays a message window that contains the following information, or a variant thereof: "Probably inadequate: patient rarely eats a complete meal and generally eats only about 2 of any food offered. Protein intake includes only three serving of meat or dairy products per day. Occasionally patient will take a dietary supplement."—OR—"The patient receives less than the optimum amount of liquid diet or is tube feeding."

If the caregiver requests additional information about the "3" value of the patient's Braden scale nutritional component, caregiver assistance application 124 displays a message window that contains the following information, or a variant thereof: "Adequate: patient eats over half of most meals. Eats a total of four servings of protein (meat, dairy products) each day. Occasionally will refuse a meal, but will usually take a supplement if offered."—OR—"The patient is on a tube feeding or a TPN (Total Parenteral Nutrition) regimen, which probably meets most of the nutritional needs."

If the caregiver requests additional information about the "4" value of the patient's Braden scale nutritional component, caregiver assistance application 124 displays a message window that contains the following information, or a variant thereof: "Excellent: Patient eats most of every meal. Never refuses a meal. Usually eats a total of four or more servings of meat and dairy products. Occasionally eats between meals. Does not require supplementation."

After displaying second bed sore risk assessment scoring screen 536 at step 528, caregiver assistance application 124 moves to step 554 where it waits for the caregiver to assign a "1", "2", "3" or "4" value to the patient's nutritional factor. Once this value is assigned at step 556, caregiver assistance application 124 moves to step 557, where it determines if there are more factors that are to be scored as part of the bed sore risk assessment. In addition, caregiver assistance application 124 updates the running total of the scores that have been assigned to the previously displayed factors (e.g. friction & shear and nutrition).

Figures 31, 32:
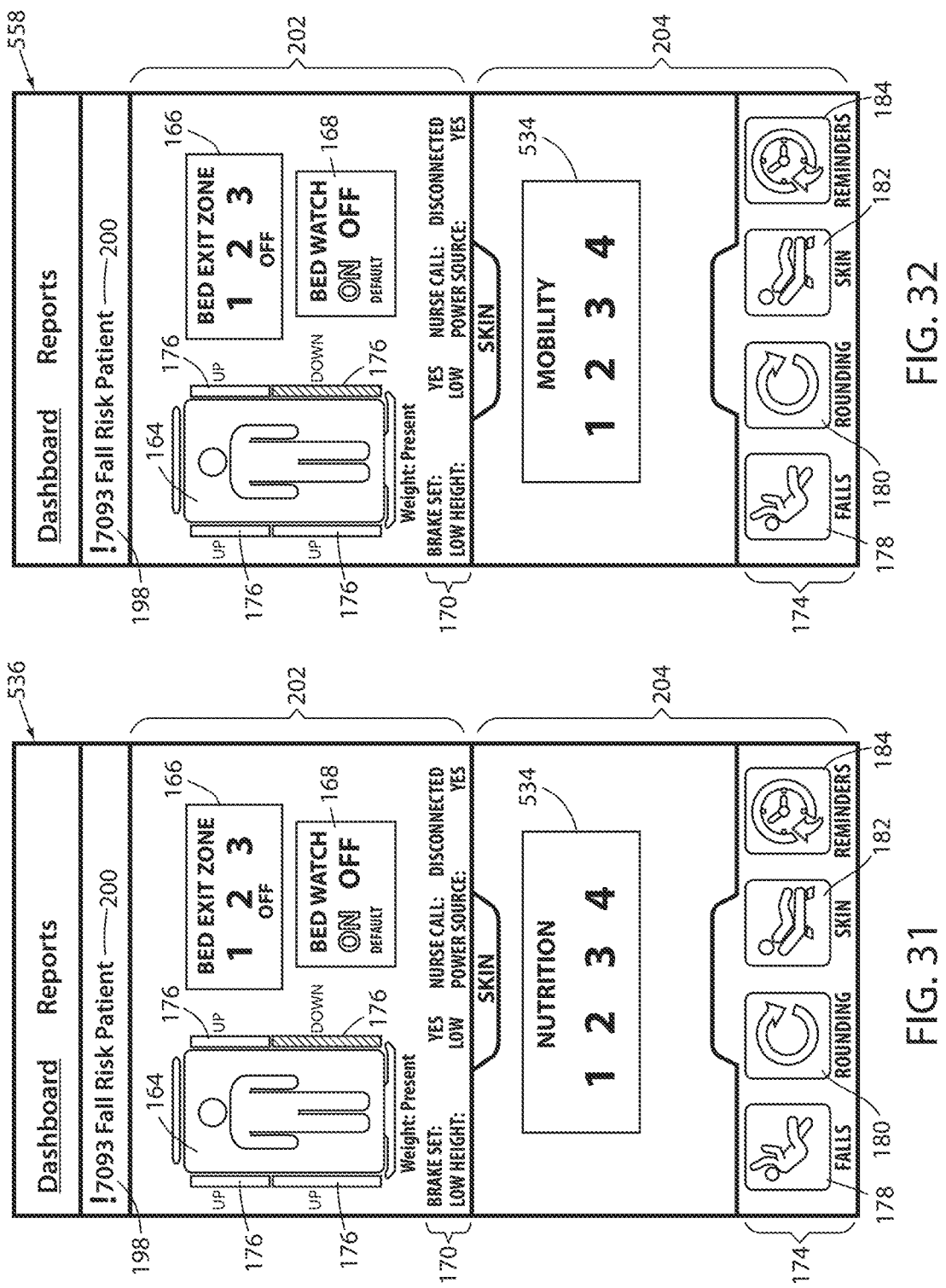
FIG. 31 is an illustrative second skin assessment question screen that is displayable on an electronic device of the caregiver assistance system.
FIG. 32 is an illustrative third skin assessment question screen that is displayable on an electronic device of the caregiver assistance system.

FIG. 32 illustrates a third bed sore risk assessment scoring screen 558. Screen 558 allows the caregiver to assign four different scoring values to the patient's mobility. As noted, the caregiver may choose the desired score value by simply touching the numeric value (e.g. "1," "2", "3", or "4") within window 534, or he or she may access additional information about the each of the particular score values, such as by double tapping on the numeric value, pressing and holding the numeric value for longer than a predetermined time period, or by other means. When the user takes the appropriate action to view this additional information, caregiver assistance application 124 responds by displaying additional informational screens in the manner described above. The content of these additional informational screens with respect to the patient's mobility is discussed below.

If the caregiver requests additional information about the "1" value of the patient's Braden scale mobility component, caregiver assistance application 124 displays a message window that contains the following information, or a variant thereof: "Completely immobile. Patient does not make even slight changes in body or extremity position without assistance."

If the caregiver requests additional information about the "2" value of the patient's Braden scale mobility component, caregiver assistance application 124 displays a message window that contains the following information, or a variant thereof: "Very limited. Patient makes occasional slight changes in body or extremity position but unable to make frequent or significant changes independently."

If the caregiver requests additional information about the "3" value of the patient's Braden scale mobility component, caregiver assistance application 124 displays a message window that contains the following information, or a variant thereof: "Slightly limited. Patient makes frequent though slight changes in body extremity position independently."

If the caregiver requests additional information about the "4" value of the patient's Braden scale mobility component, caregiver assistance application 124 displays a message window that contains the following information, or a variant thereof: "No limitations. Patient makes major and frequent changes in position without assistance."

After displaying third bed sore risk assessment scoring screen 558 at step 528, caregiver assistance application 124 moves to step 554 where it waits for the caregiver to assign a "1", "2", "3" or "4" value to the patient's mobility factor. Once this value is assigned at step 556, caregiver assistance application 124 moves to step 557, where it determines if there are more factors that are to be scored as part of the bed sore risk assessment. In addition, caregiver assistance application 124 updates the running total of the scores that have been assigned to the previously displayed factors (e.g. friction & shear, nutrition, and mobility).

Figures 33, 34:
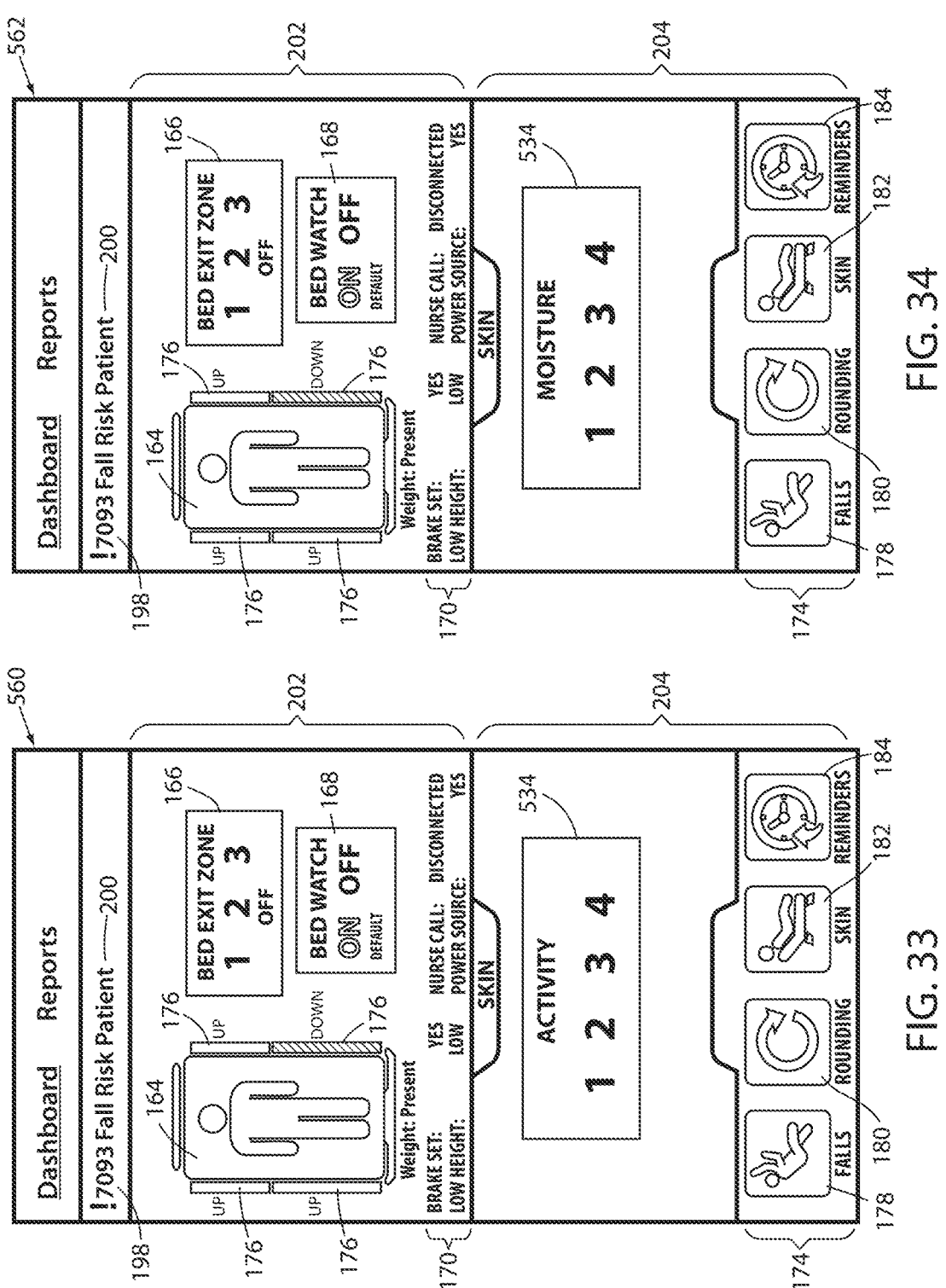
FIG. 33 is an illustrative fourth skin assessment question screen that is displayable on an electronic device of the caregiver assistance system.
FIG. 34 is an illustrative fifth skin assessment question screen that is displayable on an electronic device of the caregiver assistance system.

FIG. 33 illustrates a fourth bed sore risk assessment scoring screen 560. Screen 560 allows the caregiver to assign four different scoring values to the patient's activity levels. The caregiver chooses the desired score value by touching the numeric value (e.g. "1," "2", "3", or "4") within window 534, or he or she may access additional information about the each of the particular score values, such as by double tapping on the numeric value, pressing and holding the numeric value for longer than a predetermined time period, or by other means. When the user takes the appropriate action to view this additional information, caregiver assistance application 124 responds by displaying additional informational screens. The content of these additional informational screens with respect to the patient's activity is discussed below.

If the caregiver requests additional information about the "1" value of the patient's Braden scale activity component, caregiver assistance application 124 displays a message window that contains the following information, or a variant thereof: "Bedfast. Patient confined to bed."

If the caregiver requests additional information about the "2" value of the patient's Braden scale activity component, caregiver assistance application 124 displays a message window that contains the following information, or a variant thereof: "Chairfast. Patient's ability to walk severely limited or non-existent. Cannot bear own weight and/or must be assisted into chair or wheelchair."

If the caregiver requests additional information about the "3" value of the patient's Braden scale activity component, caregiver assistance application 124 displays a message window that contains the following information, or a variant thereof: "Walks occasionally. Patient walks occasionally during day but for very short distances, with or without assistance. Spends majority of each shift in bed or chair."

If the caregiver requests additional information about the "4" value of the patient's Braden scale activity component, caregiver assistance application 124 displays a message window that contains the following information, or a variant thereof: "Walks frequently. Patient walks outside the room at least twice a day and inside room at least once every two hours during waking hours."

After displaying fourth bed sore risk assessment scoring screen 560 at step 528, caregiver assistance application 124 moves to step 554 where it waits for the caregiver to assign a "1", "2", "3" or "4" value to the patient's activity factor. Once this value is assigned at step 556, caregiver assistance application 124 moves to step 557, where it determines if there are more factors that are to be scored as part of the bed sore risk assessment. In addition, caregiver assistance application 124 updates the running total of the scores that have been assigned to the previously displayed factors (e.g. friction & shear, nutrition, mobility, and activity).

FIG. 34 illustrates a fifth bed sore risk assessment scoring screen 562. Screen 562 allows the caregiver to assign four different scoring values to the patient's skin moisture levels. The caregiver chooses the desired score value by touching the numeric value (e.g. "1," "2", "3", or "4") within window 534, or he or she may access additional information about the each of the particular score values, such as by double tapping on the numeric value, pressing and holding the numeric value for longer than a predetermined time period, or by other means. When the user takes the appropriate action to view this additional information, caregiver assistance application 124 responds by displaying additional informational screens. The content of these additional informational screens with respect to the patient's skin moisture is discussed below.

If the caregiver requests additional information about the "1" value of the patient's Braden scale skin moisture component, caregiver assistance application 124 displays a message window that contains the following information, or a variant thereof: "Constantly moist. Patient's skin is kept moist almost constantly by perspiration, urine, etc. Dampness is detected every time patient is moved or turned."

If the caregiver requests additional information about the "2" value of the patient's Braden scale skin moisture component, caregiver assistance application 124 displays a message window that contains the following information, or a variant thereof: "Moist. Patients' skin is often but not always moist. Linen must be changed at least once a shift."

If the caregiver requests additional information about the "3" value of the patient's Braden scale skin moisture component, caregiver assistance application 124 displays a message window that contains the following information, or a variant thereof: "Occasionally moist. Patient's skin is occasionally moist, requiring an extra linen change approximately once a day."

If the caregiver requests additional information about the "4" value of the patient's Braden scale skin moisture component, caregiver assistance application 124 displays a message window that contains the following information, or a variant thereof: "Rarely moist. Patient's skin is usually dry; linen requires changing only at routine intervals."

After displaying fifth bed sore risk assessment scoring screen 562 at step 528 (FIG. 28), caregiver assistance application 124 moves to step 554 where it waits for the caregiver to assign a "1", "2", "3" or "4" value to the patient's skin moisture factor. Once this value is assigned at step 556, caregiver assistance application 124 moves to step 557, where it determines if there are more factors that are to be scored as part of the bed sore risk assessment. In addition, caregiver assistance application 124 updates the running total of the scores that have been assigned to the previously displayed factors (e.g. friction & shear, nutrition, mobility, activity, and skin moisture).

FIG. 35 illustrates a sixth bed sore risk assessment scoring screen 564. Sixth screen 564 is the final screen for the particular skin assessment (i.e. Braden scale) used in this example, but, as noted, caregiver assistance application 124 may utilize different skin assessments, may use customized assessment questions and/or scores, and/or may be modified in other manners. Screen 564 allows the caregiver to assign four different scoring values to the patient's skin sensory perception levels. The caregiver chooses the desired score value by touching the numeric value (e.g. "1," "2", "3", or "4) within window 534, or he or she may access additional information about the each of the particular score values, such as by double tapping on the numeric value, pressing and holding the numeric value for longer than a predetermined time period, or by other means. When the user takes the appropriate action to view this additional information, caregiver assistance application 124 responds by displaying additional informational screens. The content of these additional informational screens with respect to the patient's skin moisture is discussed below.

If the caregiver requests additional information about the "1" value of the patient's Braden scale sensory perception component, caregiver assistance application 124 displays a message window that contains the following information, or a variant thereof: "Unresponsive to painful stimuli due to diminished level of consciousness or sedation."—OR— "Limited ability to feel pain over rest of body surface."

If the caregiver requests additional information about the "2" value of the patient's Braden scale sensory perception component, caregiver assistance application 124 displays a message window that contains the following information, or a variant thereof: "Very limited. Patient responds only to painful stimuli. Cannot communicate discomfort except by moaning or restlessness."—OR—"Has a sensory impairment which limits the ability to feel pain or discomfort over 2 of body."

If the caregiver requests additional information about the "3" value of the patient's Braden scale sensory perception component, caregiver assistance application 124 displays a message window that contains the following information, or a variant thereof: "Slightly limited. Patient responds to verbal commands but cannot always communicate discomfort or need to be turned."—OR—"Has some sensory impairment which limits ability to feel pain or discomfort in 1 or 2 extremities."

If the caregiver requests additional information about the "4" value of the patient's Braden scale sensory perception component, caregiver assistance application 124 displays a message window that contains the following information, or a variant thereof: "No impairment. Patient responds to verbal commands. Has no sensory deficit which would limit ability to feel or voice pain or discomfort."

After displaying sixth bed sore risk assessment scoring screen 564 at step 528 (FIG. 28), caregiver assistance application 124 moves to step 554 where it waits for the caregiver to assign a "1", "2", "3" or "4" value to the patient's sensory perception factor. Once this value is assigned at step 556, caregiver assistance application 124 moves to step 557, where it determines if there are more factors that are to be scored as part of the bed sore risk assessment. In addition, caregiver assistance application 124 updates the running total of all of the scores that have been assigned by the caregiver to the assessment factors (friction & shear, nutrition, mobility, activity, skin moisture, and sensory perception).

It will be understood that, although screens 532, 536, 558, 560, 562, and 564 have been referred to herein as first, second, third, fourth, fifth, and sixth screens, respectively, the particular order of these screens is immaterial and may be varied. Thus, the numeric labels ("first," "second," "third," etc.) have merely been used to distinguish the screens from other ones of the bed sore risk assessment screens, not to indicate any particular significance to their sequential order.

Caregiver assistance application 124, after repeating all of the steps of the assessment scoring subroutine (steps 528, 554, 556, and 558) until all of the risk factors have been scored, then moves to step 568 (FIG. 28) where it assesses the patient's bed sore risk. Although different methods of scoring may be used (and/or customized by a particular healthcare facility), in some embodiments caregiver assistance application 124 converts the numeric bed sore scoring total into a qualitative rating, such as: severe risk, high risk, moderate risk, mild risk, and low risk. For this particular set of qualitative ratings, caregiver assistance application 124 may be configured to assign a "severe risk" rating for numeric scores less than 9, a "high risk" rating for scores of 10-12, a "moderate risk" rating for scores of 13-14, a "mild risk" rating for scores of 15-18, and a "low risk" rating for scores over 18. Other qualitative ratings may be used and/or other score ranges may be selected for matching quantitative scores with qualitative scores. Further, the point values assigned to each individual risk factor may also be varied from that described above.

After determining the patient's qualitative bed sore risk rating, caregiver assistance application sends either or both of the qualitative and quantitative bed sore risk ratings to the EMR server 98 at step 568 (FIG. 28). The bed sore risk rating(s) is/are sent by caregiver assistance application 124 along with one or more identifiers that identify which particular patient the just-completed bed sore risk rating corresponds to. The particular patient to whom the bed sore risk rating is assigned may be determined in any of the manners previously described, such as by correlating the room number of the patient with the patient's ID, correlating the patient support apparatus's identifier 186 with the room and/or the patient's ID, and/or by performing still other correlations. In this regard, it is to be noted that caregiver assistance application 124 displays the room number (and specific bed bay identifier if the room is a shared room) of the patient to whom the bed sore risk rating applies during the display of the screens shown in FIGS. 29-38. In the particular example shown, the room number is "7093," and all of the answers to the bed sore risk questions shown in these screens are assigned to the patient who has been assigned to room 7093. The caregiver therefore is provided with a reminder during the bed sore risk assessment process of the room number (and thus ultimately the specific patient) to which (or whom) the bed sore risk assessment is applicable. In some embodiments, caregiver assistance application 124 may be configured to retrieve the actual patient's name from ADT server 98 and display it during the bed sore risk assessment process so that the caregiver is informed of the specific patient whose bed sore risk they are assessing. Whether displaying the specific patient name or the specific room number, the caregiver ensures that the bed sore risk assessment is attributed to the correct individual by checking that the room number, or patient's name, displayed on the screens 532, 536, 558, 560, 562, and 564 corresponds to the patient (or the patient's room) the caregiver is evaluating for bed sore risk.

After sending the bed sore risk assessment and the corresponding patient identifier to EMR server 98 at step 568, caregiver assistance application 124 displays the qualitative bed sore risk rating at step 530 (FIG. 28). One example of the manner in which the qualitative bed sore risk rating may be displayed is to put a label, such as "high bed sore risk," in the status indicator 160 (e.g. FIG. 8) area of the room listing screen 156. Another option is to put the qualitative bed sore risk in the status location 200 of the various screens (see, e.g. FIG. 39 which shows a fall risk qualitative score in status location 200, but which could be replaced by, or supplemented with, a bed sore qualitative risk score in status location 200). Still other locations may be used for showing the patient's qualitative bed sore risk score.

After completing the bed sore risk assessment, caregiver assistance application 124 displays the quantitative bed sore risk score at step 530. One manner of displaying this score is shown in the bed sore risk score screen 570 of FIG. 39. Bed sore risk score screen 570 includes a score window 572 that contains not only the numeric score of the bed sore risk assessment, but also an identifier identifying the particular risk assessment utilized (i.e. "Braden score") and an "interventions" link that, when pressed, causes caregiver assistance application 124 to display one or more suggested interventions (i.e. risk-reduction steps) for reducing the likelihood of the patient developing bed sores. That is, if the caregiver touches on the "see interventions" link of FIG. 39, caregiver assistance application 124 responds by suggesting one or more steps that the caregiver should take (or consider taking, depending upon the policy of the particular healthcare facility in which the system 106 is installed) in order to reduce the risk of the patient developing a bed sore, or worsening an existing bed sore. The suggested step(s) are based on the bed sore risk reduction protocol 95 that is stored in memory 91, or in another location accessible to caregiver assistance application 124.

Bed sore risk reduction protocol 95 specifies the steps that caregivers are to follow for patients based on their bed sore risk assessment scores. The particular steps to follow may be different for different scores of the bed sore risk assessment. In many embodiments, these steps are saved in the local rules repository 126 and are at least partially dictated by the healthcare facility in which system 106 is installed. That is, when system 106 is purchased by the healthcare facility, one or more authorized individuals load whatever steps the healthcare facility selects into bed sore risk reduction protocol 95. Caregiver assistance application 124 is therefore customizable to the particular bed sore risk reduction protocol(s) followed by a particular healthcare institution. Generally speaking, the bed sore risk reduction protocol 95 identifies one or more steps to be taken with respect to the patient's mattress 38. Additionally, protocol 95 may also specify other steps, such as, but not limited to, applying one or more pressure reduction devices to one or more portions of the patient's body (e.g. a boot heel protector, one or more foam wedges, etc.), turning the patient, and/or other steps.

At step 574 (FIG. 28), caregiver assistance application 124 retrieves bed sore risk reduction protocol 95 from memory 91 (or from whatever other location it may be stored at). After retrieving protocol 95, caregiver assistance application 124 moves to step 576 where it displays the one or more interventions that are to be followed by the caregiver in order to reduce the patient's risk of developing and/or aggravating a bed sore. One example of the manner in which caregiver assistance application 124 may display these interventions is shown in a general intervention screen 578 depicted in FIG. 40. As shown therein, general intervention screen 578 includes an intervention window 580. Within intervention window 580, caregiver assistance application 124 displays those portions of protocol 95 that correspond to the particular fall risk assessment score of that particular patient. In this case, the interventions within window 580 correspond to the interventions of protocol 95 that are specific to a patient scoring a "12" on the Braden scale. As can be seen therein, the general interventions of window 580 specify that the caregiver should "consider a protocol that increases frequency of turning; supplements turning with small shifts in position; facilitates maximal remobilization; protects the patient's heels; provides a pressure-reducing support surface; provides foam wedges for 30 degree lateral support." Other intervention or risk-reduction steps can, of course, be included within window 580.

Figure 41:
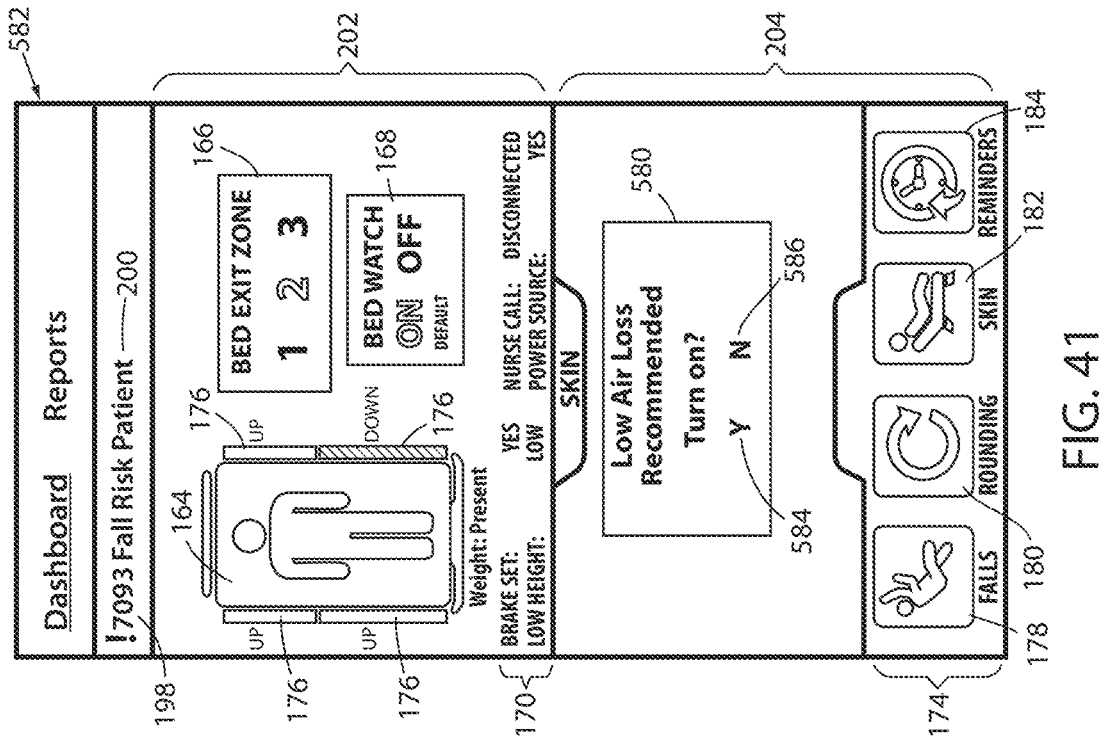
FIG. 41 is an illustrative specific intervention screen that suggests setting the patient's mattress to a low air loss mode and that is displayable on an electronic device of the caregiver assistance system.

For example, in some embodiments, caregiver assistance application 124 is configured to suggest more specific steps to take with regard to mattress 38. These specific steps include setting the mattress 38 to one or more specific states and/or implementing one or more therapies utilizing mattress 38. As noted previously, such therapies may include percussion, lateral rotation, turn assistance, low air loss, maximum inflation, etc. One example of a specific intervention screen 582 is shown in FIG. 41. Specific intervention screen 582, like general intervention screen 578 of FIG. 40, may be displayed by caregiver assistance application 124 in response to the caregiver touching the "see interventions" link in window 572 of screen 570 (FIG. 39), or it may be displayed automatically a predetermined time period after displaying the bed sore risk assessment score at step 530, or it may be displayed in response to other triggers.

Specific intervention screen 582, in the example shown in FIG. 41, suggests to the caregiver that he or she turn on a low air loss feature of mattress 38 as part of the protocol 95 for reducing the patient's risk of developing or exacerbating a bed sore. Window 580 allows the caregiver to select whether he or she wishes to implement this mattress feature or not by touching either the "Y" icon 584 (yes) or the "N" icon 586 (no). The selection of "Y" icon 584 or "N" icon 586 corresponds to step 588 of bed sore risk reduction algorithm 141 (FIG. 28). If the caregiver selects "Y" icon 584, caregiver assistance application 124 proceeds to step 590. If the caregiver selects "N" icon 586, caregiver assistance application 124 proceeds to step 592.

It will be understood that the specific intervention screen 582 is merely one example of the type of screen that may be displayed as part of step 588 of algorithm 141. Depending upon the bed sore risk reduction protocol 95 of a particular healthcare facility, as well as the risk assessment score for the particular patient, as well as the features available for that patient's mattress 38, one or more interventions screens 582 may be displayed at step 588 that include different content within intervention window 580. Further, the interventions suggested by caregiver assistance application 124 may include multiple settings or commands related to the mattress 38, and those multiple settings and/or commands may be displayed serially as part of step 588, with the caregiver selecting "yes" or "no" to each one of the suggested interventions. Still other manners of displaying the suggested interventions and allowing the caregiver to select such interventions may also be implemented.

If the caregiver selects the "Y" icon 584 at step 588, caregiver assistance application 124 proceeds to step 590 where it sends a command to patient support apparatus 20 that corresponds to the particular suggestion the caregiver accepted at step 588. In the example illustrated in FIG. 41, the particular suggested intervention is to turn on a low air loss feature of mattress 38. In at least one embodiment, caregiver assistance application 124 is configured to distinguish between commands that call for movement of a component of the patient support apparatus 20 and commands that do not call for movement of a component of the patient support apparatus 20. In such embodiments, caregiver assistance application 124 only sends commands to patient support apparatus 20 for actions that do not involve movement. For those actions that involve movement, caregiver assistance application 124 sends an informational message to patient support apparatus 20 that the caregiver wishes to carry out a movement action, but instructs patient support apparatus 20 to delay carrying out the desired movement action until the caregiver is physically present adjacent the patient support apparatus 20 and the caregiver physically activates the movement action (e.g. by pressing on one or more controls of one of the patient support apparatus control panels 42). In some embodiments, patient support apparatus 20 is configured to respond to such informational messages from caregiver assistance application 124 by saving the content of the informational messages and preconfiguring the patient support apparatus 20 to carry out the desired movement action in response to a single physical input from the caregiver, or some other reduced number of physical inputs. In other words, in some embodiments, patient support apparatuses 20 are configured to take all necessary steps in preparation for the movement action such that the caregiver only needs to physically press on the control panel 42 once, or another reduced set of times. This helps reduce the amount of work required of the caregiver to carry out the suggested intervention.

In the example shown in FIG. 41, the low air loss setting of mattress 38 is considered a non-movement action, and caregiver assistance application 124 is configured in at least one embodiment to allow the caregiver to remotely start the low air loss function of mattress 38 (i.e. while the caregiver is not present in the room of patient support apparatus 20) using either mobile electronic device 104a or stationary electronic device 104b. Thus, when the user selects "Y" icon 584 in screen 582, caregiver assistance application 124 sends a command to the corresponding patient support apparatus 20 instructing the corresponding controller 48 to turn on the low air loss feature of its mattress 38. In response, controller 48 turns on this air loss feature and sends an acknowledgement back to caregiver assistance application 124, which displays the acknowledgement on the specific electronic device 104a, 104b from which the caregiver sent the low air loss command. This acknowledgement is sent at step 594 of algorithm 141 (FIG. 28). The display of the acknowledgement on the screen of the corresponding electronic device 104a, 104b is performed at step 596.

After receiving and displaying the acknowledgement from patient support apparatus 20 at steps 594 and 596, caregiver assistance application 124 proceeds to step 598 of algorithm 141 (FIG. 28). At step 598, caregiver assistance application 124 may receive one or more updates from patient support apparatus 20 regarding the settings and/or therapies being carried out by mattress 38. For example, such updates may include: low-air loss therapy started, or low-air loss therapy unable to start, or low-air loss therapy interrupted. The updates, of course, are modified according to the particular mattress feature or function to which they pertain and the particular type of status being updated. In some cases, no updates are provided and caregiver assistance application 124 proceeds from step 596 to step 592. However, if any update is received at step 598, caregiver assistance application 124 displays the update at step 600 on the screen of the electronic device 104 from which the command was sent at step 590.

In some embodiments, caregiver assistance application 124 is configured to display the update at step 600 on any and/or all other electronic devices 104 that are configured to display data for that particular patient and/or that particular room. Thus, for example, if a caregiver A sends a command at step 590 to a patient support apparatus 20 that is located in ward B of the healthcare facility and caregiver A is being supervised by caregiver C (or sharing responsibility for that particular patient with caregiver C), caregiver assistance application 124 is configurable by authorized personnel of the healthcare facility (e.g. person 136) to send out and display updates at steps 598 and 600 to not only the electronic device 104 associated with caregiver A, but also the electronic device 104 associated with caregiver C and, in some cases, one or more stationary electronic devices 104b that are associated with ward B. Regardless of the specific list of recipients of the update at steps 598 and 600, caregiver assistance application 124 proceeds to step 592 after completing step 600.

At step 592 of skin care algorithm 141 (FIG. 28), caregiver assistance application 124 continues to monitor whether the interventions suggested at step 576 have been implemented or not, as well as to issue reminders to complete the steps and to issue notifications of any alerts that arise from the interventions. In general, caregiver assistance application 124 adds at step 592 one or more tasks to the task list 886 (FIG. 57) that is continuously monitored by reminder algorithm 145. The added tasks are for generating reminders for caring out the steps suggested at step 576, including, in at least some cases, reminders for steps that have not been accepted by the caregiver. Thus, for example, if the caregiver selects "no" at step 588 to a particular step or task, caregiver assistance application 124 is configured to add a reminder for this task to the task list 886 monitored by reminder algorithm 145 so that the caregiver is periodically issued reminders regarding the step or task that they elected not to implement at step 588.

Similar reminders are added to task list 886 for interventions that involve motion actions in those embodiments where caregiver assistance application 124 is configured such that motion actions for patient support apparatuses 20 cannot be carried out remotely. In such embodiments, reminder algorithm 145 continues to monitor status outputs from the patient support apparatuses 20 to see when the caregiver physically touches the appropriate control(s) on the control panel(s) 42 to activate the motion action, and if the caregiver does not implement the motion action within a prescribed time period (which may vary depending on the action and/or the bed sore risk assessment score), reminder algorithm 145 sends a reminder to the caregiver to complete the suggested motion action.

From step 592, caregiver assistance application 124 proceeds to step 526, which takes the application back to main algorithm 226. It will be understood that, although algorithm 141 is depicted in FIG. 28 as returning to main algorithm 226 at step 526, at least step 592 of skin care algorithm 141 continues to run in the background of main algorithm 226 such that the caregivers are apprised of changes in the status of skin care interventions and/or receive updates regarding their progress.

As was discussed previously, skin care algorithm 141 can be used to perform other functions besides those discussed above, such as, but not limited to, controlling one or more features of the mattress 38 separately from the risk-reduction steps (i.e. interventions) that are automatically suggested at step 576. Such mattress control functionality is selected at step 538 of the algorithm 141 by touching any one of the mattress control icons displayed on, for example, skin care overview screen 502 (FIG. 29). In the example shown in FIG. 29, these mattress control icons include patient turn icon 508, max inflate icon 512, and low air loss icon 514. It will be understood that, depending upon the particular features of the mattress 38 for a particular patient, the control icons displayed on screen 502 will vary such that the displayed control icons match the controllable features of the corresponding mattress 38. In other words, with respect to the example of FIG. 29, if the patient support apparatus 20 of room 7093 has a mattress 38 that does not include a max inflate function, max inflate icon 512 will not be included on screen 502. Alternatively, if that mattress 38 includes a percussion function, a lateral rotation function, or some other mattress therapy function, caregiver assistance application 124 will display corresponding control icons on screen 502.

Figure 42:
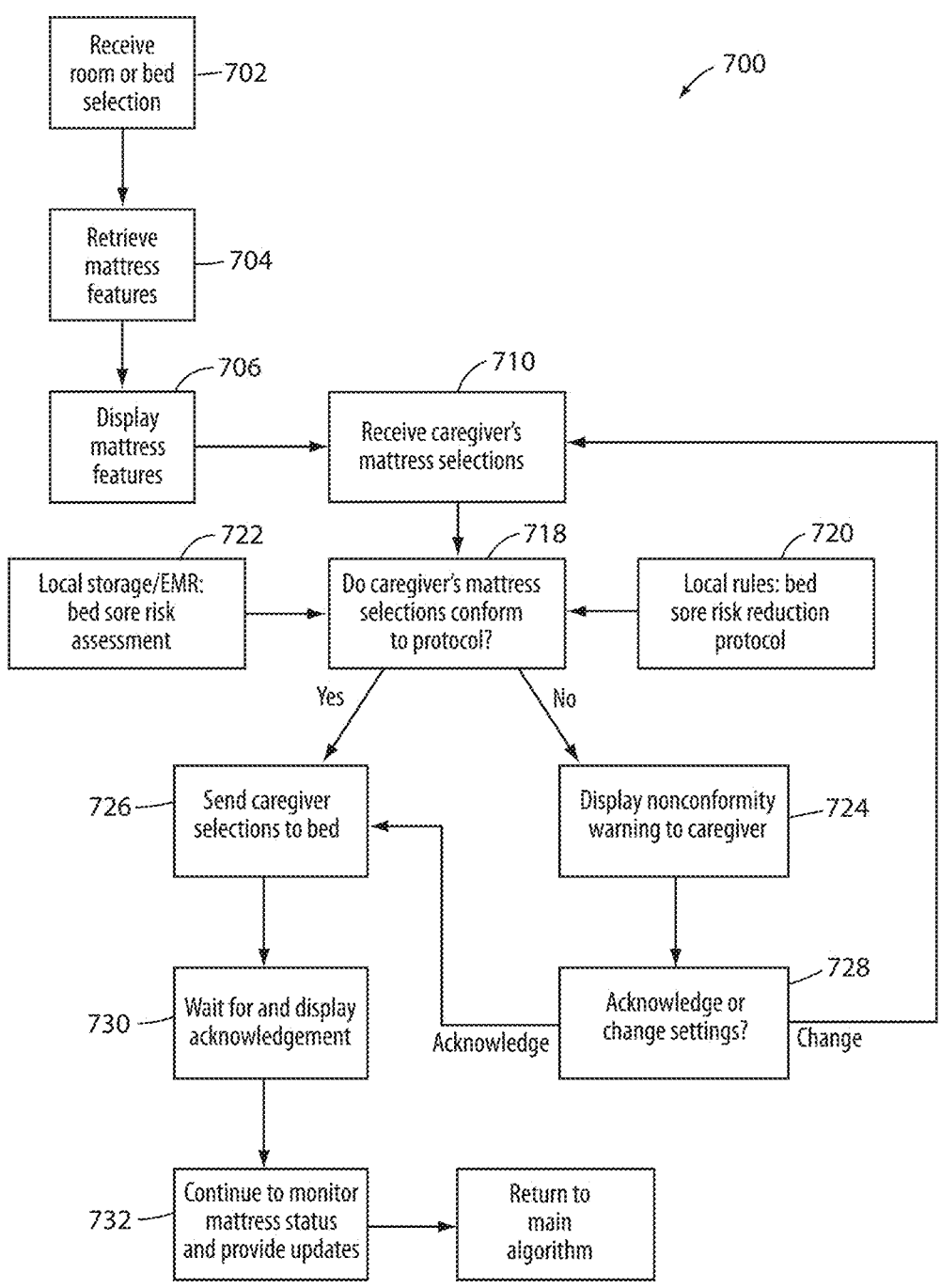
FIG. 42 is a flow diagram of a mattress control algorithm that may be executed by the caregiver assistance application.

If the caregiver selects any of the mattress control icons of screen 502 (FIG. 29), caregiver assistance application 124 commences mattress control algorithm 700, one example of which is shown in FIG. 42. Mattress control algorithm 700 may alternatively be started in other manners. Regardless of how started, algorithm 700 starts at step 702 where caregiver assistance application 124 determines which room or bed bay the mattress 38 to be controlled is located in. In most instances, this information is already known from the room number and/or bed bay number displayed in room identifier location 198. Therefore, the caregiver doesn't have to do anything for step 702 unless the caregiver wishes to control the mattress 38 of a patient support different from the one that is identified in the skin care overview screen 502 (or the caregiver navigates to screen 502 from another screen that doesn't have a room, bed bay, and/or patient identifier associated with it).

After identifying the room or bed selection at step 702, caregiver assistance application 124 proceeds to step 704 where it retrieves the mattress features that are available for the particular mattress 38 that is to be controlled. In some embodiments, such as those discussed above, step 704 is carried out in association with screen 502 of FIG. 29 (or before screen 502 of FIG. 29 is displayed) so that caregiver assistance application 124 knows which control icons to display with the skin care menu 504 of screen 502. In still other embodiments, step 704 may be performed automatically whenever a patient support apparatus 20 is communicatively coupled to caregiver assistance application 124, every time a new patient is assigned to a patient support apparatus 20, every time a new mattress 38 is detected at a patient support apparatus 20, periodically, or in response to other factors. Regardless of the specific time at which step 704 occurs, caregiver assistance application 124 receives a message from each patient support apparatus 20 that identifies what features the mattress 38 supported thereon possesses. In some embodiments, the patient support apparatus 20 sends one or more messages that identify the specific features of the mattress, while in other embodiments, the patient support apparatuses 20 identify the make and/or model of the mattress 38 (or some other identifier), and caregiver assistance application 124 determines the features of that mattress 38 from a database of mattress information (which may be saved as part of data repository 128, or stored elsewhere).

At step 706, caregiver assistance application 124 displays the features of the corresponding mattress 38 on the electronic device 104a or 104b that the caregiver is using to access caregiver assistance application 124. In most embodiments, a separate control icon is displayed for each feature or function, and the user simply selects which feature or function to control by touching the corresponding control icon. Other manners of displaying the features or functions, as well as other manners of allowing the caregiver to select those features or functions may, of course be utilized. FIGS. 43-49 depict several examples of the various manners in which caregiver assistance application 124 may display mattress control screens associated with mattress control algorithm 700. It will be understood that caregiver assistance application 124 is configured in some embodiments to carry out additional mattress control functions beyond those illustrated in these figures.

Figures 43, 44:
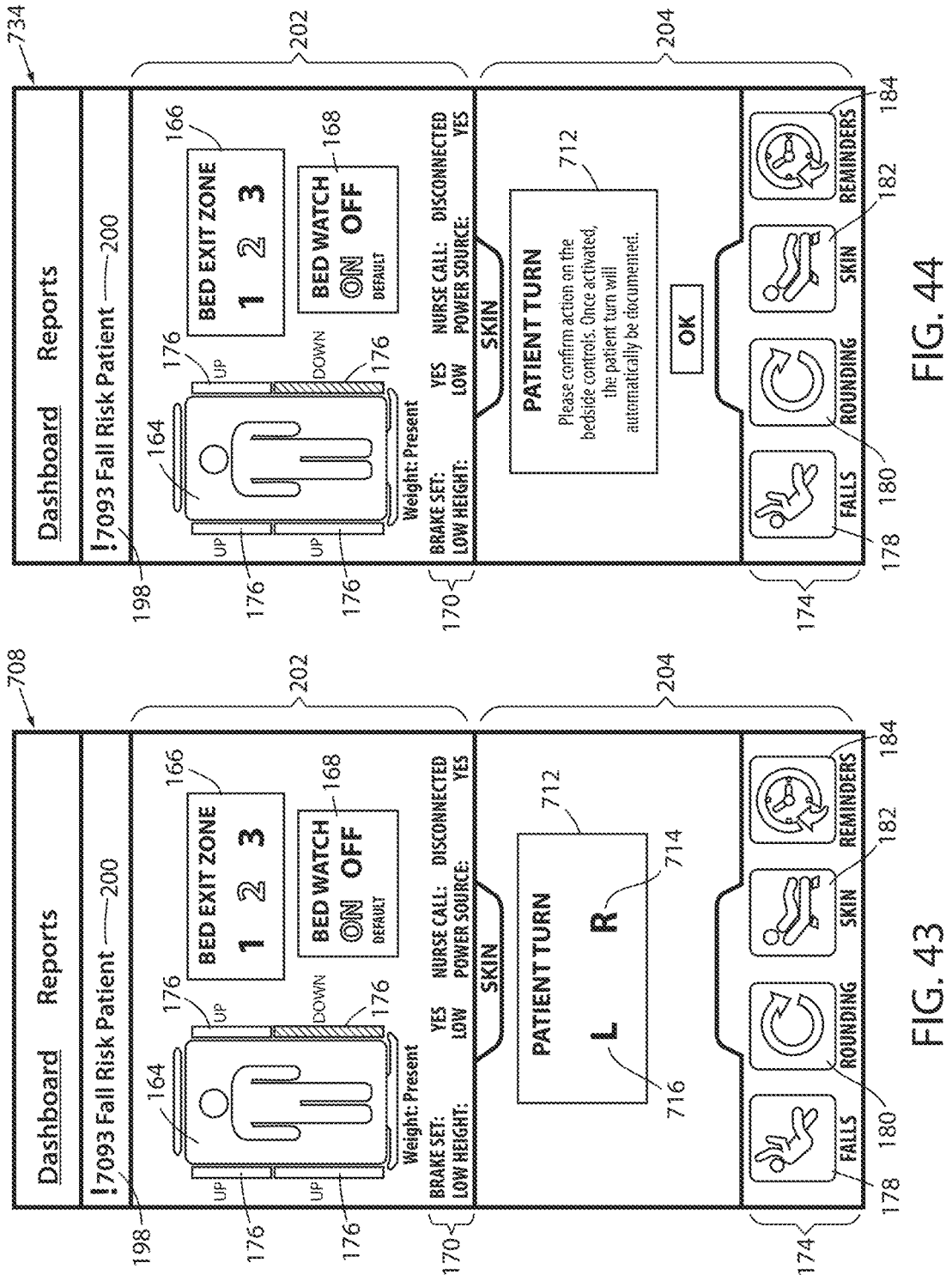
FIG. 43 is an illustrative first patient turning screen that is displayable on an electronic device of the caregiver assistance system.
FIG. 44 is an illustrative second patient turning screen that is displayable on an electronic device of the caregiver assistance system.

FIG. 43 illustrates one manner of displaying a patient turn control screen 708. Patient turn control screen 708 is displayed in response to the caregiver selecting the turn control icon (not shown) at step 710 of algorithm 700. Patient turn control screen 708 includes a turn window 712 having an "R" icon 714 and an "L" icon 716. The caregiver selects the "R" icon 714 if the caregiver wants the mattress 38 to turn the patient toward his or her right, and the caregiver selects the "L" icon 714 if the caregiver wants the mattress 38 to turn the patient toward his or her left. The caregiver selects both if he or she wants the patient turned to both the right and the left.

After making the selections of the "R" icon 714, "L" icon 716, and/or both at step 710, caregiver assistance application 124 proceeds to step 718 of algorithm 700. At step 718, caregiver assistance application 124 checks to see if the mattress setting or therapy selected at step 710 conforms to the bed sore risk reduction protocol 95 given the patient's fall risk assessment score. Thus, caregiver assistance application 124 completes step 718 with an input 720 from the bed sore risk reduction protocol 95 and an input 722 from the bed sore risk assessment score. Both of these inputs are taken from either the local rules 126, data repository 128, and/or EMR server 98. Using these inputs, caregiver assistance application 124 determines if the selection made at step 710 is in conformance with the intervention (bed sore-risk reduction) steps dictated by the bed sore risk reduction protocol 95 for that patient's particular bed sore risk score. Caregiver assistance application 124 therefore double checks to see if the caregiver is controlling the mattress 38 in a manner that is consistent with the bed sore risk reduction protocol 95 or not. If the mattress control function selected at step 710 does not conform to the risk reduction steps of the protocol 95, caregiver assistance application 124 proceeds to step 724. If the mattress control function selected at step 710 does conform to the risk reduction steps of the protocol 95, caregiver assistance application 124 proceeds to step 726.

Turning first to step 724 (FIG. 42), if the risk reduction step selected by the caregiver at step 710 does not conform to the bed sore risk reduction protocol 95, caregiver assistance application 124 displays a non-conformity notification screen (not shown) at step 724. The non-conformity notification screen alerts the caregiver to the fact that his or her selection at step 710 is not in conformance with the healthcare facility's risk reduction protocol 95. The screen includes an "acknowledgement" control and a "change" control such that the caregiver can either acknowledge the notification of non-conformity and proceed in spite of the notification, or the user can go back to step 710 and change the mattress control selection. Thus, at step 728 the caregiver is presented with the option of returning to step 710 ("change") or continuing with the mattress control feature originally selected at step 710 ("acknowledge"). If the user selects the "change" option, caregiver assistance application 124 returns to step 710 of algorithm 700 and proceeds in the manner previously described.

If the caregiver selects the "acknowledge" option at step 728, caregiver assistance application 124 proceeds to step 726 where it sends the caregiver's mattress control selection(s) to the corresponding patient support apparatus 20. After sending these selections, caregiver assistance application 124 waits at step 730 for an acknowledgement from the patient support apparatus 20 indicating that the patient support apparatus 20 received the selections. Caregiver assistance application 124 also displays a message at step 730 on the corresponding electronic device 104 indicating the acknowledgement was received from the patient support apparatus 20. From step 730, caregiver assistance application 124 proceeds to step 732 where it continues to monitor the status of the mattress 38, continues to receive updates from the mattress 38, and continues to provide alerts and/or notifications to the caregiver of any changes to the status of mattress 38. From step 732, caregiver assistance application 124 returns back to main algorithm 226 or to skin care algorithm 141. As with many of the other algorithms discussed herein, the return of algorithm 700 back to main algorithm 226 and/or to skin care algorithm 141 does not mean the caregiver assistance application 124 discontinues the monitoring of the mattresses 38. Instead, caregiver assistance application 124 continues to perform step 732 in the background while caregiver assistance application 124 is being used by the caregiver for other tasks.

FIG. 44 illustrates an example of a second patient turning screen 734 that is displayable in those embodiments of caregiver assistance application 124 that do not permit a caregiver to remotely control a motion function of the patient support apparatus 20. Second patient turning screen 734 includes a turning window 712 in which is contained a reminder to the caregiver that motion commands cannot be carried out remotely, but instead must be performed locally at the patient support apparatus 20 using one of the control panels 42. In the specific example shown in FIG. 44, the motion command selected by the caregiver is a turning function, which involves inflating one side of the mattress in order to partially turn the patient while he or she is positioned on the mattress 38. Because this moves both the patient and a side of the mattress, it involves motion, and therefore must be carried out locally (in at least one embodiment) using the controls of the patient support apparatus 20, not the electronic devices 104.

As was noted previously, caregiver assistance application 124 is configured to send the turning information selected by the caregiver at step 710 to the patient support apparatus 20, even if the turning information involves the selection of a motion function. In such situations, patient support apparatus 20 is configured to save the selections received and automatically implement those saved selections at the time the caregiver activates the corresponding mattress control using one of the control panels 42 on the patient support apparatus 20. Thus, for example, in the case of the turning function, caregiver assistance application 124 is configured to send to patient support apparatus 20 data indicating whether the patient is to be turned to the right, to the left, in both directions, and/or other information (e.g. for how long, with what intervals, for how many times, to what angular extent, etc.). Patient support apparatus 20 receives this information and, when the caregiver activates the turning function locally using a control panel 42, controller 48 automatically uses the turning information received from the caregiver via caregiver assistance application 124. This allows the caregiver to remotely prepare the patient support apparatus 20 for a movement function.

Figures 45, 46:
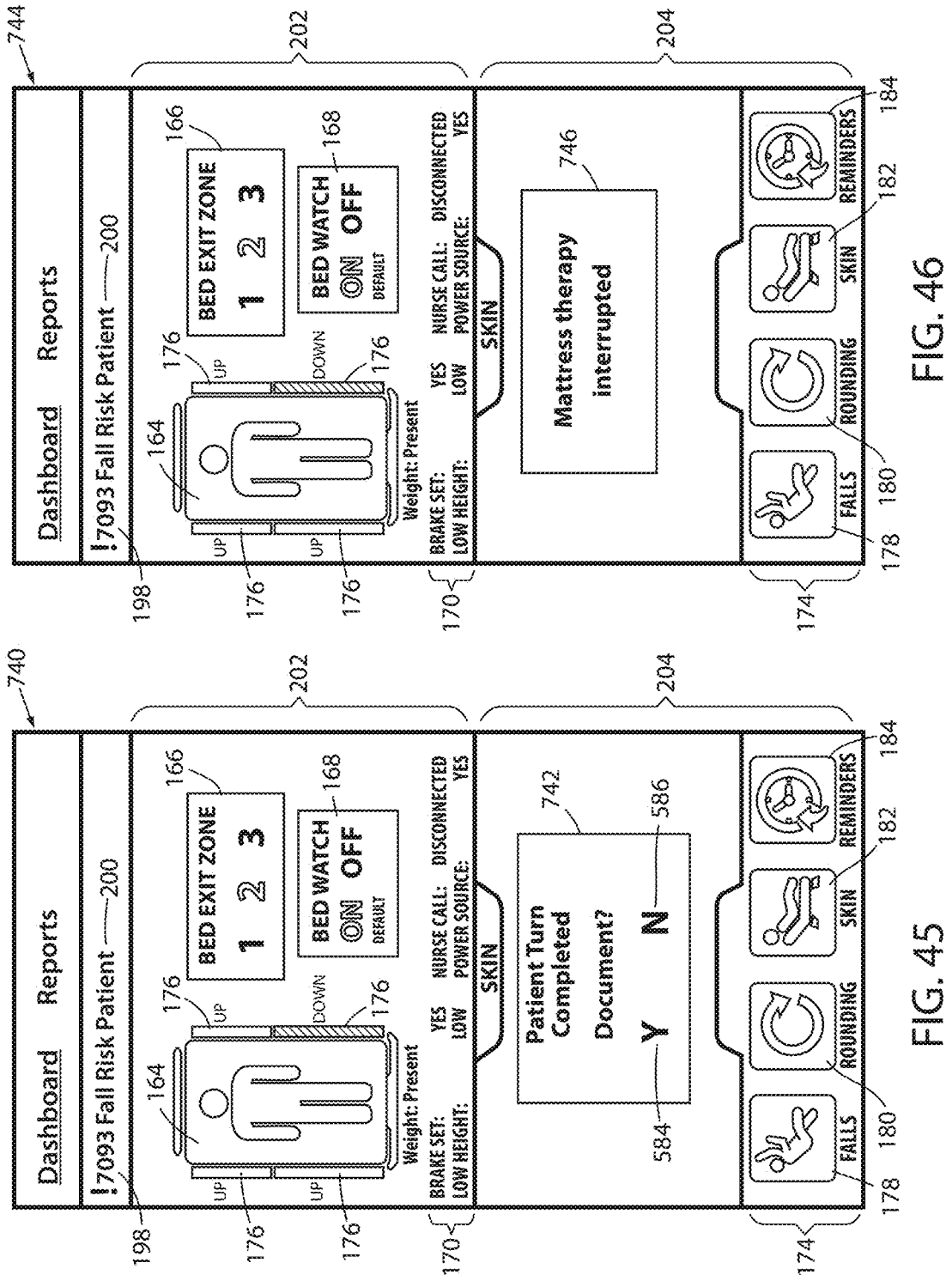
FIG. 45 is an illustrative documentation confirmation screen that is displayable on an electronic device of the caregiver assistance system.
FIG. 46 is an illustrative mattress therapy status screen that is displayable on an electronic device of the caregiver assistance system.

FIG. 45 illustrates an example of a documentation confirmation screen 740 that is displayable on one or more of the electronic devices 104 of system 106 when a mattress therapy has been completed for a patient. Although FIG. 45 illustrates an example specifically for patient turning, it will be understood that caregiver assistance application 124 is configured to display similar screens for other mattress therapies and/or mattress functions as well. Caregiver assistance application 124 displays confirmation screen 740, or one like it, when it detects the completion by patient support apparatus 20 of a mattress therapy. This is detected by the patient support apparatus 20 sending a message to caregiver assistance application 124 which forwards the message to the appropriate electronic device(s) 104. Documentation confirmation screen 740 includes a documentation window 742 in which a "Y" icon 584 and an "N" icon 586 are displayed. Documentation confirmation screen 740 allows the caregiver to select whether or not the completion of the mattress therapy (e.g. turning) should be sent to the EMR server 98 for documentation purposes. In order to do so, the caregiver selects the "Y" icon 584 and caregiver assistance application, in response thereto, sends data regarding the completed mattress therapy to EMR server 98. If the caregiver does not wish to document the therapy to the EMR, he or she selects the "N" icon 586 and caregiver assistance application 124 returns to whatever task/display screen it was previously displaying.

FIG. 46 illustrates an example of a mattress therapy status screen 744 that is displayable on one or more of the electronic devices 104 of system 106 when an update to a mattress therapy session is received by the corresponding electronic device 104. Although FIG. 46 illustrates an example specifically for patient turning, it will be understood that caregiver assistance application 124 is configured to display similar screens for other mattress therapies and/or mattress functions as well. Caregiver assistance application 124 displays a status update window 746 on screen 744 when it receives a message from the corresponding patient support apparatus 20 indicating a change in the status of the mattress therapy. Depending upon the particular change in the therapy, status update window 746 may include additional information about the status change, such as, but not limited to, the cause of the change, one or more commands to send back to the patient support apparatus 20, an acknowledgement control icon, etc. After the caregiver acknowledges status update window 746, or takes other action in response thereto, caregiver assistance application 124 may return to displaying the screen that it was previously displaying prior to its interruption by status screen 744.

Figure 47:
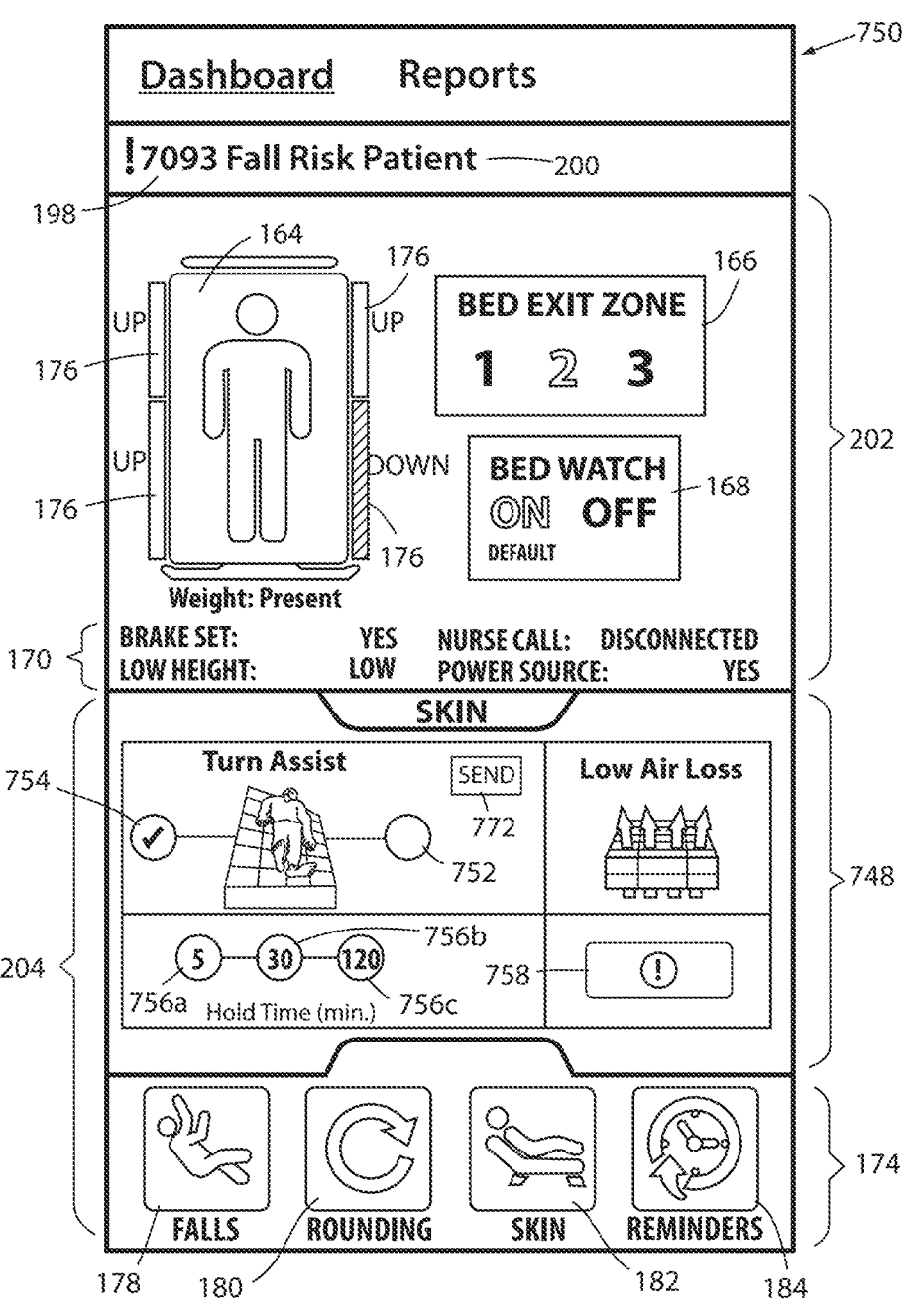
FIG. 47 is an illustrative first mattress parameter selection that is displayable on an electronic device of the caregiver assistance system.
Figure 48:
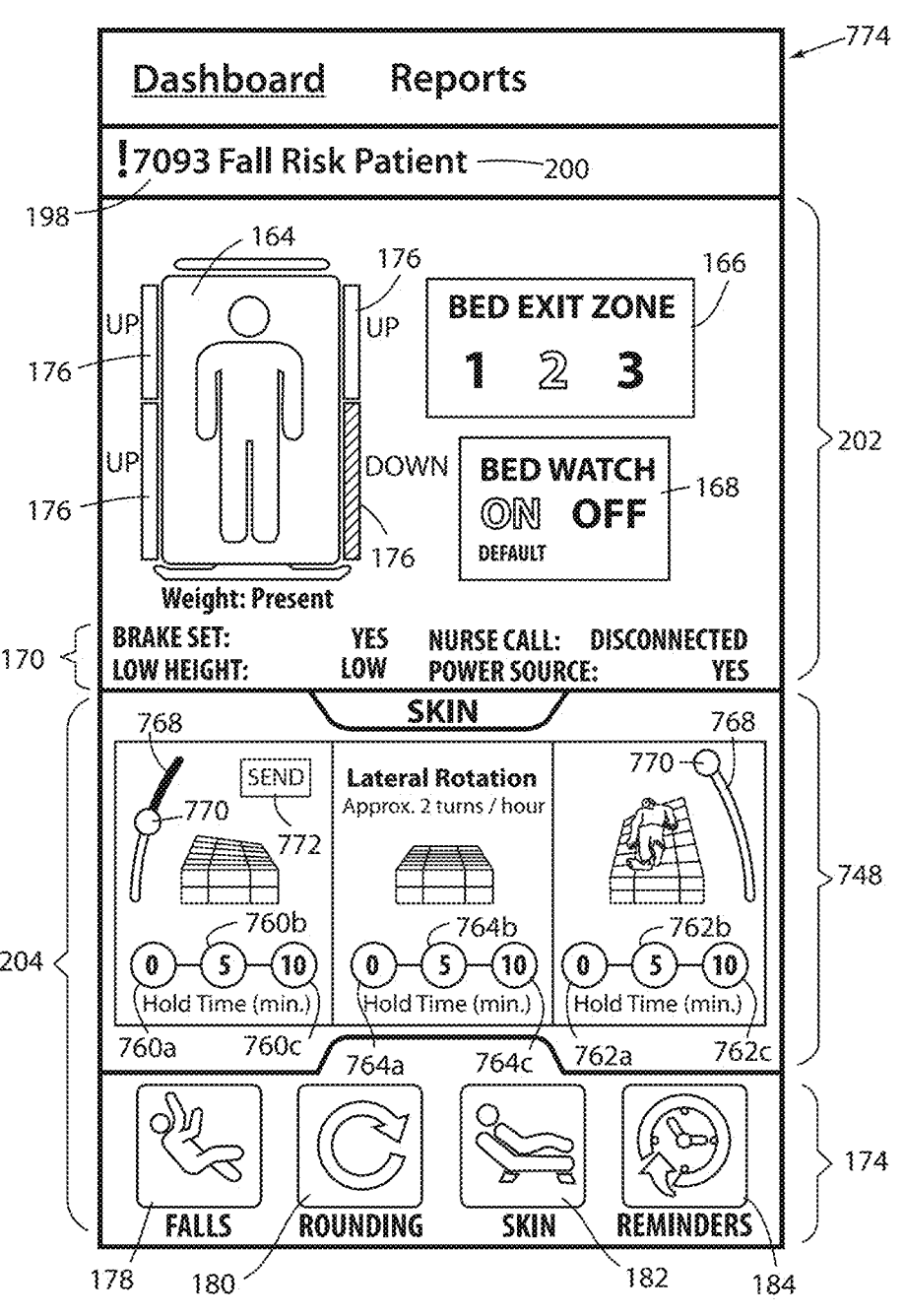
FIG. 48 is an illustrative second mattress parameter selection that is displayable on an electronic device of the caregiver assistance system.
Figure 49:
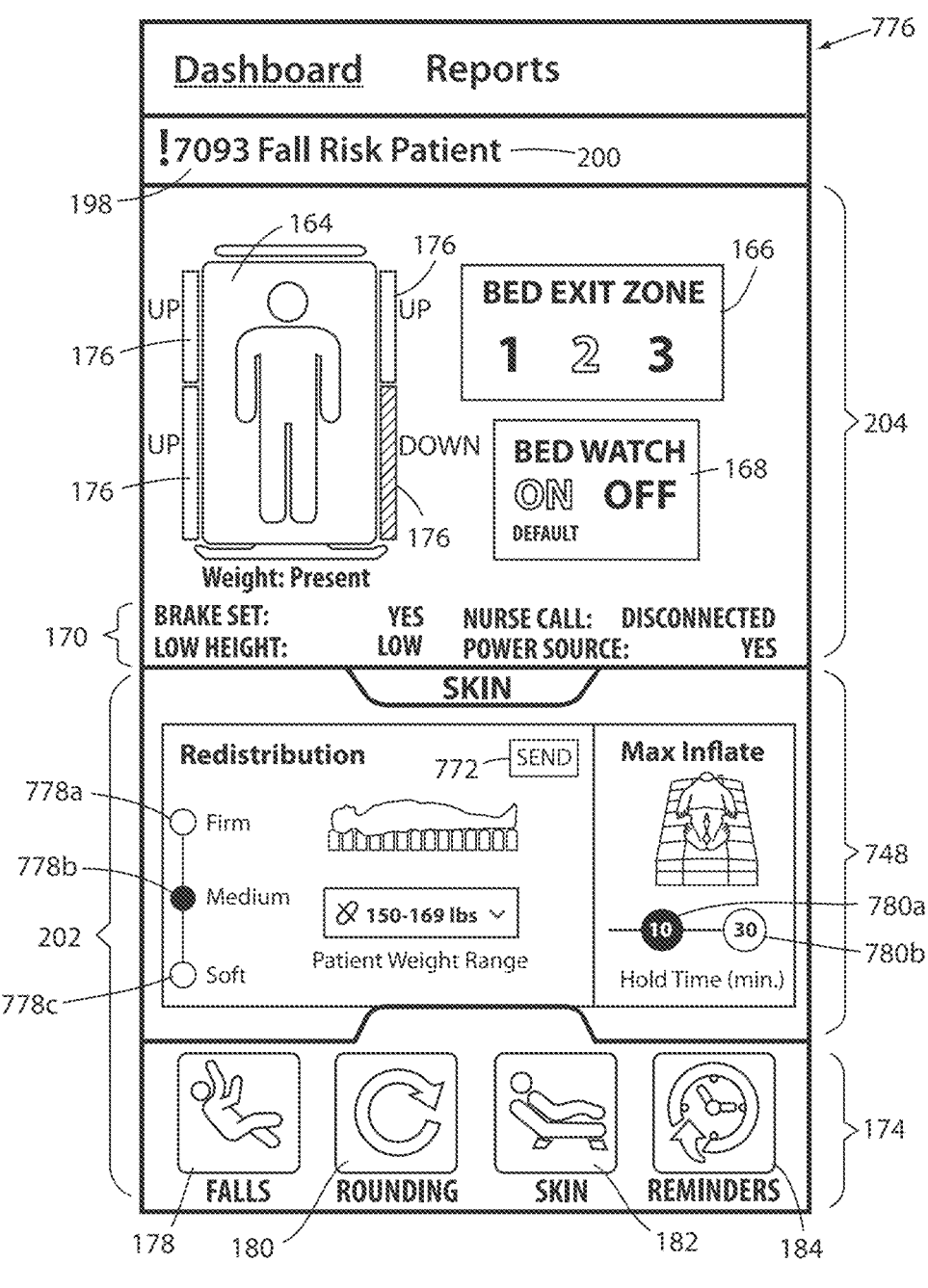
FIG. 49 is an illustrative third mattress parameter selection that is displayable on an electronic device of the caregiver assistance system.

FIGS. 47-49 illustrate several examples of additional mattress control parameters that may be selected by the caregiver using caregiver assistance application 124 and one or more of the corresponding electronic devices 104a, 104b. In some embodiments, patient support apparatuses 20 are configured to not only send the control features of their respective mattresses 38, but they are configured to send control graphics and/or other control information that is to be displayed on the screens of devices 104a, 104b by caregiver assistance applications. In such embodiments, caregiver assistance application 124 displays a control area 748 of the mattress parameter selection screens on devices 104 in the same visual manner as it is displayed on the control panel(s) 42 of the patient support apparatus 20, thereby making it easier for the caregiver to recognize the controls and relieving the caregiver of the task of having to learn a new control layout. By manipulating the various control icons within the control area 748, the caregiver is able to carry out remote control of those features of the mattress 38 that do not involve motion. Further, by manipulating the various control icons within the control area 748, the caregiver is able to remotely set up one or more mattress parameters for those features of the mattress 38 that do involve motion, thereby preparing the patient support apparatus 20 for such motion when the caregiver reaches the patient support apparatus 20, and thereby reducing the amount of work needed by the caregiver when he or she reaches the patient support apparatus 20 and wishes to start the motion feature of the mattress 38.

Turning first to a first mattress parameter selection screen 750 shown in FIG. 47, caregiver assistance application 124 displays various control parameters related to both a turn assist function and a low air low function. More specifically, control area 748 includes a right turn icon 752, a left turn icon 754, and three hold time icons 756a-c. If the user wishes to set up patient support apparatus 20 for turning the patient to the right, he or she presses the right turn icon 752. If the caregiver wishes to set up patient support apparatus 20 for turning the patient to the left, he or she presses the left turn icon 754. If the caregiver wishes to set up patient support apparatus 20 for performing both right and left turns, he or she selects both icons 752 and 754. The caregiver is also able to use control area 748 to select the duration of the turns by selecting one of the three hold time icons 756a-c. The caregiver is also able to turn on/off the low air loss function of the mattress using a low air loss control icon 758. Further control icons may be included in control area 748, depending upon the particular turn assist features and low air loss features of the mattress 38. Also, as noted above, the graphics and/or layout of control area 748 may vary, depending upon the patient support apparatus 20 and the visual graphics and layouts it displays on its control panel 42 for controlling the mattress 38.

After making these desired selections related to turning and low air loss, the caregiver presses a send control icon 772 on screen 760. The send control icon 772 causes caregiver assistance application 124 to send the selected mattress parameters to the patient support apparatus 20. Patient support apparatus 20 stores these parameters in its memory and uses them to prepare the mattress 38 for executing a turn assist function according to the selected parameters. As a result, when the caregiver approaches the patient support apparatus 20, all he or she needs to do is to touch a turn assist control and controller 48 will start changing the inflation states of one or both of the sides of mattress 38 in order to help turn the patient in accordance with the parameters that the caregiver selected using his or her electronic device 104.

FIG. 48 illustrates a second mattress parameter selection screen 774. Control area 748 of second mattress parameter selection screen 774 includes a plurality of control icons for selecting a plurality of mattress control parameters related to a lateral rotation function that periodically turns the patient to his or her side. In particular, control area 748 of screen 774 includes a plurality of left hold time icons 760a-c, a plurality of right hold time icons 762a-c, a plurality of flat hold time icons 764a-c, a left angular slide bar 766, and a right angular slide bar 768. Each of the angular slide bars 766 and 768 includes an angle selector 770. By touching and sliding the angle selector 770 to different locations along the length of the corresponding slide bar 766 or 768, the caregiver is able to select the angle at which the patient will be rotated. If the caregiver doesn't wish the patient to be turned to the left, for example, he or she can slide angle selector 770 all the way to the bottom of left slide bar 766, which corresponds to an angle of zero, and therefore causes the mattress (when the lateral rotation function is activated) to not rotate the patient to the left. In contrast, if the caregiver wishes to rotate the patient to the left the maximum amount (e.g. the largest angle that mattress 38 is capable of), he or she slides the angle selector 770 all the way to the top of left slide bar 766.

Control area 748 of mattress parameter selection screen 774 therefore enables the caregiver to select not only the rotation directions (right/left), but also the angular extent of those rotations (using slide bars 766, 768), as well as the length of time that the patient is held at each of the selected angular orientations (hold time icons 760a-c and 762a-c) and the length of time the patient is held flat between such rotations (hold time icons 764a-c). After making these selections, the caregiver presses the send control icon 772 and caregiver assistance application 124 sends the selected mattress parameters to the patient support apparatus 20. Patient support apparatus 20 stores these parameters in its memory and uses them to prepare the mattress 38 for executing a lateral rotation therapy session according to the selected parameters. As a result, when the caregiver approaches the patient support apparatus 20, all he or she needs to do is to touch a lateral rotation activation control and controller 48 will start providing lateral rotation therapy via mattress 38 in accordance with the parameters that the caregiver selected via one of the electronic devices 104 using caregiver assistance application 124.

FIG. 49 illustrates a third mattress parameter selection screen 776. Control area 748 of third mattress parameter selection screen 776 includes a plurality of control icons for selecting a plurality of mattress control parameters related to the inflation state of mattress 38. In particular, control area 748 of screen 776 includes a plurality of mattress firmness selection icons 778a-c and a plurality of maximum inflation hold time icons 780a-b. If the caregiver wishes to change the inflation level of mattress 38 from "firm" or to "medium" or to "soft," he or she simply presses the corresponding firmness selection icon 778a-c. If the caregiver wishes to utilize the maximum inflation feature of mattress 38, he or she touches one of the hold time icons 780a-b (or touches one of them a second time to toggle the selection off, and thereby turn off the maximum inflation function). Once the caregiver has made his or her selections, he or she presses the send control icon 772 and caregiver assistance application 124 sends the selected mattress parameters to the patient support apparatus 20. Patient support apparatus 20 stores these parameters in its memory and uses them to prepare the mattress 38 for executing a mattress firmness change and/or a maximum inflation therapy session. As a result, when the caregiver approaches the patient support apparatus 20, all he or she needs to do is to touch a firmness change control and/or a maximum inflation control and controller 48 will start to implement the selected feature using the parameters that the caregiver selected.

It will be understood that screens 750, 774, and/or 776 may be modified in a variety of different manners. For example, any one or more of them may include additional control icons allowing the caregiver to navigate from one of these screens to another. In such embodiments, when the caregiver is finished making his or her selections on a first one of these screens, he or she can easily navigate to another one of these screens if he or she wishes to send additional mattress control parameters to the patient support apparatus 20. Once the caregiver has completed his or her selections, touching the send control icon 772 once causes caregiver assistance application 124 to send all of the selected parameters to patient support apparatus 20 from all of the screens 750, 774, and/or 776 that were accessed by the caregiver. Still other modifications are possible.

It will also be understood that the number of mattress parameter selection screens may be varied from the three shown in FIGS. 47-49. Further, there is no significance to the terms "first," second, and "third used to describe these three screens 750, 774, and 776. The sequence in which these screens are displayed may, of course, be varied, and the content of any one or more of these screens may be combined with others of these screens, or modified in still other manners.

From the foregoing description of mattress control algorithm 700, it can be seen that caregiver assistance application 124 automatically checks to see if the mattress control parameters selected by the caregiver conform to the bed sore risk reduction protocol 95. Further, this automatic conformance checking occurs both when the caregiver uses application 124 to perform a bed sore risk assessment (via algorithm 141) and when the caregiver skips the bed sore risk assessment function and instead proceeds directly to controlling the mattress 38 using the mattress control algorithm 700. Caregiver assistance application 124 therefore helps ensure that all of the mattress therapy functions that are implemented by a caregiver are in accordance with the healthcare facility's standards for treating patients having elevated bed sore risk levels.

Caregiver assistance application 124 is also configured to send alerts and/or notifications to the caregiver (and other personnel) if the caregiver uses one of the control panels 42 of a patient support apparatus 20 to implement a mattress therapy function that is not in accordance with the bed sore risk reduction protocol. Whenever a patient support apparatus 20 controls mattress 38 in a manner prescribed by inputs from one of its control panels 42, it sends a message to caregiver assistance application 124 indicating the mattress function it is performing, as well as details about the parameters it is using for that function (e.g. turn angle, hold time, etc.). Caregiver assistance application 124 checks this data to ensure that it complies with the bed sore risk reduction protocol 95 and, if it does not, it sends a message to the caregiver and/or to other authorized personnel (e.g. the caregiver's supervisor). In this manner, caregiver assistance application 124 monitors and ensures that all mattress control commands—whether input remotely via an electronic device 104a, 104b, or input locally via one of control panels 42—are in conformance with the bed sore risk reduction protocol 95.

As part of this conformance checking process, caregiver assistance application 124 also monitors the absence of any mattress control functions being implemented on a particular mattress 38. This absence monitoring refers to the absence of a mattress control function implemented either remotely using one of the electronic devices 104 or directly using one of the control panels 42 located on the patient support apparatus 20. Thus, for example, if a patient has an elevated risk of developing bed sores and none of the desired mattress therapies and/or state changes of bed sore risk reduction protocol 95 are implemented, caregiver assistance application 124 sends a reminder and/or other message to the appropriate caregiver(s).

Figure 50:
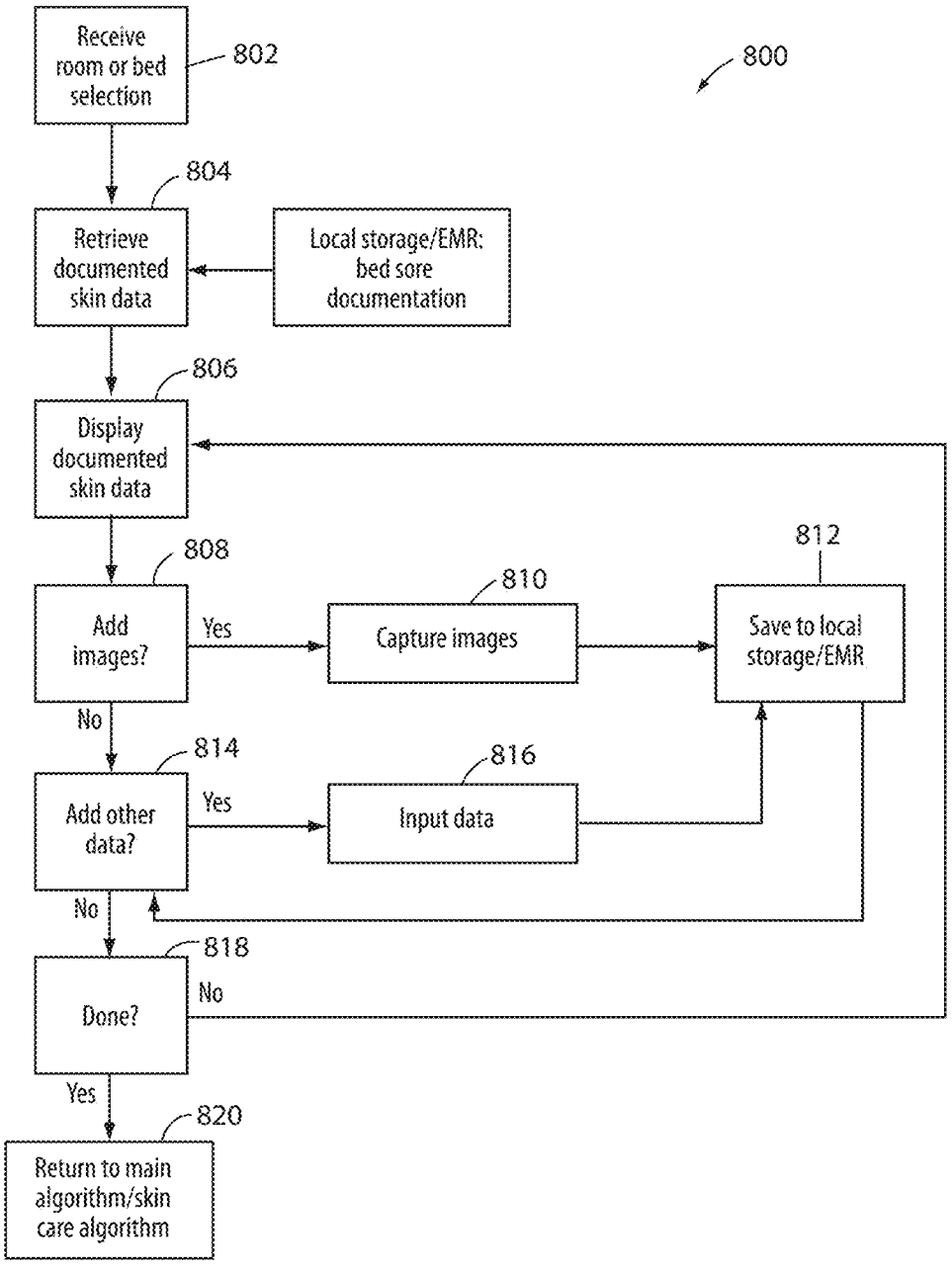
FIG. 50 is a flow diagram of a skin care documentation algorithm that may be executed by the caregiver assistance application.

If the caregiver selects the skin documentation icon 510 of screen 502 (FIG. 29), caregiver assistance application 124 commences skin documentation algorithm 800, one example of which is shown in FIG. 50. Skin documentation algorithm 800 may alternatively be started in other manners. Regardless of how started, algorithm 800 starts at step 802 where caregiver assistance application 124 determines which room or bed bay the patient is located in whose skin condition is to be documented. In most instances, this information is already known from the room number and/or bed bay number displayed in room identifier location 198. Therefore, the caregiver doesn't have to do anything for step 802 unless the caregiver wishes to document a skin condition of a patient who is located in a room or bed bay different from the one that is identified in the skin care overview screen 502 (FIG. 29), or unless the caregiver starts algorithm 800 from a screen that doesn't have a room, bed bay, and/or patient identifier associated with it.

After step 802 of skin documentation algorithm 800 (FIG. 50), caregiver assistance application 124 proceeds to step 804 where it retrieves any skin documentation that has been previously saved for that particular patient. Such prior skin documentation may be saved both on EMR server 98 and within data repository 128, and caregiver assistance application 124 checks both locations and retrieves whatever skin documentation data is saved at either or both of these locations. After retrieving this data, application 124 proceeds to step 806 where it displays the retrieved skin care documentation. Depending upon the volume of data that has been previously documented, caregiver assistance application 124 may initially display only a portion of the data along with navigation tools (e.g. forward and backward arrows, page jump icons, etc.) that enable the caregiver to use electronic device 104 to efficiently view all of the documentation that has been previously been saved.

At step 808 (FIG. 50), caregiver assistance application 124 displays a prompt, indicator, or other selection control that enables the caregiver to choose whether he or she wishes to add any image data to the skin documentation. Such image data includes pictures taken of one or more locations of the patient's skin using a digital camera. If the caregiver wishes to add one or more of such images, he or she selects the image addition option and caregiver assistance application 124 proceeds to step 810. At step 810, the caregiver uses the built-in camera of his or her mobile electronic device 104a to capture one or more images of the patient's skin. After the caregiver has finished taking digital images, application 124 proceeds to step 812 where it saves the images to the patient's medical records by sending them to EMR server 98. In some embodiments, caregiver assistance application 124 may also save the images to data repository 128.

After completing step 812, caregiver assistance application 124 proceeds to step 814 where it inquires whether the caregiver wishes to add any other data regarding the patient' skin conditions. Such other data may include measurements, notes, or other information that is not captured, or is otherwise not easily seen from, the image data captured at step 810. If the caregiver wishes to add such additional data, application 124 proceeds to step 816 where the caregiver enters the additional data. After step 816, application 124 returns to step 812 and sends the additional data to EMR server 98 and/or data repository 128.

After the caregiver has added image data and/or other data to the medical record of the patient at steps 810 and 816, caregiver assistance application 124 proceeds to step 818 where it inquires of the caregiver whether he or she is finished adding such data. If the caregiver is not finished, application 124 returns to step 806 and proceeds in the manner previously described. If the caregiver is finished, application 124 proceeds to step 820 where it returns back to executing main algorithm 226, bed sore risk reduction algorithm 141, and/or mattress control algorithm 700.

FIGS. 51-56 illustrate several examples of different screens that may be displayed by caregiver assistance application 124 on electronic devices 104 during the execution of skin documentation algorithm 800. It will be understood that these screens are merely illustrative examples of several types of screens that caregiver assistance application 124 may be configured to display. Additional screens may be displayed and/or fewer screens may be displayed. Further, the content of whatever screens are displayed may be modified from the examples shown in FIGS. 51-56. Finally, the reference to "first," "second," "third," etc. with respect to the screens of FIGS. 51-56 is not meant to signify any sequential order to these screens, but instead is used merely to distinguish one screen from another.

Figures 51, 52:
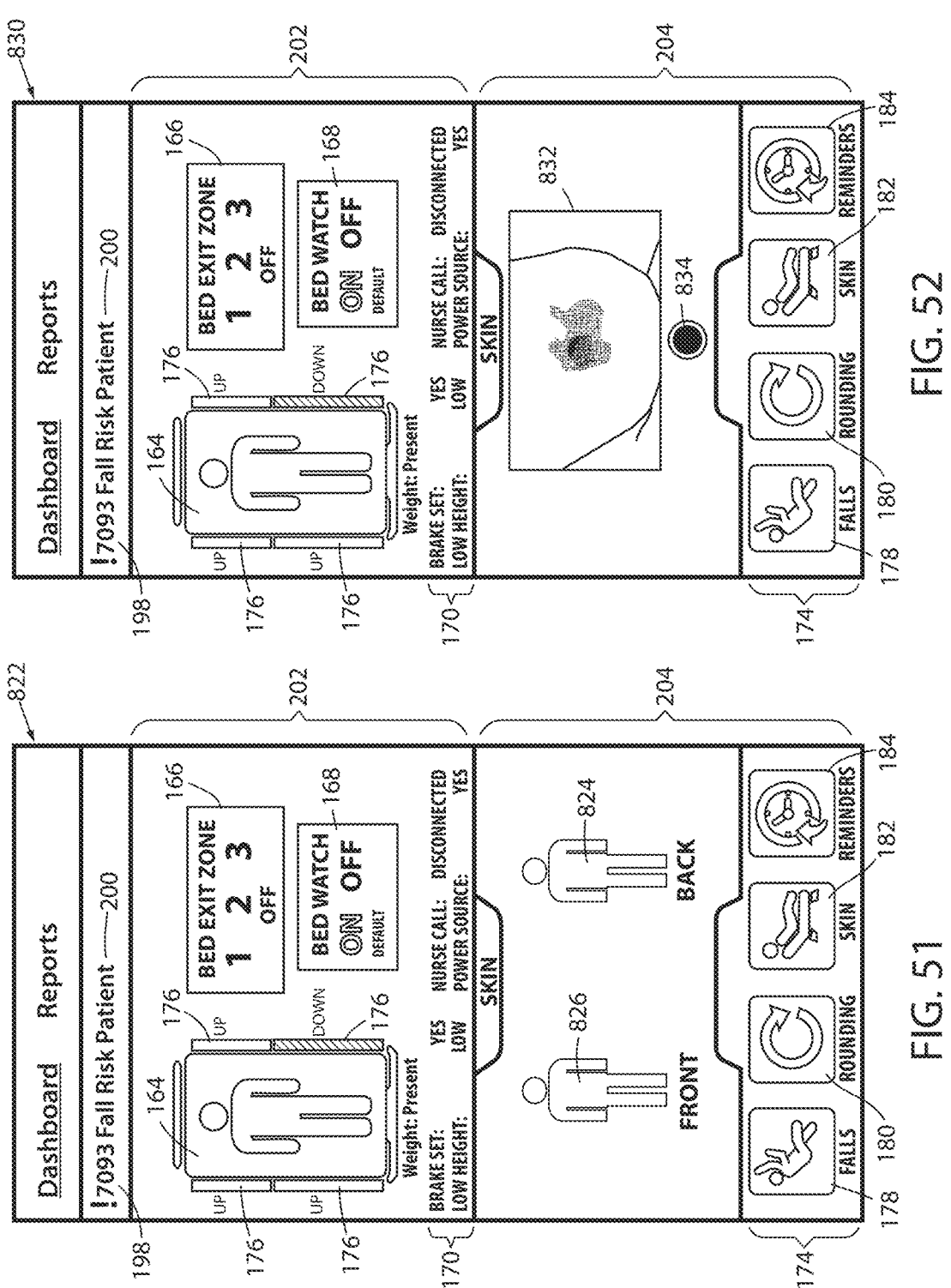
FIG. 51 is an illustrative first skin care data input screen that is displayable on an electronic device of the caregiver assistance system.
FIG. 52 is an illustrative skin care image input screen that is displayable on an electronic device of the caregiver assistance system.

FIG. 51 illustrates a first skin care data input screen 822. First skin care data input screen 822 is displayed by caregiver assistance application 124 during step 810 or 816 in order to document which side of the patient the skin data being entered corresponds to. If the caregiver wishes to enter data regarding a skin condition located on the back of the patient, the caregiver presses a back icon 824. If the caregiver wishes to enter data regarding a skin condition that is located on the front of the patient, he or she presses a front icon 826. Screen 822 may be modified to allow a user to specify the location of the skin condition with even greater granularity, or additional screens may be included for specifying this additional granularity. Such additional granularity may include icons for specifying that the skin condition is located on the patient's right or left leg, right or left arm, right or left hand, right or left foot, head, torso, and/or at other more specific locations. Once the user makes the desired selection, caregiver assistance application 124 associates the data that is subsequently added to the patient's medical record (or that was immediately previously added, in some embodiments) as corresponding to the selected location on the patient's body. Thus, the location selection function of screen 822 enables the caregiver to easily and graphically specify the location of the skin condition he or she is documenting, and this information is included as part of the data that is sent at step 812.

FIG. 52 illustrates a second skin care data input screen 830. Second skin care data input screen 830 is displayed by caregiver assistance application 124 during step 810 when the caregiver wishes to add image data to the patient's medical documentation. Screen 830 includes an image window 832 and a capture icon 834. The image window 832 shows the image that the built-in camera of the electronic device 104 is currently sensing. Image window 832 thus changes dynamically as the caregiver moves the electronic device 104 to different locations and/or orientations. The capture icon 834 is touched by the caregiver when the caregiver wishes to take and save a picture corresponding to the image currently shown in window 832. After the user touches the capture icon 834, the captured image is sent at step 812 to the EMR server 98 and/or data repository 128.

It will be understood that second skin care data input screen is only functional for those electronic devices 104 that include built-in cameras, which is typically the case for smart phones 104a, tablets 104a, and/or laptops 104a. Stationary electronic devices 104b and certain other mobile electronic devices 104a, however, might not include such a camera. For such electronic devices 104, screen 830 is either not functional or caregiver assistance application 124 may be configured to not display screen 830 at all (as well as any other screens associated with step 810).

Figures 53, 54:
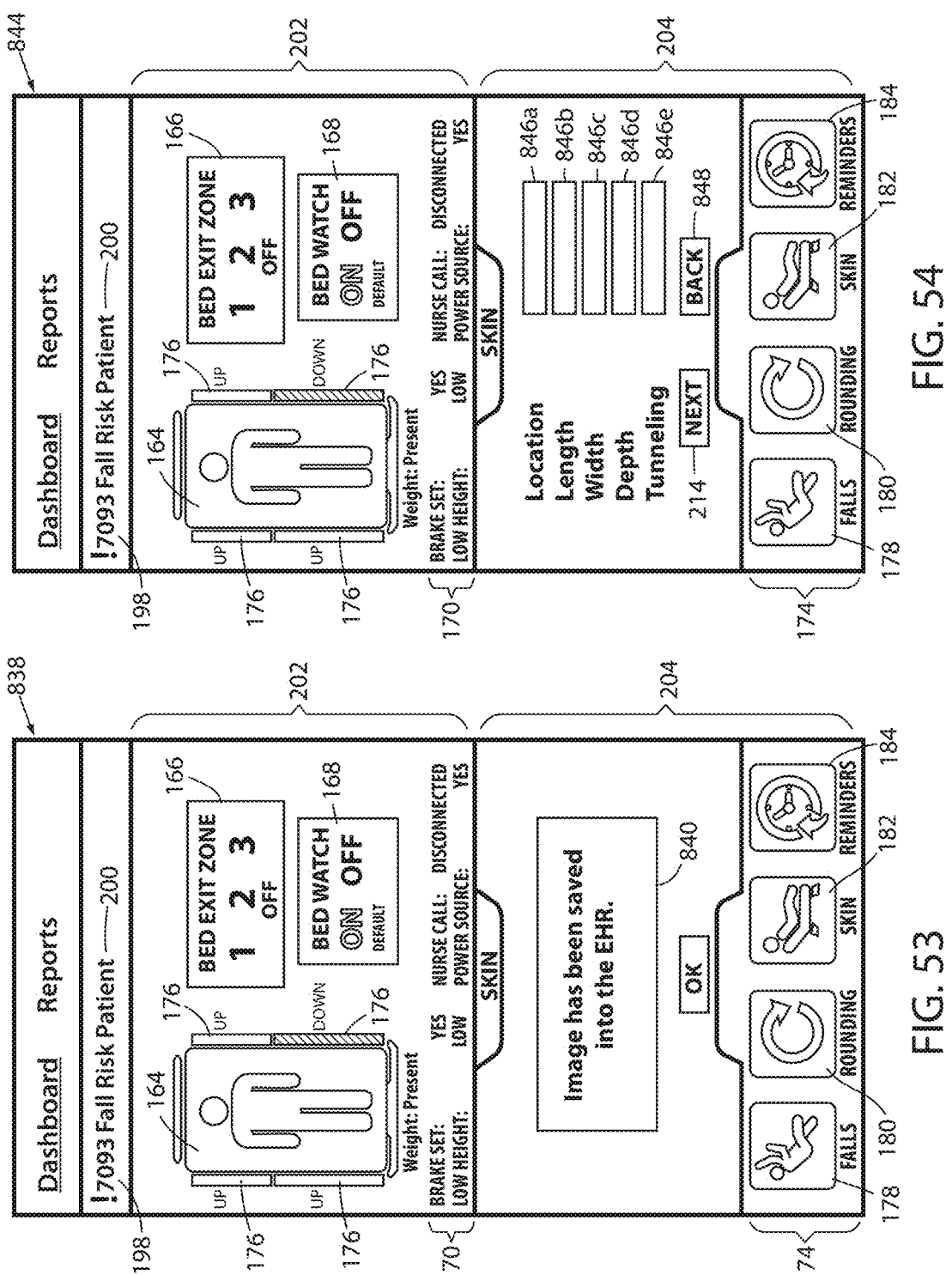
FIG. 53 is an illustrative skin care documentation confirmation screen that is displayable on an electronic device of the caregiver assistance system.
FIG. 54 is an illustrative second skin care data input screen that is displayable on an electronic device of the caregiver assistance system.

FIG. 53 illustrates a documentation confirmation screen 838 that is displayed by caregiver assistance application 124 after the caregiver has sent data to the EMR server 98 and/or data repository 128 at step 812 of algorithm 800. Documentation confirmation screen 838 includes an information window 840 in which caregiver assistance application 124 displays information regarding the status of the information sent to EMR server 98 and/or data repository 128. That is, once the data is sent at step 812, caregiver assistance application 124 awaits an acknowledgement from either or both recipients and, once received, displays information within window 840 confirming that the sent data was received and saved. If no acknowledgement is received, or there is another error in the transmission or receipt of the data, caregiver assistance application 124 displays other information about the error within window 840. Caregiver assistance application 124 therefore provides information to the caregiver that either confirms the documentation of skin data and/or lets the caregiver know if there was an error in the documentation process.

FIG. 54 illustrates a third skin care data input screen 844. Third skin care data input screen 844 is displayed on an electronic device 104 by caregiver assistance application 124 during the data input step 816. Third skin care data input screen 844 includes a plurality of data input windows 846a-e. Although the specific data input windows 846a-e shown in FIG. 54 are used by the caregiver to input data regarding an existing bed sore, it will be understood that other data input windows 846 may be displayed in association with screen 844 in order to input other data regarding one or more conditions of the patient's skin. In the specific example shown in FIG. 54, data input window 846a is used to specify the location of the patient's existing bed sore; data input window 846b is used to specify the length of the existing bed sore; data input window 846c is used to specify the width of the existing bed sore; data input window 846d is used to specify the depth of the bed sore; and data input window 846e is used to specify whether the bed sore is tunneling or not. In order to input data into these windows 846, the caregiver may use either the physical keypad of the electronic device 104 (if there is one) or a virtual keypad that is displayed on the screen (not shown) after the user presses on one of the windows 846. After the caregiver is finished inputting the desired data, the caregiver can select either the "next" icon 214 or a "back" icon 848. Touching "next" icon 214, in some embodiments, takes the caregiver to a screen like screen 850 of FIG. 55. Touching "back" icon 848, in some embodiments, takes the caregiver back to one of the previously described data input screens (e.g. screen 822 or 830).

Figures 55, 56:
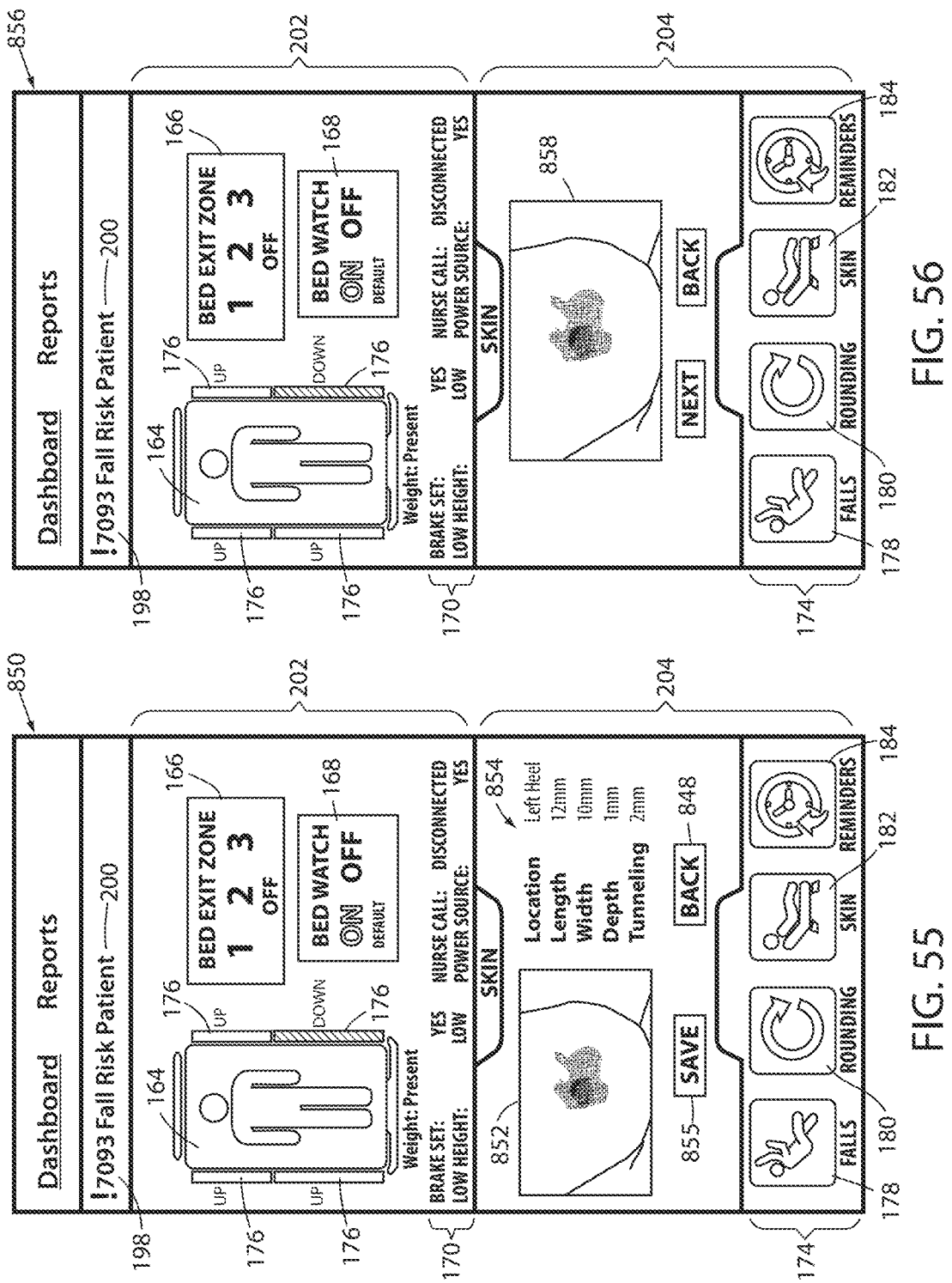
FIG. 55 is an illustrative third skin care data input screen that is displayable on an electronic device of the caregiver assistance system.
FIG. 56 is an illustrative saved images review screen that is displayable on an electronic device of the caregiver assistance system.

FIG. 55 displays a fourth skin care data input screen 850. Fourth skin care data input screen 850 is displayed after a caregiver has entered at least one image and data regarding that image, the latter of which may be entered via screen 844 of FIG. 54. Fourth skin care data input screen 850 includes both a captured image window 852 and a data summary area 854. Capture image window 852 displays one of the images captured at step 810 using $2^{nd}$ data input screen 830 of FIG. 52. Data summary area 854 displays the data input as part of step 810 (or step 816) that relates to the image shown in window 852. This data may be input using third skin care data input screen 844 (FIG. 54). Screen 850 therefore displays both a captured image of the patient' skin, as well as information about that image. Screen 850 also includes a "save" icon 855 and "back" icon 848. The user touches "save" icon 856 when the user wishes to save the data shown in window 852 and summary area 854 to the EMR server 98 and/or data repository 128. Touching "save" icon 855 thus corresponds to step 812 of algorithm 800. If the user does not wish to save the data illustrated in screen 850, or wishes to make modifications to it before saving it, he or she may touch "back" icon 848, which returns the caregiver to one of the screens previously described and shown in FIG. 51, 52, or 54, or still another screen.

FIG. 56 illustrates a saved images review screen 856 that is displayable by caregiver assistance application 124 after one or more images have been captured of the patient's skin condition. Screen 856 may be displayed as part of 810 (e.g. after one or more images have been captured at step 810). Screen 856 includes a saved image window 858 in which a previously captured image is displayed, as well as "next" icon 214 and "back" icon 848. Touching the "next" icon 214 causes caregiver assistance application 124 to display the next image in the set of captured images. Touching the "back" icon 848 causes caregiver assistance application 124 to display an earlier image in the set of captured images, or alternatively takes the caregiver back to another screen that was displayed prior to screen 856. Screen 856 may be further modified to allow a user to select one of the saved images in order to add additional data to it, such as the additional data which is input in FIG. 54. In one embodiment, touching and holding a particular image within window 858 causes caregiver assistance application 124 to display screen 844 of FIG. 54, thereby allowing the caregiver to enter additional data regarding the selected image. Screen 856 may be used in still other manners and/or display still other information.

It will be understood that screens 822, 830, 838, 844, 850, and/or 856 may be modified in a variety of different manners. For example, any one or more of these screens may include additional control icons allowing the caregiver to navigate from one of these screens to another. In such embodiments, when the caregiver is finished making his or her selections on a first one of these screens, he or she can easily navigate to another one of these screens if he or she wishes to input additional data or images, review previously input images or data, or edit previously input images or data.

Once the caregiver has completed his or her data input, touching the save icon, such as "save" icon 855 of FIG. 55, causes caregiver assistance application 124 to send all of the input data to EMR server 98 and/or data repository 128. The sending of this data may also involve time stamping the data when it is sent, and/or caregiver assistance application 124 may automatically time stamps the input data at the moment it is input or captured. Still other modifications are possible.

Figure 57:
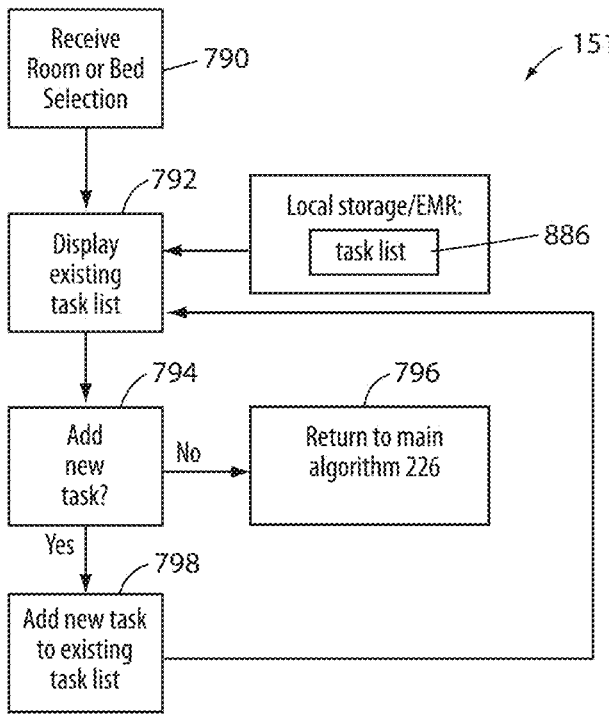
FIG. 57 is a flow diagram of a manual task list modification algorithm that may be executed by the caregiver assistance system.

FIG. 57 illustrates one example of a manual task list modification algorithm 151 that is executed by caregiver assistance application 124. Task list modification algorithm is executed by caregiver assistance application 124 when a caregiver presses on reminder task icon 184, which is displayed at the bottom of most of the screens of caregiver assistance application 124 (see, e.g. FIGS. 51-56). Manual task list modification algorithm 151 allows a caregiver to see what tasks are associated with a particular patient as well as to manually add (or remove) tasks from the task list for that patient. Manual task list modification algorithm 151 begins at step 790 where a room, bed, bed bay, or patient is selected. This selection of a room, bed, bed bay, or patient is carried out in any of the same manners discussed above with respect to step 192 of rounding algorithm 140, step 340 of fall risk reduction algorithm 143, and/or step 500 of skin care algorithm 141.

After selecting a room, bed, bed bay, or patient at step 790, caregiver assistance application 124 proceeds to step 792 where it displays a task list 886 for the selected patient (if a bed, bed bay, or room are selected at step 790, caregiver assistance application 124 correlates the selection to a specific patient and displays that patient's task list). Task list 886 is stored either locally in the data repository 128 or it is stored in EMR server 98. After displaying the task list at step 792, caregiver assistance application 124 proceeds to step 794 where it allows the caregiver to manually add (or delete) a task to (or from) the task list 886. In addition, at step 794, caregiver assistance application 124 allows the caregiver to modify a deadline associated with any one or more of the tasks in task list 886 (or any task that is added at step 794), and/or a reminder schedule associated with a deadline. The reminder schedule refers to the timing, frequency, content, and type of reminders that are sent for a particular task and its associated deadline (or, for some tasks, multiple deadlines).

If the caregiver chooses not to add a new task or delete an existing task (or modify a deadline or its associated reminder schedule), caregiver assistance application 124 exits algorithm 151 and returns back to main algorithm 226 and/or returns to the previously displayed screen. If the caregiver chooses to add a new task or delete an existing task (and/or modify a deadline or reminder schedule), caregiver assistance application 124 proceeds to step 798 where it modifies task list 886 in accordance with caregiver's manual inputs. After making these modifications, application 124 proceeds back to step 792 where it displays the modified task list and allows the caregiver to make further changes. As will be discussed in greater detail below, caregiver assistance application 124 is also configured to automatically make changes to task list 886 that do not require a caregiver to utilize algorithm 151. The changes that are automatically made to task list 886, however, are reflected in the list of tasks that are displayed at step 792.

FIGS. 58 and 59 illustrate several examples of different screens that may be displayed by caregiver assistance application 124 on electronic devices 104 during the execution of manual task list modification algorithm 151. It will be understood that these screens are merely illustrative examples of several types of screens that caregiver assistance application 124 may be configured to display. Additional screens may be displayed and/or fewer screens may be displayed. Further, the content of whatever screens are displayed may be modified from the examples shown in FIGS. 58-59.

FIG. 58 illustrates an example of an alternative room overview screen 162a. In some embodiments, room overview screen 162a is displayed in response to the user starting manual task list modification algorithm 151. That is, in some embodiments, whenever the caregiver starts algorithm 151, caregiver assistance application 124 is configured to display a room overview screen that lists the tasks for that room/patient. Alternatively, room overview screen 162a may be displayed at any of the same times as room overview screen 162 of FIG. 9 is displayed. In either case, room overview screen 162a is provided herein to show another example of the information content that may be included within a room overview screen.

Room overview screen 162a (FIG. 58) differs from room overview screen 162 of FIG. 9 in that it includes a rounding reminder indicator 888. Indicator 888 may be displayed by application 124 at steps 790 or 792 of algorithm 151. Similarly, patient turning indicator 890 of FIG. 58 may also displayed by application 124 as part of steps 790 or 792 of algorithm 151. Both indicators 888 and 890 may also be displayed automatically whenever the caregiver navigates to a room overview screen, regardless of whether he or she has started algorithm 151 or not. It will be understood that the rounding indicator 888 and turning indicator 890 that are shown in FIG. 58 are only a fraction of the types of reminders that may be displayed in summary area 172 of room overview screen 162a. Other tasks that may be displayed herein, as well as the time at which such tasks are due, include any of the risk assessments, risk re-assessments, configuration changes that are to be made to patient support apparatus 20 or mattress 38, and/or still other tasks.

FIG. 59 illustrates an example of an alternative room listing screen 156a. In some embodiments, room listing screen 156a is displayed in response to the user starting manual task list modification algorithm 151 (instead of room overview screen 162a). That is, in some embodiments, whenever the caregiver starts algorithm 151, caregiver assistance application 124 is configured to display a room listing screen that lists all of the rooms and their associated tasks that have been assigned to that particular caregiver. Alternatively, room listing screen 156a may be displayed at any of the same times as room listing screen 156 of FIG. 8 is displayed. In either case, room listing screen 156a is provided herein to show another example of the information content that may be included within a room overview screen.

Room listing screen 156a (FIG. 59) differs from room listing screen 156 of FIG. 8 in that it includes a next task column 892. Next task column 892 may be displayed by application 124 at steps 790 or 792 of algorithm 151, or it may be displayed automatically whenever the caregiver navigates to a listing screen, regardless of whether he or she has started algorithm 151 or not. Next task column 892 lists the time until the next task is to be completed for the corresponding room/patient. That is, column 892 is divided into multiple rows wherein each row corresponds to a particular room or patient. In that row, caregiver assistance application 124 computes the amount of time until the next task for that patient or room is due. If multiple tasks are due, caregiver assistance application 124 chooses the next task that is due the soonest.

It will be understood that, in some embodiments, caregiver assistance application 124 is configured such that the order of rows within column 892 can be automatically sorted in ascending or descending order. The caregiver can therefore easily see which room has the soonest upcoming task deadline. If the user wishes to see more detail about the next upcoming task, he or she may touch the corresponding row of column 892 and caregiver assistance application 124 is configured to display a room overview screen 162 (or 162a) that displays additional information about the upcoming task. It will be understood that the tasks identified in rows of room listing screen 156a of FIG. 59 are merely a subset of all of the types of reminders that may be displayed on room listing screen 156a. Any of the other tasks discussed herein may also or alternatively be displayed there.

Figure 60:
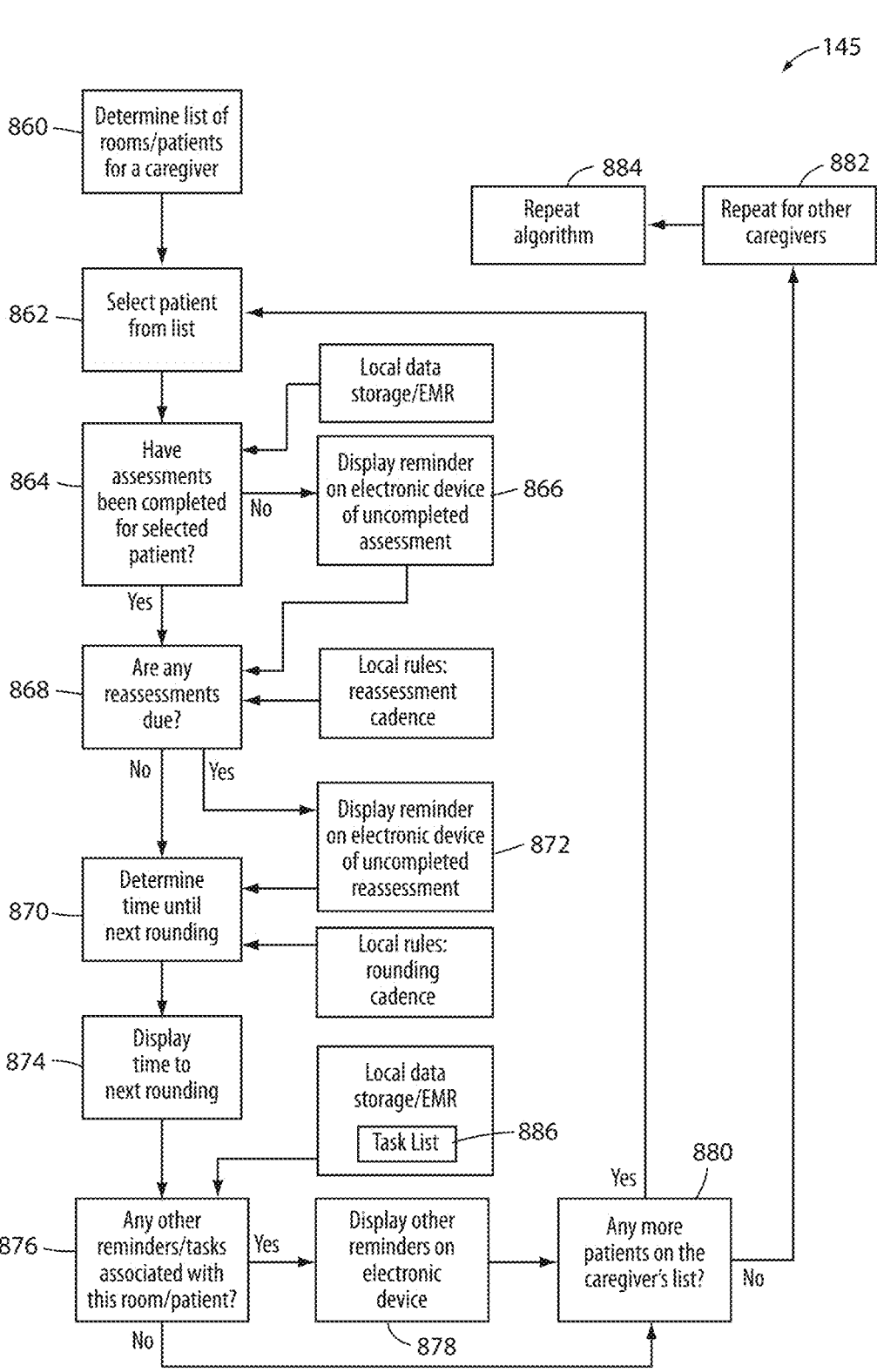
FIG. 60 is a flow diagram of a reminder algorithm that may be executed by the caregiver assistance application.

FIG. 60 illustrates one example of a reminder algorithm 145 that may be executed by caregiver assistance application 124. Reminder algorithm 145 is executed by caregiver assistance application 124 automatically in the background while the caregiver assistance application 124 is performing other tasks (such as any of the algorithms 140, 141, 143, etc.), and/or while caregiver assistance application 124 is otherwise idle with respect to other tasks. Reminder algorithm 145 provides reminders to caregivers of various tasks that they are responsible for while the caregivers are performing other duties and/or using caregiver assistance application 124 for other tasks.

Reminder algorithm 145 begins at a step 860 where caregiver assistance application 124 determines the list of rooms and/or patients that are associated with a particular caregiver. More specifically, algorithm 145 begins at step 860 by determining the list of rooms and/or patients that are associated with a specific electronic device 104, and caregiver assistance application 124 executes algorithm 145 for each device 104 that is used within system 106. Thus, for example, if a specific mobile electronic device 104a is used by caregiver A, caregiver assistance application 124 determines at step 860 the list of rooms and/or patients to whom caregiver A has been assigned. After determining this list, caregiver assistance application 124 moves to step 862.

At step 862 (FIG. 60), caregiver assistance application 124 selects one of the patients from the list that was obtained at step 860. Generally speaking, application 124 picks the first patient in the list obtained at step 862 and thereafter, when returning back to step 862, picks the next patient and the next patient until algorithm 145 has been executed for each patient on the list, as will be discussed more below with respect to step 880. Further, as will be explained more below with respect to step 884, algorithm 145 repeats itself automatically in the background for all caregivers within the healthcare facility and all of their assigned patients (as well as other electronic devices 104 that might not be assigned to a particular caregiver—e.g. a stationary electronic device 104b).

After selecting a patient at step 864 from the list of patients for a particular caregiver, application 124 proceeds to step 864 where it checks to see if a fall risk assessment and a bed sore risk assessment have been completed for the selected patient. Caregiver assistance application 124 performs step 864 by consulting both EMR server 98 and data repository 128. Caregiver assistance application 124 may be customized by the healthcare facility to check for additional patient assessments at this step as well. If application 124 determines at step 864 that one or both of the fall risk and bed sore risk assessments have not been completed, it proceeds to step 866 where it issues a reminder to the caregiver to complete either or both of these assessments.

The reminder may take on several different forms, and the forms may change depending upon how much time has passed since the task was originally supposed to be performed. In some embodiments, the reminder is merely added to room listing screen 156 (see room 7092 of FIG. 8). In other embodiments, the reminder is added to other locations, such as the status location 200 and/or the room status summary area 172 (see FIG. 9). Still further, in some embodiments, if the assessment is overdue by more than a threshold, caregiver assistance application 124 may be configured to display a popup screen that appears on top of the currently displayed screen and that reminds the caregiver to perform the overdue assessment. Alternatively, or additionally, if a task is overdue by more than a threshold, caregiver assistance application 124 may invoke alert algorithm 149 in order to send an email, text, or phone call to the caregiver. Still other manners of issuing the reminder to the caregiver may be implemented.

After completing step 866 (or if the results of step 864 is a yes), caregiver assistance application 124 proceeds to step 868. (FIG. 60) At step 868, caregiver assistance application 124 determines if there are any risk re-assessments due for the patient. In many healthcare facilities, not only are patients supposed to have their fall risk and/or bed sore risk evaluated at the time they are admitted (or within a prescribed time thereafter), but they are also supposed to have these risks re-evaluated at certain time periods thereafter. The cadence at which these assessments are intended to be re-performed is dictated by the particular healthcare facility, and data defining this cadence is stored in data repository 128. Caregiver assistance application 124 therefore uses this stored cadence data at step 868 to see if any risk re-assessments are due for the patient. If the answer is yes, application 124 proceeds to step 872 where it issues a reminder to the caregiver. The reminder may be implemented in any of the same ways discussed above with respect to the reminder issued at step 866.

If no risk re-assessments are determined to be due at step 868, or after caregiver assistance application 124 has issued a reminder for the overdue risk re-assessment at step 872, caregiver assistance application 124 proceeds to step 870. At step 870, application 124 determines if the patient is due to be visited by the caregiver for another set of rounding tasks. As with the risk re-assessments, the data defining the cadence at which the rounding tasks are to be completed is defined by the healthcare facility and stored in data repository 128. As was noted above in the discussion of the rounding algorithm 140, the rounding cadence is often set to about once every two hours, although it will be understood that this may be varied by individual healthcare facilities, and may further be varied based upon other factors such as, but not limited to, the location of the patient, the medical condition of the patient, and/or the score of one or more of the risk assessments.

After determining the time until the next rounding task is to be performed, application 124 proceeds to step 874 (FIG. 60) where it displays the time until the next rounding task. This time may be displayed in different locations, such as by adding it to an alternative room listing screen 156a of FIG. 59 (see the task column therein). In other embodiments, the time until the next rounding task is added to other locations, such as the status location 200 and/or the room status summary area 172 (see alternative room overview screen 162a of FIG. 58). Still further, in some embodiments, if the rounding task is overdue by more than a threshold, caregiver assistance application may be configured to invoke alerting algorithm 149 and send an email, text, or phone call to the caregiver, and/or to display a popup screen that appears on top of the currently displayed screen and that reminds the caregiver to perform the overdue rounding task. Still other manners of communicating the rounding reminder to the caregiver may be implemented.

After completing step 874, caregiver assistance application 124 proceeds to step 876 where it checks to see if any other tasks associated with the patient are scheduled to be performed. If there are any other such tasks, application 124 proceeds to step 878 (FIG. 60). If there are no such tasks, it proceeds to step 880. The other tasks that are evaluated at step 876 include tasks that are manually added by a caregiver to the caregiver's task list 886, as well as tasks that are automatically added by caregiver assistance application 124 to the caregiver's task list 886 during the execution of rounding algorithm 140, skin care algorithm 141, and/or fall risk reduction algorithm 143. That is, fall risk and bed sore risk reduction algorithms 143, 141 automatically add tasks for which reminders are to be sent when these algorithms detect, or are informed, of conditions that require caregiver actions which are not immediately addressed by the caregiver while he or she is using the application. Such tasks include, but are not limited to, changing one or more states of the components of patient support apparatus 20, changing one or more states of the mattress 38 on patient support apparatus 20, carrying out one or more therapies using mattress 38, and/or performing other tasks that are entered either by the caregiver into the application 124 or by an authorized administrator.

If caregiver assistance application determines at step 876 that there are other tasks to remind the caregiver about, it proceeds to display those other tasks at step 878. The display of these tasks may be carried out in any of the same manners by which the rounding and/or risks assessments (or re-assessment) reminders are displayed at steps 866, 872, and/or 874. After displaying the reminder (or sending a text, email, or phone call) at step 876, caregiver assistance application 124 proceeds to step 880. At step 880, caregiver assistance application 124 determines if there are other patients on the list of patients identified at step 860. If there are, caregiver assistance application 124 returns to step 862 and repeats the previously described steps (and continues to repeat them until all of the patients for that particular caregiver have had their reminders updated). If there are not, caregiver assistance application 124 proceeds to step 882 where it selects another caregiver and repeats steps 860 through 880 for that new caregiver. After completing step 882, algorithm 145 proceeds to step 884 where it repeats the whole process over again for all of the caregivers. The effect of step 884 is that caregiver assistance application 124 continues to monitor the tasks associated with all of the patients in the healthcare facility and to issue reminders to the appropriate caregivers at the appropriate times, thereby ensuring that the caregivers receive timely reminders throughout their workday. Although not shown in algorithm 145, caregiver assistance application also automatically removes tasks from task list 886 once they are completed.

Figure 61:
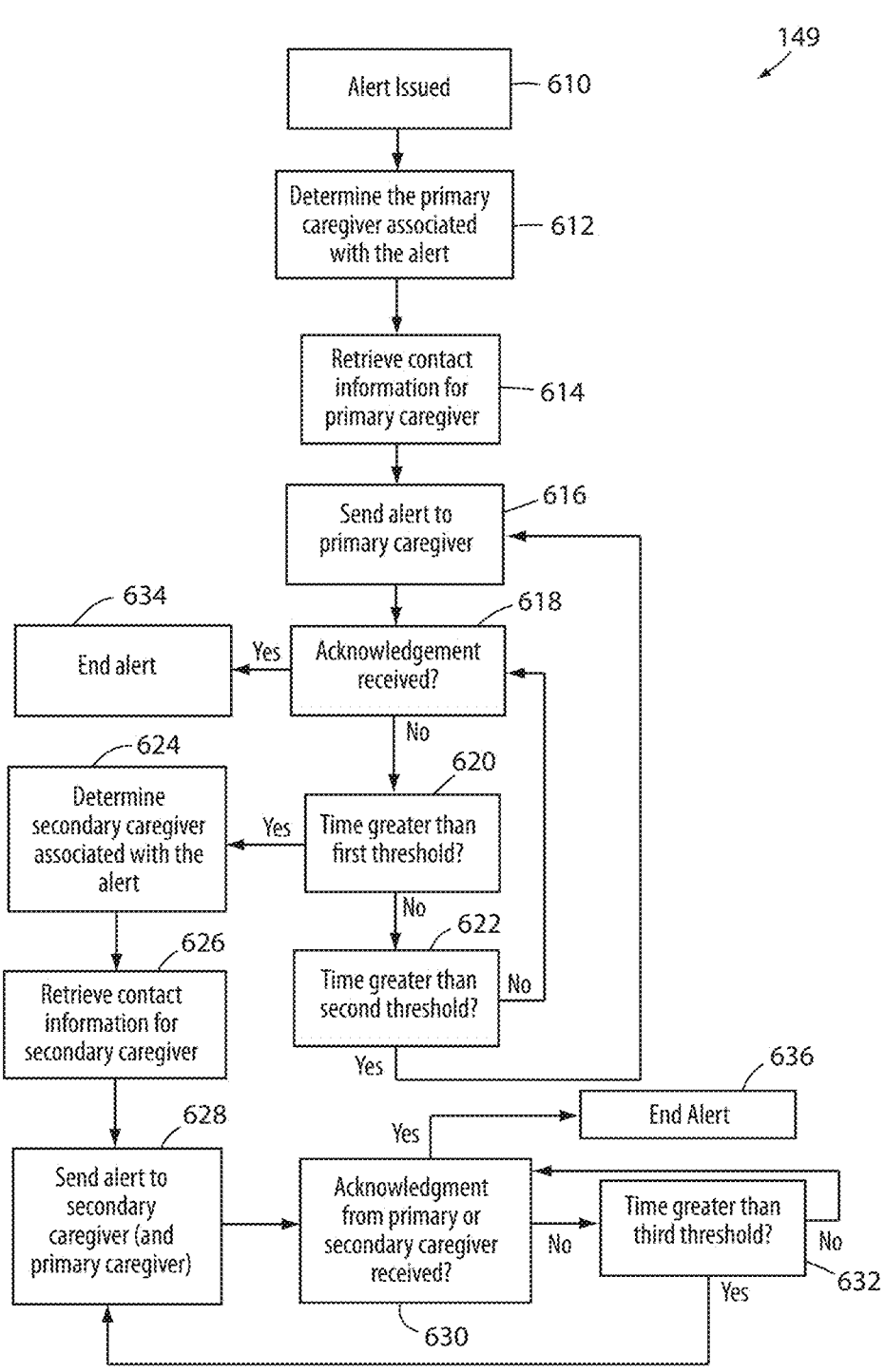
FIG. 61 is a flow diagram of an alerting algorithm that may be executed by the caregiver assistance application.

FIG. 61 illustrates one example of an alerting algorithm 149 that may be executed by caregiver assistance application 124. Alerting algorithm 149 is invoked by caregiver assistance application 124 whenever any of the other algorithms discussed herein (such as, but not limited to, any of algorithms 140, 141, 143, etc.) detect a condition for which an alert is to be issued. Alerting algorithm begins at a step 610 when such a condition is detected by caregiver assistance application 124. After step 610, caregiver assistance application 124 proceeds to step 612 where it determines who the primary caregiver is who is associated with the alert. This information is stored in either local rules repository 126 or data repository 128 (or a combination of both).

In general, caregiver assistance application 124 maintains a table (or other data format) in which each patient is listed in a row and various data corresponding to that patient is listed in a plurality of columns. In one example, separate columns are included for each of the following data items: the patient support apparatus identifier 186 of the patient's patient support apparatus 20; the room number of the patient; the bed bay identifier of the patient's patient support apparatus 20 (if there are semi-private rooms in the healthcare facility); the primary caregiver for that patient; contact information for that primary caregiver (e.g. email address, phone number, an identifier of the caregiver's mobile electronic device 104a, etc.); the secondary caregiver for that patient, and contact information for that secondary caregiver. The designations of the primary and secondary caregivers are performed by the healthcare facility and may be automatically read by caregiver assistance application 124 by sending an inquiry to the appropriate server (or servers) on network 74 where such information is stored (e.g. nurse call server 96). Alerting algorithm 149 uses the information in this table to carry out various steps of algorithm 149, as will now be further described.

At step 612 of algorithm 149, caregiver assistance application 124 determines who the primary caregiver is for the patient associated with the alert. In those situations where the alert is from a patient support apparatus 20, or it relates to a condition of the patient support apparatus 20, algorithm 149 uses the aforementioned table to identify the patient assigned to that particular patient support apparatus 20, and from that information the primary caregiver associated with that patient. In other situations, the alert may arise from a condition directly associated with a patient and caregiver assistance application 124 may not need to utilize any patient support apparatus 20 information to determine the primary caregiver who is to be alerted.

After determining the primary caregiver at step 612 (FIG. 61), caregiver assistance application 124 proceeds to step 614 where it retrieves the contact information for the primary caregiver identified at step 612. As noted, this contact information may include, but is not limited to, the caregiver's email address, phone number, device ID (of mobile electronic device 104a), instant messaging contact information, etc. After obtaining this information, caregiver assistance application 124 proceeds to step 616 where it sends the alert to the primary caregiver. The sending of the alert may include displaying a pop-up on the screen of the caregiver's mobile electronic device 104a (and, in some embodiments, on any stationary electronic devices 104b that are configured to display alerts associated with the primary caregiver's patients), sending an email, a text, an instant message, and/or placing a phone call.

Regardless of how sent, caregiver assistance application 124 checks at step 618 for an acknowledgement from the primary caregiver indicating that the alert was received and that the caregiver has acknowledged it. If the acknowledgement has been received, caregiver assistance application 124 proceeds to step 634 and ends the alert. If no acknowledgement has yet been received, caregiver assistance application 124 proceeds to step 620 where it compares the amount of time that has passed since the alert was sent at step 616 to a first threshold amount of time. The first threshold amount of time is configurable by authorized individuals (e.g. person 136) and, as will be explained, defines how much time is allowed to pass before caregiver assistance application 124 proceeds to send the alert information to the patient's secondary caregiver.

If the elapsed time is determined at step 620 to be less than the first threshold, caregiver assistance application 124 proceeds to step 622 where it compares the elapsed time to a second threshold. The second threshold is also configurable by authorized individuals. In the illustrated embodiment of algorithm 149 shown in FIG. 61, the second threshold is for a shorter amount of time than the first threshold. If the elapsed time has not yet reached this shorter time threshold, caregiver assistance application 124 returns back to step 816 where it checks again to see if the acknowledgement has yet been received and, if not, continues to cycle through steps 620 and 622 until the elapsed time eventually reaches the smaller, second threshold. When the total elapsed time since the alert was sent at step 616 reaches or exceeds the second threshold of step 622, caregiver assistance application 124 returns back to step 616 and re-sends the alert. After re-sending the alert, application proceeds to step 681 and, if no acknowledgement has been received, to steps 620 and/or 622. When caregiver assistance application 124 reaches steps 620 and/or step 622 after the alert was sent for the second time at step 616, it compares the total elapsed time since the alert was first issued at step 616 to the thresholds. That it, no matter how many times the alert was re-sent to the caregiver at step 616, caregiver assistance application 124 always uses the total elapsed time since the first alert was sent at step 616 for comparisons purposes at steps 620 and 622. By doing this, eventually the elapsed time will exceed the larger first threshold (assuming no acknowledgment is received), at which point caregiver assistance application 124 proceeds to step 624.

At step 624, caregiver assistance application 124 determines who the secondary caregiver is for the patient who is (or the patient support apparatus 20 that is) the cause of the alert. This is done in the same manner that the primary caregiver is determined, which, as discussed above with respect to step 612, utilizes a table of correlations between caregivers, patients, patient support apparatuses 20, contact information, etc. After identifying the secondary caregiver, caregiver assistance application 124 proceeds to step 626 where it retrieves the secondary caregiver's contact information. This information, in most situations, is stored in the same location as the primary caregiver's contact information, and step 626 is therefore carried out in the same manner as step 614 (discussed above).

After retrieving the secondary caregiver's contact information, caregiver assistance application 124 proceeds to step 628 (FIG. 61) where it sends an alert to the secondary caregiver (and in some embodiments, another alert to the primary caregiver). As with the alert to the primary caregiver, this alert may be a pop-up window on the screen of the secondary caregiver's mobile electronic device 104a, a text, an email, an instant message, and/or a phone call. After sending the alert to the secondary caregiver (and primary caregiver) at step 628, caregiver assistance application 124 proceeds to step 630 where it checks to see if either of the alerts sent at steps 628 and 616 have been acknowledged. If one or both of them have been acknowledged, it proceeds to step 636 where it ends the alert. If neither of them have been acknowledged, it proceeds to step 632 where it checks to see if the amount of time that has elapsed since sending the alert to the secondary caregiver at step 628 is greater than a third threshold. If it is, it returns to step 628 and resends the alert to the secondary (and primary) caregiver and proceeds to step 630. If the elapsed time does not exceed the third threshold at step 632, caregiver assistance application 124 returns to step 630 and checks again for acknowledgements from either the primary or secondary caregiver. From step 630, caregiver assistance application 124 continues to proceed in the manner just described.

Third threshold of step 632 may be the same as either of the first or second thresholds, or it may have a different value. The elapsed time which is compared to the third threshold at step 632 is reset every time another alert is sent at step 628 to the primary and secondary caregiver. Thus, unlike the elapsed amount of time that is used in steps 620 and 622 and which is the amount of time since an alert was first sent at step 616, the total amount of elapsed time that is compared to the third threshold at step 632 is the amount of elapsed time since step 628 was last executed.

It will be understood that alerting algorithm 149 (FIG. 61) may be modified in a variety of different manners. Such variations include, but are not limited to, the following: algorithm 149 may skip re-sending the alert to the primary caregiver and instead proceed directly to escalating the alert to the secondary caregiver if the first alert is not acknowledged; algorithm 149 may escalate the alert beyond a secondary caregiver and send alerts to a tertiary caregiver, or still other caregivers (or one or more stationary electronic devices 104b); algorithm 149 may break up the alert sent at steps 616 and/or 628 into separate steps, such as, first sending a popup window, then sending a text, then placing a phone call, etc.; algorithm 149 may initially send the alert to both primary and secondary caregivers (and/or other devices); algorithm 149 may skip re-sending one or more of the alerts and instead, either continue to wait for an acknowledgement or escalate the alert to still other individuals, such as an administrator or supervisor; and/or algorithm 149, to the extent it sends an alert to a stationary electronic device 104b, may cause the stationary electronic device 104b to flash the room, and/or change the color of the room of the alert (if it is displaying a room listing screen) and/or flash the background and/or change the color of the entire screen, or a portion thereof (if it is displaying a room overview screen). Such modifications to algorithm 149 may also, or alternatively, include the emission of one or more predetermined sounds.

The particular manner in which algorithm 149 is implemented in a particular healthcare facility can be customized by authorized individuals 136 to match the alerting priorities and protocols of that particular healthcare facility. Such customization includes defining and/or modifying alerting algorithm 149 in different manners for different caregivers, different floors of the healthcare facility, different wings or other sections of the healthcare facility, and/or for different times of the day.

FIG. 62 illustrates one embodiment of an access algorithm 153 that may be executed by caregiver assistance application 124. As mentioned previously, access algorithm 153 is executed at step 171 of main algorithm 226 (FIG. 5), in at least one embodiment of caregiver assistance application 124. Access algorithm 153 begins at an initial step 640 where it checks the credentials of the user who has just logged in at step 152 of main algorithm 226. That is, caregiver assistance application 124 checks the username corresponding to the user who has just logged in against a list of valid usernames stored within data repository 128. If the username (and corresponding password) are on the list of valid usernames, caregiver assistance application 124 proceeds to step 642. If the username is not valid, algorithm 153 may display a message to the user regarding an invalid username and return to main algorithm 226 (such as step 152), or take other action.

At step 642, caregiver assistance application 124 checks the access level that has been assigned to the user whose username was confirmed as valid at step 640. During the initial setup of caregiver assistances system 106, each username is assigned an access level corresponding to that particular individual's authorization and/or expected usage of system 106. In the embodiment of access algorithm 153 shown in FIG. 62, there are three levels of access corresponding to three different types of users: caregivers, administrators, and technicians. It will be understood that access algorithm 153 may be modified to include greater numbers of classifications and/or fewer classifications.

Figure 64:
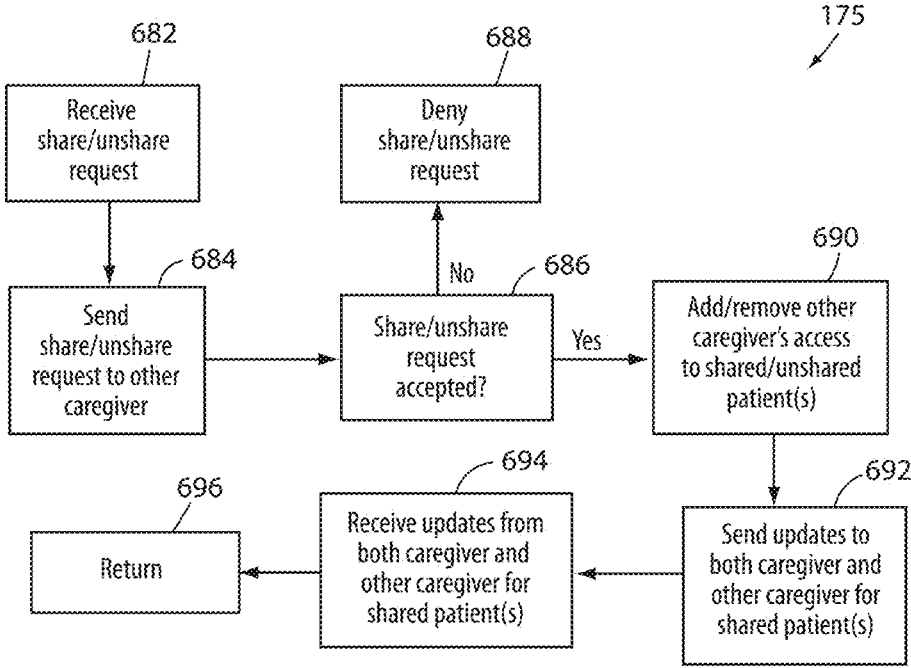
FIG. 64 is a flow diagram of a sharing algorithm that may be executed by the caregiver assistance application.

In the embodiment shown in FIG. 62, caregiver assistance application 124 proceeds to step 644 if the username corresponds to a caregiver, proceeds to step 648 if the username corresponds to an administrator, and proceeds to step 652 if the username corresponds to a technician. Turning first to users who are classified as caregivers, caregiver assistance application 124 proceeds from step 644 to step 646 where it determines which patients the particular caregiver is assigned to. That is, caregiver assistance application 124 determines the set of patients to which that particular caregiver is assigned and only allows access to the data corresponding to that set of patients. Thus, if caregiver A is assigned to care for patients C, D, E, F, and G, caregiver assistance application 124 only displays data regarding patients C, D, E, F, and G, as well as data from the patient support apparatuses 20 assigned to these patients, on the screens of the mobile electronic device 104a that is assigned to caregiver A. Such data may be displayed in any of the ways discussed above (e.g. room listing screens, room overview screens, and/or any of the other various screens described above, as well as still other screens). Unless caregiver A receives or sends a share request (discussed further below with respect to sharing algorithm 175; FIG. 64), caregiver A will not be allowed to see any data on his or her mobile electronic device 104a from caregiver assistance application 124 corresponding to, for example, patients X, Y, and/or Z.

If caregiver assistance application 124 determines at steps 642 and 648 (FIG. 62) that the username corresponds to an administrator, caregiver assistance application 124 proceeds step 650 where it grants the administrator access to all of the patient data. Thus, the administrator is allowed to see patient data and patient support apparatus data for all of the patients in the entire healthcare facility.

If caregiver assistance application 124 determines at steps 642 and 652 that the username corresponds to a technician, caregiver assistance application 124 proceeds to step 654 where it grants the technician access only to patient support apparatus data. That is, technicians are not allowed to see any patient data, but instead are only allowed to see data from patient support apparatuses 20. In some embodiments, the data viewable by technicians is greater than the data shown and described previously herein. That is, in addition to status information about the state of the brake, siderails 36, exit detection system 46, bed watch system, height of litter frame 28, state of mattress 38, etc., caregiver assistance application 124 may also display to a technician information about the software versions of the software onboard the patient support apparatus 20, usage statistics of the components of the patient support apparatus 20, and/or a service history for the patient support apparatuses 20. As will be discussed in greater detail below, in some embodiments, a technician is able to view the service history and/or usage statistics for a particular patient support apparatus 20 by utilizing caregiver assistance application 124 to access a separate, standalone remote equipment management system that gathers and stores this maintenance and usage data. This is discussed in greater detail below with respect to FIGS. 71-73. Still further, in addition to granting a technician access to this patient support apparatus data at step 654, caregiver assistance application 124 is configured in some embodiments to also allow the technician to upload servicing data to caregiver assistance application 124, thereby allowing the technician to enter and store servicing data with caregiver assistance application 124.

It will be understood that access algorithm 153 (FIG. 62) may be modified in a variety of different manners. As but one example, algorithm 153 may be modified to include a supervisor classification (or the like) that allows the user to see all of the patient data corresponding to the set of caregivers that he or she is supervising, but not all of the patients in the entire healthcare facility. Alternatively, or additionally, there may be a classification that allows a user to see all of the patients corresponding to a particular ward, wing, floor, or other section of the healthcare facility. Still other classifications are possible. Caregiver assistance application 124 may also classify stationary electronic devices 104*b* with a separate classification that is stored in data repository 128 during the installation of system 106. These classifications, in some embodiments, cause caregiver assistance application 124 to display only patient and/or patient support apparatus data for a pre-configured set of rooms that correspond to the location of the particular stationary electronic device 104*b*. Thus, for example, a particular stationary electronic device 104*b* that is positioned in the maternity ward of a healthcare facility may be configured via local rules 126 and/or corresponding data with repository 128 to display only the data corresponding to the rooms of the maternity ward. The username and password for that particular stationary electronic device may be shared with all of the caregiver assigned to that ward, and/or the stationary electronic devices 104*b* may be configured to not utilize usernames and/or passwords, but instead display a preconfigured set of data based on their ID. Still other variations are possible for stationary electronic devices 104*b*.

Figure 63:
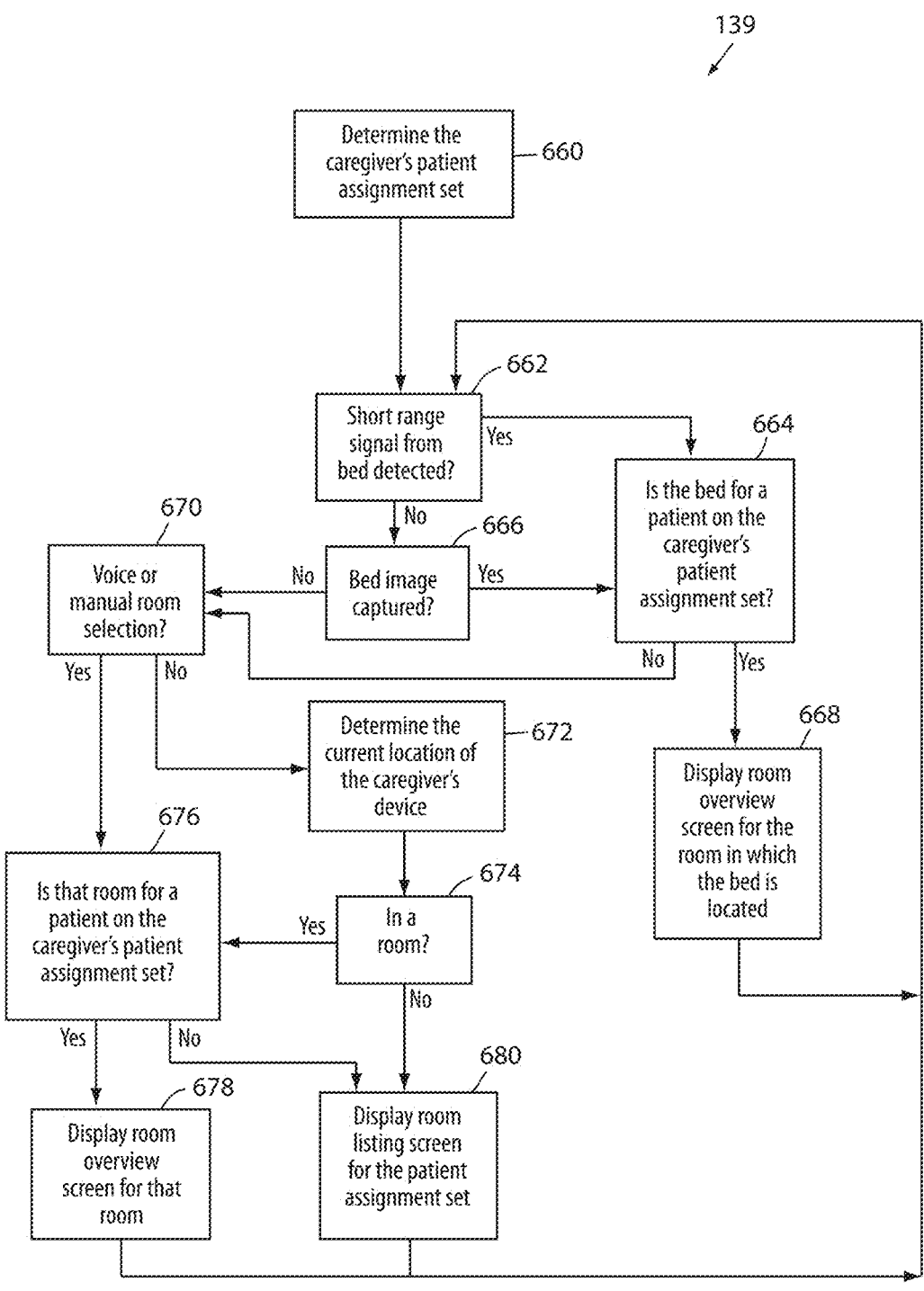
FIG. 63 is a flow diagram of a screen selection algorithm that may be executed by the caregiver assistance application.

FIG. 63 illustrates one embodiment of a screen selection algorithm 139 that may be executed by caregiver assistance application 124. As mentioned previously, screen selection algorithm 139 is executed at step 173 of main algorithm 226 (FIG. 5), in at least one embodiment of caregiver assistance application 124. Screen selection algorithm 139 is only executed by caregiver assistance application 124 for mobile electronic devices 104*a*, and not for stationary electronic devices 104*b*. Screen selection algorithm 139 begins at step 660 where caregiver assistance application 124 determines the set of patients to which the particular caregiver using caregiver assistance application 124 is assigned. In other words, caregiver assistance application 124 executes algorithm 139 for each individual caregiver and automatically changes the screens displayed on each of the mobile electronic devices 104*a* for each of the individual caregivers. Thus, at step 660, caregiver assistance application 124 identifies which caregiver it is executing algorithm 139 with respect to, and then identifies the patients assigned to that particular caregiver. Step 660 is therefore carried out in a similar manner to, or in the same manner as, step 646 of access algorithm 153 (FIG. 62).

After determining the caregiver's assigned set of patients at step 660, caregiver assistance application 124 proceeds to step 662 where it determines if the caregiver's mobile electronic device 104*b* has detected any short range signals from a patient support apparatus 20. As described below with respect to caregiver assistance systems 106*a*, 106*b*, and/or 106*c*, patient support apparatuses 20 may be modified to include a short range transceiver 320 that sends out short range signals that are detectable by mobile electronic devices 104*a* when the mobile electronic device 104*a* is positioned in proximity to such a modified patient support apparatus 20. Such proximity may refer to being in the same room as, or positioned next to, the particular patient support apparatus 20 that is equipped with such a short range transceiver 320. Step 662 therefore is only executed in those embodiments of caregiver assistance system 106 in which at least one patient support apparatus 20 is equipped with such a short range transceiver 320.

If the mobile electronic device 104*a* detects a short range signal from a patient support apparatus 20 at step 662, it notifies caregiver assistance application 124 and proceeds to step 664. At step 664, caregiver assistance application 124 checks to see if the short range signal received at step 662 was from a patient support apparatus 20 whose patient is one of the patient's on the caregiver's assigned set of patients. This is accomplished, in at least some embodiments, by configuring patient support apparatuses 20 to send out a unique identifier (e.g. identifier 186) via the short range transceiver 320 that uniquely identifies that particular patient support apparatus 20. This unique identifier is forwarded by the mobile electronic device 104*a* to caregiver assistance application 124 and caregiver assistance application 124 uses the identifier at step 664 to determine if that particular patient support apparatus 20 has been assigned to a patient who is part of the patient assignment set for the caregiver associated with that particular mobile electronic device 104*a*. In other words, caregiver assistance application 124 determines if the patient onboard that particular patient support apparatus 20 is one of the caregiver's patients, or if the patient is another caregiver's patient. If the patient is the responsibility of another caregiver, caregiver assistance application 124 proceeds to step 670. If the patient is one of the caregiver's patients, caregiver assistance application 124 proceeds to step 668.

At step 668 (FIG. 63), caregiver assistance application 124 automatically displays the room overview screen corresponding to the patient support apparatus 20 whose short range signal was received at step 662. As described previously, FIGS. 9 and 58 illustrate two examples of room overview screens 162 and 162*a*. Other types of room overview screens may alternatively be used. The effect of steps 662, 664, and 668 is that, if a caregiver walks into a room in which one of his or her assigned patients is located, caregiver assistance application 124 will automatically display a room overview screen (162, 162*a*) on his or her mobile electronic device 104*a* that corresponds to the room in which he or she just entered (assuming the patient support apparatus 20 is configured with a short range transceiver 320). Further, if the caregiver walks into a room that contains a patient support apparatus 20 having a short range transceiver 320, but the patient support apparatus 20 is assigned to a different caregiver, caregiver assistance application 124 will not display the room overview screen for that room because, as determined at step 664, the patient in that room is not assigned to that particular caregiver. Still further, when the caregiver exits the room, the short range signal will no longer be detected and algorithm 175 will therefore switch to displaying a room listing screen when the caregiver is in the hallway (or anywhere else outside of an assigned patient's room), as will be discussed further below.

Returning to step 662 of screen selection algorithm 139 (FIG. 63), if the caregiver's mobile electronic device 104*a* does not detect any short range signals from a patient support apparatus 20 at step 662, it proceeds to step 666 where it checks to see if any images of a particular patient support apparatus 20 have been captured. Such images are captured using the camera app onboard the mobile electronic device 104*a*. Such images include, but are not limited to, images that uniquely identify a particular patient support apparatus 20. For example, such images include a bar code, a QR code, or some other visual identifier that is either permanently displayed somewhere on the patient support apparatus 20, or that is selectively displayed on display 70 of the patient support apparatus 20. If the user captures an image of such a visual identifier, caregiver assistance application 124 proceeds to step 664 where it analyzes the image. The analysis of the image is carried out at step 664 to determine if that particular patient support apparatus 20 corresponds to a patient to whom the caregiver is assigned. That is, step 664 is carried out in the same manner previously described except, instead of utilizing identifier 186 received via short range transceiver 320, caregiver assistance application 124 uses a visual identifier (which may visually identify identifier 186) to determine if the patient support apparatus 20 has been assigned to one of the caregiver's patients. If it has been, caregiver assistance application 124 proceeds to step 668 where it displays the corresponding room overview screen for that particular room. If it has not, caregiver assistance application 124 proceeds to step 670.

The effect of steps 666, 664, and 668 is to allow the caregiver to control what room overview screen 162, 162*a* is displayed on his or her mobile electronic device 104*a* by taking a picture of a visually unique identifier on a particular patient support apparatus 20. If the unique visual identifier corresponds to a patient support apparatus 20 for one of his or her assigned patients, then application 124 automatically displays the room overview screen 162 for that particular room. If it does not, application 124 proceeds to step 670.

At step 670 of algorithm 139 (FIG. 63), caregiver assistance application 124 checks to see if it has received either a manual selection of a room number and/or, in some embodiments, an audio (voice) selection of a particular room number. The manual selection may occur in different manners, such as, but not limited to, the caregiver typing in a particular room number using a keypad (physical or virtual) onboard his or her mobile electronic device 104*a*, the caregiver selecting a particular room from amongst those listed on a room listing view screen (e.g. screens 156, 156*a*, 156*b*, 156*c*, etc.), or by other means. In some embodiments, caregiver assistance application 124 includes, or otherwise utilizes, voice recognition software that enables the caregiver to speak a room number (or other room identifier) into the microphone onboard his or her mobile electronic device 104*a* and then processes the audio signals to determine a corresponding room number (or other room identifier). Caregiver assistance application 124 determines at step 670 whether any of these methods of selecting a particular room have occurred. If one has occurred, it proceeds to step 676. If none have occurred, it proceeds to step 672.

Turning first to step 672, caregiver assistance application 124 determines the current location of the caregiver at step 672. Step 672 is only included in those embodiments of caregiver assistance application 124 that utilize a real time locating server 100 (FIG. 4). As was described previously, real time location server 100 may be a conventional server that keeps track of the current locations of caregivers using one or more badges, beacons, and/or other devices. Regardless of the specific manner in which real time locating server 100 keeps track of caregiver locations, caregiver assistance application 124 sends a request for the caregiver's current location at step 672 of algorithm 139. Upon receiving a reply to this request, caregiver assistance application 124 proceeds to step 674. At step 674, it determines if the caregiver is currently located in a room, or outside of a room (e.g. a hallway, a nurses' station, etc.) If the caregiver is not located within a room, caregiver assistance application 124 proceeds to step 680 where it automatically displays a room listing screen, such as one of the room listing screens 156, 156*a*, 156*b*, 156*c*, etc.

If the real time locating server 100 indicates that the caregiver's current location is within a room (as determined at step 674 of algorithm 139; FIG. 63), caregiver assistance application 124 proceeds from step 674 to step 676. At step 676, caregiver assistance application 124 determines if the room in which the caregiver is currently located corresponds to a room in which one of his or her assigned patients is located. If it does, caregiver assistance application 124 displays a room overview screen for that particular room on the caregiver's mobile electronic device 104*a*. If it does not, caregiver assistance application 124 proceeds to step 680 where it displays a room listing screen on the caregiver's mobile electronic device 104*a*.

Returning back to step 670 of screen selection algorithm 139 (FIG. 63), caregiver assistance application 124 proceeds from step 670 to step 676 if the caregiver manually selects a room number, either aurally or by physically touching the screen (or other controls) on his or her mobile electronic device 104*a*. At step 676, caregiver assistance application 124 checks to see if the room manually entered by the caregiver at step 670 corresponds to a room in which one of his or her assigned patients is located. If it does, caregiver assistance application 124 proceeds to step 678 where it displays the room overview screen for that particular room. If it does not, caregiver assistance application 124 proceeds to step 680 where it displays the room listing screen for that particular caregiver.

The effect of all of the steps of screen selection algorithm 139 is that caregiver assistance application 124 will display the room overview screen of a patient assigned to that particular caregiver whenever the caregiver enters the room of that patient. This will be done either automatically (via step 662, 666, or 672) or manually (via step 670). Further, in those embodiments in which caregiver assistance application 124 communicates with real time locating server 100 and/or patient support apparatuses 20 include a short range transceiver 320, caregiver assistance application 124 will automatically switch to displaying a room listing screen whenever the caregiver leaves the room, or otherwise is positioned outside of a patient's room. In these embodiments, the caregiver is therefore automatically presented with a screen listing all of the rooms he or she is responsible for when he or she is positioned outside of a room, and automatically presented with the room overview screen when he or she enters a room.

It will be understood that screen selection algorithm 139 (FIG. 63) is configured in some embodiments to not change whatever screen is being displayed on mobile electronic device 104*a* if no room selection inputs are received at steps 662, 666, 670, or 672. In such embodiments, the screen that caregiver assistance application 124 displays is only changed automatically if the caregiver's location changes from being inside a room to being outside a room, or vice versa.

Still further, caregiver may also pause for a predetermined period of time before making any automatic change to the screen displayed on mobile electronic device 104*a*. During the pause, caregiver assistance application 124 monitors mobile electronic device 104*a* for any inputs by the caregiver. If any inputs are detected, the automatic screen switch is delayed or cancelled. If no user inputs are detected during the pause period, then caregiver assistance application 124 automatically switches the screen after the pause period time has expired. The inclusion of such a pause period helps reduce or eliminate interrupting the displayed screen while the caregiver is using caregiver assistance application 124. In other words, caregiver assistance application 124 only changes the screen automatically if the mobile electronic device 104*a* has been idle for predetermined amount of time.

In another modified embodiment of screen selection algorithm 139, caregiver assistance application 124 may be configured to prompt the caregiver to allow the change of the displayed screen before making such a change. The prompt may include a popup window, or some other message, that asks the caregiver for permission to change the displayed screen. In such embodiments, only if the user accepts the screen change (or, in some embodiments, if no response is received within a predetermined time period), does caregiver assistance application 124 automatically change the screen displayed on the corresponding mobile electronic device 104*a*.

It will be understood that still other modifications may be made to screen selection algorithm 139. Such modifications include, but are not limited to, omitting step 662 completely (particularly if patient support apparatuses 20 do not include a short range transceiver 320), omitting step 666 (particularly if patient support apparatuses 20 are not configured to visually display a unique identifier), and/or omitting step 672 completely if caregiver assistance application 124 is not configured to communicate with a real time locating server 100 (or the particular healthcare facility does not have a real time locating server 100). Still further, it will be understood that the order in which the steps of algorithm 139 are executed may be varied from what is shown in FIG. 63.

It will be understood that in all of the embodiments of screen selection algorithm 139, the screen automatically selected by algorithm 139 in only the initial screen that is initially displayed when the caregiver enters a room (or selects a particular patient support apparatus) and/or leaves a room. That is, the caregiver is still free to select different screens after caregiver assistance application 124 has initially selected a room overview screen or a room listing screen at steps 668, 678, and/or 680. Thus, for example, if a caregiver initially walks into a patient's room and caregiver assistance application 124 initially displays a room overview screen for that particular room, the caregiver is free to press on any of the task icons 178, 180, 182, and/or 184 to bring up other screens for carrying out these tasks, or to manually change the room overview screen to a room listing screen (or vice versa), or to make still other manual changes to the screen displayed. Algorithm 139 is therefore included to help reduce the amount of work required by the caregiver in selecting a particular initial screen, but not to limit the screens that are available to the caregiver.

Figures 65, 66:
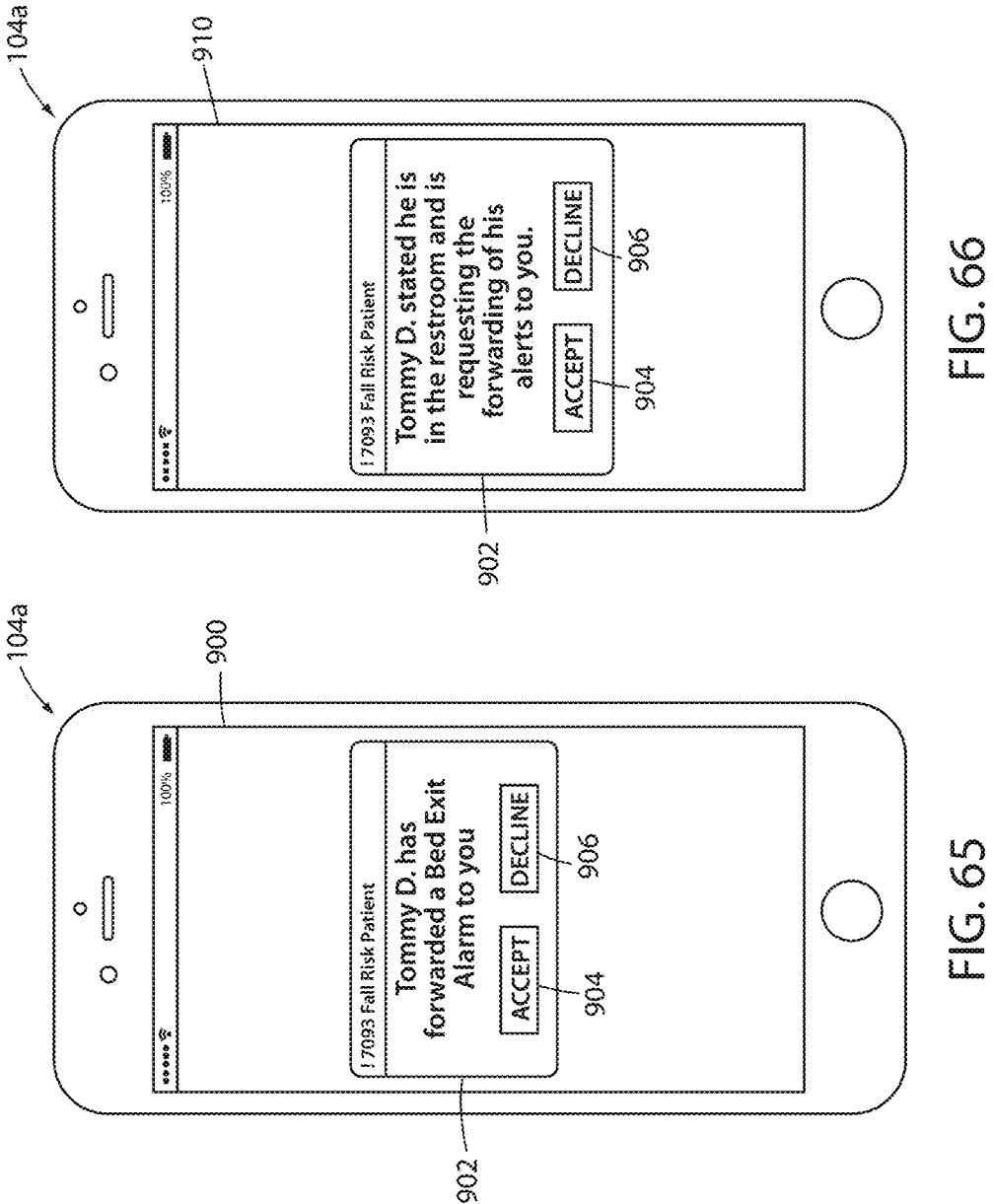
FIG. 65 is a first illustrative sharing request screen that is displayable on an electronic device of the caregiver assistance system.
FIG. 66 is a second illustrative sharing request screen that is displayable on an electronic device of the caregiver assistance system.
Figure 67:
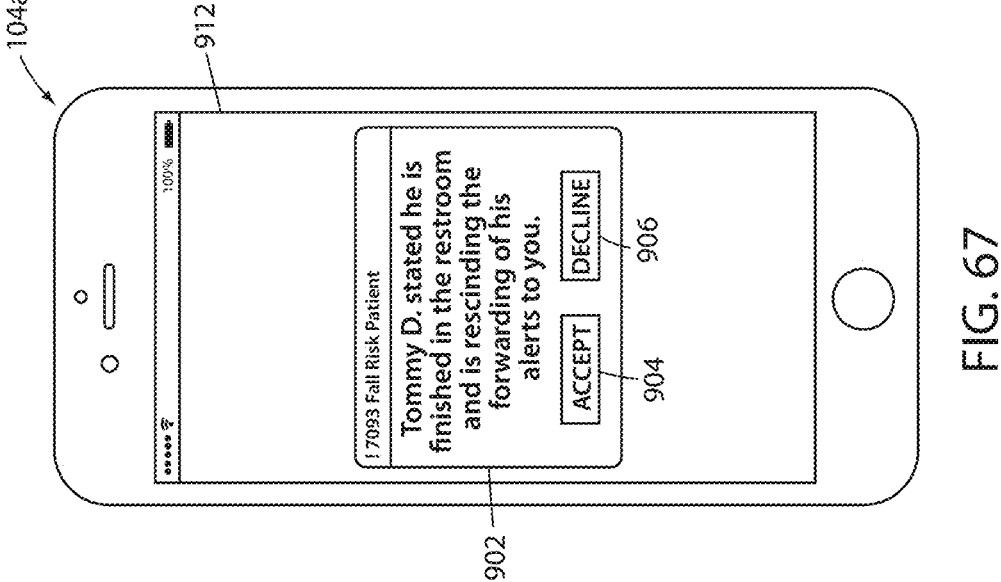
FIG. 67 is an illustrative unsharing request screen that is displayable on an electronic device of the caregiver assistance system.

FIGS. 64-67 illustrate several drawings related to a patient sharing feature that may be included in some embodiments of caregiver assistance system 106. More particularly, FIG. 64 illustrates one embodiment of a sharing algorithm 175 implemented by some embodiments of caregiver assistance application 124, and FIGS. 65-67 illustrate examples of the types of screens that may be displayed by caregiver assistance application 124 on electronic devices 104 during the execution of sharing algorithm 175. It will be understood that modifications to either or both of the algorithm 175 displayed in FIG. 64 and the associated screens shown in FIG. 65-67 may be implemented.

Sharing algorithm 175 may be initiated at any time by a caregiver after he or she has successfully logged into caregiver assistance application 124. Typically, sharing algorithm 175 is initiated by a caregiver pressing on, or otherwise selecting, a sharing icon (not shown) that is displayed on one or more of the screens associated with caregiver assistance application 124. For example, a sharing icon may be added to task menu 174, or it may be added elsewhere. Regardless of where added, sharing algorithm 175 is not shown as being included within the main algorithm 226 (FIG. 5) because it is intended to be initiated at any time in response to user input.

In general, sharing algorithm 175 allows a caregiver to transfer complete or partial responsibility for one or more of the patients to whom he or she has been assigned to another caregiver. Sharing algorithm 175 may therefore affect other ones of the algorithms discussed herein. For example, if caregiver A transfers complete responsibility for patient X to caregiver B, then after that transfer has taken place, caregiver B will be considered the primary caregiver for purposes of alerting algorithm 149. The transfer of complete responsibility for patient X to caregiver B will also enlarge the patient assignment set for caregiver B used at steps 664 and/or 676 of algorithm 139 (FIG. 63) and, in some embodiments, reduce the patient assignment set for caregiver A at steps 664 and/or 676 of algorithm 139. In other situations, algorithm 175 may be selected by a caregiver to transfer one or more specific tasks, such as the task of responding to a particular alarm or performing a patient assessment (e.g. fall risk or bed sore risk). In such cases, complete responsibility for the patient is not transferred, but instead only responsibility for the particular task identified). The effect of algorithm 175 on the other algorithms discussed herein may therefore be limited to only a specific task, or set of tasks. Algorithm 175 may influence the other algorithms discussed herein in still other manners.

Sharing algorithm 175 begins at a step 682 where it receives a request from a first caregiver to share one or more of his or her responsibilities with a second caregiver. As noted, the first caregiver can select whether to share all of his or her responsibilities, or just a subset of his or her responsibilities. Further, as noted, the request for sharing these responsibilities may be implemented by a caregiver selecting a sharing icon displayed on one or more of the screens displayed on his or her mobile electronic device 104*a*. After the caregiver has initiated the request at step 682, caregiver assistance application 124 proceeds to step 684 where it sends the request to the second caregiver. In some embodiments, the first caregiver specifically selects the second caregiver. In other embodiments, the first caregiver may select a set of recipients of the share request. In either embodiment, caregiver assistance application 124 forwards the request at step 684 to the mobile electronic device(s) 104*a* of the second caregiver(s) identified by the first caregiver. This forwarding is implemented by displaying on the screen of the second caregiver(s) an indication that that the first caregiver has initiated a share request. One example of such a share request that is received by a second caregiver is shown in FIG. 65.

First share request screen 900 of FIG. 65 is an example of a share request for a specific task, not a share request for complete responsibility of a patient. In this particular example, screen 900 includes a window 902 in which a share request message is contained. The share request message identifies the particular task, or tasks, that the first caregiver is requesting the second caregiver to accept responsibility for. In this particular example, the share-requested task is the task of responding to an exit detection alert from an exit detection system 46 onboard one of the patient support apparatuses 20. Window 902 includes an "accept" icon 904 and a "decline" icon 906. If the second caregiver is willing to take responsibility for the share-requested task (e.g. an exit detection alarm), he or she touches the "accept" icon 904. If the second caregiver does not wish to take responsibility for the share-requested task, he or she touches the "decline" icon 906.

Sharing algorithm 175 determines if the second caregiver has accepted the share-requested task or not at step 686. If the second caregiver declines the share request by selecting the "decline" icon 906, caregiver assistance application 124 proceeds from step 686 to step 686 where the sharing request is denied. The denials of the sharing request is accompanied by a message to the first caregiver indicating that the share request has either been denied by the second caregiver (if the second caregiver has selected the "decline" icon 906) or not acknowledged by the second caregiver (if the second caregiver does not select either the "accept" icon 904 or the "decline" icon 906 within a predetermined amount of time after window 902 has been displayed on the second caregiver's mobile electronic device 104a). After denying the share request at step 688, caregiver assistance application 124 makes no changes to the alerting, notifications, and/or other aspects of the share-requested task(s), but instead continues to provide such alerts, notifications, and/or other information associated with the share-requested task(s) to the first caregiver.

If the second caregiver accepts the share-requested task at step 686, such as by touching the "accept" icon 904, caregiver assistance application 124 proceeds to step 690 where it adds the share-requested task to the list of tasks/patients for which second caregiver has access to, and is responsible for. This allows the second caregiver access to the share-requested task(s), and such access includes not only information regarding the share-requested task, but also alerts and/or notifications regarding the share-requested task. That is, at step 692, caregiver assistance application 124 adds the second caregiver to the list of caregivers who are to be notified of any alerts, reminders, or other notifications associated with the share-requested task. Thus, for instance, if the first caregiver requests that the second caregiver take over responsibility for performing the next rounding task associated with a particular patient, and the second caregiver accepts, not only will the second caregiver be given access to a room overview screen for that particular patient, but he or she will have the share-requested rounding task added to his or her task list 886, and will therefore receive reminders and/or alerts regarding the share-requested task(s).

In the example of FIG. 65, the patient support apparatus exit alert that was forwarded to the second caregiver will therefore be displayed on the second caregiver's mobile electronic device 104a. Further, the second caregiver will be temporarily assigned the same status as the first caregiver was with respect to this alert. For example, if the first caregiver was the primary caregiver, then the second caregiver will temporarily be considered the primary caregiver, and will accordingly receive alerts in the manner specified for primary caregivers in alerting algorithm 149. Alternatively, if the first caregiver was the secondary caregiver, then the second caregiver will be temporarily considered the secondary caregiver, and will accordingly receive alerts in the manner specified for secondary caregivers in alerting algorithm 149.

In the embodiment shown in FIG. 64, sharing algorithm 175 continues to send the updates, alerts, and/or reminders regarding the share-requested task to both the first caregiver and the second caregiver at step 692. It will be understood that, in some embodiments, algorithm 175 is modified such that, after a share-requested task has been accepted by a second caregiver, the first caregiver no longer receives updates, alerts, and/or reminders regarding that particular share-requested task(s).

After step 692, caregiver assistance application 124 proceeds to step 694 where it receives updates from either of the first or second caregivers regarding the share-requested task. Thus, in the example of FIG. 65, if the second caregiver responds to the patient support apparatus exit alert, caregiver assistance application 124 will update the mobile electronic devices 104a of both the first and second caregivers to reflect the fact that the exit alert has been terminated. As another example, if the shared task is an assessment, caregiver assistance application 124 allows either the first or second caregiver to input the assessment information at step 694. As yet another example, caregiver assistance application 124 also allows both the first and second caregiver to send commands to the patient support apparatus 20 at step 694. Still other data may be input by the first or second caregivers at step 694. After completing step 694, caregiver assistance application 124 returns at step 696 to whatever action it was previously performing prior to starting algorithm 175 at step 682. Any alerts, notifications, and/or reminders that are generated thereafter that are related to the share-requested task continue to be forwarded to the second caregiver's mobile electronic device 104a until the share-requested task is unshared.

Before turning to the process of unsharing a share-requested task, it will be understood that the share-requested task need not be limited to a specific task. Indeed, as noted before, caregiver assistance application 124 is configured to allow a caregiver to transfer complete responsibility for one or more patients to a second caregiver. Still further, caregiver assistance application 124 is also configured to allow a user to share sets of tasks. One example of a set of tasks to be shared is illustrated in FIG. 66. FIG. 66 illustrates a second share request screen 910 that is displayed by caregiver assistance application 124 at step 686. Second share request screen 910 requests that the second caregiver take over responsibility for a set of tasks, rather than an individual task. In the particular example shown in FIG. 66, window 902 identifies the set of tasks as responding to any alerts that would otherwise be issued to the first caregiver. Thus, second share request screen 910 requests that the second caregiver take over responsibility for responding to all alerts—rather than just the patient support apparatus exit alert of FIG. 65—that would otherwise be sent to the first caregiver. If the second caregiver accepts this request, he or she touches the "accept" icon 904 and caregiver assistance application 124 proceeds from step 686 to step 690 of algorithm 175. If the second caregiver does not accept this request, he or she touches the "decline" icon 906 and caregiver assistance application 124 proceeds to step 688 of algorithm 175.

Sharing algorithm 175 is configured to send and receive unshare requests in the same manner as discussed above with respect to share requests. Thus, instead of sending a share request at step 684, algorithm 175 may cause caregiver assistance application 124 to send an unshare request to a second caregiver at step 684. The unshare request asks the second caregiver to rescind a previously shared task, set of tasks, or responsibilities. One example of an unshare request message that may be displayed by caregiver assistance application 124 as part of step 686 is shown in FIG. 67.

Unshare request screen 912 of FIG. 67 shows an example of an unshare request that seeks to rescind the share request example of FIG. 66. Thus, unshare request screen 67 may be displayed by caregiver assistance application 124 after the second caregiver initially accepted the share-requested tasks of FIG. 66 and the first caregiver has since decided to reclaim responsibility for those shared tasks. As with the share request screens, unshare request screen 912 includes an "accept" icon 904 and a "decline" icon 906, enabling the second caregiver to accept or deny the unshare request. In some embodiments, caregiver assistance application 124 is configured to automatically implement unshare requests and simply notify the second caregiver of the unsharing (rather than giving the second caregiver the opportunity to deny the unsharing request). Still further, in some embodiments, if the unshare request is not accepted or denied within a prede-termined time period by the second caregiver, the unshare request may be automatically implemented, in which case all of the data associated with the previously shared task(s) is reverted back to being displayed only on the first care-giver's mobile electronic device 104a.

It will be understood that sharing algorithm 175 may modified in a number of different manners. For example, in one modified embodiment, any share requests have to first be approved by a supervisor or other administrator. In such cases, the request is first sent to the supervisor or adminis-trator's mobile electronic device 104a and then forwarded, if allowed by that individual, to the second caregiver's mobile electronic device 104a. In another modified embodi-ment, only certain types of sharing requests (configurable via an authorized administrator changing local rules 126) are required to have approval of a supervisor or administrator before being sent to a second caregiver. In still other modified embodiments, shared tasks may automatically be rescinded after a predetermined time period and/or after a predetermined event. For example, if an alert is shared with a second caregiver, caregiver assistance application 124 may automatically unshare that task with the second caregiver after the alert has been responded to. Still other variations are possible.

A variety of structural modifications may be made to caregiver assistance system 106 beyond those previously discussed herein. For example, although caregiver assis-tance system 106 has been described herein as utilizing a caregiver assistance application 124 executed on caregiver assistance server 90 and accessed by electronic devices 104 having conventional web-browser applications stored thereon, caregiver assistance system 106 may be modified to include one or more native applications that execute on the electronic devices 104a or *b* themselves. In some of these modified embodiments, the caregiver does not need to open up the web-browser to access caregiver assistance applica-tion 124, but instead opens up a local caregiver assistance software application on the electronic device 104 that inter-acts with the caregiver assistance application 124 being executed on caregiver assistance server 90. In such embodi-ments, it may be easier to provide alerts to the caregiver by having the electronic device vibrate, emit an audible sound, and/or illuminate one or more lights on the device. Such alerts may be more difficult to communicate to a caregiver when caregiver assistance system 106 is implemented using browser-connected electronic devices 104, particularly if the caregiver has the browser application closed and/or running in the background and/or is not looking at the information currently being displayed on the screen of the electronic device 104. Such native applications may be programmed for execution with the Android or iOS operating systems, or still other operating systems utilized by the electronic device 104.

It will be understood by those skilled in the art that, although caregiver assistance application 124 has been pri-marily described herein with reference to a single caregiver using a single electronic device 104, caregiver assistance application 124 is not limited to use by only a single caregiver and/or a single electronic device 104. Further, caregiver assistance application 124 is not limited to use with only a single patient support apparatus 20 or a single patient. Instead, caregiver assistance application 124 is configured to be used, if desired, with all of the patient support apparatuses 20 within the healthcare facility, as well any or all of the caregivers within the healthcare facility. Such use of caregiver assistance application 124 by multiple caregivers can occur simultaneously. That is, multiple care-givers may be logged into caregiver assistance application 124 at the same time. In such cases, caregiver assistance application 124 is configured to display the room, patient, and/or patient support apparatus information discussed above for the set of rooms, patients, and/or patient support apparatuses 20 assigned to that particular caregiver. In other words, each caregiver (other than those with administrative access) is only able to view the room, patient, and patient support apparatus information for the rooms and/or patients assigned to that particular caregiver. Unless otherwise con-figured by an authorized individual, alerts associated with those patients, rooms, and/or patient support apparatuses 20 are only communicated by caregiver assistance application 124 to the mobile electronic device 104a associated with that caregiver (and, in some cases, to the stationary elec-tronic device 104b that is associated with that particular room or patient).

Stationary electronic devices 104b are typically not used to perform rounding tasks and/or patient risk assessments because they cannot be carried with the caregiver to a patient's room, and thus are difficult to use for capturing images or assessment information and/or performing other tasks in the patient's presence. Nevertheless, stationary electronic devices 104b are capable of displaying all of the screens previously described and associated with caregiver assistance application 124, and receiving all of the data that is input on these screens, including not only answers to rounding and/or assessment questions, but also commands to change components on the patient support apparatuses 20. Further, authorized individuals 136 can configure caregiver assistance application 124 as they see fit with respect to what, if any, alerts are displayed on the stationary electronic devices 104b. For example, if a particular stationary elec-tronic device 104b is associated with a particular wing of the healthcare facility, then the authorized individual 136 may configure caregiver assistance application 124 to notify the stationary electronic device 104b whenever any alert from any room or patient support apparatus 20 within that wing is issued. This can be configured even if the different rooms and/or patient support apparatuses 20 are assigned to dif-ferent caregivers. As a result, caregiver A may receive alerts on his or her mobile electronic device 104a for a first set of rooms in that particular wing; caregiver B may receive alerts on his or her mobile electronic device 104a for a second set of rooms in that particular wing; and the stationary electronic device 104b associated with that wing may receive alerts for both the first and the second sets of rooms (and any other rooms in that particular wing). Still other variations are possible.

The data flows of caregiver assistance system 106 between caregiver assistance server 90, patient support apparatuses 20, and electronic devices 104 are illustrated in greater detail in FIG. 2. As shown therein, patient support apparatuses 20 transmit patient support apparatus messages 310 to patient support apparatus server 86 (or directly to caregiver assistance server 90) via network transceivers 60 and wireless access points 76. The patient support apparatus data contained within messages 310 includes such things as the status of the exit detection system 46 (armed or disarmed), the status of the siderails 36 (up or down), the status of the electrical power cord 102 (plugged in or not), the status of the nurse call cable 78 (plugged in or not), the status of the brake (on or off), the height of the litter frame 28, the status of mattress 38 (including any current therapy protocols being implemented using mattress 38), the status of the bed watch monitoring system, any existing alerts, and/or other data about patient support apparatus 20.

Caregiver assistance server 90, after receiving the data in these messages, transmits outbound messages 312 to selected ones of the electronic device 104 (FIG. 2). The content of the outbound messages 312 includes all or selected portions of the patient support apparatus data received via messages 310. Most of this patient support apparatus data is displayed on the screens in top portion 202. The outbound messages 312 also include the data content for the display screens shown as part of main algorithm 226, rounding algorithm 140, skin care algorithm 141, and fall risk reduction algorithm 143. This data content includes, among other things, the rounding questions that are identified in the rounding display screens of FIGS. 10-13, the skin care scoring data shown in FIGS. 29-41, the mattress control information of the screens shown in FIGS. 43-49, the fall risk assessment questions that are displayed in the fall risk screens of FIGS. 19-24, any reminders, room numbers, alerts, and other data discussed herein.

Caregiver assistance server 90 receives inbound message 314 from the electronic devices 104 in which it is in communication (FIG. 2). Inbound messages 314 include rounding data, patient support apparatus commands, fall-risk and/or bed sore-risk assessment data, and/or verification data. The rounding data includes the answers and/or acknowledgements corresponding to the rounding questions displayed on first through fourth rounding screens 190, 220, 230, and 240, and the fall-risk assessment data includes the answers to the fall risk questions that are asked as part of algorithm 143. The bed sore risk assessment data includes any of the data entered by the caregiver using the various screens associated with the bed sore risk reduction algorithm 141, including the documentation algorithm 800. The patient support apparatus commands include any commands input by the caregiver into the electronic device 104 to change a state of the corresponding patient support apparatus 20. As discussed previously, such commands include commands to arm exit detection system 46 and/or commands to arm a bed watch system, as well as other commands.

Inbound messages 314 may also include verification data, which is data gathered by mobile electronic device 104a that verifies the actual physical presence of the caregiver adjacent the patient support apparatus whose patient the caregiver is performing rounding duties for. More specifically, the verification data includes the images of the QR code, bar code, patient support apparatus, and/or caregivers that are captured by the mobile electronic device 104a and sent to caregiver assistance application 124, as was previously described above with respect to FIGS. 15-17.

Figure 68:
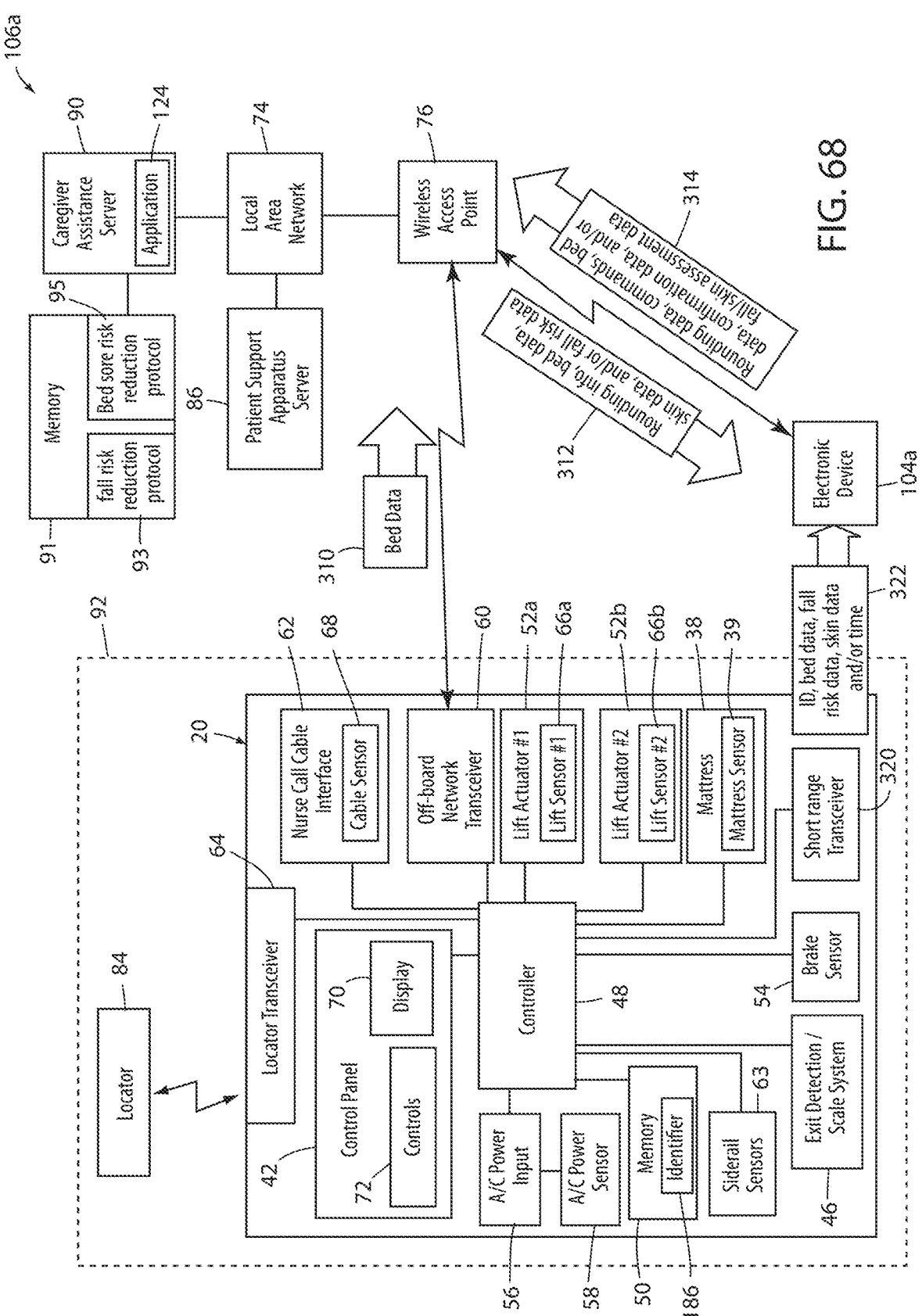
FIG. 68 is a block diagram of a second embodiment of the caregiver assistance system of the present disclosure showing a detailed set of components of a patient support apparatus usable therein, as well as a portion of a local area network in which the patient support apparatus is in communication.

It will be understood that the data flows illustrated in FIG. 2 may be modified significantly. For example, FIG. 68 illustrates a caregiver assistance system 106a according to another embodiment of the present disclosure. Caregiver assistance system 106a differs from caregiver assistance system 106 of FIG. 2 in that caregiver assistance system 106a includes different flows of messages sent between the caregiver assistance server 90, the mobile electronic devices 104a, and the patient support apparatuses 20. Caregiver assistance system 106a also differs from caregiver assistance system 106 of FIG. 2 in that it includes modified patient support apparatuses 20a that, unlike patient support apparatuses 20, include a short range transceiver 320. Further aspects of caregiver assistance system 106a are described below.

Patient support apparatuses 20a of caregiver assistance system 106a include all of the same components of patient support apparatuses 20 of caregiver assistance system 106. Those common components have been labeled with common numbers in FIG. 2 and, unless explicitly stated to the contrary below, the description of those components previously made above is equally applicable to these components. Caregiver assistance system 106a differs from caregiver assistance system 106 primarily in the source of various data (such as verification data, skin care data, fall risk assessment data, etc.) that is sent by electronic device 104 to caregiver assistance server 90 for use with rounding algorithm 140. In some embodiments, this altered data flow enables a control panel on the patient support apparatus 20 to receive any of the data input by the caregiver into mobile electronic device 104a to be input into a control panel 42 on the patient support apparatus 20. The patient support apparatus 20 can then send the input data to mobile electronic device 104a for forwarding to server 90, or it may send it to server 90 via its direction connection with the wireless access points 76. In some cases, system 106a is implemented such that the rounding verification data comes not from the images captured and illustrated in FIGS. 15-17, but from the short range transceiver 320 that is built into patient support apparatus 20a.

Short range transceiver 320 (FIG. 68) is adapted to wirelessly communicate with electronic devices 104 over a relatively short range. The short range is, in some embodiments, no larger than the typical size of a healthcare facility room such that, when a caregiver leaves a particular room, the caregiver's mobile electronic device 104a is no longer within range of the short range transceiver 320, and therefore no longer able to communicate with the short range transceiver 320. In some embodiments, short range transceiver 320 is an infrared transceiver adapted to communicate in line-of-sight situations with a corresponding infrared transceiver built into the mobile electronic device 104a. In other embodiments, short range transceiver 320 is a near field transceiver adapted to communicate with a near field transceiver built into mobile electronic device 104a. In still other embodiments, short range transceiver 320 is an RF transceiver having a relatively small power output such that communications are limited to within a short range of patient support apparatus 20a. Such RF transceivers may include, but are not limited to, Bluetooth transceivers.

Regardless of the specific short range transceiver 320 utilized by patient support apparatus 20a, controller 48 of patient support apparatus 20a is configured to transmit one or more patient support apparatus messages 322 using transceiver 320 to a nearby mobile electronic device 104a (FIG. 68). The messages 322 contain one or more of the following pieces of information: the unique identifier 186 of the corresponding patient support apparatus 20a; the current time; and/or sufficient patient support apparatus data to indicate whether the current status of the patient support apparatus 20 is in compliance with its desired settings or not. This information is transmitted periodically and repetitively in some embodiments of patient support apparatus 20a. In other embodiments, this information is transmitted only in response to an interrogation signal received from a mobile electronic device 104a. In still other embodiments, this information may be transmitted both repetitively and in response to interrogation signals.

Mobile electronic device 104a receives message(s) 322 when it is positioned within the vicinity of patient support apparatus 20a (FIG. 68). Mobile electronic device 104a uses the message 322 for carrying out the verification and/or compliance steps of rounding algorithm 140, for carrying out one or more aspects of bed sore risk reduction algorithm 141, and/or for carrying out one or more aspects of the fall risk reduction algorithm 143. With respect to patient rounding, in some embodiments, messages 322 are sent and captured by mobile electronic device 104a as part of step 252 of algorithm 140. The sending of messages 322 to mobile electronic device 104a takes the place of, or supplements (in some embodiments), the capturing of image data that otherwise occurs at step 252 of algorithm 140. Mobile electronic device 104a uses the messages 322, particularly the patient support apparatus ID and/or time, to verify that it was physically present adjacent patient support apparatus 20a when the rounding occurred. This verification is handled, in some embodiments, internally via the programming of caregiver assistance application 124 such that the caregiver does not need to enter any information, or take any manual steps (other than positioning mobile electronic device 104a within range of transceiver 320) for this verification data to be received by mobile electronic device 104a and forwarded to caregiver assistance application 124. In other embodiments, in order to prevent a user (or electronic device 104a) from modifying the data contained within messages 322, the data is encrypted with an encryption algorithm that caregiver assistance application 124 is able to decrypt, but not mobile electronic device 104a. In still other embodiments, patient support apparatus 20a may be further modified to send a second message to caregiver assistance application 124 via network transceiver 60 whenever it transmits message 322 via short range transceiver 320. This second message confirms to caregiver assistance application 124 that message 322 was sent and, in some embodiments, contains the same information. If caregiver assistance application 124 does not receive this second message, it does not accept the verification data sent from mobile electronic device 104a.

With respect to bed sore risk reduction algorithm 141 and fall risk reduction algorithm 143, patient support apparatus messages 322 may identify the particular patient support apparatus 20 to mobile electronic device 104a (and thus caregiver assistance application 124) that the caregiver is currently positioned next to. This allows caregiver assistance application 124 to automatically, in at least some embodiments, bring up a screen that corresponds to that particular patient support apparatus 20 and the patient assigned thereto. This automatic screen selection may be part of the screen selection algorithm 139 described previously. If the caregiver wishes to perform a risk assessment (bed sore and/or fall) for a particular patient, he or she merely needs to walk within range of messages 322 and press the fall task icon 178. In response to pressing fall task icon 178, caregiver assistance application 124 automatically displays screen 400 (or a screen like it) with full knowledge of which patient (and/or which patient support apparatus 20) the answers to the fall risk questions are applicable to. The caregiver therefore is relieved of the task of manually identifying a specific room or a specific patient before proceeding to the risk assessment process of algorithms 141 and/or 143. Instead, caregiver assistance application 124 uses the specific patient support apparatus identifier 186 received within message 322 to determine which patient the subsequent risk assessment applies to. Risk reduction algorithms 141 and/or 43 may also use data from messages 322 for other aspects.

Regardless of whether they are used by rounding algorithm 140, bed sore risk reduction algorithm 141, and/or fall risk reduction algorithm 143, messages 322 (FIG. 68) also include patient support apparatus data. In some embodiments, the patient support apparatus data only includes an indicator indicating whether the patient support apparatus 20 is in a compliant or non-compliant state. In other embodiments, the patient support apparatus data includes actual data about the state of each of the components of the patient support apparatus 20 and the determination of whether the patient support apparatus is in a compliant or non-compliant state is made by caregiver assistance application 124 based on the data communicated in message 322, as well as data stored in rules repository 126 defining the criteria for compliance. In either embodiment, the patient support apparatus data sent in message 322 is used by algorithm 140 to perform step 254 (FIG. 6) and/or by risk reduction algorithms 141 and/or 143 to perform step 360 (FIG. 18).

In some embodiments, message 322 may also include the current time. If included, this time information is also forwarded to caregiver assistance application 124. Caregiver assistance application 124 uses this time information to confirm the time that the caregiver was actually present at the patient's bedside when a rounding task was completed (or, in some embodiments, to record when another task was completed, such as a fall risk assessment). This time information is sent to EMR server 98 in some embodiments so that the time at which the rounding task, or other task, is recorded in the patient's electronic medical record. In other embodiments, patient support apparatus 20 may skip transmitting a time in message 322 and mobile electronic device 104a may append a time of receipt of message 322 in the data it sends to caregiver assistance application 124. As yet another alternative, both patient support apparatus 20 and mobile electronic device 104a may omit sending any time information and caregiver assistance application 124 can instead record the time at which it receives the inbound messages 314 from mobile electronic device 104a. In any of these embodiments (which may be wholly or partially combined), the time is used by caregiver assistance application 124 to determine and/or record when the caregiver completed his or her rounding task (or other task) for the particular patient assigned to the patient support apparatus 20 that sent message 322.

Figure 69:
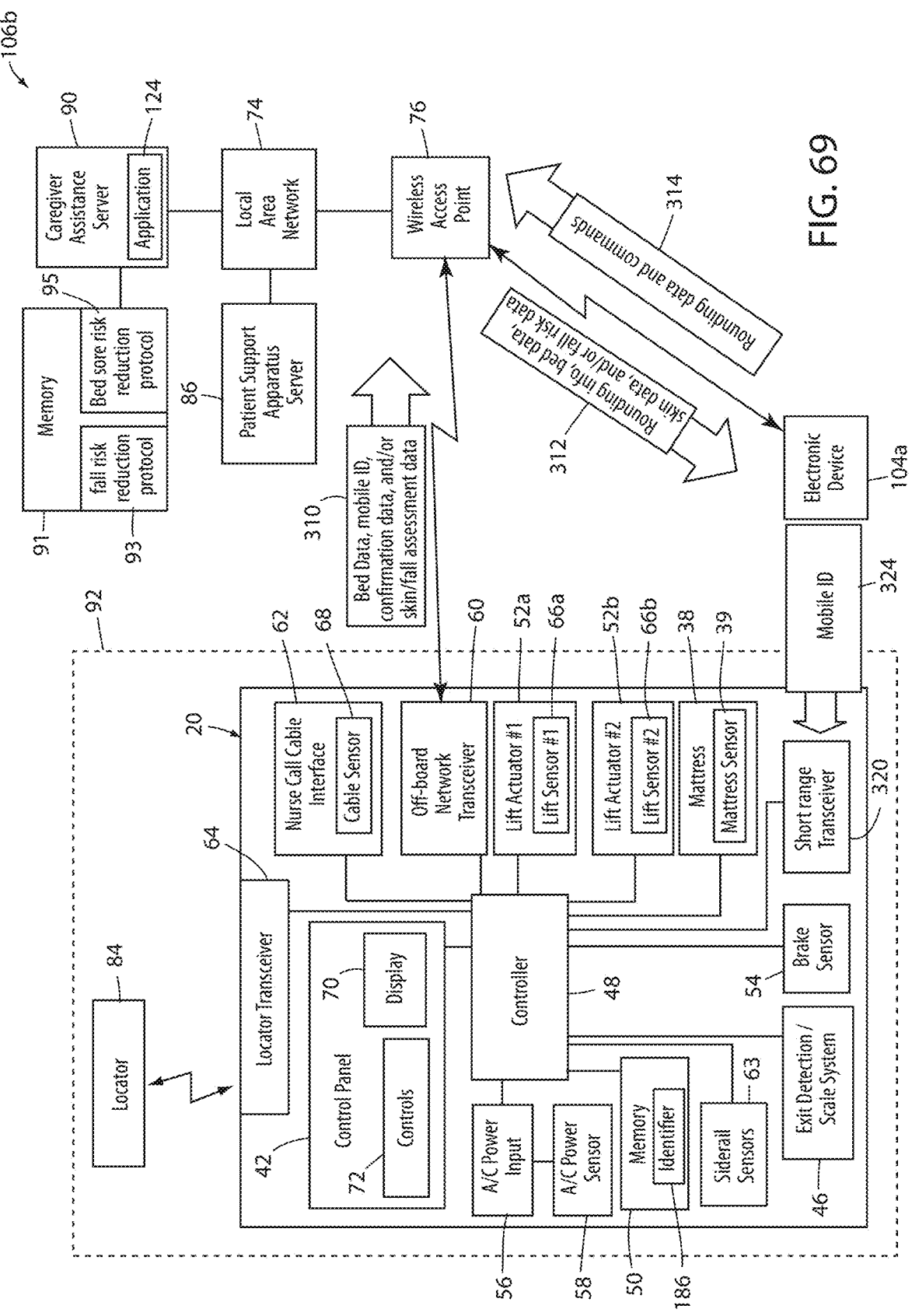
FIG. 69 is a block diagram of a third embodiment of the caregiver assistance system of the present disclosure showing a detailed set of components of a patient support apparatus usable therein, as well as a portion of a local area network in which the patient support apparatus is in communication.

FIG. 69 illustrates a caregiver assistance system 106b according to another embodiment of the present disclosure. Caregiver assistance system 106b differs from caregiver assistance systems 106 and 106a of FIGS. 2 and 68, respectively, in that mobile electronic device 104*a* sends an electronic device message 324 to patient support apparatus 20*a* that is used by caregiver assistance system 106*b* for one or more purposes. With respect to rounding algorithm 140, message 324 is used by patient support apparatus 20 to verify that the caregiver was present at the patient's bedside during the caregiver's performance of his or her rounding duties. With respect to risk reduction algorithms 141 and/or 143, messages 324 may be used to correlate the risk assessment to a specific patient or patient support apparatus 20, or it may be used to send a command to the patient support apparatus 20 directly in order to change a state of any of the bed sore risk components (e.g. mattress 38) or fall-risk components of patient support apparatus 20.

As shown more clearly in FIG. 69, mobile electronic device 104*a* is adapted in caregiver assistance system 106*b* to send out a short range message 324 to a nearby short range transceiver 320 of patient support apparatus 20*a*. The short range message 324 is sent as a result of any one or more of the following: in response to a user manipulating an input on mobile electronic device 104*a*, an expiration of a periodic time interval, an interrogation signal sent from short range transceiver 320 of patient support apparatus 20*a*, a signal from RTLS server 100 to mobile electronic device 104*a* indicating that it is currently in a room with one or more patient support apparatuses 20*a*, a combination of one or more of these triggering conditions, and/or in response to still other triggering conditions.

The content of electronic device message 324 includes a unique identifier that uniquely identifies the mobile electronic device 104*a*. This may be a serial number of the device 104*a*, a MAC address, or some other identifier that distinguishes that particular mobile electronic device 104*a* from other mobile or stationary electronic devices 104*a*, 104*b* that are part of system 106*b*, and/or other electronic devices that are not part of system 106*b* but which may utilize the same protocol and/or communication channel as transceiver 320.

As with patient support apparatus message 322 (FIG. 68), electronic device message 324 may be sent via infrared, near field communication, low power RF (e.g. Bluetooth), or some other protocol that limits the range of message 324 such that it is not detected by patient support apparatuses 20*a* that are positioned outside of the room in which the caregiver is currently located.

In response to receiving the electronic device message 324, controller 48 of patient support apparatus 20*a* forwards a message to caregiver assistance application 124 informing application 124 of the receipt of the message 324, including the mobile ID contained within the message 324. Caregiver assistance application 124 uses the receipt of this information at step 252 of rounding algorithm 140. That is, caregiver assistance application 124 waits for receipt of this message from patient support apparatus 20*a* and, if it does not receive it, it concludes that there has been no verification of the caregiver's presence beside the patient when performing his or her rounding task. If the caregiver assistance application 124 receives the message, then it concludes that there has been verification and proceeds to step 254 of algorithm 140. In some embodiments, caregiver assistance application 124 proceeds from step 250 directly to step 254 and doesn't wait for the receipt of the mobile ID from patient support apparatus 20. In such embodiments, caregiver assistance application 124 checks to see if the mobile ID has been received from the patient support apparatus 20*a* after performing step 254 and/or the steps of path 280 and/or 282 have been completed (but prior to step 256).

In the caregiver assistance system 106*b* of FIG. 69, mobile electronic device 104*a* does not need to include any verification data in the inbound messages 314 it sends to caregiver assistance server 90 because such verification data is contained within the patient support apparatus messages 310 sent by network transceiver 60. In some embodiments, the verification data contained within message 310 includes only the mobile electronic device ID, while in other embodiments, the verification data includes additional information, such as, but not limited to, the time at which the electronic device message 324 was received. Of course, all of the messages 310 sent from patient support apparatus 20*a* (and patient support apparatuses 20) via network transceiver 60 to caregiver assistance server 90 include the patient support apparatus ID.

In the caregiver assistance system 106*b* of FIG. 69, the messages 314 sent by mobile electronic device 104*a* to caregiver assistance server 90 may omit patient support apparatus data that is used to determine whether the patient support apparatus 20*a* is in a compliant state or not. This information may be omitted because patient support apparatus 20*a* sends its status data directly via messages 310, and this status data is used by caregiver assistance application 124 to determine at step 254 whether the patient support apparatus 20*a* is in a compliant state or not.

Caregiver assistance system 106*b* of FIG. 69 may be modified to replace the short range communication between mobile electronic device 104*a* and transceiver 320 of patient support apparatus 20*a*. In such modified embodiments, rather than having a wireless signal transmitted to patient support apparatus 20*a* to verify the caregiver's presence adjacent the patient support apparatus 20*a*, the patient support apparatus 20*a* is modified to accept a physical input from the caregiver, such as a button, switch, or the like, that the caregiver presses during the rounding task. The physical input may be included as an icon on a touchscreen of patient support apparatus 20*a*, or it may be a dedicated control, or it may some combination of the two. As an alternative to a physical input, a wireless signal may be utilized for verification purposes that does not involve mobile electronic device 104*a*. For example, the input may involve a caregiver swiping a card with a magnetic strip along a card reader built into patient support apparatus 20*a*, or it may involve positioning a near field communication card adjacent a near field communication transceiver built into patient support apparatus 20*a*. Still other variations are possible.

Regardless of how the input to patient support apparatus 20 is implemented, when the caregiver physically or wirelessly activates the verification control on patient support apparatus 20*a*, controller 48 sends a message 310 to caregiver assistance application 124 that includes verification data indicating that the caregiver was present adjacent patient support apparatus 20*a*. The message 310 may include a time at which the verification input was activated by the caregiver. In this modified embodiment of system 106*b*, short range transceiver 320 of patient support apparatus 20*a* may be omitted and/or modified, and mobile electronic device 104*a* need not include a transceiver that is compatible with transceiver 320.

It will be noted that, as shown in FIG. 69, caregiver assistance system 106*b* does not show electronic device 104 forwarding any fall risk assessment or bed risk assessment data to caregiver assistance server 90 via wireless access point 76. Although caregiver assistance system 106*b* can be configured to forward such data in the manner previously described, caregiver assistance system 106*b* can alternatively be configured such that the risk assessment data (fall or bed sore) gathered by these algorithms 141 and/or 143 are gathered via a control panel 42 on patient support apparatus 20. Thus, instead of displaying screens such as those shown in FIGS. 19-24 and/or FIGS. 29-41 on the display of electronic device 104, caregiver assistance application 124 can be configured to work with a patient support apparatus 20 that displays screens like those shown in these figures on one of its own displays (e.g. display 70). The data input via these screens is then sent by patient support apparatus 20 to caregiver assistance application 124 and used in the manner specified by algorithm 141 and/or algorithm 143. In this particular embodiment, the patient support apparatus 20 is used to perform either or both of the risk assessments, and the electronic device 104 is used to receive and display alerts if the fall risk reduction protocol is not being followed. In still another alternative embodiment, the risk assessment screens may be displayed and on either or both of display 70 of patient support apparatus 20 or the display of the electronic device 104.

Figure 70:
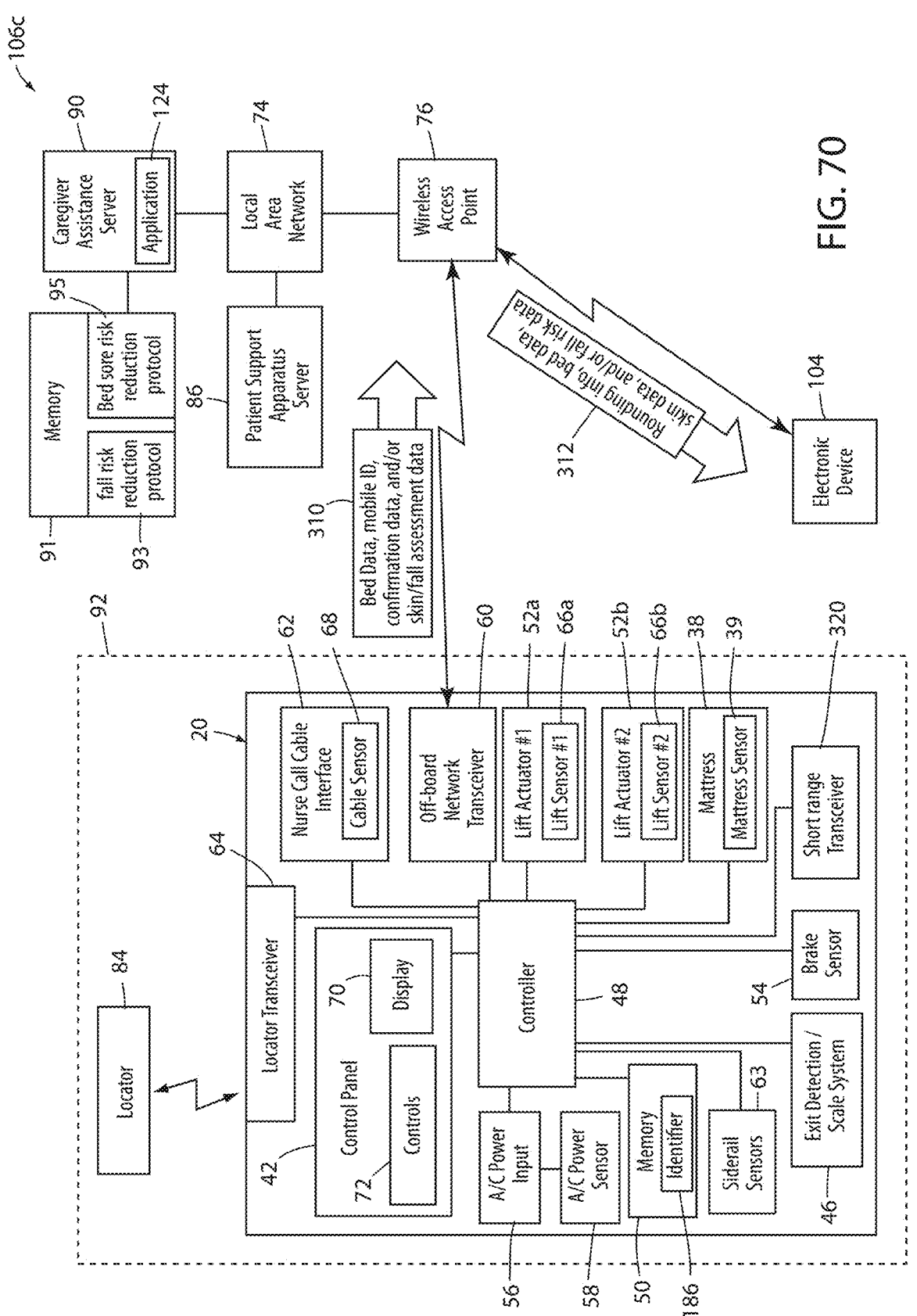
FIG. 70 is a block diagram of a fourth embodiment of the caregiver assistance system of the present disclosure showing a detailed set of components of a patient support apparatus usable therein, as well as a portion of a local area network in which the patient support apparatus is in communication.

FIG. 70 illustrates another caregiver assistance system 106c according to yet another embodiment of the present disclosure. Caregiver assistance system 106c differs from caregiver assistance systems 106, 106a, and 106b of FIGS. 2, 68, and 69, respectively, in that mobile electronic device 104a does not send any rounding data, fall risk assessment data, bed sore risk assessment data, commands, and/or patient support apparatus data back to caregiver assistance application 124. Instead, such data is communicated to caregiver assistance server 90 via patient support apparatus 20a. Caregiver assistance system 106c also differs from the other caregiver assistance systems 106, 106a, and 106b in that it can utilize either patient support apparatus 20 or patient support apparatus 20a. That is, the patient support apparatuses usable with caregiver assistance system 106c can include short range transceiver 320, or they may omit short range transceiver 320. Indeed, in some embodiments, caregiver assistance system 106c may be implemented in a healthcare facility wherein some of the patient support apparatuses includes short range transceiver 320 and others do not.

In the embodiment of FIG. 70, system 106c uses mobile electronic devices 104a (and/or stationary electronic devices 104b (not shown)) primarily to display information regarding the patient support apparatuses 20 and/or 20a, as well as, in some embodiments, to display rounding information, fall risk protocol compliance information, and/or skin care protocol compliance information. The caregiver, however, does not utilize mobile electronic device 104a (or device 104b) to input rounding information, verification data, fall risk assessment data (e.g. answer to fall risk questions), bed sore risk assessment data (e.g. bed sore risk scores) and/or compliance data. Instead, all of this data is entered via a user interface of patient support apparatus 20 or 20a. Stated alternatively, in the embodiment of caregiver assistance system 106c of FIG. 70, all of the screens shown in at least FIGS. 10-14, 19-27, and/or 29-41 are adapted to be displayed on the display 70 of patient support apparatus 20, or 20a, rather than (or in addition to) the display of the electronic devices 104. Controller 48 of system 106c is therefore configured to execute a software application that displays the information shown in these screens on display 70 and provides the same functionality as those screens. The caregiver, for example, enters the patient's pain level using plus and minus icons 210 and 212 and a next icon 214 that are displayed on display screen 70 of the corresponding patient support apparatus 20 or 20a (see FIG. 10).

In the embodiment of FIG. 70, mobile electronic device 104a does not need to receive any compliance data from the patient support apparatus 20 or 20a because this information is sent from the patient support apparatus 20 to caregiver assistance application 124 (via messages 310). Indeed, in some embodiments of system 106c, mobile electronic devices 104a may be dispensed with entirely, or used only to receive alerts and/or status updates. Alternatively, mobile electronic devices 104a may be used to display information about the rounding status and/or patient support apparatus status, but not accept any inputs regarding patient rounding and/or fall risk assessments (and, in some embodiments, not accept any commands for commanding the patient support apparatus).

In the embodiment of FIG. 70, patient support apparatus 20 or 20a may be configured to require a user to enter a username and/or a password before allowing the caregiver to input the rounding information and/or risk assessment data into patient support apparatus 20 or 20a. Such access may be carried out in the same or similar manner to what is illustrated in FIGS. 7 and 8. Alternatively, in some embodiments, patient support apparatus 20 or 20a may be configured to allow the caregiver to enter rounding data and/or risk data without first establishing his or her credentials.

In the caregiver assistance system 106c of FIG. 70, neither mobile electronic device 104a nor patient support apparatus 20 (or 20a) sends any verification data to caregiver assistance server 90. This is because the rounding data comes to caregiver assistance server 90 via messages 310 from patient support apparatus 20 or 20a. Because such messages 310 are specifically received from patient support apparatus 20 or 20a, and are only sent in response to the caregiver manipulating one or more controls on the patient support apparatus 20 or 20a, the very sending of such messages 310 is verification that the caregiver is present adjacent the patient support apparatus 20 or 20a. In other words, because messages 310 originate from patient support apparatuses 20 or 20a in response to caregiver actions, such messages inherently provide their own verification of the caregiver's presence.

It will be understood that caregiver assistance system 106c of FIG. 70 may be modified in a number of different manners. For example, in at least one modified embodiment, rounding algorithm 140 is modified so that no rounding questions, fall risk assessment questions, and/or bed sore scoring screens are displayed, and/or caregiver assistance application 124 does not wait for receipt of any answers for the rounding questions in algorithm 140. In this modified embodiment, it is assumed that the caregivers will ask the proper questions for either or both of the rounding task and the fall risk assessment task while they are present in the patient's room. It is also, or alternatively, assumed that the caregiver knows the different score levels that are to be assigned to the different components of the bed sore risk assessment, and therefore application 124 may omit the screens of FIGS. 30-35, or condense the information in these screens to a smaller number of screen. Therefore, system 106c assumes that rounding questions and rounding tasks are properly asked and implemented whenever the caregiver is present in a patient's room, and also assumes that whenever it receives a fall risk assessment score, that the proper fall risk assessment questions are asked; and/or that the proper bed sore risk components are known and properly scored. As a result of one or more of these assumptions, this modified embodiment of system 106c concludes that a caregiver has properly performed a rounding task whenever his or her presence within a patient's room is detected (while the patient is present in that room), and/or it concludes that the caregiver has properly determined the fall risk of a patient without having seen the specific questions used in the fall risk assessment, and/or it concludes that the caregiver has properly assessed the patient's bed sore risk without seeing all of the information shown on the screens of FIGS. 30-35. Accordingly, in this modified embodiment, patient support apparatus 20 or 20a is configured to send a rounding confirmation message 310 to caregiver assistance server 90 whenever it detects the presence of a caregiver. The message includes data indicating the detection of the caregiver's presence, and caregiver assistance application 124 interprets this data as an indication that the caregiver has completed a round with that particular patient. If the message includes risk assessment data, or a separate message 310 is sent that includes risk assessment data, caregiver assistance application 124 interprets this assessment data as properly reflecting the patient's fall or bed sore risk according to the questions and/or scores utilized by that particular healthcare facility.

In this modified embodiment of system 106c, the presence of a caregiver within a room can be detected in a variety of different manners. In one implementation, patient support apparatus 20 or 20a is modified to send a message 310 whenever a button or control is activated on one of the caregiver control panels 42a or 42c. For example, if the scale controls are used to weigh the patient, or a therapy control is used to implement a mattress therapy, or the exit detection system is armed, controller 48 of patient support apparatus 20 or 20a sends a message 310 to caregiver assistance server indicating that a caregiver has activated a control on patient support apparatus 20 or 20a. The message 310 is sent because system 106c assumes that such button or control activations are the result of a caregiver's actions, not the patient's actions. As a result, the message 310 includes data indicating that a caregiver is present in the room. The message 310 may include data identifying the specific control that has been activated and/or a time at which the control was activated. Alternatively, message 310 may simply indicate that a caregiver control was activated without specifying which one and/or without specifying a time.

In another implementation of this modified embodiment of system 106c, the caregiver carries a card (an RF ID card, a card with a magnetic strip, a near field communication card, or another type of card) that is detected by a corresponding sensor on the patient support apparatus 20 or 20a when the caregiver is within relatively close proximity to the patient support apparatus 20 or 20a (e.g. within the same room, or closer). In response to detecting the card, patient support apparatus 20 or 20a sends a message 310 to caregiver assistance application 124 indicating the presence of the caregiver, and caregiver assistance application 124 treats that message 310 as proof that the caregiver has completed a round with the patient. The message 310 may also include patient support apparatus data that caregiver assistance application 124 uses to determine if the patient support apparatus 20 or 20a is in a compliant or non-compliant state. This data (the compliancy data and rounding completion data) is then sent to EMR server 98, as discussed above with respect to step 256 of algorithm 140.

In this modified embodiment of caregiver assistance system 106c, patient support apparatus 20 (or 20a) and/or mobile electronic device 104a can be designed to omit the display of any rounding questions and/or rounding related screens shown in FIGS. 10-17. In other words, in this modified embodiment, because the caregiver is assumed to perform his/her rounding duties correctly whenever present in the patient's room, there is no need to display the questions shown in FIGS. 10-13 and/or receive answers to those questions. The display of these screens can therefore be omitted. The same is true for the fall risk assessment questions and associated screens and the bed sore risk assessment screens. That is, they may be omitted in some embodiments, but retained in other embodiments. Further, there is no need to include the verification screens of FIGS. 15-17 because the caregiver's presence is inherently verified in this embodiment (i.e. the caregiver's presence is the trigger in this embodiment for concluding that a rounding task has been completed). Indeed, in this embodiment, the web API 132 of caregiver assistance server 90 can be omitted entirely, if desired, along with need for any devices (electronic devices 104a, 104b, or patient support apparatuses 20 or 20a) to log into this modified version of system 106c.

Figure 71:
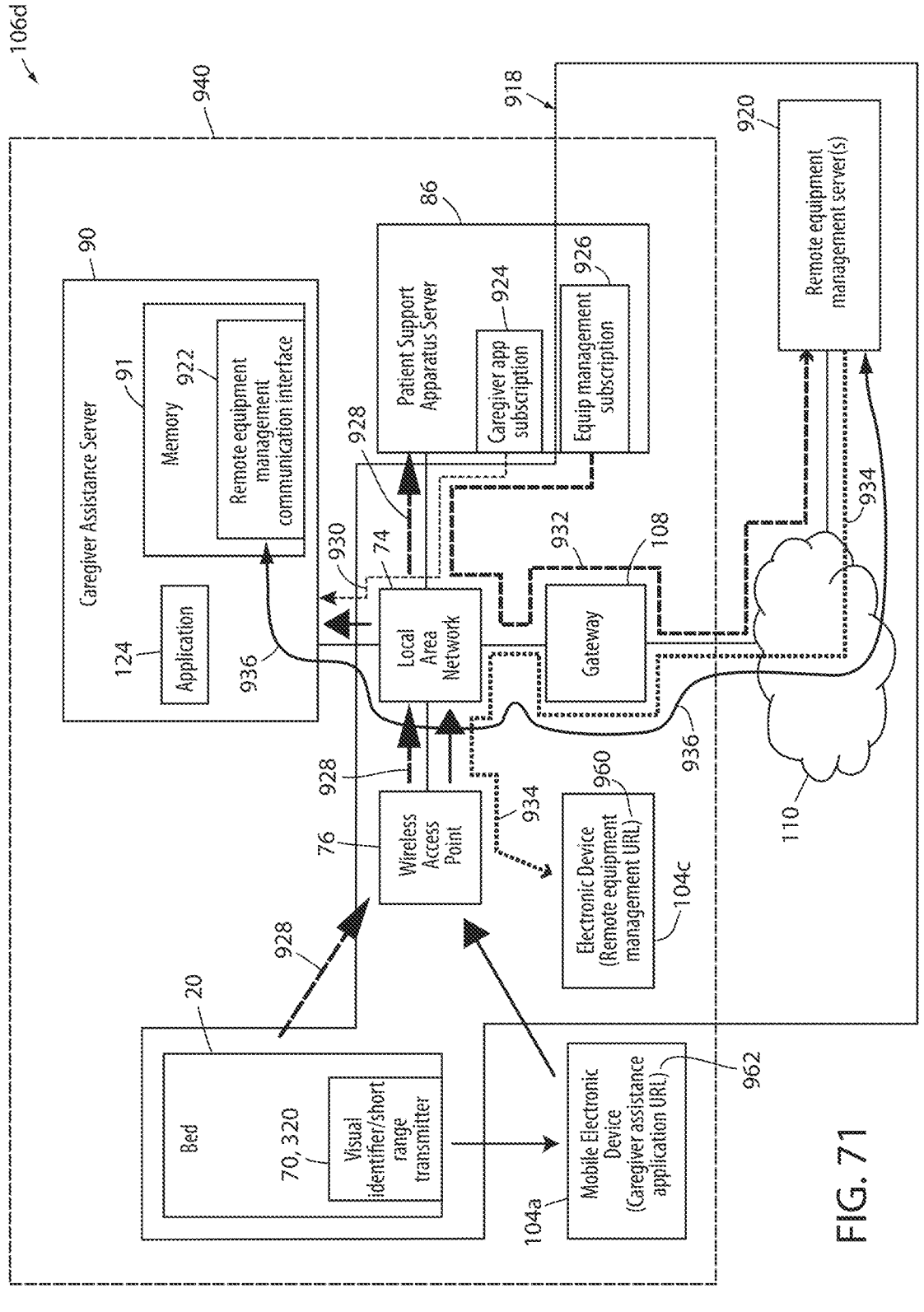
FIG. 71 is a block diagram of a fifth embodiment of the caregiver assistance system of the present disclosure showing a caregiver assistance application adapted to operate in conjunction with a remote equipment management system.

FIG. 71 illustrates another caregiver assistance system 106d according to yet another embodiment of the present disclosure. Caregiver assistance system 106d differs from caregiver assistance systems 106, 106a, 106b, and 106c of FIGS. 2, 68, 69, and 70, respectively, in that it includes a remote equipment management interface 922 that is adapted to enable caregiver assistance application 124 to work in conjunction with a standalone remote equipment management system 918. The remote equipment management system 918 may be a conventional, standalone equipment management system that repetitively receives updates from equipment within the healthcare facility (e.g. patient support apparatuses 20) regarding their usage, maintenance, servicing, battery state, etc. In at least one embodiment, the remote equipment management system 918 is implemented in any of the forms disclosed in commonly assigned PCT patent publication WO 2018-013666 filed Jul. 12, 2017, by inventors David Becker et al. (Int'l app. #: PCT/US2017/041681) and entitled EQUIPMENT MANAGEMENT SYSTEM, the complete disclosure of which is incorporated herein by reference in its entirety. Caregiver assistance application 124 may be configured to interface with other equipment management systems as well.

As shown in FIG. 71, remote equipment management system 918 includes one or more remote equipment management servers 920 (positioned outside of a healthcare facility 940) that communicate with one or more pieces of medical equipment, such as patient support apparatuses 20. Remote equipment management server 920 communicates with the equipment using various structures of the healthcare facility's local area network 74, such as, but not limited to, patient support apparatus server 86, wireless access points 76, and internet gateway 108 that couples local area network 74 to the Internet 110. Remote equipment server 920 is located at an Internet accessible location that is therefore able to communicate with LAN 74 via gateway 108.

Each patient support apparatus 20 that is part of remote equipment management system 918 is configured to send its data to patient support apparatus server 86. Patient support apparatus server 86 is configured to allow one or more services to subscribe to the patient support apparatus data that it receives. In the embodiment shown in FIG. 71, both caregiver assistance application 124 and remote equipment management system 918 include a subscription to this patient support apparatus data. Thus, as a result of a caregiver assistance application subscription 924, patient support apparatus server 86 forwards patient support apparatus data to server 90 and caregiver assistance application 124. This data includes the data described above, such as, but not limited to, the data displayed in the top portion 202 of various of the caregiver assistance screens (see, e.g., top portion 202 of screen 190 of FIG. 10). As a result of a remote equipment management system subscription 926, patient support apparatus server 86 also sends the patient support apparatus data it receives from patient support apparatuses 20 to remote equipment management server 920.

It will be understood that the subscriptions 924 and 926 may be for the same sets of patient support apparatus data, or they may include subscriptions to different data sets. Still further, it will be understood that, in some embodiments, patient support apparatuses 20 may be configured to send their patient support apparatus data to remote equipment management system server 920 directly (i.e. without passing through server 86).

In the embodiment shown in FIG. 71, the patient support apparatus data travels from a patient support apparatus 20 to patient support apparatus server 86 along a first path 928. After arriving at patient support apparatus server 86, the data is forwarded to server 90 and caregiver assistance application 124 via a second path 930. Further, the patient support apparatus data received at patient support apparatus server 86 (or a subset of it) is forwarded by server 86 to remote equipment management server 920 via a third path 932. The data that is stored at remote equipment management server 920, or a subset of it, is accessible to users of the remote equipment management system 918 via one or more electronic devices 104c. Electronic devices 104c include smart phones, tablets, laptops, desktops, and browser enabled displays. Electronic devices 104c may be the same as any of devices 104a and/or 104b, or they may be different. Whether the same or different, a direct user of remote equipment management system 918 uses the electronic device 104c to access remote equipment management server 920 by navigating to a specific remote equipment management URL 960. In contrast, a user of caregiver assistance system 106d accesses caregiver assistance application 124 by navigating to a separate caregiver assistance application URL 962. For each URL, the user must present separate login credentials.

Thus, for a user to access the equipment management data stored at server 920 (the contents of which are described in greater detail in the aforementioned PCT patent publication WO 2018-013666), the user enters valid login information (e.g. username and password) into the electronic device 104c and that information is communicated directly (via access point 76, gateway 108, and Internet 110) to server(s) 920. If the login information is valid, the user is able to view the equipment management data stored at server 920 on his or her electronic device 104c. This data is communicated to the electronic device 104c via a fourth path. As shown in FIG. 71, fourth path 934 bypasses caregiver assistance application 124 and server 90.

Because remote equipment management system 918 is a separate system that utilizes different users with different login information, and because it stores different sets of data than caregiver assistance application 124, a user who directly accesses server 920 via electronic device 104c is not able to access any of the data of caregiver assistance application 124. Similarly, a user of caregiver assistance application 124 is not able to send his or her caregiver assistance system login information to server 920 in order to gain access to the data stored therein. However, as will now be discussed, caregiver assistance server 90 of system 106d is constructed so that users of caregiver assistance application 124 are able to gain access to the data of remote equipment management system 918.

In order for a user of caregiver assistance application 124 to access the data of remote equipment management system 918, he or she must be validly logged into caregiver assistance application 124. Once logged in there, he or she may send a request for patient support apparatus data to caregiver assistance application 124. Caregiver assistance application 124 receives this request and uses remote equipment management communication interface 922 to communicate the request to remote equipment management server 920. Interface 922 is configured with a list of authorized users who are permitted to access remote equipment management system 918, as well as the communication protocols used to communicate with remote equipment management server 920. Further, interface 922 includes, or has access to, the IP address(es) and/or URL(s) of remote equipment management server(s) 920. Caregiver assistance application 124 is therefore able to act as an authorized user of remote equipment management system 918 for all of, or a set of, the users of caregiver assistance application 124. This allows those user to access data from remote equipment management server 920. Further, in some embodiments, caregiver assistance application 124 is configured to allow an authorized user of caregiver assistance application 124 to upload data, such as, but not limited to, servicing data to remote equipment management server(s) 920.

The data communicated between caregiver assistance server 90 and remote equipment management server 920 follows a fifth path 936. As a result, if a user of caregiver assistance application 124 is logged into caregiver assistance application 124 on a mobile electronic device 104a (see FIG. 71), he or she is able to access equipment data stored at server 920 by sending a request to server 90. The request is forwarded via fifth data path 936 to server 920, and server 920 responds to server 90 via fifth path 936. This response is then forwarded to mobile electronic device 104a via local area network 74 and an appropriate wireless access point 76. In contrast, if a user is logged into remote equipment management system 918 directly on his or her electronic device 104c, they are able to access the data of remote equipment management server 920 by bypassing server 90 and caregiver assistance application 124. That is, the communication between electronic device 104c and server 920 takes place via path 934, and path 934 does not utilize caregiver assistance application 124 or server 90.

Interface 922 of caregiver assistance application 124 therefore allows users of caregiver assistance application 124 to utilize one or more electronic devices 104a or 104b to access data stored at remote equipment management system 918 without having to separately log into system 918, or to manually input any other data necessary for viewing this data. As a result, a single user interface of electronic devices 104a, 104b is able to provide the user with the functionality of both caregiver assistance application 124 and remote equipment management system 918. The user therefore does not need to download separate applications to utilize both systems, log into separate systems, and/or direct their web browser to separate URL's in order to enjoy the advantages of both systems.

Figures 72, 73:
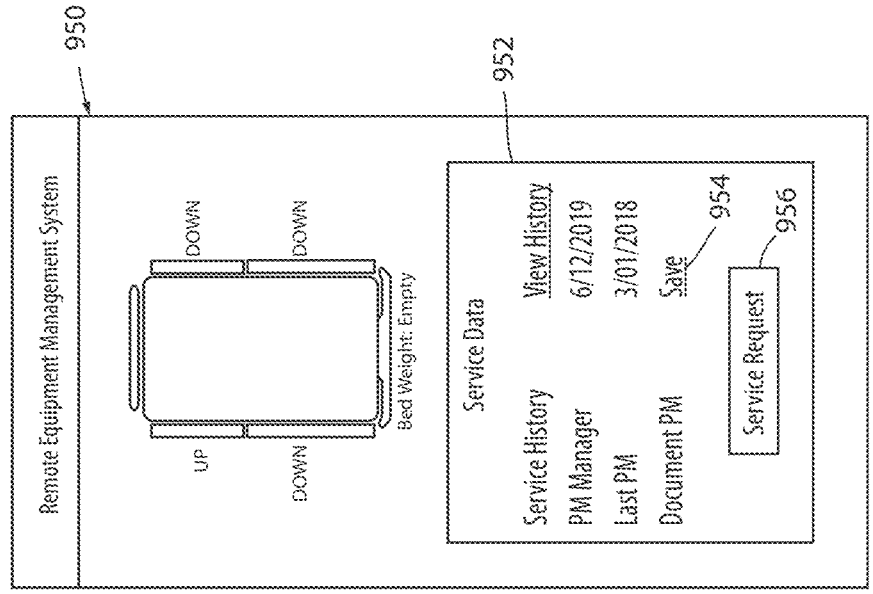
FIG. 72 is an illustrative bed identification screen that is displayable on an electronic device of the caregiver assistance system of FIG. 71.
FIG. 73 is an illustrative bed maintenance screen that is displayable on an electronic device of the caregiver assistance system of FIG. 71.

FIG. 72 depicts one example of a manner in which a user of caregiver assistance application 124 can utilize his or her electronic device 104a to gain access to the data stored at remote equipment management server 920. More particularly, FIG. 72 depicts a remote equipment management system access screen 942 that includes an image window 944 and a capture icon 946. Image window 944 and capture icon 946 may operate in the same manner as previously described with respect to image window 272 and capture icon 274 of FIG. 15. That is, the user uses screen 942 to capture an image of a QR code, or other unique visual identifier on a particular patient support apparatus 20. After capturing the image, the image is either locally processed on device 104*a* to determine the identity of the corresponding patient support apparatus 20, or it is sent to caregiver assistance application 124 to determine the identity of the corresponding patient support apparatus 20. After the identity of the patient support apparatus 20 is determined, caregiver assistance application 124 sends a request to remote equipment management server 920 for data corresponding to that particular patient support apparatus 20. Server 920 sends the requested data back to caregiver assistance application 124 via path 936 and caregiver assistance application 124 then displays this data (or a portion of it) on the screen of the mobile electronic device 104*a*.

FIG. 73 illustrates one example of a remote equipment management data display screen 950. Remote equipment management data display screen 950 displays patient support apparatus data that is obtained from remote equipment management server(s) 920. More particularly, screen 950 includes a service data window 952 that displays various data regarding the servicing of the patient support apparatus 20. This service data includes, but is not limited to, data indicating the service history of that patient support apparatus, data indicating the last time preventative maintenance was performed on the patient support apparatus 20, and/or data indicating who is responsible for performing one or more types of service on the patient support apparatus 20.

In addition, screen 950 may also include a"document" icon 954 and a "service request" icon 956. The "document" icon 954 is touched when the user has performed a particular service on the patient support apparatus 20. Pressing this icon causes caregiver assistance application 124 to send information to remote equipment management server 920 indicating that that particular patient support apparatus 20 was serviced. This information includes, but is not limited to, the type of service performed, the person who performed the server, and the date (and time) of the service.

If the user selects the "service request" icon 956, caregiver assistance application 124 sends a message to remote equipment management server 920 indicating that service has been requested for that particular patient support apparatus 20. Server 920 forwards this message to appropriate personnel, as described in more detail in the aforementioned PCT patent publication WO 2018-013666).

In order for a user to access remote equipment management screen 942, or one like it, caregiver assistance application 124 may be modified to include a remote equipment management system icon that is selectable by a user. The icon may be included as part of task menu 174, or it may be included elsewhere. In addition, caregiver assistance application 124 may be configured to allow a user to access remote equipment management system 918 in other manners besides the use of image capturing, such as the image capturing illustrated in FIG. 72. These other manners include, but are not limited to, having the user manually input a particular patient support apparatus ID (e.g. 186), automatically capturing the patient support apparatus's ID from a short range transceiver 320, and/or using a real time location server 100 to determine the specific patient support apparatus 20 that is currently closest to the user. Still other manners of accessing remote equipment management system 918 are possible.

In addition to, or in lieu of, interfacing caregiver assistance system 106*d* with a remote equipment management system 918, any of the caregiver assistance systems 106, 106*a*, 106*b*, 106*c* and/or 106*d* described herein may be further modified to interface with a patient support apparatus configuration system. In such systems, the mobile electronic device 104*a* may be used as a configuration tool that enables the user to change configuration settings onboard one or more of the patient support apparatuses 20. In such embodiments, caregiver assistance application 124 allows the user of a mobile electronic device 104*a* to use the mobile electronic device 104*a* as a configuration tool in any of the same manners as the configuration tools are used in commonly assigned U.S. patent application Ser. No. 16/057,928 filed Aug. 8, 2018, by inventors Marco Constant et al. and entitled FIELD CONFIGURABLE PATIENT SUPPORT APPARATUSES, the complete disclosure of which is incorporated herein by reference.

For example, in this modified embodiment, caregiver assistance application 124 may be configured to interface with the information system 174 disclosed in the aforementioned '928 application. Interfacing with system 174 enables mobile electronic device 104*a* to receive configuration settings for a particular patient support apparatus 20 and to transfer those to the particular patient support apparatus 20. Further, this interfacing with a configuration system allows a user of caregiver assistance application 124 to use his or her mobile electronic device 104*a* to configure the patient support apparatus 20 to communicate with a specific type of nurse call system; and/or input desired presets into the patient support apparatus 20 (e.g. default transfer height, default bed watch system settings, default bed locking/ unlocking settings, etc.). Indeed, in some of these embodiments, caregiver assistance application 124 is configured to allow a user to send messages to a patient support apparatus 20 that enable the patient support apparatus 20 to carry out any of the configuration changes that are disclosed in commonly assigned U.S. patent application Ser. No. 16/272, 332 filed Feb. 11, 2019, by inventors Krishna Bhimavarapu et al. and entitled PATIENT SUPPORT APPARATUSES WITH RECONFIGURABLE COMMUNICATION, the complete disclosure of which is incorporated herein by reference.

It will be understood by those skilled in the art that any of the components, functions, and/or features of the different embodiments of caregiver assistance systems 106, 106*a*, 106*b*, 106*c* and 106*d* may be combined together, substituted, and/or mixed in any manner. As but one non-limited example, system 106 may be modified to omit the display of any rounding questions, similar to modified system 106*c*, and the patient support apparatuses 20 of system 106 may be modified to display a code that identifies the bed and the current time. In this modified system, the caregiver is assumed to ask the desired rounding questions and take care of the desired rounding tasks, and the modified system merely verifies the caregiver's presence in the patient's rooms. This presence is verified by the modified patient support apparatus displaying the code and the caregiver capturing an image of this code using his or her mobile electronic device 104*a* that sends the captured image to caregiver assistance server 90. In some embodiments, the code includes both the bed ID and time, while in other embodiments the code includes only the bed ID. In still other embodiments, the bed ID and/or time are not coded at all, but merely displayed so that an image of them can be captured by the caregiver's mobile electronic device 104*a*. In a variation on this embodiment, the patient support apparatus 20 may be configured to not display the ID and/or time (or the code) or the patient support apparatus ID if the patient support apparatus is not currently in a compliant state, or it may simultaneously display the fact that it is not in a compliant state along with the ID and/or time (or a code with such information).

It will also be understood that, in any of the embodiments discussed above that utilize one or more near field transceivers incorporated into any of the patient support apparatuses 20 or 20*a*, such patient support apparatuses 20 or 20*a* may be constructed to include such near field transceivers and/or utilize the near field transceivers in any of the manners disclosed in commonly assigned U.S. Pat. No. 9,966,997 issued May 8, 2018, to inventors Michael Hayes et al. and entitled COMMUNICATION SYSTEMS FOR PATIENT SUPPORT APPARATUSES, the complete disclosure of which is incorporated herein by reference.

Still further, it will be understood that any of the embodiments of the caregiver assistance system may omit one or more of the algorithms shown in FIG. 3, and/or these algorithms may be supplemented with additional algorithms. Thus, for example, in some modified embodiments, caregiver assistance system 106 (or 106*a*, 106*b*, 106*c*, or 106*d*) is only configured to implement fall risk reduction algorithm 143 without implementing rounding algorithm 140 and/or skin care algorithm 141, or vice versa. In still other embodiments, still other combinations of two or more of the algorithms shown in FIG. 3 may be implemented by the system. Further, it will be understood that additional modifications may be made to individual algorithms beyond those already discussed above, such as, but not limited to, modifying fall risk reduction algorithm 143 to omit the fall risk assessment questions, or to include additional fall risk screens beyond those illustrated herein.

Still further, in any of the embodiments discussed above, caregiver assistance application 124 may be modified to prevent rounding data, or other patient data, to be entered until an overdue task is completed, such as, but not limited to, one or both of the fall risk and bed sore risk assessments. Additionally, or alternatively, in any of the embodiments discussed above, any of the data that is shown on the screens of electronic devices 104 may alternatively or additionally be shown on the screen of the display 70 of patient support apparatus 20. Thus, for example, if a patient is determined to be a fall risk, that fall risk category may be added to the display of the corresponding patient support apparatus 20 so that the caregiver is reminded of the patient being a fall risk whenever he or she uses the control panel 42 of the patient support apparatus. Still further, indicators may be added to the screens of mobile electronic devices 104*a* and/or patient support apparatuses 20*a* whenever they are in sufficient proximity to communicate with each other using short range transceiver 320.

In yet another modified embodiment, short range transceivers 320 on patient support apparatuses 20 may be used by mobile electronic devices 104*a* to automatically select the correct room, bed bay, and/or patient when a caregiver walks into a room and up to the patient's patient support apparatus 20. In such embodiments, the mobile electronic device 104*a* receives the short range message 322 (FIG. 68) from the patient support apparatus 20, sends it to caregiver assistance application 124, and caregiver assistance application 124 uses it to identify the patient, patient support apparatus, room, and/or bed bay that the caregiver is currently located next to or in. This information is used, in some embodiments, by caregiver assistance application 124 to automatically select the corresponding room information to display on one of the screens of caregiver assistance application 124, thereby relieving the caregiver of having to manually select a room or bed bay. In other words, if a caregiver walks into room 700*a* and approaches patient B who is positioned in bed bay 2 of room 700*a*, caregiver assistance application 124 uses the data contained within short range message 322 to automatically select a screen for displaying on the mobile electronic device 104*a* that corresponds to patient B (or bed bay 2 of room 700*a*). Thus, the short range message 322 is used, in at least some embodiments, to automate any one or more of the following: step 192 of algorithm 140, step 340 of algorithm 143, step 500 of algorithm 141, step 790 of algorithm 141, step 702 of algorithm 700, and/or step 802 of algorithm 800.

It will also be understood that any of the embodiments of caregiver assistance system 106, 106*a-d* may be further modified to display additional screens beyond those described above, and/or that the screens described herein may be modified and/or replaced with other screens. FIGS. 74-81 and 83-84 illustrate several examples of additional screens that may be displayed on the mobile and/or stationary electronic devices 104*a*, 104*b* of any of the caregiver assistance systems disclosed herein. More specifically, FIGS. 74-79 illustrate different manners in which bed icon 164 may be modified to include different graphical indications regarding the presence/absence of a patient on the patient support apparatus 20, as well as different graphical indications regarding different sensitivity levels of exit detection system 46. FIGS. 80-81 and 83-84 illustrate additional data, such as patient support apparatus status data, that may be displayed on any of the screens discussed herein.

Figures 74, 75:
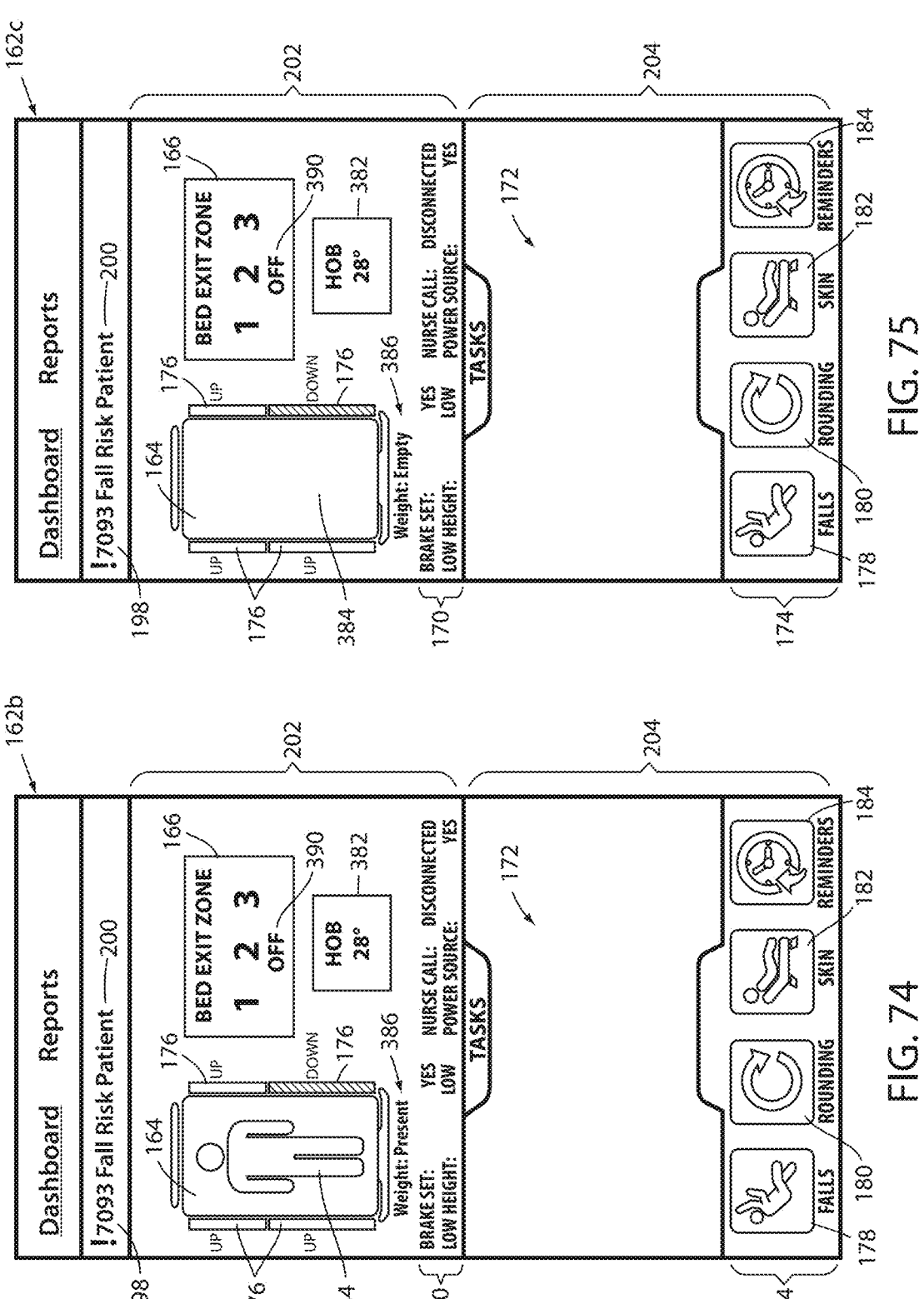
FIG. 74 is another alternative room overview screen that is displayable on an electronic device of any of the caregiver assistance systems disclosed herein that include at least one bed having no bed watch monitoring feature.
FIG. 75 is the room overview screen of FIG. 74 showing that the patient is not currently present on the bed.

Turning specifically to FIG. 74, it shows an alternative room overview screen 162*b* that may be displayed on any of the caregiver assistance system embodiments discussed herein. Room overview screen 162*b* differs from room overview screens 162 of FIGS. 9 and 162*a* of FIG. 58 in that it includes a head of bed (HOB) angle indicator 382 instead of the bed watch status indicator 168. It will be understood that room overview screens 162, 162*a*, and/or 162*b* could be modified to include both HOB angle indicator 382 and bed watch status indicator 168. HOB angle indicator 382 indicates the current angle of head section 40 of the corresponding patient support apparatus 20. In the example shown in FIG. 74, HOB angle indicator 382 is indicating that the HOB angle of the patient support apparatus 20 is currently at twenty-eight degrees.

Caregiver assistance application 124 determines the HOB angle based upon information detected by the HOB angle sensor 69 aboard patient support apparatus 20. As was noted previously, controller 48 forwards the readings from HOB angle sensor 69 to caregiver assistance application 124 using network transceiver 60 (which forwards the readings to wireless access point 76, which in turns forwards them to caregiver assistance server 90 and caregiver assistance application 124). In response to these readings, caregiver assistance application 124 determines which mobile electronic devices 104*a* and/or stationary electronic devices 104*b* have access to this data, such as in the manner described above with respect to access algorithm 153. Caregiver assistance application 124 then sends messages to the corresponding electronic devices 104 with the HOB angle readings. In this manner, remote caregivers can check either their associated mobile electronic device 104*a* or a nearby stationary electronic device 104*b* to ascertain the HOB angle reading of patient support apparatus 20.

Room overview screen 162*b* (FIG. 74) also illustrates bed icon 164 with a patient symbol 384 positioned thereon. Patient symbol 384 is solidly colored in the example shown in FIG. 74. The solid coloring of patient symbol 384 indicates that the patient associated with that particular patient support apparatus 20 (e.g. the one in room 7093 in the example of FIG. 74) is currently located in that patient support apparatus 20. The presence of the patient in the bed is also indicated by a weight indicator 386. The states of weight indicator 386 and patient symbol 384 are controlled by caregiver assistance application 124 based upon readings from scale/exit detection system 46, in at least one embodiment. In such embodiments, scale/exit detection system 46 repetitively takes weight readings from its associated force sensors (e.g. load cells) and compares them to a threshold to see if the current weight readings exceed the threshold. If they do, controller 48 concludes that the patient is present on litter frame 28. If the weight reading is less than the threshold, controller 48 concludes that the patient is not present on the litter frame 28. In some embodiments, the weight threshold may be set to roughly 50 pounds or so, although it will be understood that different thresholds may be used based upon a number of different factors (e.g. patient support apparatuses 20 in a children's ward may have a smaller threshold.

In some embodiments where weight indicator 386 and patient symbol 384 are displayed in a manner that is based upon weight readings from scale/exit detection system 46, controller 48 of patient support apparatus 20 may be configured to send a message to caregiver assistance application 124 (either directly or indirectly through patient support apparatus server 86) whenever the weight readings indicate a change in the patient's presence (i.e. either the previously present patient has left, or the previously absent patient has entered litter frame 28). It will be understood that the weight readings used for determining the content of weight indicator 386 and patient symbol 384 are not dependent upon exit detection system 46 being armed. Instead, the weight readings used to determine patient presence are repetitively taken by controller 48 regardless of whether or not the exit detection system 46 is armed.

In alternative embodiments, the determination of whether a patient is present on litter frame 28 or not may be carried out in alternative manners. For example, in some embodiments, the patient's presence/absence may be detected by sensing the presence/absence of the patient's vital signs. In these embodiments, detecting a patient's vital signs may be carried out in any of the manners disclosed in commonly assigned U.S. patent application Ser. No. 62/253,167, filed Nov. 10, 2015, by inventors Marko Kostic et al. and entitled PERSON SUPPORT APPARATUSES WITH ACCELERATION DETECTION; or commonly assigned U.S. Pat. No. 7,699,784 issued to Wan Fong et al. and entitled SYSTEM FOR DETECTING AND MONITORING VITAL SIGNS, the complete disclosures of which are both hereby incorporated herein by reference. Still other methods and/or sensors can be used to detect a patient's vital signs, and thereby determine if a patient is present on patient support apparatus 20 or not.

Detecting a patient's vital signs may also be performed in other manners. For example, in some embodiments, patient presence sensors are incorporated into mattress 38, such as the mattress disclosed in commonly assigned U.S. patent application Ser. Nos. 13/836,813 and 61/697,010, entitled INFLATABLE MATTRESS AND CONTROL METHODS and PATIENT SUPPORT, respectively, the former of which was filed Mar. 15, 2013 and the latter of which was filed Sep. 5, 2012, the complete disclosures of both of which are hereby incorporated herein by reference. When incorporated into a mattress, the patient's presence is determined, in some embodiments, by detecting the patient's respiration and/or heart rates using one or more pressure sensors included within the mattress that detect fluid pressure changes within one or more bladders contained within the mattress. Such fluid pressure changes are filtered for frequencies within those of the normal heart rate and breathing rate and processed, such as through Fourier analysis, or otherwise, to yield a heart rate and/or respiration rate. In embodiments using the mattress construction disclosed in the above-referenced Ser. No. 13/836,813 and/or 61/697,010 applications, the mattress also includes a plurality of depth sensors that measure the depth which the patient has sunk into the mattress. These depth sensor signals may be combined with the air pressure signals to determine a patient's breathing rate and or heart rate.

In other embodiments, the detection of the patient's presence on litter frame 28 may be carried out in manners that do not detect the patient's vital signs. For example, in some embodiments, patient support apparatus 20 may include one or more thermal sensors that detect the absence/presence of the patient and/or the position of the patient's head on the patient support apparatus 20. Further details of such a thermal sensing system are disclosed in commonly assigned U.S. patent application Ser. No. 14/692,871 filed Apr. 22, 2015, by inventors Marko Kostic et al. and entitled PERSON SUPPORT APPARATUS WITH POSITION MONITORING, the complete disclosure of which is incorporated herein by reference.

In still other embodiments, patient support apparatus 20 may be configured to detect the absence or presence of a patient using one or more of the methods disclosed in commonly assigned U.S. patent application Ser. No. 14/928,513 filed Oct. 30, 2015, by inventors Richard Derenne et al. and entitled PERSON SUPPORT APPARATUSES WITH PATIENT MOBILITY MONITORING, the complete disclosure of which is also hereby incorporated herein by reference. In still other embodiments, one or more video and/or infrared cameras may be used to detect an occupant's presence, absence, and/or position, such as disclosed in commonly assigned U.S. patent application Ser. No. 14/578,630 filed Dec. 22, 2014, by inventors Richard Derenne et al. and entitled VIDEO MONITORING SYSTEM, the complete disclosure of which is also hereby incorporated herein by reference. Such cameras are positioned onboard patient support apparatus 20 in some embodiments; positioned off-board patient support apparatus 20 in other embodiments; and include both one or more on-board cameras and one or more off-board cameras in still other embodiments.

In yet another alternative embodiment, patient support apparatus 20 senses the presence, absence, and/or position of a patient using a pressure sensing mat on which, or above which, the patient lies. The pressure sensing mat may be positioned on top of, or underneath, mattress 38, such as is disclosed in commonly assigned U.S. patent application Ser. No. 14/003,157 filed Mar. 2, 2012, by inventors Joshua Mix et al. and entitled SENSING SYSTEM FOR PATIENT SUPPORTS, the complete disclosure of which is also incorporated herein by reference. This pressure sensing mat is also able to detect the overall shape of the patient's weight or the object's weight (e.g. the weight footprint) when positioned on the mattress. This overall shape is processed by either controller 48, or a controller within the flexible pressure sensing mat, to determine whether the shape corresponds to a human or an object. The result of this determination is used by controller 48 to distinguish between the objects and humans moving onto or off the patient support apparatus.

In yet another embodiment, patient support apparatuses 20 may be adapted to detect a bracelet, tag, or other radio-frequency object worn by the patient using one or more near field transceivers incorporated into patient support apparatus 20. In such embodiments, patient support apparatus 20 includes one or more sensors that are able to communicate via near field communication with near field tags, bracelets, etc. worn by the patients. Examples of near field transceivers that may be incorporated into patient support apparatuses and used to detect patient-worn tags, bracelets, etc. are disclosed in commonly assigned U.S. patent application Ser. No. 13/802,992, filed Mar. 14, 2013 by applicants Michael Hayes et al., and entitled COMMU-NICATION SYSTEMS FOR PATIENT SUPPORT APPA-RATUSES, the complete disclosure of which is hereby incorporated herein by reference. Still other types of sensors that detect the patient's presence in other manners may be used.

Regardless of the specific manner, or manners, in which patient support apparatus 20 detects the absence or presence of the patient on patient support apparatus 20, controller 48 forwards the results of this determination to caregiver assistance application 124, and caregiver assistance application 124 displays these results on the corresponding room over-view screen (and/or other screens). If no patient is currently detected, caregiver assistance application 124 may be con-figured to display bed icon 164 in the manner illustrated in the modified room overview screen 162c of FIG. 75. As shown therein, patient symbol 384 is not colored in. Instead, only the outline of the patient is shown for patient symbol 384. Further, weight indicator 386 has changed from indi-cating "present" to indicating "empty." These two changes (when compared to FIG. 74) convey to the caregiver that the patient is currently not present on patient support apparatus 20.

Figures 76, 77:
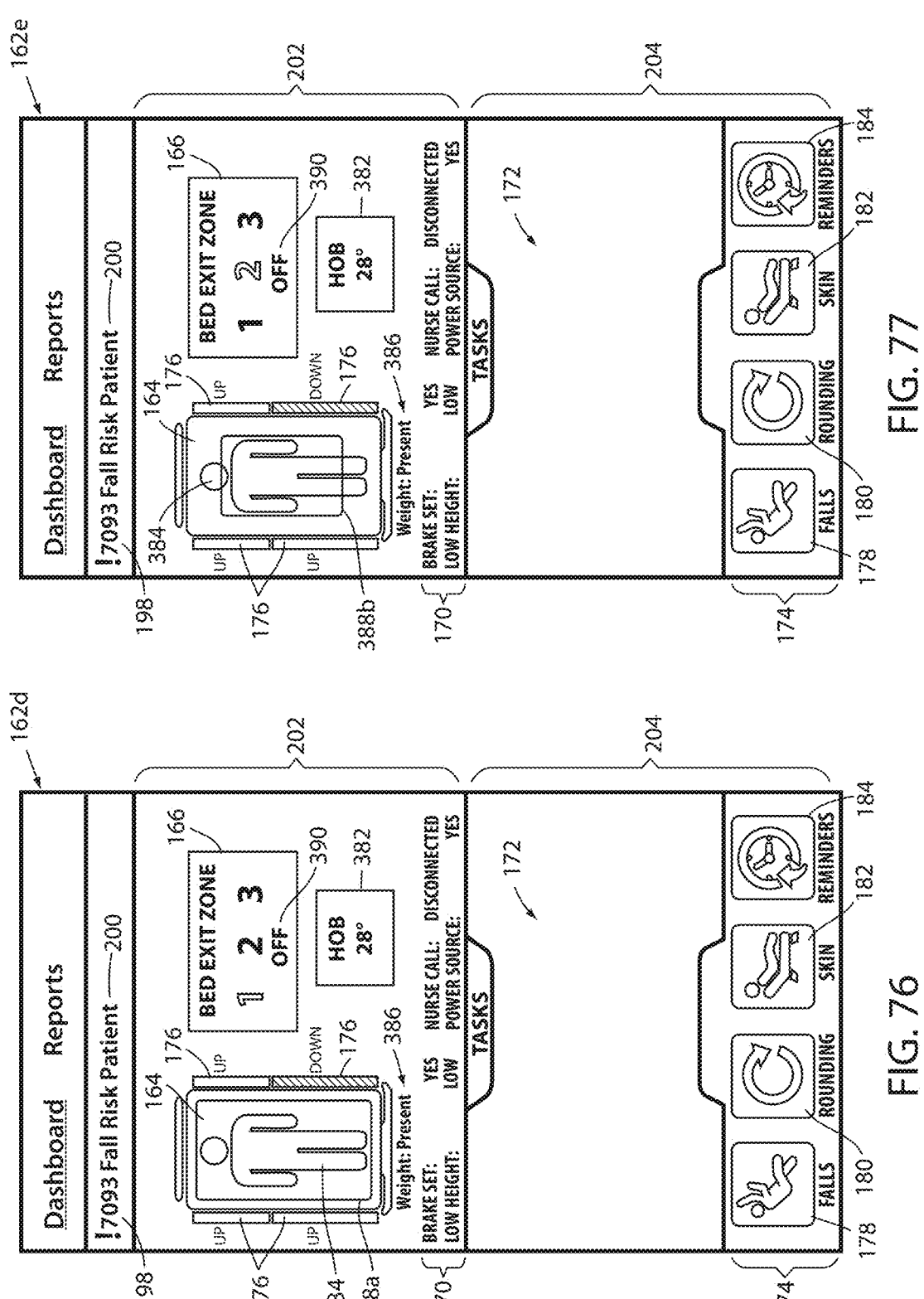
FIG. 76 is the room overview screen of FIG. 74 showing a graphical representation of a first sensitivity level of the exit detection system.
FIG. 77 is the room overview screen of FIG. 74 showing a graphical representation of a second sensitivity level of the exit detection system.
Figures 78, 79:
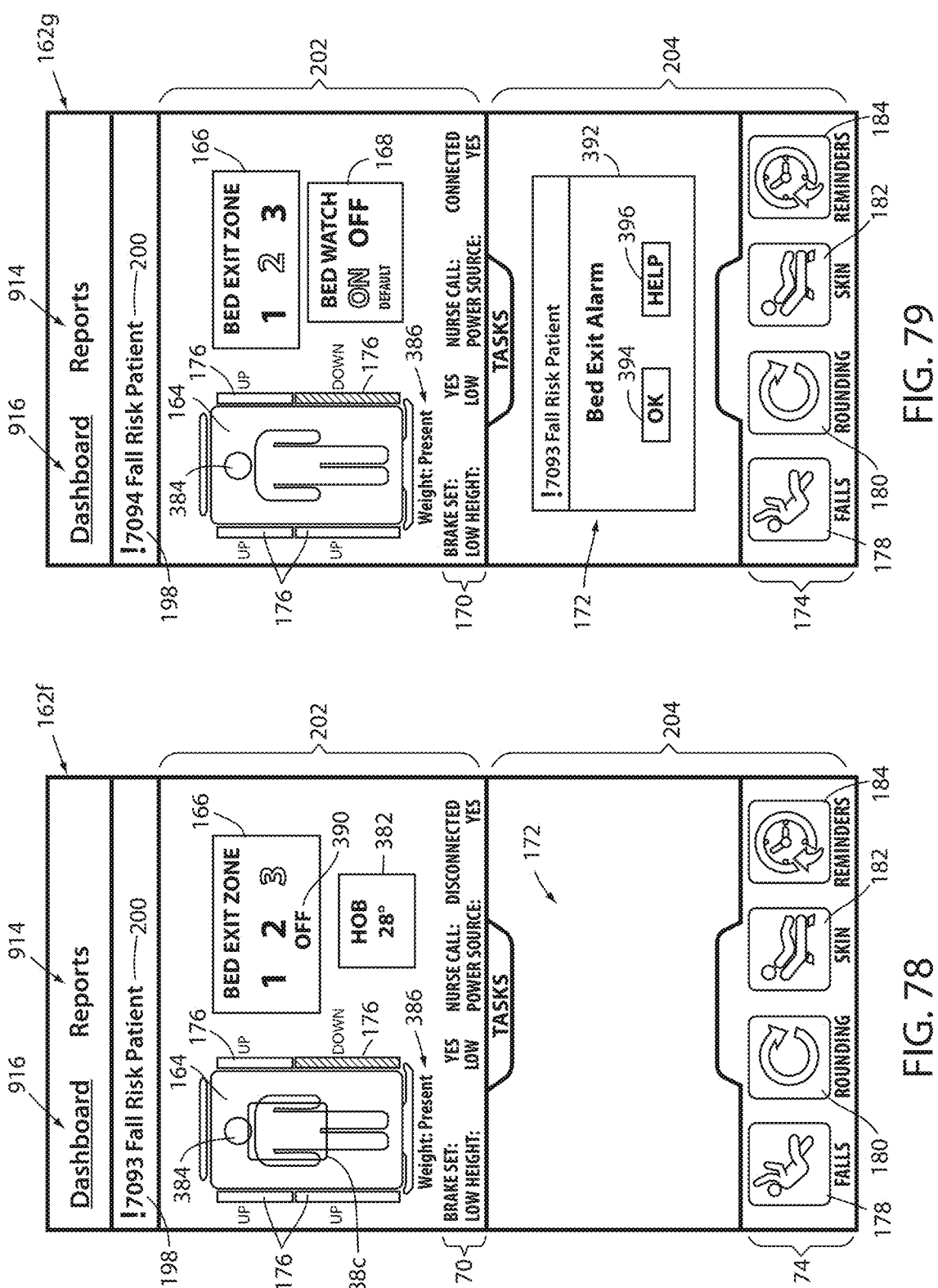
FIG. 78 is the room overview screen of FIG. 74 showing a graphical representation of a third sensitivity level of the exit detection system.
FIG. 79 is another illustrative room overview screen that is displayable on an electronic device of any of the caregiver assistance systems disclosed herein when an exit detection alert is issued.

FIGS. 76-78 illustrate alternative room overview screens 162d-f that may be displayed on the displays of any of the electronic devices 104a, 104b of any of the caregiver assistance systems 106, 106a-d disclosed herein. In particu-lar, these FIGS. illustrate different manners in which bed icon 164 may be modified to include different graphical indications regarding different sensitivity levels of exit detection system 46. As was noted previously, exit detection system 46 of patient support apparatus 20 is implemented, in at least some embodiments, using a plurality of load cells that determine the center of gravity of the patient. If the center of gravity of the patient moves outside of a defined zone, an exit alert is issued. In many of these embodiments, patient support apparatus 20 is configured such that the caregiver can select different zones that are used to trigger the exit alert. Each of the zones corresponds to a different level of sensitivity of the exit detection system 46.

For example, if the caregiver wishes to have an exit alert issued only if the patient approaches the very edge of the litter frame 28 (and thus give the patient a wide degree of movement latitude before triggering an alert), he or she can arm exit detection system 46 using a first zone that has a relatively large area. If the caregiver wishes to have an exit detection alert issued with less movement, he or she can arm exit detection system 46 using a second zone that has a smaller area than the first zone. Still further, if the caregiver wishes to have an exit detection alert triggered with very little movement at all, he or she can arm exit detection system 46 with a third zone that has a relatively small size. The caregiver can therefore choose what level of movement by the patient will trigger an exit alert.

In those embodiments of caregiver assistance system 106 (or 106a-d) in which one or more of the patient support apparatuses 20 are configured to allow a caregiver to select different sensitivity levels for exit detection system 46 (e.g. different zones), caregiver assistance application 124 is configured to modify the composition of bed graphic icon 164 so as to indicate information about the currently selected sensitivity level of the exit detection system 46. FIGS. 76-78 illustrate three examples of the manner in which bed graphic icon 164 may be modified to identify which zone, or sensitivity level, the exit detection system 46 of the patient support apparatus 20 is currently armed at.

Bed graphic icon 164 of room overview screen 162d (FIG. 76) includes a first zone indicator 388a. First zone indicator 388a is generally rectangular shaped and is posi-tioned on bed graphic icon 164 at a location that loosely corresponds to the location of the first zone of exit detection system 46. Further, the size of first zone indicator 388a loosely corresponds to the allowed movement of the patient's center of gravity that does not trigger an exit alert. In other words, if the center of gravity of the patient remains within the area defined by first zone indicator 388a, exit detection system 46 will not issue an alert. It can also be seen in the exit detection system status indicator 166 of FIG. 76 that zone 1 of the exit detection system 46 has been selected (although not armed). This is indicated by coloring the "1" in indicator 166 a different color from the "2" and "3" in indicator 166. By including first zone indicator 388a on bed graphic icon 164, a caregiver is able to visually and rapidly determine the relative amount of freedom of movement the patient is permitted when exit detection system 46 is armed and zone 1 (the least sensitive alarming level) has been selected by the caregiver.

If the caregiver selects zone 2-which corresponds to a more sensitive alarming level-caregiver assistance applica-tion 124 is configured to display, at least in some embodi-ments, a screen such as the room overview screen 162e of FIG. 77. As shown therein, bed icon 164 includes a second zone indicator 388b that corresponds to zone 2 of the exit detection system 46. Second indicator 388b is smaller than first indicator 388a, and this size difference indicates that the patient is allowed less freedom of movement before trig-gering an exit alert.

If the caregiver wishes to select an even more restrictive level of movement freedom, he or she can select a third zone (zone 3) of the exit detection system 46. Room overview screen 162f of FIG. 78 illustrates the selection of such a third zone. As shown therein, zone indicator 388c has an even smaller size than zone indicator 388b of FIG. 77. This corresponds to the smaller amount of permitted movement of the patient before an exit alert is triggered. Accordingly, if the caregiver wishes to have an alert issued based upon a small amount of patient movement, he or she can arm exit detection system 46 with the third zone selected. As was noted previously, such arming of the exit detection system 46 can be carried out remotely using one of electronic devices 104. Further, the selection of a particular zone can also be carried out remotely using one of electronic devices 104. In some embodiments, the arming of the exit detection system 46 is carried out by touching an indicator 390 within the status indicator 166. Repetitively touching this indicator 390 toggles the exit detection system 46 between an armed and a disarmed state. To change the selected zone, the user can touch the "1", "2", or "3" shown within indicator 166. Other manners of arming and disarming the exit detection system 46, as well as other manners of selecting the sensi-tivity level may, of course, be used.

It will be understood that the room overview screens 162b-f of FIGS. 74-78 are all shown with summary area 172 blank, but that this has been done merely for purposes of visual simplification. Summary area 172 may include any of the data discussed herein and/or shown in any of the summary areas 172 of any of the screens shown in the other FIGS. included herein. Also, in some embodiments, exit detection system 46 may be implemented in any of the manners, and/or include any of the features of, the exit detection system disclosed in commonly assigned U.S. patent publication 2016/0128610 published May 12, 2016, and filed by inventors Marko Kostic et al. and entitled EXIT DETECTION SYSTEM WITH COMPENSATION, the complete disclosure of which is incorporated herein by reference. Other manners of implementing the exit detection system 46 of patient support apparatuses 20 may also or alternatively be used.

It will also be understood that the exit detection systems 46 incorporated into the multiple patient support apparatuses 20 need not be uniform across the healthcare facility's set of patient support apparatuses 20. That is, some patient support apparatuses 20 may have a first kind of exit detection system 46, while other patient support apparatuses 20 may have a different kind of exit detection system. In such embodiments, caregiver assistance application 124 displays room overview screens 162 that correspond to the type of exit detection system 46 for that particular patient support apparatus. In addition to varying exit detection systems 46 for different patient support apparatuses 20, it will also be understood that individual patient support apparatuses 20 may vary from each other in still other manners for a given caregiver assistance system. Thus, a particular healthcare facility may have a first set of patient support apparatuses 20 having a first set of capabilities and/or sensors, a second set of patient support apparatuses 20 having a second set of capabilities and/or sensors, a third set, and so on. Caregiver assistance application 124 is configurable to display whatever information each set of patient support apparatuses 20 is capable of generating, and to indicate, in some embodiments, what features are not available for those particular patient support apparatuses 20 that are lacking one or more features of the other patient support apparatuses 20.

FIG. 79 illustrates an example of a room overview screen 162g that may be displayed in any of the caregiver assistance system embodiments disclosed herein. Room overview screen 162g is displayed when an exit alert is issued by a patient support apparatus 20 (in this example, the patient support apparatus 20 located in room 7094). Room overview screen 162g includes an alert window 392 that is displayed within summary area 172. Alert window 392 indicates that an exit alarm has been issued for the patient support apparatus and includes an "OK" icon 394 and a "Help" icon 396. If the caregiver wishes to acknowledge the alert, he or she touches the "OK" icon 394 and the alert window 392 will disappear. If the caregiver wishes to ask another caregiver for assistance in responding to the alert, he or she may touch the "help" icon 396. In response to touching the "help" icon 396, caregiver assistance application displays a screen and/or window (not shown) that allows the caregiver to send a request to another caregiver's mobile electronic device asking him or her to respond to the exit alert. In some embodiments, this request for assistance function is accomplished through the sharing algorithm 175 discussed above.

In some embodiments, caregiver assistance application 124 is configured to re-issue an exit detection alert of the kind shown in FIG. 79 if the caregiver does not respond to the exit alert within a user-configurable amount of time. This response time may be measured in different manners. In one embodiment, the location of the caregiver is tracked via real time location server 100 and if the caregiver's location does not coincide with the location of the patient support apparatus 20 that issued the alert within the prescribed time period, the alert is re-issued. In another embodiment, the patient support apparatuses 20 are configured to continue to issue the exit alert locally (i.e. on patient support apparatus 20 itself) until a caregiver disables the alert. In these instances, if the exit alert is not disabled by a caregiver within a prescribed period of time, patient support apparatus 20 sends a message to caregiver assistance application 124 and caregiver assistance application 124 re-issues the alert.

It will be understood that the exit alert issued by caregiver assistance application 124 and communicated to appropriate electronic devices 104 operates completely independently of the exit alert that is communicated to the nurse call system 80 via nurse call cable 78. Caregiver assistance system 106 (and systems 106a-d) are separate systems from the nurse call system 80, and in some instances are able to be implemented completely separately from a healthcare facility's existing nurse call system. In other embodiments, as discussed herein, caregiver assistance systems 106 (and 106a-d) may send queries to the nurse call system 80 to determine caregiver room assignments and/or other information. Even in those embodiments, however, caregiver assistance system 106 (and systems 106a-d) provide a completely separate communication channel for conveying information to caregivers that is independent of the existing nurse call system, thereby providing redundancy of certain alarm notifications (e.g. bed exit) and enabling caregivers to be notified of information even if the patient support apparatus 20 is not properly connected to the nurse call system (e.g. nurse call cable 78 is not plugged into the nurse call outlet 82). Healthcare facilities that implement caregiver assistance system 106 (or 106a-d) are therefore provided with a redundant mechanism of alerting caregivers of patient exits, and in some instances—depending upon the capabilities of the nurse call system—other patient support apparatus alerts.

Figures 80, 81:
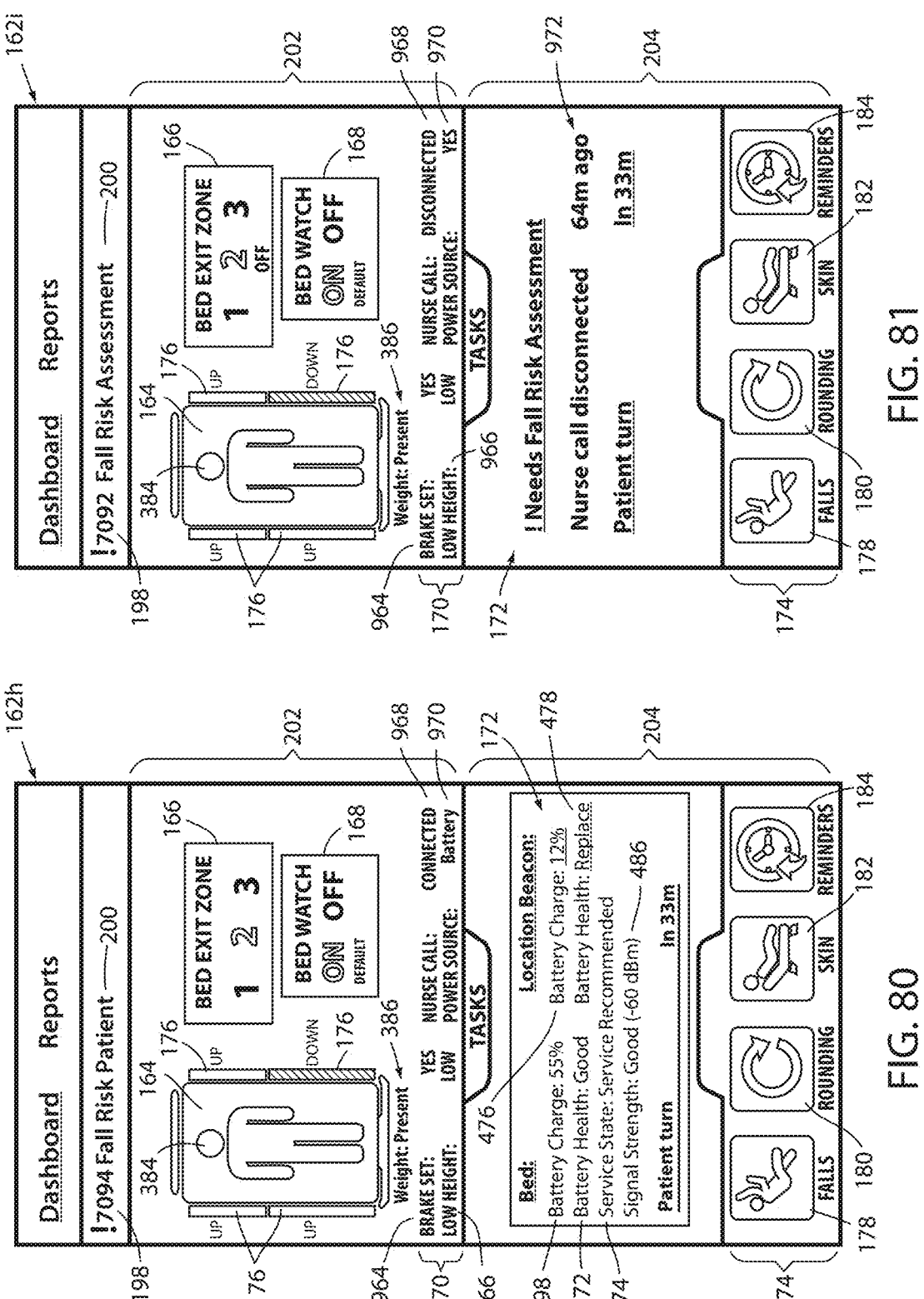
FIG. 80 is another illustrative room overview screen that is displayable on an electronic device of any of the caregiver assistance systems disclosed herein and that illustrates additional status information regarding the bed.
FIG. 81 is another illustrative room overview screen that is displayable on an electronic device of any of the caregiver assistance systems disclosed herein and that illustrates still other information about the patient and bed.

FIG. 80 illustrates another example of a room overview screen 162h that may be displayed in any of the caregiver assistance system embodiments disclosed herein. Room overview screen 162h is provided herein to illustrate a number of additional examples of data that may be displayed in summary area 172 that have not been previously described. It will be understood that the particular combination of data shown in summary area 172 of room overview screen 162h is merely an illustrative example, and that different combinations of this data and/or other data may be displayed in summary area at different times during the usage of caregiver assistance application 124.

Summary area 172 of room overview screen 162h (FIG. 80) includes a battery charge indicator 398, a battery health indicator 472, a service state indicator 474, a beacon battery charge indicator 476, a beacon battery health indicator 478, and a signal strength indicator 486. Battery charge indicator 398 indicates a current charge level of battery 71. Battery charge indicator 398 is shown in FIG. 80 to indicate the current charge percentage of battery 71, but it will be understood that battery charge indicator 398 could be modified to indicate the charge of battery 71 in manners other than a percentage, such as, for example, a bar graph and/or another type of graphical indicator. Further, if patient support apparatus 20 includes multiple batteries 71 (e.g. one or more for general use and one or more for specific use with a propulsion system), summary area 172 may be modified to include multiple battery charge indicators 398—one for each battery 71 and/or each set of batteries onboard patient support apparatus 20.

Battery health indicator 472 (FIG. 80) indicates one or more aspects about the general health of battery 71. Battery health indicator 472 is generally only displayed when battery 71 is a rechargeable battery. Battery health indicator 472 therefore informs the caregiver when it may be time to replace battery 71, rather than merely recharge battery 71. The information displayed by battery health indicator 472 comes from battery monitor 73 onboard patient support apparatus 20. More specifically, it is sent to caregiver assistance application 124 via network transceiver 60, and from caregiver assistance application 124, a caregiver accesses this data using—in at least some embodiments—a conventional web browser onboard one of devices 104 to navigate to a URL associated with caregiver assistance application 124, which then displays the information on that device using conventional web technology (e.g. hypertext markup language, etc.). As with battery charge indicator 398, if patient support apparatus 20 includes more than one battery 71, more than one battery health indicator 472 may be displayed in order to inform the caregiver of the health of each of the batteries 71.

Service state indicator 474 (FIG. 80) provides an indication to the caregiver if any service should be performed on patient support apparatus 20. Although such service is typically not performed by caregivers, including the information in summary area 172 can remind the caregivers to contact the appropriate technicians or other service personnel to have patient support apparatus 20 services. Alternatively, in some embodiments, service state indicator 474 may be displayed only on the displays of electronic devices 104 which have been accessed by technicians (rather than caregivers), as discussed above with respect to access algorithm 153. Regardless of where displayed, service state indicator 474 is displayed based off of information received from usage monitor 77 of patient support apparatus 20.

Beacon battery charge indicator 476 and beacon battery health indicator 478 may also be displayed in summary area 172 of any of the room overview screens, such as room overview screen 162h of FIG. 80. Beacon battery charge indicator 476 and beacon battery health indicator 478 display the charge status and health status of beacon battery 79. As noted previously, location beacon 84 sends the charge status of its beacon battery 79 and its health (as determined by beacon battery monitor 81) to patient support apparatus 20 via its onboard transmitter. This information is received by location transceiver 64 and then forwarded (and, in some instances, also displayed on display 70) by network transceiver 60 to caregiver assistance application 124, which displays it on the corresponding electronic devices 104. Indicators 476 and 478 therefore alert the caregivers and/or other personnel within the healthcare facility of any needs to change, recharge, and/or otherwise service the batteries 79 within location beacons 84.

Signal strength indicator 486 displays the current signal strength of the wireless connection between network transceiver 60 and the wireless access point 76 with which it is currently in communication. Signal strength indicator 485 is displayed using information derived from signal strength detector 75 of patient support apparatus 20. As with the other indicators shown in FIG. 80, as well as those shown elsewhere, signal strength indicator 485 may be represented graphically, or it may be supplemented with a graphical indication of the current strength of patient support apparatus 20's wireless connection with local area network 74.

FIG. 81 illustrates yet another example of a room overview screen 162i that may be displayed in any of the caregiver assistance system embodiments disclosed herein. Room overview screen 162i is provided herein to illustrate some additional variations of the data that may be displayed in summary area 172 and/or bed status bar 170. It will be understood that the particular combination of data shown in room overview screen 162i is merely another illustrative example provided herein for a more complete understanding of the capabilities of the caregiver assistance systems disclosed herein, and that different combinations of this data and/or other data may be displayed on any of the room overview screens disclosed herein.

Room overview screen 162i includes a bed status bar 170 that comprises a brake indicator 964, a height indicator 966, a nurse call cable indicator 968, and a power source indicator 970. Brake indicator 964 indicates whether the brake onboard patient support apparatus 20 is currently activated or not, and is based off of information detected by brake sensor 54 and forwarded to caregiver assistance application 124 via network transceiver 60. Height indicator 966 indicates whether litter frame 28 is at its lowest height or not, and is based off of information detected by lift sensors 66a, 66b and forwarded to caregiver assistance application 124 via network transceiver 60. Nurse call cable indicator 968 indicates whether the nurse call cable 78 is currently plugged into the nurse call outlet 82 or not, and is based off of information detected by cable sensor 68 and forwarded to caregiver assistance application 124 via network transceiver 60. Power source indicator 970 indicates whether patient support apparatus 20 is currently receiving electrical power from an A/C outlet (via cable 102) or from battery 71. This information is detected by power source sensor 58 and forwarded to caregiver assistance application 124 via network transceiver 60.

It can also be seen from FIG. 81 that caregiver assistance application 124 is configured in at least some embodiments to include a disconnection time indicator 972 within summary status area 172 when it detects that nurse call cable 78 is not connected to nurse call system outlet 82. Nurse call disconnection time indicator 972 indicates how long ago the disconnection of nurse call cable 78 from nurse call system outlet 82 was detected. This time information is displayed to the caregiver in order for the caregiver to better assess how quickly he or she may wish to take corrective action with respect to the nurse call cable 78. In some embodiments, the timer used to populate nurse call disconnection time indicator 972 is maintained by caregiver assistance application 124, while in other embodiments, the time may be maintained on patient support apparatus 20, or in both locations.

In some embodiments, caregiver assistance application 124 is adapted to provide an indication to the caregiver if the patient support apparatus 20 loses its wireless connection to caregiver assistance application 124. Such a disconnection may be the result of losing the connection between network transceiver 60 and a wireless access point 76, or it may be due to other issues. Regardless of the cause, caregiver assistance application 124 is adapted in some embodiments to send an alert to the appropriate electronic device(s) 104 indicating that the connection has been lost. In some embodiments, caregiver assistance application 124 is configured to send such an alert any time it loses a communication with any patient support apparatus 20. In this embodiment, however, caregiver assistance application 124 may end up sending alerts for patient support apparatuses 20 that are not being used, that are in storage, that have been turned off, and/or that are otherwise not of concern to the caregiver. In order to avoid such nuisance alerts, caregiver assistance application 124 may be configured to implement a wireless disconnection detection algorithm, such as wireless disconnection detection algorithm 990 shown in FIG. 82.

Wireless disconnection detection algorithm 990 is adapted to send alerts for only those disconnected patient support apparatuses 20 that have a patient assigned to them, thereby avoiding potential nuisance alerts for unused patient support apparatuses 20 that have ceased communication with caregiver assistance application 124. Wireless disconnection detection algorithm 990 begins at an initial step 992 after which it proceeds to step 994. At step 994, caregiver assistance application 124 retrieves a list of all of the patient support apparatuses 20 within the healthcare facility. This list may be retrieved in a variety of different manners. In one manner, every time a patient support apparatus 20 is purchased, or otherwise added to a healthcare facility, the identity of that patient support apparatus (e.g. identifier 186) is manually added to data repository 128 via one or more authorized persons 136 using a computer 134 and/or one of the electronic devices 104. In another embodiment, caregiver assistance application 124 automatically populates this list every time it first detects communication with a patient support apparatus 20, and keeps adding to this list each time it detects a new patient support apparatus 20. Although this latter method doesn't add patient support apparatuses 20 to the list until they make successful communication with caregiver assistance application 124, it will eventually include a complete listing of the patient support apparatuses 20 within the healthcare facility. Still other manners of populating the list of patient support apparatuses 20 may also or alternatively be used.

After retrieving the list of patient support apparatuses 20 within the healthcare facility at step 994, caregiver assistance application 124 proceeds to step 996 where it determines if it is in communication with all of the patient support apparatuses 20 on the list retrieved at step 996. Step 996 may be accomplished in different manners. In one embodiment, each patient support apparatus 20 sends a periodic heartbeat message either to server 90 and caregiver assistance application 124, or to patient support apparatus server 86, which then forwards information regarding their receipt to caregiver assistance application 124. In such embodiments, if no heartbeat message are received for more than a threshold amount of time, the patient support apparatus 20 is considered to no longer be in communication with caregiver assistance application 124. In another embodiment, caregiver assistance application 124 may be configured to query each wireless access point 76 for a list of the patient support apparatuses 20 it is currently in communication with. Still other methods may be used to determine what patient support apparatuses 20 are currently in communication with caregiver assistance application 124.

If all of the patient support apparatuses 20 are determined to currently be in communication with caregiver assistance application 124 at step 996, then caregiver assistance application 124 returns back to initial step 992, where it repeats algorithm 990 at whatever frequency it has been configured to do so. If there are any patient support apparatuses 20 that are not currently in communication with caregiver assistance application 124, then caregiver assistance application 124 proceeds from step 996 to step 998. At step 998, caregiver assistance application 124 sends a query to ADT server 94 requesting an up-to-date listing of all of the rooms to which patients have been assigned. After receiving this information from ADT server 94 at step 998, caregiver assistance application 124 proceeds to step 1000.

At step 1000, caregiver assistance application 124 determines the room location of each patient support apparatus 20 that it is in communication with caregiver assistance application. This current room location information may be supplied in a variety of different manners. In one embodiment, locations are determined using locator beacons 84. In another embodiment, caregiver assistance application 124 consults real time location server 100. In still other embodiments, caregiver assistance application 124 may combine both of these methods, and/or use still other methods.

After obtaining the room location of each communicative patient support apparatus 20 at step 1000, caregiver assistance application 124 proceeds to step 1002 where it determines if there is a communicative bed in each of the rooms to which a patient has been assigned. If there is, then caregiver assistance application 124 concludes that the non-communicative patient support apparatus(es) 20 are not assigned to any patients, and therefore does not issue an alert for them. Thus, caregiver assistance application 124 returns back to step 992.

On the other hand, if caregiver assistance application 124 determines at step 1000 that there are one or more rooms to which a patient has been assigned, but there is no communicative patient support apparatus 20 in that location, caregiver assistance application 124 proceeds to step 1004 and issues an alert to the appropriate caregivers. One manner in which this alert may be conveyed to the caregiver is discussed below with respect to FIG. 82. After sending the alert (which may be issued via alerting algorithm 149), caregiver assistance application 124 returns to step 992 and repeats algorithm 990. As noted, the frequency at which caregiver assistance application 124 repeats algorithm 990 may be configured by authorized personnel 136 of the healthcare facility.

Figure 83:
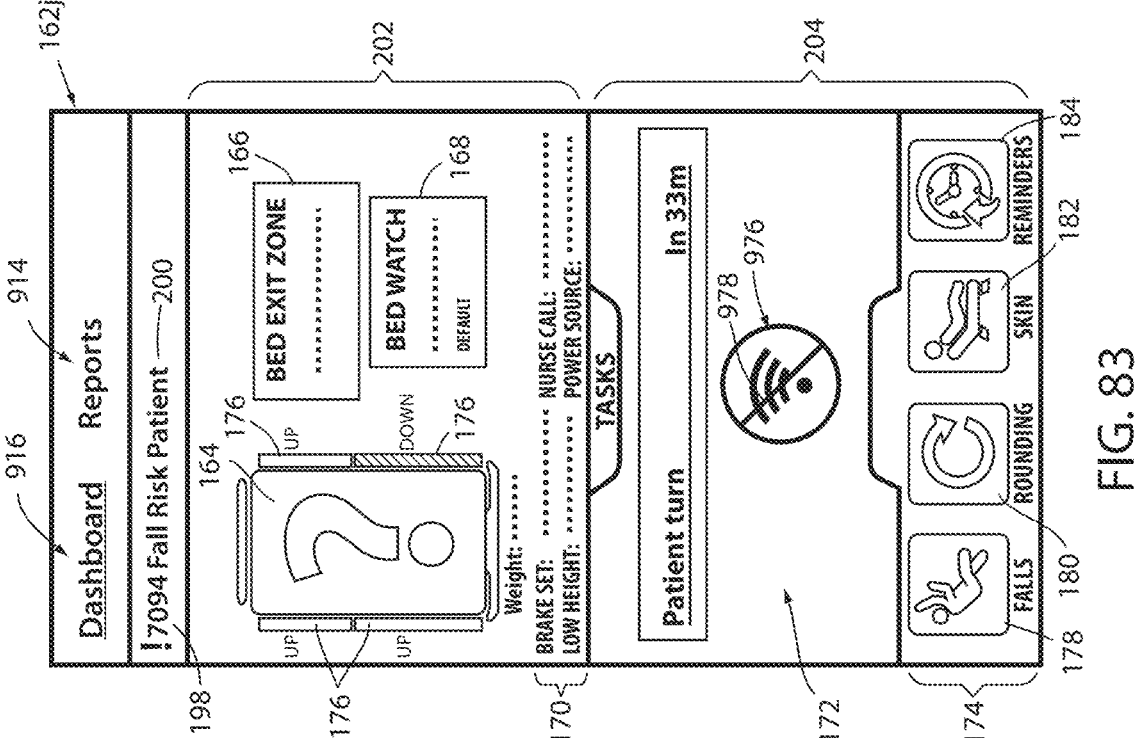
FIG. 83 is an illustrative room overview screen that is displayable on an electronic device of any of the caregiver assistance systems disclosed herein and that illustrates an absent communication connection.

FIG. 83 illustrates an example of a room overview screen 162j that is displayable in any of the caregiver assistance system embodiments disclosed herein. Room overview screen 162j may be displayed when caregiver assistance application 124 determines, using algorithm 990 or another algorithm, that it is not in wireless communication with a patient support apparatus 20. As shown therein, the information within bed exit status indicator 166, bed watch status indicator 168, bed icon 164, and bed status bar 170 is all empty. This is because this data is all supplied to caregiver assistance application 124 via network transceiver 60, and when caregiver assistance application 124 loses communication with the patient support apparatus 20, it no longer is able to receive this data.

In the particular example shown in FIG. 83, patient symbol 384 has been replaced with a question mark to indicate that the occupancy, or lack of occupancy, of the patient support apparatus 20 by the patient cannot be determined. Further, in the particular example shown in FIG. 83, a wireless disconnection symbol 976 is displayed to provide a graphical indication to the caregiver that the patient support apparatus 20 that should be in the indicated room (room 7094 in this example) is not communicating with caregiver assistance application 124. Until this communication disconnection is remedied, caregiver assistance application 124 may be configured to continue to display room overview screen 162j in the manner shown in FIG. 83 (although the caregiver may be free to navigate away from this screen).

It should be noted that, although caregiver assistance application 124 has lost communication with the patient support apparatus 20 in the example shown in FIG. 83, this lack of communication does not stop caregiver assistance application 124 from displaying reminders about upcoming tasks and/or events. Thus, although caregiver assistance application 124 does not supply any patient support apparatus 20 information on screen 162j, it still includes a reminder to the caregiver to turn the patient in thirty-three minutes. Other reminders, such as reminders for performing rounding tasks, risk assessments, or other tasks may also still be displayed in summary area 172 while the patient support apparatus 20 has lost communication with caregiver assistance application 124.

It will be understood that, in some embodiments, caregiver assistance application 124 is configured to display a wireless communication indicator in at least two different forms, depending upon whether a particular patient support apparatus 20 is able to currently communicate with caregiver assistance application 124 or not. In such embodiments, the wireless communication indicator may take on a first form, such as that of the disconnection indicator 976 shown in FIG. 83, when the patient support apparatus 20 is unable to communicate, and a second form when the patient support apparatus 20 is able to communicate. In some embodiments, the second form is similar to disconnection indicator 976 but does not include a cross bar 978 (FIG. 83) through the middle of the indicator 976 (or also does not include both the cross bar 978 and the circle around the wireless symbol). In other embodiments, the first and second forms may take on different representations, such as, but not limited to, a plain text indication of "connected" and "disconnected." Still other forms are possible. Further, in some embodiments, any of the room overview screens 162 and/or room listing screens 156 may include the second form thereon when the patient support apparatus 20 is currently in communication with caregiver assistance application 124, thereby providing a positive indication of the communication connection (as opposed to only displaying the disconnection indicator when a patient support apparatus 20 loses its communication connection).

Figure 84:
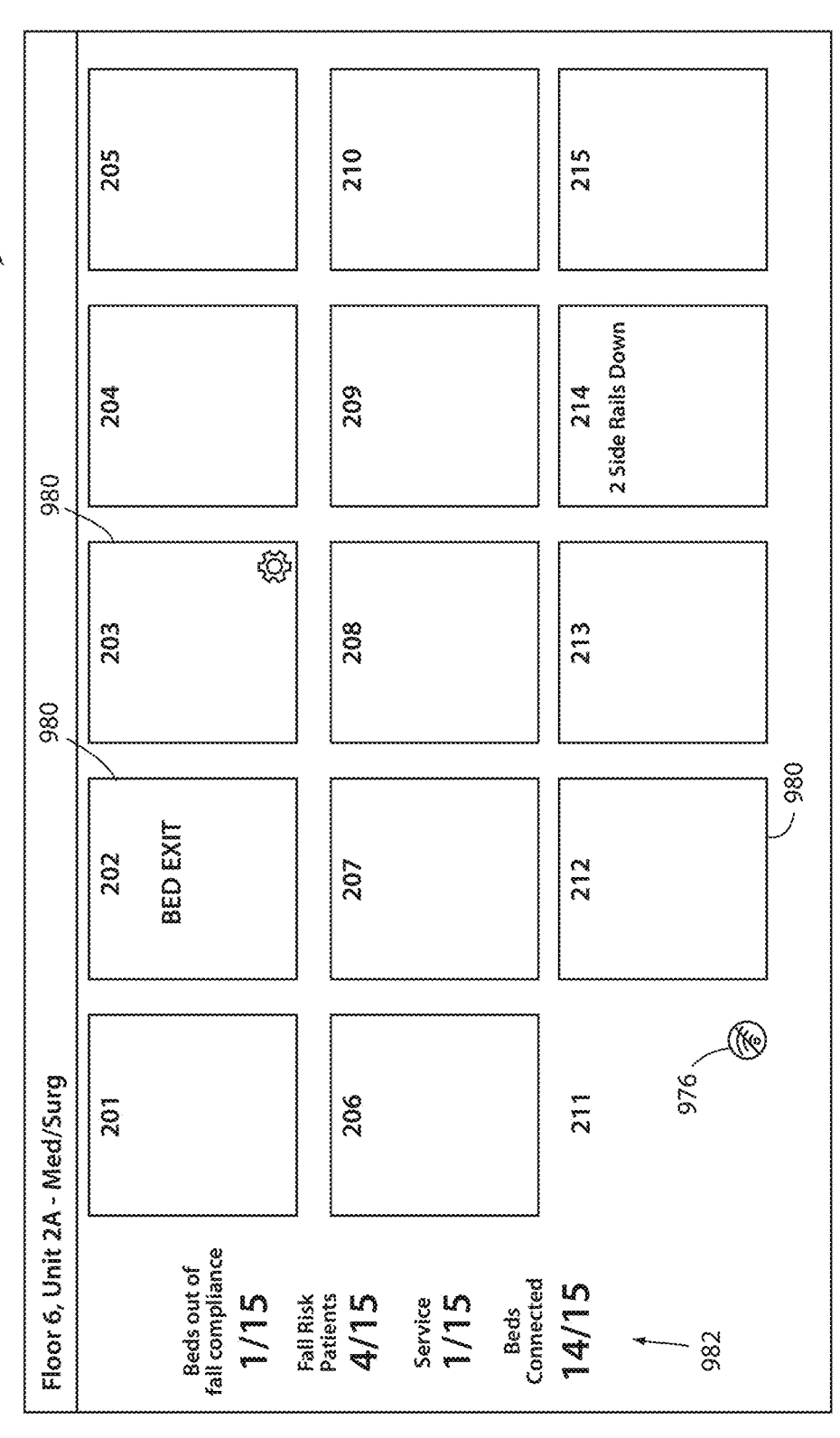
FIG. 84 is an illustrative room listing screen that may be displayed on a stationary electronic device of any of the caregiver assistance systems disclosed herein.

FIG. 84 illustrates an alternative example of a room listing screen 156b that is particularly suited for being displayed on electronic devices 104 having larger sized displays, such as many of the stationary electronic devices 104b. It will, however, be understood that room listing screen 156b may also be displayed on mobile electronic devices 104a. Room listing screen 156b may be displayed as an alternative to any of room listing screens 156 and/or 156a. In such embodiments, room listing screen 156b is displayed at any of the same times as room listing screen 156 of FIG. 8 and/or room listing screen 156a of FIG. 59 are displayed, as described above. Room listing screen 156b is provided herein to show another example of the information content that may be included within a room listing screen. In some embodiments, any of the information on any of room listing screens 156, 156a, 156b (and/or 156c, discussed below) may be combined in any desirable manner.

Room listing screen 156b (FIG. 84) differs from room listing screen 156 of FIG. 8 and room listing screen 156a of FIG. 59 in that it includes a plurality of room icons 980 and a status area 982. Room icons 980 correspond to particular rooms within the healthcare facility and may include status information about the patient and/or bed associated with that room. For example, room 211 in the example of FIG. 84 includes a disconnection symbol 976 indicating that the patient support apparatus 20 associated with that room is not in communication with caregiver assistance application 124. Room 214 in the example of FIG. 84 indicates that the siderails of the patient support apparatus 20 in that room are lowered. Room 202 in the example of FIG. 84 indicates that an exit detection alert has been issued by that particular patient support apparatus 20. It will be understood that still other information may be listed for each room icon. Further, caregiver assistance application 124 may be configured to color code each room icon in different colors, depending upon whether an alert has been issued for that room, whether a task is overdue or the patient support apparatus 20 is not in a state of compliance, or whether the patient support apparatus is compliant and there are not tasks due with respect to the patient. Still other color coding may also be used.

In at least one embodiment, touching on any of the room icons 980 causes caregiver assistance application 124 to display further information about that room, such as any of the information shown in the room overview screens 162 disclosed herein.

Status area 982 displays a summary of information regarding the collection of patients and patient support apparatuses 20 associated with the displayed room icons. Thus, for example, caregiver assistance application 124 may display in this area the number of patient support apparatuses 20 that are in a compliant state, the number of fall risk patients, the number of patient support apparatuses 20 that need service, the number of patient support apparatuses 20 that do not have their nurse call cables 78 coupled to the corresponding nurse call outlet 82, and/or other information about the collection of room icons 980.

Figures 85, 86:
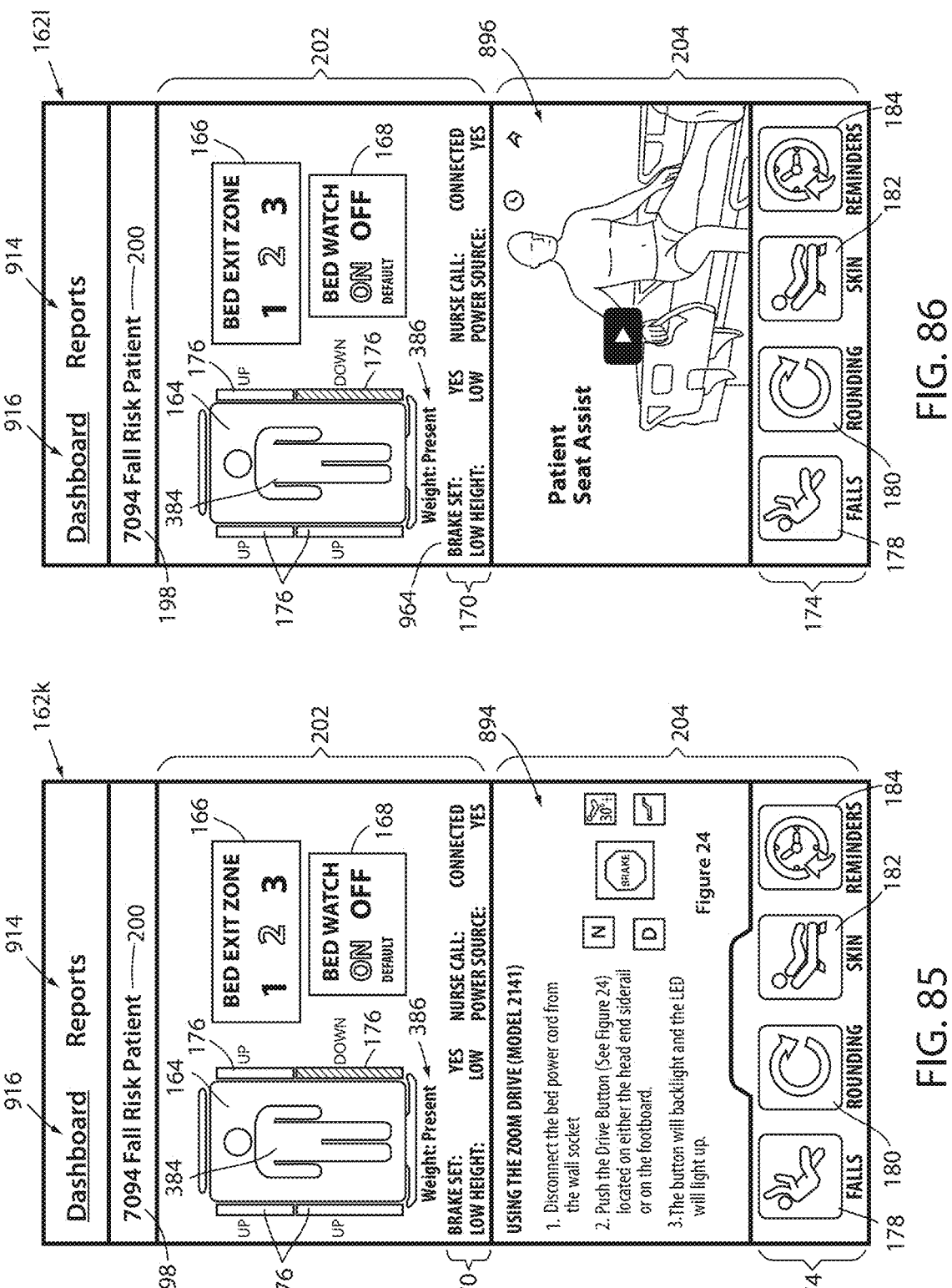
FIG. 85 is another illustrative room overview screen that is displayable on an electronic device of any of the caregiver assistance systems disclosed herein and that illustrates instructions for using a feature of the specific bed positioned within the corresponding room.
FIG. 86 is another illustrative room overview screen that is displayable on an electronic device of any of the caregiver assistance systems disclosed herein and that illustrates a video explaining the use of one or more features of the specific bed positioned within the corresponding room.

FIG. 85 illustrates an example of a room overview screen 162k that is displayable in any of the caregiver assistance system embodiments disclosed herein. Room overview screen 162k may be displayed when a caregiver requests instructions for using a particular feature of patient support apparatus 20. Room overview screen 162k includes an instruction window 894 in which instructions are shown for explaining to the caregiver how to use a feature of patient support apparatus 20. In the particular example shown in FIG. 85, the instructions are for using a propulsion system of patient support apparatus 20; however, it will be understood that this is merely one example of instructions, and that caregiver assistance application 124 is capable of displaying instructions for using any feature or function of patient support apparatus 20, as well as any feature or function of caregiver assistance system 106 (or 106a-d).

In some embodiments, caregiver assistance system 106 (or 106a-d) is configured such that caregiver assistance application 124 adds an instructions task icon (not shown) to the task menu 174 that is selectable by a user. In such an embodiment, screens like room overview screen 162k are displayable on the corresponding electronic device 104 in response to the user selecting the instructions task icon. When initially selecting this icon, caregiver assistance application 124 may initially display a main menu and/or a graphic depiction of the bed in which the user can select different portions of the bed to receive instructions for using the selected portion. Still other manners of selecting instructions for a particular feature may be utilized.

In some embodiment, caregiver assistance application 124 stores in data repository 128 the entire user's manual and/or other manuals that correspond to patient support apparatus 20, and the contents of that user's manual, or other manual, are accessed by caregiver assistance application 124 to display the instructions shown in instruction window 894. In other embodiments, additional instructional data may be included and/or different sources of data.

Regardless of which specific data is stored in data repository 128, caregiver assistance application 124 is configured to display in window 894 instructions that are specific to the particular bed identified in the corresponding room overview screen 162. Thus, for example, in the room overview screens 162k of FIG. 85, the identified room is room 7094 and caregiver assistance application 124 is configured to display instructions in window 894 that are specific to the specific bed in room 7094 of that particular healthcare facility. If a healthcare facility happens to have different types of patient support apparatuses 20, and/or different models of patient support apparatuses 20, caregiver assistance application 124 is configured to display instructions that are specific to the type, model, and/or other characteristics of the particular patient support apparatus 20 within the corresponding room. In some embodiments, caregiver assistance application 124 utilizes the patient support apparatus identifier 186 to match specific patient support apparatuses 20 to specific instructions. In other embodiments, other techniques may be used to correlate instructions to specific patient support apparatuses 20.

It will also be understood that caregiver assistance application 124 may be modified to display instructions for operating other items besides patient support apparatuses 20. The other items include, but are not limited to, caregiver assistance application 124 itself, location beacons 84, mattresses 38, Deep Vein Thrombosis compression pumps, heel care boots, etc.

FIG. 86 illustrates an example of a room overview screen 1621 that is displayable in any of the caregiver assistance system embodiments disclosed herein. Room overview screen 1621 may be displayed in addition to, or as an alternative to, room overview screen 162*k*. Room overview screen 1621 includes a video window 896. Video window 896 displays one or more videos that a user can play on the corresponding electronic device 104. In some embodiments, the videos that are available for display in video window 896 may include instructional videos for operating patient support apparatuses 20 and/or for any of the other devices discussed above with respect to instructional window 894. The available videos for display in video window 896 may also include videos for assisting the caregiver in performing other dues, such as, but not limited to, videos explaining one or more procedures and/or tasks that administrators of the healthcare facility expect their caregivers to perform, as well as still other videos.

The library of all of the videos displayable within video window 896 may be stored in data repository 128, along with the data for all of the instructions for instructional window 894. If any of the videos are specific to a particular type of patient support apparatus 20, or another device, situation, task, or other subject, caregiver assistance application 124 flags the video with an association identifier so that the video will be displayed for the correct patient support apparatus, 20, other device, situation, task, or other subject. In some embodiments, video window 896 may be larger than what is shown in FIG. 86, such as, but not limited to, a window that consumes the entire screen of the electronic device 104.

Accessing and selecting a video for viewing may be carried out in any of the same manners discussed above for accessing and viewing instructions. That is, caregiver assistance application 124 may display an "video" icon (not shown) on task menu 174 that, when selected, results in a display of one or more menus for selecting an appropriate video. Alternatively, the menu for selecting videos may be mixed with the menu for selecting instructions. Still further, in some embodiments, help icons may be displayed next to one or more graphics or other icons on the various screens and when a caregiver selects the help icon, one or more instructions and/or videos are identified which the caregiver can view, if desired. Still other manners of accessing the videos may be utilized.

Figure 87:
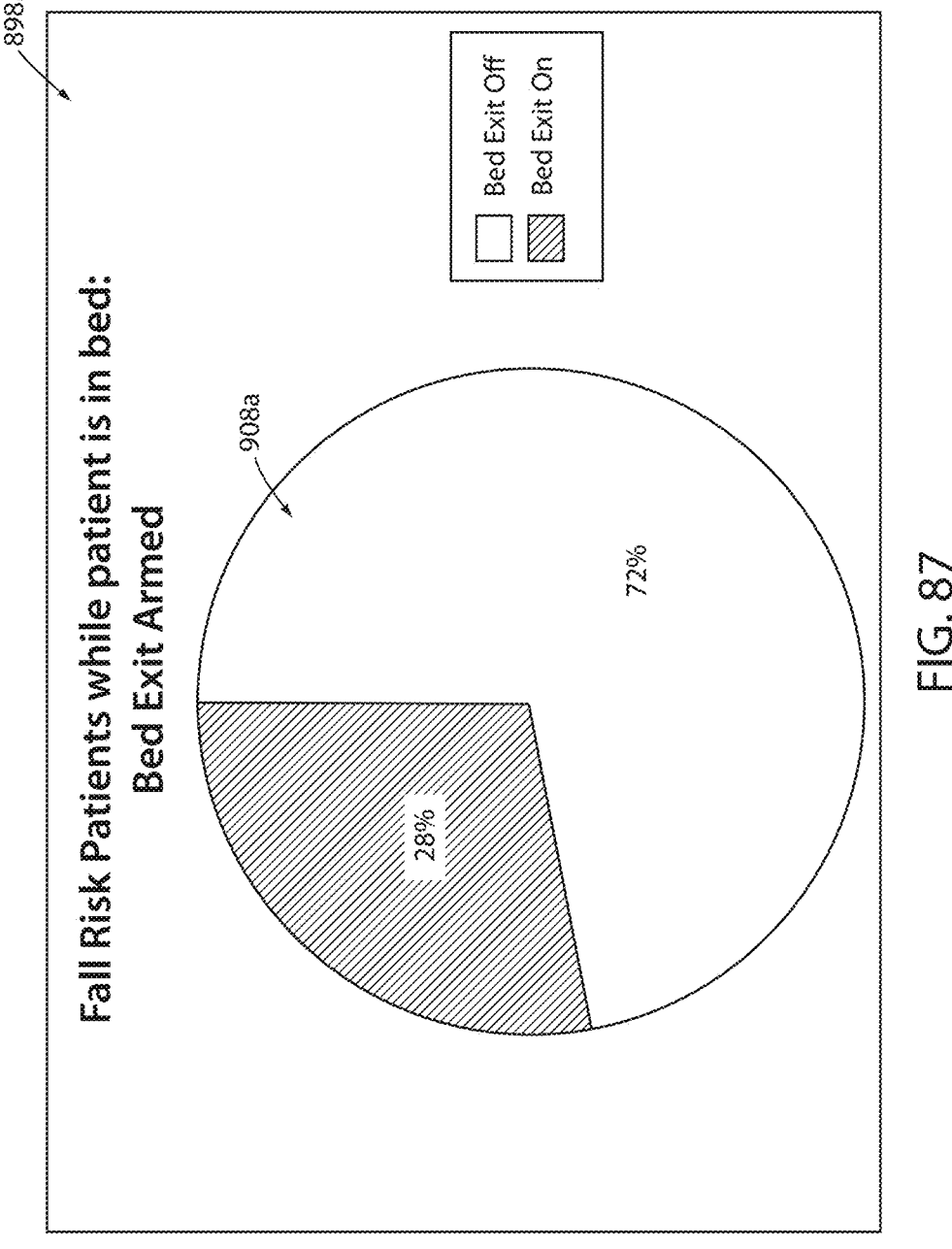
FIG. 87 is an illustration of a first type of report that may be generated by any of the caregiver assistance systems disclosed herein and that illustrates a pie chart of bed exit arming compliance.

FIG. 87 illustrates an example of a first type of report 898*a* that may be generated by caregiver assistance application 124. Report 898*a* includes a pie chart 908*a* that illustrates how often (in percentages) the exit detection system 46 is armed on the patient support apparatuses 20 that are assigned to patients who have a high fall risk. Report 898*a* therefore gives administrators and/or other personnel of a particular healthcare facility an indication of how often the caregivers are arming the exit detection system 46 for high fall risk patients. In most healthcare facilities, arming the exit detection system 46 while a high fall risk patient is present on the patient support apparatus 20 is part of the healthcare facility's fall risk reduction protocol 93. Accordingly, report 898*a* provides an indication of how often caregivers are following fall risk reduction protocol 93 (or at least a portion of fall risk reduction protocol 93).

Report 898*a* is generated by caregiver assistance application 124 by recording when a patient is present on each patient support apparatus 20. This is known from messages transmitted from each patient support apparatus 20 to caregiver assistance application 124 (either directly or through patient support apparatus server 86) indicating when a patient enters patient support apparatus 20, as well as when the patient exits patient support apparatus 20. These messages are generated in response to the sensor(s) onboard each patient support apparatus 20 that are also used to populate patient presence indicator 386 (see FIGS. 85, 86) of the various room overview screens 162. Such sensors, in some embodiments, are the same load cells, or other force sensors, that are part of the exit detection system 46. However, patient support apparatuses 20 are configured to transmit patient-present and patient-absent messages to caregiver assistance application 124 based on these sensor regardless of whether exit detection system 46 is armed or not. That is, in such embodiments, exit detection system 46 transmits patient-present and patient-absent messages to caregiver assistance application 124 any time the status of the patient's presence changes, and these messages are transmitted both when exit detection system 46 is armed and when exit detection system 46 is disarmed. When exit detection system 46 is armed and the patient's absence is first detected, then patient support apparatus 20 also issues an exit detection alert.

Caregiver assistance application 124 records the time intervals (and, in at least some cases, the actual dates and times) between receiving a patient-presence message (indicating the patient is present on patient support apparatus 20) and receiving a patient-absence message (indicating the patient is absent from patient support apparatus 20) for each patient support apparatus 20. These time intervals are then summed together and a running amount of patient-presence time is accumulated. Caregiver assistance application 124 further checks one or more of EMR server 98, ADT server 94, or data repository 128 to see which patients have an elevated fall risk (e.g. a fall risk sufficiently high to dictate—based on one or more of the fall risk reduction protocols 93—that the exit detection system 46 of their patient support apparatus 20 be armed every time they are on patient support apparatus 20). For those patients with the elevated fall risk, caregiver assistance application 124 determines how much time the patient spends on patient support apparatus 20 with the exit detection system 46 armed and how much time the patient spends on patient support apparatus 20 with exit detection system 46 disarmed. The ratio of these two is values is then shown in pie chart 908*a*.

In order to calculate the ratio shown in pie chart 908*a*, caregiver assistance application 124 uses messages 310 from patient support apparatuses 20 that, in addition to the patient-present and patient-absent messages, include messages indicating when exit detection system 46 is armed and when exit detection system 46 is disarmed. That is, each patient support apparatus 20 is configured to send at least four types of messages that are used for generating pie chart 908*a*: (1) the patient is present; (2) the patient is absent; (3) exit detection system 46 is armed; and (4) exit detection system 46 is disarmed. From this data, caregiver assistance application 124 is able to calculate pie chart 908*a*.

Caregiver assistance application 124 is able to calculate pie chart 908*a* in a variety of different manners. In one manner, pie chart 908*a* is calculated for all of the patient support apparatuses 20 (more specifically, for all patient support apparatuses 20 that have, or have had, a high fall risk patient on them) over a given time period. When calculated in this manner, caregiver assistance application 124 provides an overview of how well all of its caregivers are implementing at least one aspect of its fall prevention protocol 93. Caregiver assistance application 124, however, allows administrators, or other users of caregiver assistance application 124, to calculate pie chart 908*a* in other ways. For example, caregiver assistance application 124 is also able to calculate pie chart 908*a* for an individual caregiver, or for a selected set of caregivers. Alternatively, caregiver assistance application 124 can calculate pie chart 908*a* for a particular wing, ward, floor, or other section of the healthcare facility. Still further, the time period over which pie chart 908*a* is calculated is selectable by the user.

In some embodiments, caregiver assistance application 124 is further configured to enable the user to compute multiple pie charts 908*a* and simultaneously display them, thereby allowing the user to make easier visual comparisons between multiple pie charts 908*a*. For example, caregiver assistance application 124 can be instructed by a user to calculate a first pie chart 908*a* for an individual caregiver and display it next to a second pie chart 908*b* for all of the caregivers within the healthcare facility, thereby providing a visual comparison of how often a particular caregiver follows fall risk reduction protocol 93 in comparison to the rest of the caregivers of that healthcare facility. As another example, different pie charts 908*a* may be simultaneously displayed that show different time periods, thereby enabling a user to easily see how well the healthcare facility's compliance levels have changed over time. Still other types of pie charts 908*a* may be simultaneously displayed. It will further be understood that caregiver assistance application 124 may be configured to display other types of reports 898*a* than ones involving pie charts 908*a* (e.g. reports 898*a* may involve bar graphs, line graphs, text, etc.)

In order to display one or more reports 898*a*, the user may touch on a report icon 914 that is displayed, in at least one embodiment, near the top of almost all, if not all, of the screens of caregiver assistance application 124 (see, e.g. FIGS. 85-86). Once touched, the user is presented with a menu (not shown) allowing the user to select a type of report and the parameters used to populate the report (e.g. select the time period and what data will be used to populate the report (such as whether the report will be for a particular caregiver, or a set of caregivers, etc.)). At any point during the usage of the report-generating features of caregiver assistance application 124, if the user wishes to return to viewing any of the screens discussed above, he or she can touch the dashboard icon 916 that is also displayed on most, if not all, of the screens of caregiver assistance application 124 (see, e.g. FIGS. 85-86).

In some embodiments, the report icon 914 is only displayed on the screens of users who log into caregiver assistance application 124 as administrators (see the above discussion of access algorithm 153). In other embodiments, the report icon 914 and the reports that can be generated using caregiver assistance application 124 are shown on the caregiver's screens and caregiver are allowed to see and/or generate reports using this functionality of caregiver assistance application 124. In still other embodiments, a healthcare facility is able to customize which people are able to view and use the report generating features of caregiver assistance application 124, and/or what reports of caregiver assistance application 124 they are able to generate.

Figure 88:
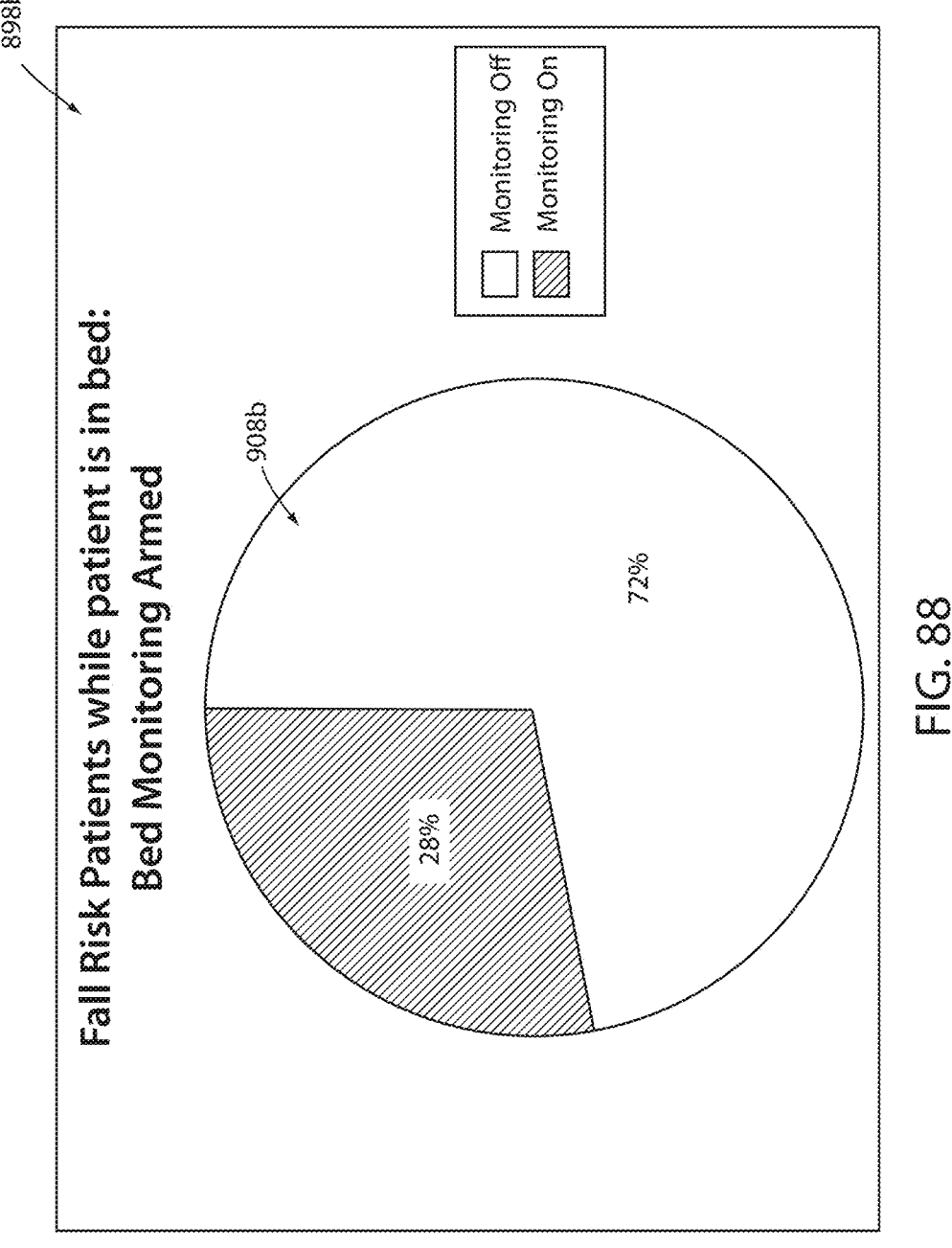
FIG. 88 is an illustration of a second type of report that may be generated by any of the caregiver assistance systems disclosed herein and that illustrates a pie chart of bed monitoring arming compliance.

FIG. 88 illustrates an example of a second type of report 898*b* that may be generated by caregiver assistance application 124. Report 898*b* includes a pie chart 908*b* that illustrates how often (in percentages) the bed monitoring system is armed on the patient support apparatuses 20 that are assigned to patients who have a high fall risk. As was noted previously, the bed monitoring system is a system that may be built into one or more of patient support apparatuses 20 that monitors, when armed, the state of various components of patient support apparatus 20 (e.g. brake, litter height, exit detection system 46, siderails 36) and issues an alert if any of these components change out of their desired states. Caregiver assistance application 124 is configured to generate report 898*b* and pie chart 908*b* in the same manner as it generates report 898*a* and pie chart 908*a*. That is, each patient support apparatus 20 that includes a bed watch monitoring system sends at least four types of messages 310 to caregiver assistance application 124 that are used by caregiver assistance application 124 to generate report 898*b*: (1) the patient is present; (2) the patient is absent; (3) the bed monitoring system is armed; and (4) the bed monitoring system is disarmed. Caregiver assistance application 124 uses these messages, as well as data from EMR server 98, ADT server 94, and/or data repository 128 indicating which patients have an elevated fall risk, to generate report 898*b*.

Caregiver assistance application 124 is configured to allow the user to change the parameters of report 898*b* in any of the same manners discussed above with respect to report 898*a* (e.g. these can be customized to show data for individual caregivers, for groups of caregivers, for particular locations of the healthcare facility, and for user-selectable time periods). Access to reports 898*b* is also controlled in the same manners as access to reports 898*a* (e.g. by selecting the "reports" icon 914), and reports 898 can be also be changed to different formats (e.g. bar graph, line graph, text, etc.). Caregiver assistance application 124 is also able to display one or more reports 898*b* simultaneously with one or more reports 898*a* (or other types of reports), if desired.

Figure 89:
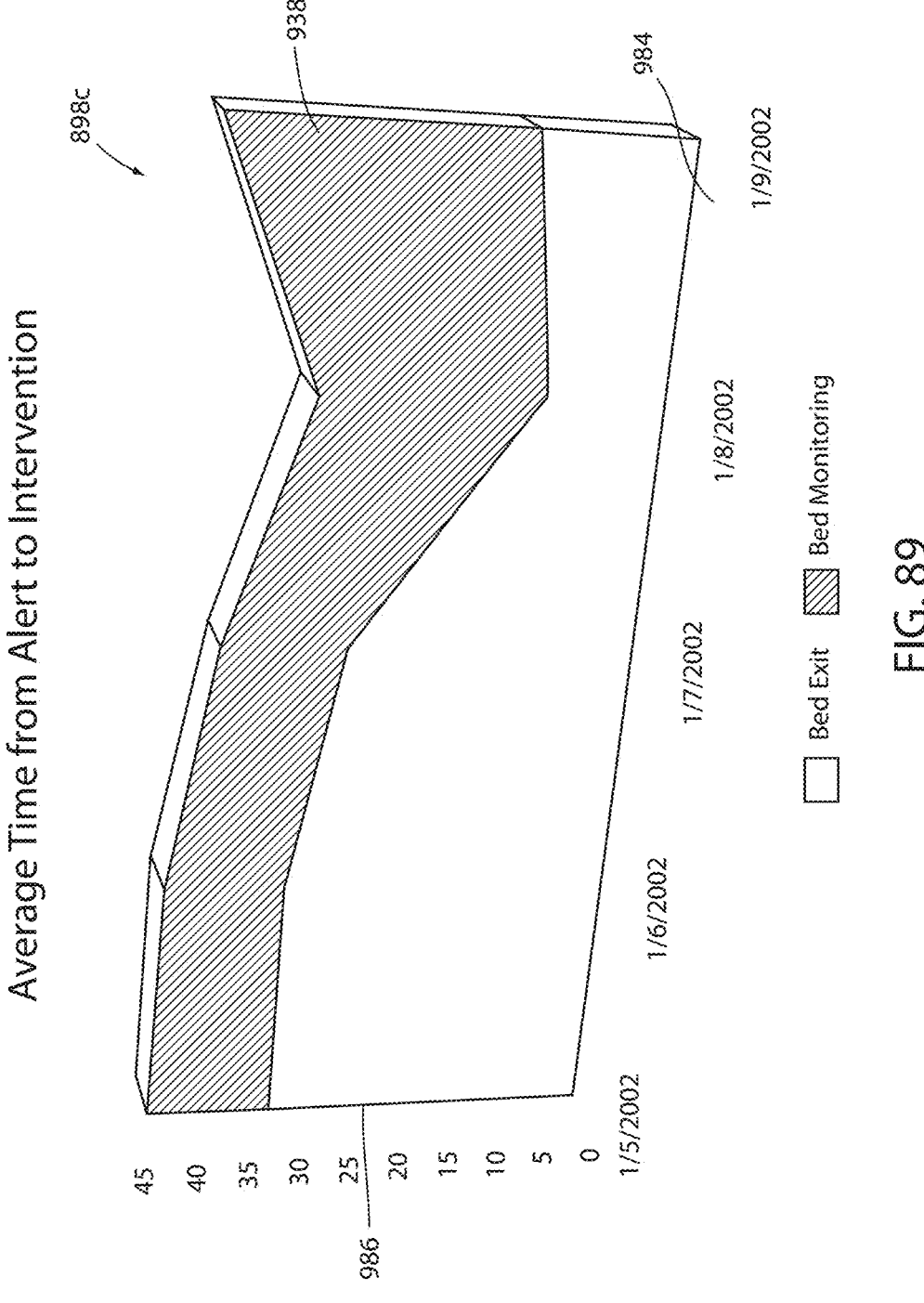
FIG. 89 is an illustration of a third type of report that may be generated by any of the caregiver assistance systems disclosed herein and that illustrates a graph of response times between alerts and caregiver intervention.

FIG. 89 illustrates an example of a third type of report 898*c* that may be generated by caregiver assistance application 124. Report 898*c* includes a line graph 938 having an X-axis 984 and a Y-axis 986. The X-axis 984 has units of time (dates, in this particular case) and the Y-axis has units of time (minutes, in this case). Line graph 938 plots the average time, for each day shown on X-axis 984, between an alert being issued from a patient support apparatus 20 and the caregiver arriving at the patient support apparatus 20 and shutting off the alert. In this specific example shown in FIG. 89, line graph 938 displays this time interval for two different types of alerts: exit detection alerts and bed monitoring alerts. The exit detection alerts are alerts issued when exit detection system 46 detects a patient exiting the patient support apparatus 20 while the exit detection system 46 is armed. The bed monitoring alerts are alerts issued when any of the components of patient support apparatus 20 that are monitored by the monitoring system changed to an undesired state.

Caregiver assistance application 124 generates reports such as report 898c utilizing two outputs from patient support apparatuses 20 for each of the different alerts. In other words, caregiver assistance application 124 generates that portion of report 898c corresponding to the exit detection alerts using two outputs and that portion of report 898c corresponding to the bed monitoring alert using another two outputs.

In particular, caregiver assistance application 124 generates the exit detection portion of report 898c by measuring the time between the receipt of a particular first message from a patient support apparatus 20 and a particular second message from the patient support apparatus 20. The first message is the alert message that is sent by patient support apparatus 20 when the patient is detected by exit detection system 46 to be exiting, or has exited from, patient support apparatus 20. The second message is sent by patient support apparatus 20 when a control on patient support apparatus 20 is activated (by the caregiver) that terminates the alert. The first message is sent substantially at the moment the exit alert is detected and the second message is sent substantially at the moment the exit alert is terminated by a caregiver. By monitoring the time interval between receipt of the first and second messages, caregiver assistance application 124 is able to determine how long it took the caregiver to respond to that particular exit detection alert. This time interval is recorded for each exit detection alert that occurs within the healthcare facility (as well as the time and/or date at which the exit alert happened). Each of the time intervals that occur on the same day (or within some other user-designated time period) are averaged together and the average is displayed for each day on report 898c.

Caregiver assistance application 124 generates the bed monitoring portion of report 898c in the same manner as the exit detection alert portion, except the first and second messages that are sent by patient support apparatus 20 for this portion of the report 898c are sent in response to the bed monitoring system being alerted and being terminated. That is, each patient support apparatus 20 also sends a first message to caregiver assistance application 124 whenever its bed monitoring system alerts, and it also sends a second message to caregiver assistance application 124 whenever a caregiver terminates the bed monitoring system alert. Because these messages are sent substantially at the same time as these respective events occur, caregiver assistance application 124 is able to determine the time interval between the alert being issued and the alert being terminated based upon the time interval between the receipt of these two messages. Caregiver assistance application 124 averages all of the time intervals together that occur on a particular day (or other user-designated time period) and displays the average on the line graph 938 of report 898c.

It will be understood that, as with reports 898a and 898b, report 898c can be modified by the user. Thus, for example, instead of averaging together all of the alert response times (i.e. intervals between the alert being issued and the alert being terminated) that occur anywhere within the healthcare facility on a given day, the user can average only those alerts for a particular caregiver or set of caregivers, or those alerts for a particular location within the healthcare facility. Further, multiple reports 898c can be simultaneously displayed, and/or one or more reports 898c can be simultaneously displayed with one or more reports 898a and/or 898b. Access to reports 898c is carried out in the same manners as access to reports 898a and 898b, which was described above and need not be repeated herein.

It will also be understood that report 898c can be generated in other manners besides the manners discussed above. For example, in one embodiment, caregiver assistance application 124 is configured to determine the response time to a particular alert by measuring the time interval between an alert issuing and the moment the caregiver enters the room in which the alert is issuing. In this particular embodiment, if the caregiver enters the room and chooses to first attend to the patient (rather than terminating the alert), the time spent attending to the patient until the caregiver terminates the alert is not counted as part of the response time. This particular embodiment may be implemented in a variety of different manners. One manner involves querying RTLS server 100 (if present in a healthcare facility) to determine when the caregiver enters a particular room. Another manner involves automatically detecting one or more short range signals between the caregiver's mobile electronic device 104a and the patient support apparatus 20 that is issuing the alarm. Another manner involves tracking the location of the caregiver's mobile electronic device 104a, or the caregiver itself, using triangulation from the known locations of the various wireless access points 76 positioned within the healthcare facility. Such triangulation techniques are described in greater detail in commonly assigned U.S. Pat. No. 9,838,836 issued to Hayes et al. and entitled PATIENT SUPPORT APPARATUS COMMUNICATION SYSTEMS, the complete disclosure of which is hereby incorporated herein by reference. Still other manners of determining the caregiver's presence may be utilized.

Figure 90:
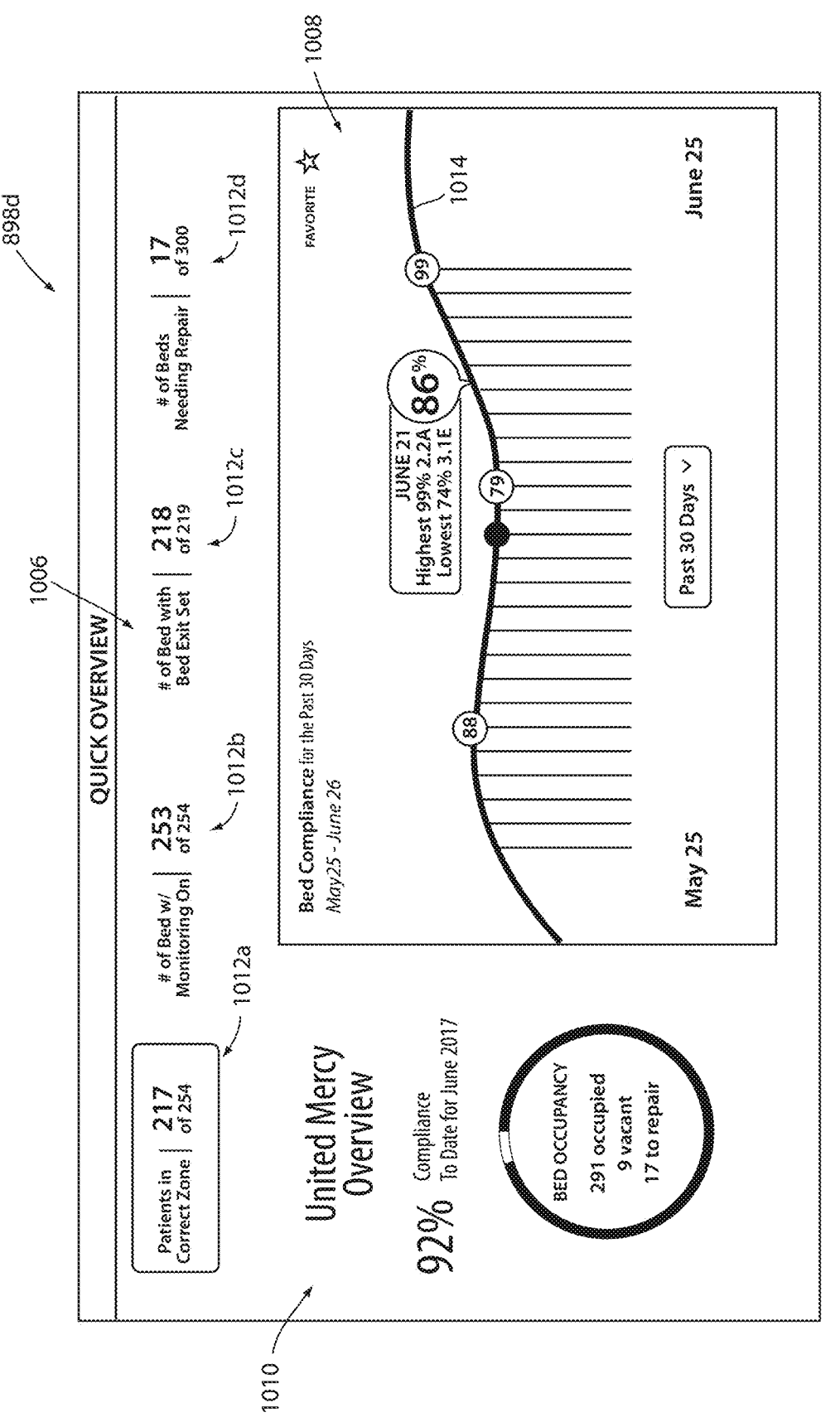
FIG. 90 is an illustration of a fourth type of report that may be generated by any of the caregiver assistance systems disclosed herein and that illustrates a number of statistics regarding the beds in a healthcare facility.

FIG. 90 illustrates an example of a fourth type of report 898d that may be generated by caregiver assistance application 124. Report 898d is a more comprehensive report than reports 898a, b, or c, and includes a quick overview area 1006, a graph area 1008, and a compliance summary area 1010. Quick overview area 1006 includes a first statistic 1012a, a second statistic 1012b, a third statistic 1012c, and a fourth statistic 1012d. First statistic 1012a indicates how many patient support apparatuses 20 are currently reporting the location of the patient thereon within a correct zone of patient support apparatus 20 (in some embodiments, the bed monitoring system monitors the patient's location on the support deck 30 and reports that information to caregiver assistance application 124). The correct zone may be defined as part of the fall risk reduction protocol 93, the bed sore risk reduction protocol, and/or another protocol.

Second statistic 1012b indicates how many of the patient support apparatuses 20 currently have their respective bed monitoring system armed. Third statistic 1012c indicates how many of the patient support apparatuses 20 currently have their respective exit detection system 46 armed. Fourth statistic 1012d indicates how many of the patient support apparatuses 20 currently need to be repaired and/or have some service work performed. All of statistics 1012a-d are based on messages sent to caregiver assistance application 124 from patient support apparatus 20. Fourth statistic 1012d may also, or alternatively, be based upon information obtained from equipment management system 918 (FIG. 71).

Graph area 1008 includes a graph 1014 that, in the particular example shown in FIG. 90, graphs a level of compliance of the patient support apparatuses 20 with respect to time. It will be understood that graph area 1008 may alternatively, or additionally, include any of the graphs and/or other information shown in any of reports 898a, b, and/or c. Compliance graph 1014 shows how many patient support apparatuses 20 are in compliance with one or more of the healthcare facility protocols (e.g. fall risk reduction protocol 93, bed sore risk reduction protocol 95, a Ventilator Associated Pneumonia (VAP) protocol (discussed below), a rounding frequency protocol, a mattress turning protocol, or another healthcare facility protocol). Graph 1014 is generated by caregiver assistance application 124 by determining which patients are subject to a particular healthcare facility protocol (e.g. high fall risk patients), what steps are to be taken with respect to those patients and/or their patient support apparatuses 20, and determining if such steps are taken within a timely manner. If one or more steps are not taken in a timely manner, caregiver assistance application 124 determines that the corresponding patient support apparatus 20 is not in compliance. If the one or more steps are taken in a timely manner, caregiver assistance application 124 determines that the corresponding patient support apparatus 20 is in compliance.

Compliance summary area 1010 indicates how many beds are in compliance for a particular date. It may also indicate how many beds are currently occupied, how many are vacant, and/or how many are in need of repair or servicing. Still other information may be displayed within compliance summary area 1010, and/or any of the other areas of report 898d.

It will be understood that additional reports and/or statistics beyond those illustrated in the accompanying drawings and described above may be generated by caregiver assistance application 124. Such additional reports and/or data include, but are not limited to, daily lists of activities (tasks, reminders, etc.) that were completed and/or not completed, patient information, patient support apparatus 20 alerts, EMR data, rounding data, and other types of data.

In some embodiments, caregiver assistance application 124 is configured to determine if patient support apparatuses 20 are in compliance with a VAP healthcare facility protocol. Such VAP protocols are designed to help reduce the risk of a patient developing VAP. In some embodiments, the VAP protocol specifies that the patient support apparatus 20 is to have an angular lockout armed when the corresponding patient is on a ventilator. The angular lockout, when armed, prevents the angle of head section 40 from being lowered below a certain threshold. In such embodiments, patient support apparatuses 20 send a message to caregiver assistance application 124 indicating when the angular lockout is activated and when the angular lockout is not activated. If the patient support apparatus 20 does not have this lockout armed when the patient is on a ventilator (as determined by caregiver assistance application 124 based on one or more inquiries sent to EMR server 98), caregiver assistance application 124 determines that the patient support apparatus 20 is not in compliance with the VAP protocol and, in at least some embodiments, issues an alert to the assigned caregiver(s). In some embodiments, the angular lockout feature may be customizable, such as disclosed in commonly assigned U.S. patent application Ser. No. 62/783,442 filed Dec. 21, 2018, by inventors Kurosh Nahavandi et al. and entitled PATIENT SUPPORT APPARATUSES WITH MOTION CUSTOMIZATION, the complete disclosure of which is incorporated herein by reference.

Figure 91:
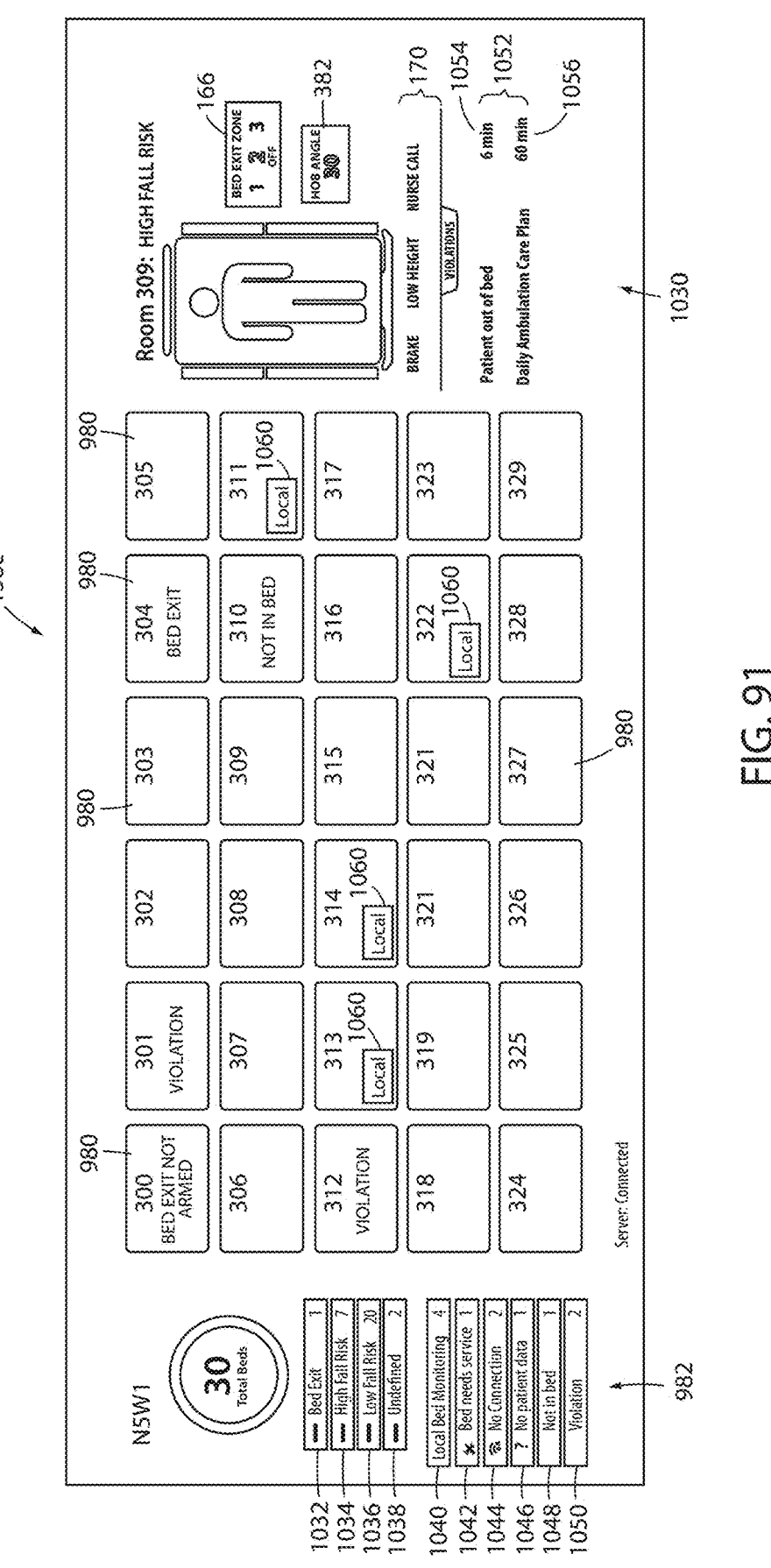
FIG. 91 is another illustrative room listing screen that may be displayed on any of the electronic devices of any of the caregiver assistance systems disclosed herein and that includes information beyond what is included on some of the other room listing screens, such as the amount of time the patient has spent out of bed.

FIG. 91 illustrates yet another alternative room listing screen 156c. Room listing screen 156c is displayed by caregiver assistance application 124 as an alternative to any of room listing screens 156, 156a, and/or 156b in some embodiments. In those embodiments, room listing screen 156c is displayed at any of the same times that room listing screens 156, 156a, and/or 156b are displayed, as described above. Room listing screen 156c is provided herein to show another example of the information content that may be included within a room listing screen. In some embodiments, any of the information on any of room listing screens 156, 156a, 156b, 156c may be combined in any desirable manner.

Room listing screen 156c (FIG. 91) differs from room listing screen 156 of FIG. 8, room listing screen 156a of FIG. 59, and room listing screen 156b of FIG. 84 in that it includes a number of additional items of information, including, but not limited to, a room detail area 1030. Room listing screen 156c also include additional information in the listing of rooms 980, as well as in its room status area 982.

Turning first to the room status area 982, caregiver assistance application 124 includes an exit summary 1032 indicating how many patient support apparatuses 20 are currently detecting a patient exit. In the particular example shown in FIG. 91, caregiver assistance application 124 has detected, and is reporting, that a single patient support apparatus 20 located in room 304 is currently detecting a patient exit condition. In some embodiments, caregiver assistance application 124 colors room icons 980 in a red, flashing color when a bed exit event is detected. Exit summary 1032 may be displayed in the same red color (and may or may not flash), or it may be displayed with a background in the same red color, in order to provide a visual indication to the user of the correlation between exit summary 1032 and any rooms 980 in which a patient support apparatus 20 is positioned whose exit detection system 46 has issued an alert. In other words, exit summary 1032 may be displayed in a color that matches the color of room 304 in FIG. 91.

Room listing screen 156c also includes a high fall risk summary 1034 in the room status area 982. High fall risk summary 1034 indicates the number of rooms 980 with patient support apparatuses 20 that have been assigned to patients who have been determined to be at a high risk for falling. In the particular example of FIG. 91, there are 7 patients who have been determined to be at a high fall risk. Caregiver assistance application 124 populates high fall risk summary 1034 by determining the fall risks of each patient in any of the manners previously discussed (e.g. by consulting ADT server 94, by consulting data repository 128, etc.). Caregiver assistance application 124 may be configured to display high fall risk summary 1034 in the same color as the rooms 980 in which a patient is located who has been determined to be a high fall risk. In at least one embodiment, caregiver assistance application 124 displays each room 980 to which a high fall risk patient has been assigned in a yellow color, and also displays high fall risk summary 1034 in the same yellow color, or with a background of the same yellow color.

Room listing screen 156c also includes a low fall risk summary 1036 in the room status area 982. Low fall risk summary 1036 indicates the number of rooms 980 with patient support apparatuses 20 that have been assigned to patients who have been determined to be at a low risk for falling. In the particular example of FIG. 91, there are twenty patients who have been determined to be at a low fall risk. Caregiver assistance application 124 populates low fall risk summary 1036 in the same manner as high fall risk summary 1034. Caregiver assistance application 124 may be configured to display low fall risk summary 1036 in the same color as the rooms 980 in which a patient is located who has been determined to be a low fall risk. In at least one embodiment, caregiver assistance application 124 displays each room 980 to which a low fall risk patient has been assigned in a green color, and also displays low fall risk summary 1036 in the same green color, or with a background of the same green color.

Room listing screen 156c also includes an undefined fall risk summary 1038 in the room status area 982. Undefined fall risk summary 1038 indicates the number of rooms 980 with patient support apparatuses 20 whose patients have not been assigned any fall rating, or whose fall rating caregiver assistance application 124 is unable to determine. In the particular example of FIG. 91, there are two patients whose fall risk has not been determined and/or made available to caregiver assistance application 124. Caregiver assistance application 124 may be configured to display undefined fall risk summary 1038 in the same color as the rooms 980 in which a patient is located whose fall risk is undetermined. In at least one embodiment, caregiver assistance application 124 displays each room 980 to which a patient with an unknown fall risk has been assigned in a gray color, and also displays undefined fall risk summary 1038 in the same gray color, or with a background of the same gray color.

Room status area 982 of room listing screen 156c further includes a local bed monitoring summary 1040, a bed service summary 1042, a no connection summary 1044, a no patient data summary 1046, an out-of-bed summary 1048, and a violation summary 1050. Local bed monitoring summary 1040 indicates how many patient support apparatuses 20 are currently being monitored locally at the patient support apparatus 20 (rather than at server 90 via caregiver assistance application 124) for changes to an undesired condition, as will be explained in greater detail below. Bed service summary 1042 indicates how many patient support apparatuses 20 currently are in need of servicing by a technician, or other service personnel. No connection summary 1044 indicates how many patient support apparatuses 20 are currently not in communication with server 90 and caregiver assistance application 124, and no connection summary 1044 may be determined by caregiver assistance application 124 in the same manner that it decides whether to display the wireless disconnection symbol 976, as discussed previously. No patient data summary 1046 indicates how many patient support apparatuses 20 caregiver assistance application 124 is currently unable to obtain patient data for, such as from ADT server 94. Out-of-bed summary 1048 indicates how many patients are currently out of their respective patient support apparatuses 20, as determined by, for example, the scale/exit detection system 46 onboard each of the patient support apparatuses detecting a weight less than a threshold (e.g. thirty pounds). Violation summary 1050 indicates how many patient support apparatuses 20 are in a state that violates one or more of the fall risk reduction protocol 93, bed sore risk reduction protocol 95, or any other defined setting that caregiver assistance application 124 is configured to monitor for compliance with a desired state and report when the patient support apparatus is in the undesired state.

Room detail area 1030 (FIG. 91) provides a summary of the status of one of the rooms 980 listed in the center area of room listing screen 156c. In the particular example shown in FIG. 91, room 309 has been selected for display in room detail area 1030. It will be understood that caregiver assistance application 124 is configured to display corresponding data for whichever room 980 a user selects from the center area of room listing screen 156c. Room detail area 1030 provides, in some embodiments, the same information that caregiver assistance application 124 provides on any of the various room overview screens 162, 162a, 162b, etc. discussed herein. In other embodiments, caregiver assistance application 124 is configured to display an abbreviated or otherwise modified version of the information of a room overview screen 162 in room detail area 1030.

In the particular example shown in FIG. 91, caregiver assistance application 124 displays the exit detection system status indicator 166, the HOB angle indicator 382, the bed status bar 170, and a text area 1052. Text area 1052 may include any of the information from any of the bottom portions 204 of any of the room overview screens 162 that have been discussed above and/or that are shown in the accompanying drawings. In the particular example of FIG. 91, text area 1052 provides information about the mobility of the patient assigned to that particular room.

In some embodiments, such as the embodiment shown in FIG. 91, caregiver assistance application 124 is configured to monitor the mobility of each of the patients. In such embodiments, caregiver assistance application 124 is configured to keep track of how much time each patient spends out of patient support apparatus 20. In one of these embodiments, caregiver assistance application 124 concludes that a patient has exited from his or her patient support apparatus 20 when the scale/exit detection system 46 of that patient support apparatus 20 indicates a weight reading below a particular threshold, such as, but not limited to, thirty pounds. In such embodiments, patient support apparatus 20 sends a message to caregiver assistance application 124 of the less than thirty-pound weight detection, and caregiver assistance application 124 records the time when this less than thirty-pound weight was first detected. When patient support apparatus 20 records a weight of more than thirty pounds, it sends another message to caregiver assistance application 124 and caregiver assistance application 124 determines the time difference between the moment the patient exited and the moment the patient returned to patient support apparatus 20. This time difference is added to any previous time differences that were previously computed and a running total of the total amount of time the patient has spent out of patient support apparatus 20 is maintained.

In some embodiments, caregiver assistance application 124 is configured to reset the running total of the patient's time out of patient support apparatus 20 every day. In other embodiments, caregiver assistance application 124 keeps a running total of the patient's time out of patient support apparatus 20 for the patient's entire stay at the healthcare facility. In still other embodiments, caregiver assistance application 124 is configurable by authorized users such that the amount of time for which the running total is maintained can be customized by a user. Still further, in some embodiments, caregiver assistance application 124 may be configured to keep multiple running totals of the amount of time the patient has spent out of patient support apparatus 20, each of which spans a different time period. For example, caregiver assistance application 124 may record the total amount of time the patient has spent out of patient support apparatus 20 for a particular day, as well as the total amount of time the patient has spent out of patient support apparatus 20 since the patient was admitted to the healthcare facility.

In some embodiments, caregiver assistance application 124 may be configured to further refine its estimate of how much time the patient spends out of patient support apparatus 20 such that the amount of time the patient spends sitting on a different patient support apparatus (e.g. a chair), or on a toilet, or on some other support is subtracted from the time spent out of patient support apparatus 20. These type of refinements provide the caregiver with a better estimate of the patient's mobility and/or how much time the patient has spent physically supporting himself or herself. These refinements may be carried out in some embodiments by having one or more chairs and/or restroom usage sensors positioned in the room 980 communicate with caregiver assistance application 124. For example, in some embodiments, caregiver assistance application 124 is configured to communicate with not only the bed(s) 20 positioned within a room, but also with one or more of the chairs positioned therein, and/or one or more sensors that detect when the patient is in the accompanying restroom.

One type of chair that may communicate with caregiver assistance application 124 is disclosed in commonly assigned U.S. Pat. No. 9,351,890 issued to Hough et al. and entitled MEDICAL SUPPORT APPARATUS, the complete disclosure of which is incorporated herein by reference. In some embodiments, the chair(s) (and/or beds 20) in the room 980 may communicate with server 86 and/or server 90 in any of the manners disclosed in commonly assigned U.S. patent publication 2013/0283529 published Oct. 31, 2013, filed by Michael Hayes et al. and entitled PATIENT SUPPORT APPARATUS COMMUNICATION SYSTEMS, the complete disclosure of which is incorporated herein by reference. Still further, in some embodiments, caregiver assistance application 124 monitors the time each patient spends out of patient support apparatus 20 in any of the same manners disclosed in commonly assigned U.S. patent publication 2016/0140827 published May 19, 2016, and filed by inventors Richard Derenne et al. and entitled PERSON SUPPORT APPARATUSES WITH PATIENT MOBILITY MONITORING, the complete disclosure of which is incorporated herein by reference.

Caregiver assistance application 124 is configured to display a total time out of bed indicator 1054 (FIG. 91) in room detail area 1030. Caregiver assistance application 124 may also be configured to display this total time out of bed indicator 1054 on any of the room overview screens 162 discussed above. Time of out bed indicator 1054 provides the caregiver with the current running total of the amount of time the patient has spent out of his or her patient support apparatus 20 (which may be the current running total for the day, for the entire visit, or for some other time period).

In some embodiments, caregiver assistance application 124 is further configured to display a desired time out of bed indicator 1056. Desired time out of bed indicator 1056 display the amount of time that a caregiver associated with the patient has set as a goal for the patient to be out of patient support apparatus 20. In some embodiments, any caregiver associated with the patient is able to set this goal using his associated mobile electronic device 104a or an adjacent stationary electronic device 104b. In other embodiments, only certain authorized caregiver are able to set this goal. Still further, in some embodiments, this goal is entered into the EMR server 98 and read automatically by caregiver assistance application 124, rather than having the user enter this goal directly into caregiver assistance application 124. Regardless of how it is conveyed to caregiver assistance application 124, caregiver assistance application displays desired time out of bed indicator 1056 adjacent to the measured time out of bed indicator 1054 so that the caregiver can easily see how much progress the patient has made toward reaching the time out of bed goal.

It will be understood that the particular set of rooms 980 displayed on any of the room listing screens (e.g. screen 156c of FIG. 91) is configurable by authorized individuals utilizing, for example, computer 134 and/or one of devices 104. Generally, the particular set of rooms 980 for a particular room listing screen 156 corresponds to a wing, ward, section, or other grouping of rooms within a hospital or other healthcare facility. Authorized individuals may configure the contents of any of these room listing screens 156 differently depending upon the particular user of a mobile electronic device 104a and/or the location of a stationary electronic device 104b. Thus, for example, caregiver assistance application 124 will respond to a caregiver who works in a pediatric ward and who presses a control on his or her mobile electronic device 104a that brings up a room listing screen 156 by displaying a set of rooms 980 that correspond to the pediatric ward. Caregiver assistance application 124 will not display rooms 980 in the maternity ward on that user's device 104, or rooms corresponding to other locations in the healthcare facility. Caregiver assistance application 124 will also display on that user's device a room status area 982 that corresponds to the pediatric patient support apparatuses 20, as well as, in some embodiments, a room detail area 1030 that provides additional details about one or more of the rooms 980 selected from the pediatric ward. In contrast, if a caregiver assigned to the surgical ward brings up a room listing screen 156 on his or her mobile electronic device 104a, caregiver assistance application 124 is configured to display a listing of rooms 980 that are assigned to the surgical ward, or that are otherwise associated with that caregiver's particular surgical duties. Caregiver assistance application 124 determines what data to populate room listing screens 156, 156a, 156b, etc. with by the login credentials that the user sends to caregiver assistance application 124, as well as the local data (stored in repository 128, for example) that correlates particular users to particular locations, patients, duties, and/or sections of the healthcare facility.

Returning to the local bed monitoring summary 1040 of room listing screen 156c (FIG. 91), caregiver assistance application 124 is configured to notify its users whenever a particular patient support apparatus 20 is being monitored by a local monitoring system that is built into the patient support apparatus 20, as opposed to the remote monitoring that is executed by caregiver assistance application 124 at server 90. In any particular caregiver assistance system 106, the particular patient support apparatuses 20 that populate the system 20 may be of different types, models, and/or brands, and some of those patient support apparatuses 20 may include an onboard local bed watch monitoring system that is built into the patient support apparatus, while others of those patient support apparatuses 20 may not include such a local bed watch monitoring system. The differences between these two types of monitoring are explained in greater detail below.

For those patient support apparatuses 20 that do include a local bed watch monitoring system built into them, the caregiver is able to turn on this local monitoring system by activating one or more controls on one or more of the patient support apparatus's control panels 42. In response to the caregiver activating this local bed watch monitoring system, the local controller 48 onboard the patient support apparatus 20 begins monitoring the state of one or more components of the patient support apparatus 20 and issues an alert when any of those monitored components are changed to an undesired state. The controller 48 then sends a message via network transceiver 60 to server 90 (either directly, or via server 86). In response, caregiver assistance application 124 reports the activation of the alert to those electronic devices 104 that are associated with that particular patient support apparatus 20.

Such local bed watch monitoring systems 20 are typically constructed such that caregiver assistance application 124 is not able to override or otherwise select the components or subsystems that are monitored on those patient support apparatuses. In other words, the patient support apparatuses 20 with the built-in monitoring systems may be constructed to monitor a set of components that cannot be changed by caregiver assistance application 124 (although they may be customizable locally using one of the control panels 42). Accordingly, the set of monitored conditions for such patient support apparatuses 20 may not necessarily be the same as the set of conditions that are monitored on other patient support apparatuses 20, such as those patient support apparatuses 20 that are monitored by the remote bed watch monitoring function built into caregiver assistance application 124 itself. Caregiver assistance application 124 therefore provides an indication of which patient support apparatuses 20 are being monitored by a local, built-in monitoring system onboard the patient support apparatus 20. In the example of FIG. 91, caregiver assistance application 124 provides this indication by a local indicator 1060 provided for each room 980 in which a patient support apparatus 20 is located that has its local bed monitoring system activated, rather than the remote monitoring that is carried out by caregiver assistance application 124.

For patient support apparatuses 20 that do not have a local, built-in monitoring system, the local controller 48 sends messages to caregiver assistance application 124 when the status of any of its components and/or subsystems changes. Caregiver assistance application 124 monitors these status updates to see if any components and/or subsystems have changed to an undesired state. If so, caregiver assistance application 124 issues an alert to the electronic device(s) 104 associated with that particular patient support apparatus 20. Thus, it can be seen that for patient support apparatuses 20 that do not have a local, built-in monitoring system, caregiver assistance application 124 is able to perform this monitoring remotely by monitoring the status updates that are repetitively fed to caregiver assistance application 124. For these patient support apparatuses 20, caregiver assistance application 124 determines what components are to be monitored and/or what states are to be considered desired and undesired. Typically, caregiver assistance application 124 will choose a set of conditions to monitor, as well as the desired states for those conditions, in a uniform manner for all patient support apparatuses 20 that have no built-in bed monitoring system and that have patients assigned to them who share the same fall risk, bed sore risk, or other risk profile. In this manner, the caregivers are assured that they will receive the same type of alerts for all patients with the same risk profile. However, as noted above, some patient support apparatuses 20 may have built-in local bed monitoring systems that provide alerts based on different criteria, and therefore caregiver assistance application 124 notifies its users of this local bed monitoring by providing local indicator 1060 for those patient support apparatuses 20.

Figure 92:
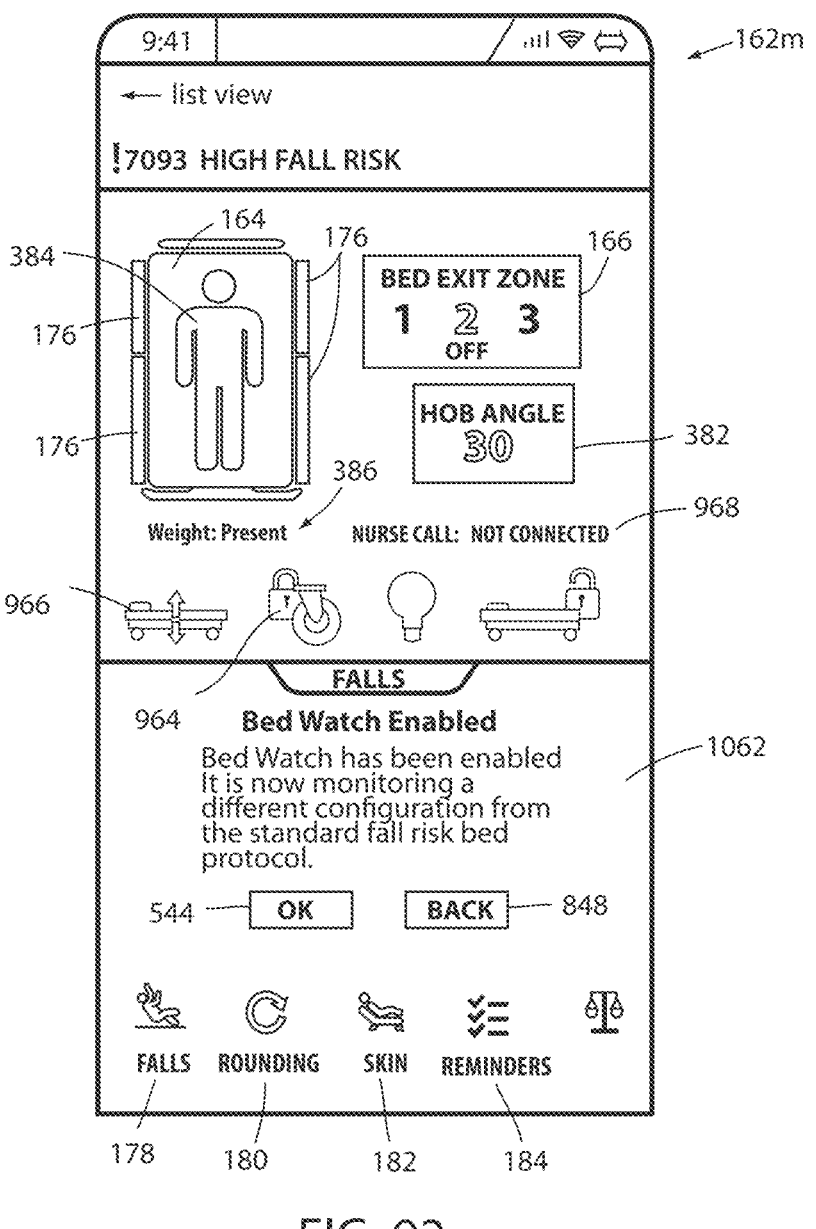
FIG. 92 is another illustrative room overview screen that is displayable on an electronic device of any of the caregiver assistance systems disclosed herein and that illustrates a notification for when a bed having a local, built-in monitoring system has had its monitoring system activated.

In addition to the local indicator 1060 that is placed on each room 980 in which a patient support apparatus 20 is located that is monitoring a set of components using its local, built-in monitoring system, caregiver assistance application 124 is also configured to provide additional notifications to the user of such local bed monitoring usage. For example, in some embodiments, caregiver assistance application 124 is configured to provide a message indicating such local bed monitoring on any of the room overview screens 162. One example of such a message is shown on room overview screen 162*m* of FIG. 92. Specifically, room overview screen 162*m* includes a message window 1062 that instructs the user that the local bed monitoring system of the patient support apparatus 20 in room 7093 has been activated, and that this local bed monitoring may be monitoring different criteria from what caregiver assistance application 124 would monitor were it to monitor that patient support apparatus. (The criteria used by caregiver assistance application 124 is defined in protocols 93, 95, and/or other protocols). If the user presses the OK icon 544, caregiver assistance application 124 allows the local bed monitoring system to be activated. If the user presses the Back icon 848, caregiver assistance application 124 sends a message to the patient support apparatus 20 instructing it not to arm its local bed monitoring system.

Room overview screen 162*m* also includes additional items of information that may be displayed on any of the other room overview screens discussed above. These additional items of information include a lockout indicator 1064 and a scale task icon 1066. Lockout indicator 1064 indicates to the user whether the corresponding patient support apparatus 20 (e.g. the bed in room 7093 in the example of FIG. 92) has had its lifts 26 locked out such that the patient is not able to change the height of litter frame 28. Scale task icon 1066, when pressed, brings the user to a scale screen (not shown) that allows the user to take a patient weight reading and/or perform other scale related functions on the patient support apparatus 20. Thus, the scale screen allows the user to remotely control one or more aspects of the scale/exit detection system 46 of the patient support apparatus 20.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A caregiver assistance system for helping a caregiver to perform patient care tasks, the caregiver assistance system comprising:

(a) a patient support apparatus comprising:
   a litter frame;
   a support deck supported on the litter frame and configured to support a patient thereon;
   a memory containing an identifier uniquely identifying the patient support apparatus;
   a nurse call cable port adapted to couple to a first end of a nurse call cable having a second end adapted to couple to a nurse call outlet to thereby enable the patient support apparatus to communicate with a nurse call system;
   a sensor adapted to detect if the nurse call cable port is electrically coupled to the nurse call system via the nurse call cable;
   a transceiver; and
   a controller in communication with the memory, the transceiver, and the sensor, the controller adapted to transmit the identifier and data from the sensor off the patient support apparatus; and (b) a caregiver assistance application adapted to be executed on a server, the caregiver assistance application adapted to receive the identifier and the sensor data from the patient support apparatus and to perform the following:

(i) forward the sensor data to a mobile electronic device associated with the caregiver assigned to the patient; and (ii) display a connection indicator on a display of the mobile electronic device, the connection indicator indicating whether or not the nurse call cable port is communicatively connected to the nurse call system.

2. The caregiver assistance system of claim 1 wherein the caregiver assistance application is further adapted to display a time on the mobile electronic device indicating when the caregiver should perform a rounding task for the patient.

3. The caregiver assistance system of claim 2 wherein the caregiver assistance application is further adapted to receive completion data from the caregiver indicating when the caregiver has completed the rounding task.

4. The caregiver assistance system of claim 3 wherein the caregiver assistance application is further adapted to forward the completion data to an electronic medical record server for entry in a patient record corresponding to the patient.

5. The caregiver assistance system of claim 3 wherein the mobile electronic device is adapted to obtain confirmation data confirming a presence of the caregiver adjacent the patient support apparatus when the caregiver completes the rounding task, and the mobile electronic device is further adapted to forward the confirmation data to the caregiver assistance application.

6. The caregiver assistance system of claim 1 wherein the patient support apparatus further comprises a battery and a battery sensor adapted to detect a status of the battery, wherein the controller is adapted to send the status of the battery to the caregiver assistance application, and the caregiver assistance application is further adapted to display on the display of the mobile electronic device a battery status indicator, the battery status indicator indicating the status of the battery.

7. The caregiver assistance system of claim 1 wherein the patient support apparatus further comprises a short range transceiver adapted to communicate with a headwall-mounted short range transmitter of a location beacon, the short range transceiver adapted to forward location data and beacon battery status data to the patient support apparatus, the location data indicative of a location of the patient support apparatus and the beacon battery status data indicative of a status of a battery of the location beacon, and wherein the patient support apparatus is adapted to forward the beacon battery status data to the caregiver assistance application and the caregiver assistance application is further adapted to display a beacon status indicator on the display of the mobile electronic device, the beacon status indicator indicating a current status of the battery of the location beacon.

8. A caregiver assistance system for helping a caregiver to perform patient care tasks, the caregiver assistance system comprising:

(a) a patient support apparatus comprising:

a litter frame;

a support deck supported on the litter frame and configured to support a patient thereon;

a memory containing an identifier uniquely identifying the patient support apparatus;

a short range transceiver adapted to communicate with a short range transmitter of a location beacon mounted to headwall of a healthcare facility room, the short range transceiver adapted to receive location data and beacon battery status data from the location beacon, the location data indicative of a location of the patient support apparatus and the beacon battery status data indicative of a current status of a battery of the location beacon;

a network transceiver; and a controller in communication with the memory, the network transceiver, and the short range transceiver, the controller adapted to transmit the identifier, the location data, and the beacon battery status data off the patient support apparatus via the network transceiver; and (b) a caregiver assistance application adapted to be executed on a server, the caregiver assistance application adapted to receive the location data and beacon battery status data and to perform the following:

(i) determine a location of the patient support apparatus using the location data;

(ii) forward the beacon battery status data to a mobile electronic device associated with the caregiver assigned to the patient; and (iii) display a beacon battery status indicator on a display of the mobile electronic device, the beacon battery status indicator indicating the current status of the battery of the location beacon.

9. The caregiver assistance system of claim 8 wherein the caregiver assistance application is further configured to perform at least two of the following:

(a) receive bed sore risk data from the caregiver regarding the patient's risk of developing bed sores and determine a bed sore risk assessment score from the bed sore risk data;

(b) receive fall risk data from the caregiver regarding the patient's risk of falling and determine a fall risk assessment score from the fall risk data;

(c) receive completion data from the caregiver indicating when the caregiver has completed a rounding task associated with the patient;

(d) display a bed sore risk assessment indicator on the display of the mobile electronic device, the bed sore risk assessment indicator indicating the patient's risk of developing bed sores;

(e) display a fall risk assessment indicator on the display of the mobile electronic device, the fall risk assessment indicator indicating the patient's risk of falling;

(f) display a time until a next rounding task is to be completed for the patient;

(g) display a reminder to perform a rounding task with the patient;

(h) display a reminder to perform a bed sore risk assessment for the patient;

(i) display a reminder to perform a fall risk assessment for the patient;

(j) arm an exit detection system onboard the patient support apparatus using the mobile electronic device; and (k) receive an exit alert when the patient exits from the patient support apparatus.

10. The caregiver assistance system of claim 9 wherein the mobile electronic device is one of a smart phone or a tablet computer.

11. The caregiver assistance system of claim 10 wherein the patient support apparatus further comprises:

a nurse call cable port adapted to couple to a first end of a nurse call cable having a second end adapted to couple to a nurse call outlet to thereby enable the patient support apparatus to communicate with a nurse call system; and a sensor adapted to detect if the nurse call cable port is electrically coupled to the nurse call system via the nurse call cable; and wherein the controller is adapted to transmit data from the sensor to the caregiver assistance application and the caregiver assistance application is further adapted to display a connection indicator on the display of the mobile electronic device, the connection indicator indicating whether or not the nurse call cable port is communicatively connected to the nurse call system.

12. The caregiver assistance system of claim 10 wherein the patient support apparatus further comprises a battery and a battery sensor adapted to detect a status of the battery, wherein the controller is adapted to send the status of the battery to the caregiver assistance application, and the caregiver assistance application is further adapted to display on the display of the mobile electronic device a battery status indicator, the battery status indicator indicating the status of the battery.

13. The caregiver assistance system of claim 10 wherein controller is further adapted to forward signal strength data to the caregiver assistance application, the signal strength data indicative of a strength of a signal between the network transceiver and a wireless access point of a healthcare facility, wherein the caregiver assistance application is further adapted to display a signal strength indicator on the display of the mobile electronic device, the signal strength indicator indicating the strength of the signal between the network transceiver and the wireless access point of the healthcare facility.

14. A caregiver assistance system for helping a caregiver to perform patient care tasks, the caregiver assistance system comprising:

(a) a patient support apparatus comprising:
   a litter frame;
   a support deck supported on the litter frame and configured to support a patient thereon;
   a memory containing an identifier uniquely identifying the patient support apparatus;
   a short range transceiver adapted to communicate with a short range transmitter of a location beacon mounted to headwall of a healthcare facility room, the short range transceiver adapted to receive location data from the location beacon;
   a network transceiver adapted to wirelessly communicate with a wireless access point of a healthcare facility network; and
   a controller in communication with the memory, the short range transceiver, and the network transceiver, the controller adapted to transmit the identifier and location data off the patient support apparatus via the network transceiver; and (b) a caregiver assistance application adapted to be executed on a server, the caregiver assistance application adapted to receive the identifier and location data from the patient support apparatus via the network transceiver and to perform the following:
   (i) determine a location of the patient support apparatus using the location data;
   (ii) forward the location to a mobile electronic device associated with the caregiver assigned to the patient;

(iii) display the location on display of the mobile electronic device; and
   (iv) display a wireless connection indicator on the display of the mobile electronic device, the wireless connection indicator comprising a first form indicating the patient support apparatus is unable to wirelessly communicate with the caregiver assistance application using the network transceiver, and a second form indicating the patient support apparatus is able to wirelessly communicate with the caregiver assistance application using the network transceiver.

15. The caregiver assistance system of claim 14 wherein the caregiver assistance application is further adapted to perform the following: query an Admission, Discharge, and Tracking server for patient-room assignment information and use the patient-room assignment information to determine if the patient support apparatus is unable to communicate wirelessly with the caregiver assistance application.

16. The caregiver assistance system of claim 14 wherein the caregiver assistance application is further configured to perform at least two of the following:
   (a) receive bed sore risk data from the caregiver regarding the patient's risk of developing bed sores and determine a bed sore risk assessment score from the bed sore risk data;
   (b) receive fall risk data from the caregiver regarding the patient's risk of falling and determine a fall risk assessment score from the fall risk data;
   (c) receive completion data from the caregiver indicating when the caregiver has completed a rounding task associated with the patient;
   (d) display a bed sore risk assessment indicator on the display of the mobile electronic device, the bed sore risk assessment indicator indicating the patient's risk of developing bed sores;
   (e) display a fall risk assessment indicator on the display of the mobile electronic device, the fall risk assessment indicator indicating the patient's risk of falling;
   (f) display a time until a next rounding task is to be completed for the patient;
   (g) display a reminder to perform a rounding task with the patient;
   (h) display a reminder to perform a bed sore risk assessment for the patient;
   (i) display a reminder to perform a fall risk assessment for the patient;
   (j) arm an exit detection system onboard the patient support apparatus using the mobile electronic device; and
   (k) receive an exit alert when the patient exits from the patient support apparatus.

17. The caregiver assistance system of claim 16 wherein the patient support apparatus further comprises:
   a nurse call cable port adapted to couple to a first end of a nurse call cable having a second end adapted to couple to a nurse call outlet to thereby enable the patient support apparatus to communicate with a nurse call system; and
   a sensor adapted to detect if the nurse call cable port is electrically coupled to the nurse call system via the nurse call cable; and
   wherein the controller is adapted to transmit data from the sensor to the caregiver assistance application and the caregiver assistance application is further adapted to display a connection indicator on the display of the mobile electronic device, the connection indicator indicating whether or not the nurse call cable port is communicatively connected to the nurse call system.

18. The caregiver assistance system of claim 17 wherein the patient support apparatus further comprises a battery and a battery sensor adapted to detect a status of the battery, wherein the controller is adapted to send the status of the battery to the caregiver assistance application, and the caregiver assistance application is further adapted to display on the display of the mobile electronic device a battery status indicator, the battery status indicator indicating the status of the battery.

19. The caregiver assistance system of claim 18 wherein the short range transceiver is further adapted to receive beacon battery status data from the location beacon, the beacon battery status data indicative of a status of a battery of the location beacon, and wherein the patient support apparatus is adapted to forward the beacon battery status data to the caregiver assistance application and the caregiver assistance application is further adapted to display a beacon status indicator on the display of the mobile electronic device, the beacon status indicator indicating a current status of the battery of the location beacon.

20. The caregiver assistance system of claim 18 wherein the caregiver assistance application is further adapted to perform the following: (a) display a time on the display of the mobile electronic device indicating when the caregiver should perform a rounding task for the patient; (b) receive completion data from the caregiver indicating when the caregiver has completed the rounding task; and (c) forward the completion data to an electronic medical record server for entry in a patient record corresponding to the patient.

*     *     *     *     *